US008513400B2

(12) United States Patent  
Ward et al.

(10) Patent No.: US 8,513,400 B2
(45) Date of Patent: Aug. 20, 2013

(54) MODULATION OF HIF1α AND HIF2α EXPRESSION

(75) Inventors: Donna T. Ward, North Chelmsford, MA (US); Kenneth W. Dobie, Del Mar, CA (US); Eric G. Marcusson, San Francisco, CA (US); Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/642,534

(22) Filed: Dec. 18, 2009

(65) Prior Publication Data

US 2011/0190370 A1  Aug. 4, 2011

Related U.S. Application Data

(63) Continuation of application No. 11/527,876, filed on Sep. 26, 2006, now abandoned, which is a continuation of application No. 10/719,370, filed on Nov. 21, 2003, now Pat. No. 7,217,572, which is a continuation-in-part of application No. 10/304,126, filed on Nov. 23, 2002, now Pat. No. 7,144,999.

(51) Int. Cl.
*C07H 21/04* (2006.01)
*C12N 15/113* (2006.01)

(52) U.S. Cl.
USPC .......................................... 536/24.5; 514/44

(58) Field of Classification Search
None
See application file for complete search history.

(56) References Cited

U.S. PATENT DOCUMENTS

| | | | |
|---|---|---|---|
| 5,695,963 A | 12/1997 | McKnight et al. | |
| 5,801,154 A | 9/1998 | Baracchini et al. | |
| 5,882,914 A | 3/1999 | Semenza | |
| 6,060,458 A | 5/2000 | Moschel et al. | |
| 6,133,246 A | 10/2000 | McKay et al. | |
| 6,395,548 B1 | 5/2002 | Lee et al. | |
| 6,432,927 B1 | 8/2002 | Gregory et al. | |
| 6,582,908 B2 | 6/2003 | Fodor et al. | |
| 6,958,240 B1 | 10/2005 | Baird et al. | |
| 7,144,999 B2 | 12/2006 | Ward et al. | |
| 7,589,190 B2 | 9/2009 | Westergaard et al. | |
| 7,737,264 B2 | 6/2010 | Thrue et al. | |
| 2001/0053519 A1 | 12/2001 | Fodor et al. | |
| 2003/0045686 A1 | 3/2003 | Kaelin, Jr. et al. | |
| 2003/0228597 A1 | 12/2003 | Cowsert et al. | |
| 2004/0086498 A9 | 5/2004 | Krissansen et al. | |
| 2004/0096848 A1 | 5/2004 | Thrue et al. | |
| 2004/0152655 A1 | 8/2004 | Yoon et al. | |
| 2004/0180357 A1 | 9/2004 | Reich et al. | |
| 2004/0220393 A1 | 11/2004 | Ward et al. | |
| 2004/0241651 A1* | 12/2004 | Olek et al. | 435/6 |
| 2005/0070474 A1 | 3/2005 | Krissansen et al. | |
| 2005/0096282 A1 | 5/2005 | Lewin et al. | |
| 2005/0148496 A1 | 7/2005 | Defranoux et al. | |
| 2005/0163781 A1 | 7/2005 | Koninckx et al. | |
| 2006/0252721 A1 | 11/2006 | Westergaard et al. | |

FOREIGN PATENT DOCUMENTS

| | | |
|---|---|---|
| EP | 0147819 | 6/1992 |
| JP | 2005529589 | 10/2005 |
| WO | WO 99/48916 | 9/1999 |
| WO | WO 99/54500 | 10/1999 |
| WO | WO 00/09657 | 2/2000 |
| WO | WO 01/62965 | 8/2001 |
| WO | WO 0177384 A2 * | 10/2001 |
| WO | WO 02/34291 | 5/2002 |
| WO | WO 02/068466 | 9/2002 |
| WO | WO 02/086497 | 10/2002 |
| WO | WO 02/094862 | 11/2002 |
| WO | WO 03/040366 | 5/2003 |
| WO | WO 03/085110 | 10/2003 |
| WO | WO 2004/042024 | 5/2004 |
| WO | WO 2005/035759 | 4/2005 |
| WO | WO 2006/050734 | 6/2006 |

OTHER PUBLICATIONS

Agrawal et al., "Antisense therapeutics: is it as simple as complementary base recognition?" Molecular Medicine Today (2000) 6:72-81.

Andrew et al., "Nickel requires hypoxia-inducibile factor-1alpha, not redox signaling, to induce plasminogen activator inhibitor-1"Am. J. Physiol. Lung Cell Ml. Physiol. (2001) 281:L607-L615.

Branch, "A good antisense molecule is hard to find" TIBS (1998) 3:45-50.

Caniggia et al., "Oxygen and Placental Development During the First Trimester: Implications for the Pathophysiology of Pre-eclampsia" Placenta (2000) 21(Suppl. 1): S25-S30.

Caniggia et al., "Hypoxia-inducible factor-1 mediates the biological effects of oxygen on human trophoblast differentiation through TGFB3" J. Clin. Invest. (2000) 105(5):577-587.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chirila et al., "The use of synthetic polymers for delivery of therapeutic antisense oligodeoxynucleotides" Biomaterials (2002) 23:321-342.

Cockman et al., "Hypoxia Inducible Factor-alpha Binding and Ubiquitylation by the von Hippel-Lindau Tumor Supressor Protein" J. Biol. Chem. (2000) 275(33):25733-25741.

(Continued)

*Primary Examiner* — Tracy Vivlemore
(74) *Attorney, Agent, or Firm* — Isis Pharmaceuticals Patent Dept.

(57) ABSTRACT

Compounds, compositions and methods are provided for modulating the expression of HIF1α and/or HIF2α. The compositions comprise oligonucleotides, targeted to nucleic acid encoding HIF1α and HIF2α. Methods of using these compounds for modulation of HIF1α and/or HIF2α expression and for diagnosis and treatment of disease associated with expression of HIF1α and/or HIF2α are provided.

18 Claims, No Drawings

(56) References Cited

OTHER PUBLICATIONS

Comerford et al., "Hypoxia-inducible factor-1-dependent regulation of the multidrug resistance (MDR1) gene" Cancer Research (2002) 62: 3387-3394.
Conrad et al., "EPAS1 trans-Activation during Hypoxia Requires p42/p44 MAPK" J. Biol. Chem. (1999) 274(47):33709-33713.
Conrad et al., "The molecular basis of )2-sensing and hypoxia tolerence in pheochromocytoma cells" Comparative Biochem. Physiol. B (2001) 128:187-204.
Crooke, "Basic Principles of Antisense Therapeutics" Antisense Research & Therapeutics (1998) Crooke (ed.) Springer-Verlag, Berlin pp. 1-50.
Drutel et al., "Two splice variants of the hypoxia-inducible factor HIF-1alpha as potential dimerization partners of ARNT2 in neurons" European J. Neuroscience (2000) 12:3701-3708.
Ema et al., "A novel bHLH-PAS factor with close sequence similarity to hypoxia-indubile factor 1alpha regulates the VEGF expression and is potentially involved in lung and vascular development" PNAS (1997) 94:4273-4278.
Favier et al., "Angiogenesis and Vascular Architecture in Pheochromocytomas" Am. J. Pathology (2002) 161(4):1235-1246.
Flamme et al., "HRF, a putative basic helix-loop-helix-PAS-domain transcription factor is closely related to hypoxia-inducible factor-1alpha and developmentally expressed in blood vessels" Mech. Dev. (1997) 63:51-60.
Flamme et al., "Up-Regulation of Vascular Endothelial Growth Factor in Stromal Cells of Hemangioblastomas is Correlated with Up-Regulation of the Transcription Factor HRF/HIF-2alpha" Am. J. Pathology (1998) 153(1):25-29.
Furuta et al., "Hypoxia-inducible Factor 1-dependent Induction of Intestinal Trefoil Factor Protects Barrier Function during Hypoxia" J. Exp. Med. (2001) 193(9):1027-1034.
Giatromanolaki et al., "Relation of hypoxia inducible factor 1alpha and 2 alpha in operable non-small cell lung cancer to angiogenic/molecular profile of tumours and survival" Br. J. Cancer (2001) 85(6):881-890.
Giatromanolaki et al., "Hypoxia inducible factor 1 alpha and 2 alpha overexpression in inflammatory bowel disease" J. Clin. Pathol. (2003) 56:209-213.
Harris, "Hypoxia—A Key Regulatory Factor in Tumour Growth" Nature Reviews Cancer (2002) 2:38-47.
Hirsila et al., "Characterization of the Human Prolyl 4-Hydroxylases That Modify the Hypoxia-inducible Factor" J. Biol. Chem. (2003) 278(33):30772-30780.
Hogenesch et al., "Characterization of a Subset of the Basic Helix-Loop-Helix-PAS Superfamily That Interacts with Components of the Dioxin Signaling Pathway" J. Biol. Chem. (1997) 272(13):8581-8593.
Huang et al., "Regulation of hypoxia-inducible factor 1alpha is mediated by an O2-dependent degradation domain via the ubiquitin-proteasome pathway" PNAS (1998) 95:7987-7992.
Iyer et al., "Cellular and developmental control of 02 homeostasis by hypoxia-inducible factor 1alpha" Genes Dev. (1998) 12:149-162.
Kakinuma et al., "Novel Molecular Mechanism of Increased Myocardial Endothelial-1 Expression in the Failing Heart Involving the Transcriptional Factor Hypoxia-Inducible Factor-lalpha Induced for Impaired Myocardial Energy Metabolism" Circulation (2001) 103:2387-2394.
Kang et al., "An antisense oligonucleotide that inhibits the expression of hypoxia-induced factor-1alpha alters hypoxia-injduced changes in proliferation and viability of human cardiac fibroblasts" Circulation, American Heart Association (2001) 104: 1157.
Koukourakis et al., "Hypoxia-Inducible Factor (HIF1A and HIF2A), Angiogenesis, and Chemoradiotherapy Outcome of Squamous Cell Head-and-Neck Cancer" Int. J. Radiation Oncology Biol. Phys. (2002) 53(5):1192-1202.
Leek et al., "Relation of Hypoxia-inducible Factor-2alpha (HIF-2a) Expression in Tumor-infiltrative Macrophages to Tumor Angiogenesis and the Oxidative Thymidine Phosphorylase Pathway in Human Breast Cancer" Cancer Res. (2002) 62:1326-1329.

Liang et al., "Activation of Vascular Endothelial Growth Factor A Transcription in Tumorigenic Glioblastoma Cell Lines by an Enhancer with Cell Type-specific Dnase I Accessibility" J. Biol. Chem. (2002) 277(22):20087-20094.
Liu et al., "Up-Regulation of Hypoxia-inducible Factor 2alpha in Renal Cell Carcinoma Associated with Loss of TSC-2 Tumor Suppressor Gene" Cancer Res. (2003) 63:2675-2680.
Maemura et al., "Generation of a Dominant-negative Mutant of Endothelial PAS Domain Protein 1 by Deletion of a Potent C-terminal Transactivation Domain" J. Biol. Chem. (1999) 274(44)31565-31570.
Maxwell et al., "The tumour suppressor protein VHL targets hypoxia-inducible factors for oxygen-dependent proteolysis" Nature (1999) 399:271-275.
Maxwell et al., "Insights into the Role of the von Hippel-Lindau Gene Product" Exp. Nephrol. (2001) 9:235-240.
Maxwell et al., "Activation of the HIF pathway in cancer" Curr. Opin. Genetics Dev. (2001) 11:293-299.
Minchenko et al., "Hypoxia-inducibile Factor-1-mediated Expression of the 6-Phosphorofructor-2-kinase/fructose-2, 6-bisphosphatase-3 (PFKFB3) Gene" J. Biol. Chem. (2002) 277(8):6183-6187.
Narravula et al., "Hypoxia-Inducible Factor 1-Mediated Inhibition of Peroxisome Proliferator-Activated Receptor Alpha Expression During Hypoxia" J. Immunol. (2001) 166:7543-8.
New England Biolabs 1998/99 Catalog (cover page and pp. 121 and 284).
Ohh et al., "Ubiquitination of hypoxia-inducible factor requires direct binding to the B-domain of the von Hippel-Lindau protein" Nature Cell Biology (2000) 2:423-427.
Opalinska et al., "Nucleic-Acid Therapeutics: Basic Principles and Recent Applications" Nature Reviews Drug Discovery (2002) 1:503-514.
Peracchi et al., "Prospects for antiviral ribozymes and deoxyribozymes" Rev. Med. Virol. (2004) 14:47-64.
Pugh et al., "The vin Hippel-Lindau tumor suppressor, hypoxia-inducible factor-1 (HIF1) degradation, and cancer pathogenesis" Seminars in Cancer Biol. (2003) 13:83-89.
Rajakumar et al., "Expression, Ontogeny, and Regulation of Hypoxia-Inducible Transcription Factors in the Human Placenta" Biol. Reproduction (2000) 63:559-569.
Rajakumar et al., "Selective Overexpression of the Hypoxia-Inducible Transcription Factor, HIF-2alpha, in Placentas from Women with Preeclampsia" Biol. Reproduction (2001) 64:499-506.
Ravi et al., "Regulation of tumor angiogenesis by p53-induced degradation of hypoxia-inducible factor 1alpha" Genes Dev. (2000) 14:43-44.
Reynolds et al., "Rational siRNA design for RNA interference" Nature Biotechnology (2004) 22(3):326-330.
Ryan et al., "HIF-1alpha is required for solid tumor formation and embryonic vascularization" EMBO J. (1998) 17(11):3005-3015.
Safran et al., "HIF hydroxylation and the mammalian oxygen-sensing pathway" J. Clin. Invest. (2003) 111(6):779-783.
Sanghvi et al., "Heterocyclic Base Modifications in Nucleic Acids and Their Applications in Antisense Oligonucleotides" Antisense Research and Applications (1993) pp. 273-288.
Sato et al., "Inducible Expression of Endothelial PAS Domain Protein-1 by Hypoxia in Human Lung Adenocarcinoma A549 Cells" Am. J. Respir. Cell Mol. Biol. (2002) 26:127-134.
Semenza, "HIF-1 and human disease: one highly involved factor" Genes Dev. (2000) 14: 1983-1991.
Semenza, "Hypoxia-induced factor 1: oxygen homeostasis and disease pathophysiolog" Trends in Mol. Med. (2001) 7(8):345-350.
Semenza, "Hypoxia-Inducible Factor 1: Control of Oxygen Homeostasis in Health and Disease" Pediatric Res. (2001) 49(5):614-617.
Sowter et al., "Predominant Role of Hypoxia-Inducible Transcription Factor (Hif)-1alpha versus HIF-2alpha in Regulation of the Transcriptional Response to Hypoxia" Cancer Res. (2003) 63:6130-6134.
Sun et al., "Gene transfer of antisense hypoxia inducible factor-1alpha enhances the therapeutic efficacy of cancer immunotherapy" Gene Therapy (2001) 8:638-645.

Sutter et al., "Hypoxia-inducible factor 1alpha protein expression is controlled by oxygen-regulated ubiquitination that is disrupted by deletions and missense mutations" PNAS (2000) 97(9):4748-4753.

Synnestvedt et al., "Ecto-5-nucleotide (CD73) regulation by hpyoxia-inducible factor-1 mediates permeability changed in intestinal epithelia" Journal of Clinical Investigation (2002) 110: 993-1002.

Talks et al., "The Expression and Distribution of the Hypoxia-Inducible Factors HIF-1 alpha and HIF-1alpha in Normal Human Tissues, Cancer and Tumors-Associated Macrophages" Am. J. Pathology (2000) 157(2):411-421.

Tanaka et al., "Endothelial PAS Domain Protein 1 (EPAS1) Induces Adrenomedullin Gene Expression in Cardiac Myocytes: Role of EPAS1 in an Inflammatory Response in Cardiac Myocytes" J. Mol. Cell. Cardiol. (2002) 34:739-748.

Thrash-Bingham et al., "aHIF: a Natural Antisense Transcript Overexpressed in Human Renal Cancer During Hypoxia" J. Natl. Cancer Inst. (1999) 91(2):143-151.

Tian et al., "Endothelial PAS domain protein 1 (EPAS1), a transcription factor selectively expressed in endothelial cells" Genes Dev. (1997) 11:72-82.

Tian et al., "The hypoxia-responsive transcription facor EPAS1 is essential for catecholamine homeostasis and protection against heart failure during embryonic development" Genes Dev. (1998) 12:3320-3324.

Wang et al., "Hypoxia-inducible factor 1 is a basic-helix-loop-helix-PAS heterodimer regulated by cellular O2 tension" PNAS (1995) 92:5510-5514.

Wang et al., "Purification and Characterization of Hypoxia-Inducible Factor 1" J. Biol. Chem. (1995) 270(3):1230-1237.

Wiesener et al., "Induction of Endothelial PAS Domain Protein-1 by Hypoxia: Characterization and Comparison with Hypoxia-Inducible Factor-1alpha" Blood (1998) 92(7):2260-2268.

Xia et al., "Regulation of Vascular Endothelial Growth Factor Transcription by Endothelial PAS Domain Protein 1 (EPAS1) and Possible Involvement of EPAS1 in the Angiogenesis of Renal Cell Carcinoma" Cancer (2001) 91(8):1429-1436.

Xia et al., "Positive Expression of HIF-2a/EPAS1 in Invasive Bladder Cancer" Urology (2002) 59:774-778.

Yu et al., "Impaired physiological responses to chronic hypoxia in mice partially deficient for hypoxia-induced factor 1a" J. Clin. Invest. (1999) 103(5):691-696.

Zagzag et al., "Expression of Hypoxia-Inducible Factor 1a in Brain Tumors" Cancer (2000) 88(11):2606-2618.

Supplementary European Search Report for EP Application No. EP03787010 dated Jan. 10, 2007.

International Search Report for PCT/US03/37383 dated Jan. 5, 2005.

Akhtar et al., "In vivo studies with antisense oligonucleotides" Trends in Pharmacological Sciences (1997) 18(1):12-18.

Hoeg et al., "Specific Down-Regulation of Hypoxia-Inducible Factor 1 Alpha (HIF1 Alpha) in a Human GlioBlastoma Cell Line by Locked Nucleic Acid (LNA) Antisense Oligonucelotides" Proceedings of the Annual Meeting of the American Association for Cancer Research (2002) 43:962.

European Search Report for application EP 10177650.8 dated Aug. 2, 2011.

* cited by examiner

SEQUENCE LISTING

```
<160> NUMBER OF SEQ ID NOS: 458

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(3)
<223> OTHER INFORMATION: 2'-O-methoxyethyl with phosphorothioate
      backbone
<220> FEATURE:
<221> NAME/KEY: misc_feature
<222> LOCATION: (13)..(20)
<223> OTHER INFORMATION: 2'-O-methoxyethyl with phosphorothioate
      backbone

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
```

```
<220> FEATURE:
<223> OTHER INFORMATION: Oligonucleotide primer
<220> FEATURE:
<221> NAME/KEY: misc_feature
<222> LOCATION: (1)..(5)
<223> OTHER INFORMATION: 2'-O-methoxyethyl with phosphorothioate
      backbone
<220> FEATURE:
<221> NAME/KEY: misc_feature
<222> LOCATION: (16)..(20)
<223> OTHER INFORMATION: 2'-O-methoxyethyl with phosphorothioate
      backbone

<400> SEQUENCE: 2
gtgcgcgcga gcccgaaatc                                                  20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(5)
<223> OTHER INFORMATION: 2'-O-methoxyethyl with phosphorioate backbone
<220> FEATURE:
<221> NAME/KEY: misc_feature
<222> LOCATION: (16)..(20)
<223> OTHER INFORMATION: 2'-O-methoxyethyl with phosphorioate backbone

<400> SEQUENCE: 3
atgcattctg cccccaagga                                                  20

<210> SEQ ID NO 4
<211> LENGTH: 3933
<212> TYPE: DNA
<213> ORGANISM: Homo sapiens
<220> FEATURE:
<221> NAME/KEY: CDS
<222> LOCATION: (265)..(2745)
<300> PUBLICATION INFORMATION:
<301> AUTHORS: Hogenesch et al.
<302> TITLE: Characterization of a subset of the basic-helix-loop-
      helix-PAS superfamily that interacts with components of the
      dioxin signaling pathway
<303> JOURNAL: J. Biol. Chem
<304> VOLUME: 272
<305> ISSUE: 13
<306> PAGES: 8581-8593
<307> DATE: 1997
<308> DATABASE ACCESSION NUMBER: U29165.1
<309> DATABASE ENTRY DATE: 1997-04-11
<313> RELEVANT RESIDUES: (1)..(3933)

<400> SEQUENCE: 4
cacgaggcag cactctcttc gtcgcttcgg ccagtgtgtc gggctgggcc ctgacaagcc         60
acctgaggag aggctcggag ccgggcccgg accccggcga ttgccgcccg cttctctcta        120
gtctcacgag gggtttcccg cctcgcaccc ccacctctgg acttgccttt ccttctcttc        180
tccgcgtgtg gagggagcca gcgcttaggc cggagcgagc ctgggggccg ccgccgtga         240 agacatcgcg gggaccgatt cacc atg gag ggc gcc ggc ggc gcg aac gac          291
                             Met Glu Gly Ala Gly Gly Ala Asn Asp
                              1               5 aag aaa aag ata agt tct gaa cgt cga aaa gaa aag tct cga gat gca         339
Lys Lys Lys Ile Ser Ser Glu Arg Arg Lys Glu Lys Ser Arg Asp Ala
 10              15                  20                  25 gcc aga tct cgg cga agt aaa gaa tct gaa gtt ttt tat gag ctt gct         387
Ala Arg Ser Arg Arg Ser Lys Glu Ser Glu Val Phe Tyr Glu Leu Ala
             30                  35                  40
```

-continued

| | | |
|---|---|---|
| cat cag ttg cca ctt cca cat aat gtg agt tcg cat ctt gat aag gcc<br>His Gln Leu Pro Leu Pro His Asn Val Ser Ser His Leu Asp Lys Ala<br>            45                    50                   55 | 435 |
| tct gtg atg agg ctt acc atc agc tat ttg cgt gtg agg aaa ctt ctg<br>Ser Val Met Arg Leu Thr Ile Ser Tyr Leu Arg Val Arg Lys Leu Leu<br>60                    65                    70 | 483 |
| gat gct ggt gat ttg gat att gaa gat gac atg aaa gca cag atg aat<br>Asp Ala Gly Asp Leu Asp Ile Glu Asp Asp Met Lys Ala Gln Met Asn<br>        75                    80                    85 | 531 |
| tgc ttt tat ttg aaa gcc ttg gat ggt ttt gtt atg gtt ctc aca gat<br>Cys Phe Tyr Leu Lys Ala Leu Asp Gly Phe Val Met Val Leu Thr Asp<br>90                    95                   100            105 | 579 |
| gat ggt gac atg att tac att tct gat aat gtg aac aaa tac atg gga<br>Asp Gly Asp Met Ile Tyr Ile Ser Asp Asn Val Asn Lys Tyr Met Gly<br>            110                   115                  120 | 627 |
| tta act cag ttt gaa cta act gga cac agt gtg ttt gat ttt act cat<br>Leu Thr Gln Phe Glu Leu Thr Gly His Ser Val Phe Asp Phe Thr His<br>                125                  130                  135 | 675 |
| cca tgt gac cat gag gaa atg aga gaa atg ctt aca cac aga aat ggc<br>Pro Cys Asp His Glu Glu Met Arg Glu Met Leu Thr His Arg Asn Gly<br>140                    145                   150 | 723 |
| ctt gtg aaa aag ggt aaa gaa caa aac aca cag cga agc ttt ttt ctc<br>Leu Val Lys Lys Gly Lys Glu Gln Asn Thr Gln Arg Ser Phe Phe Leu<br>        155                   160                  165 | 771 |
| aga atg aag tgt acc cta act agc cga gga aga act atg aac ata aag<br>Arg Met Lys Cys Thr Leu Thr Ser Arg Gly Arg Thr Met Asn Ile Lys<br>170                    175                   180                  185 | 819 |
| tct gca aca tgg aag gta ttg cac tgc aca ggc cac att cac gta tat<br>Ser Ala Thr Trp Lys Val Leu His Cys Thr Gly His Ile His Val Tyr<br>            190                   195                  200 | 867 |
| gat acc aac agt aac caa cct cag tgt ggg tat aag aaa cca cct atg<br>Asp Thr Asn Ser Asn Gln Pro Gln Cys Gly Tyr Lys Lys Pro Pro Met<br>                205                   210                  215 | 915 |
| acc tgc ttg gtg ctg att tgt gaa ccc att cct cac cca tca aat att<br>Thr Cys Leu Val Leu Ile Cys Glu Pro Ile Pro His Pro Ser Asn Ile<br>220                    225                   230 | 963 |
| gaa att cct tta gat agc aag act ttc ctc agt cga cac agc ctg gat<br>Glu Ile Pro Leu Asp Ser Lys Thr Phe Leu Ser Arg His Ser Leu Asp<br>        235                   240                  245 | 1011 |
| atg aaa ttt tct tat tgt gat gaa aga att acc gaa ttg atg gga tat<br>Met Lys Phe Ser Tyr Cys Asp Glu Arg Ile Thr Glu Leu Met Gly Tyr<br>250                    255                   260                  265 | 1059 |
| gag cca gaa gaa ctt tta ggc cgc tca att tat gaa tat tat cat gct<br>Glu Pro Glu Glu Leu Leu Gly Arg Ser Ile Tyr Glu Tyr Tyr His Ala<br>            270                   275                  280 | 1107 |
| ttg gac tct gat cat ctg acc aaa act cat cat gat atg ttt act aaa<br>Leu Asp Ser Asp His Leu Thr Lys Thr His His Asp Met Phe Thr Lys<br>                285                   290                  295 | 1155 |
| gga caa gtc acc aca gga cag tac agg atg ctt gcc aaa aga ggt gga<br>Gly Gln Val Thr Thr Gly Gln Tyr Arg Met Leu Ala Lys Arg Gly Gly<br>300                    305                   310 | 1203 |
| tat gtc tgg gtt gaa act caa gca act gtc ata tat aac acc aag aat<br>Tyr Val Trp Val Glu Thr Gln Ala Thr Val Ile Tyr Asn Thr Lys Asn<br>        315                   320                  325 | 1251 |
| tct caa cca cag tgc att gta tgt gtg aat tac gtt gtg agt ggt att<br>Ser Gln Pro Gln Cys Ile Val Cys Val Asn Tyr Val Val Ser Gly Ile<br>330                    335                   340                  345 | 1299 |
| att cag cac gac ttg att ttc tcc ctt caa caa aca gaa tgt gtc ctt<br>Ile Gln His Asp Leu Ile Phe Ser Leu Gln Gln Thr Glu Cys Val Leu<br>            350                   355                  360 | 1347 |

| | | | | | | | | | | | | | | | | |
|---|---|---|---|---|---|---|---|---|---|---|---|---|---|---|---|---|
| aaa | ccg | gtt | gaa | tct | tca | gat | atg | aaa | atg | act | cag | cta | ttc | acc | aaa | 1395 |
| Lys | Pro | Val | Glu | Ser | Ser | Asp | Met | Lys | Met | Thr | Gln | Leu | Phe | Thr | Lys | |
| | | | 365 | | | | | 370 | | | | | 375 | | | |
| gtt | gaa | tca | gaa | gat | aca | agt | agc | ctc | ttt | gac | aaa | ctt | aag | aag | gaa | 1443 |
| Val | Glu | Ser | Glu | Asp | Thr | Ser | Ser | Leu | Phe | Asp | Lys | Leu | Lys | Lys | Glu | |
| | | | 380 | | | | | 385 | | | | | 390 | | | |
| cct | gat | gct | tta | act | ttg | ctg | gcc | cca | gcc | gct | gga | gac | aca | atc | ata | 1491 |
| Pro | Asp | Ala | Leu | Thr | Leu | Leu | Ala | Pro | Ala | Ala | Gly | Asp | Thr | Ile | Ile | |
| | | 395 | | | | | 400 | | | | | 405 | | | | |
| tct | tta | gat | ttt | ggc | agc | aac | gac | aca | gaa | act | gat | gac | cag | caa | ctt | 1539 |
| Ser | Leu | Asp | Phe | Gly | Ser | Asn | Asp | Thr | Glu | Thr | Asp | Asp | Gln | Gln | Leu | |
| 410 | | | | | 415 | | | | | 420 | | | | | 425 | |
| gag | gaa | gta | cca | tta | tat | aat | gat | gta | atg | ctc | ccc | tca | ccc | aac | gaa | 1587 |
| Glu | Glu | Val | Pro | Leu | Tyr | Asn | Asp | Val | Met | Leu | Pro | Ser | Pro | Asn | Glu | |
| | | | | 430 | | | | | 435 | | | | | 440 | | |
| aaa | tta | cag | aat | ata | aat | ttg | gca | atg | tct | cca | tta | ccc | acc | gct | gaa | 1635 |
| Lys | Leu | Gln | Asn | Ile | Asn | Leu | Ala | Met | Ser | Pro | Leu | Pro | Thr | Ala | Glu | |
| | | | 445 | | | | | 450 | | | | | 455 | | | |
| acg | cca | aag | cca | ctt | cga | agt | agt | gct | gac | cct | gca | ctc | aat | caa | gaa | 1683 |
| Thr | Pro | Lys | Pro | Leu | Arg | Ser | Ser | Ala | Asp | Pro | Ala | Leu | Asn | Gln | Glu | |
| | | | 460 | | | | | 465 | | | | | 470 | | | |
| gtt | gca | tta | aaa | tta | gaa | cca | aat | cca | gag | tca | ctg | gaa | ctt | tct | ttt | 1731 |
| Val | Ala | Leu | Lys | Leu | Glu | Pro | Asn | Pro | Glu | Ser | Leu | Glu | Leu | Ser | Phe | |
| | | 475 | | | | | 480 | | | | | 485 | | | | |
| acc | atg | ccc | cag | att | cag | gat | cag | aca | cct | agt | cct | tcc | gat | gga | agc | 1779 |
| Thr | Met | Pro | Gln | Ile | Gln | Asp | Gln | Thr | Pro | Ser | Pro | Ser | Asp | Gly | Ser | |
| 490 | | | | | 495 | | | | | 500 | | | | | 505 | |
| act | aga | caa | agt | tca | cct | gag | cct | aat | agt | ccc | agt | gaa | tat | tgt | ttt | 1827 |
| Thr | Arg | Gln | Ser | Ser | Pro | Glu | Pro | Asn | Ser | Pro | Ser | Glu | Tyr | Cys | Phe | |
| | | | | 510 | | | | | 515 | | | | | 520 | | |
| tat | gtg | gat | agt | gat | atg | gtc | aat | gaa | ttc | aag | ttg | gaa | ttg | gta | gaa | 1875 |
| Tyr | Val | Asp | Ser | Asp | Met | Val | Asn | Glu | Phe | Lys | Leu | Glu | Leu | Val | Glu | |
| | | | 525 | | | | | 530 | | | | | 535 | | | |
| aaa | ctt | ttt | gct | gaa | gac | aca | gaa | gca | aag | aac | cca | ttt | tct | act | cag | 1923 |
| Lys | Leu | Phe | Ala | Glu | Asp | Thr | Glu | Ala | Lys | Asn | Pro | Phe | Ser | Thr | Gln | |
| | | 540 | | | | | 545 | | | | | 550 | | | | |
| gac | aca | gat | tta | gac | ttg | gag | atg | tta | gct | ccc | tat | atc | cca | atg | gat | 1971 |
| Asp | Thr | Asp | Leu | Asp | Leu | Glu | Met | Leu | Ala | Pro | Tyr | Ile | Pro | Met | Asp | |
| | | 555 | | | | | 560 | | | | | 565 | | | | |
| gat | gac | ttc | cag | tta | cgt | tcc | ttc | gat | cag | ttg | tca | cca | tta | gaa | agc | 2019 |
| Asp | Asp | Phe | Gln | Leu | Arg | Ser | Phe | Asp | Gln | Leu | Ser | Pro | Leu | Glu | Ser | |
| 570 | | | | | 575 | | | | | 580 | | | | | 585 | |
| agt | tcc | gca | agc | cct | gaa | agc | gca | agt | cct | caa | agc | aca | gtt | aca | gta | 2067 |
| Ser | Ser | Ala | Ser | Pro | Glu | Ser | Ala | Ser | Pro | Gln | Ser | Thr | Val | Thr | Val | |
| | | | | 590 | | | | | 595 | | | | | 600 | | |
| ttc | cag | cag | act | caa | ata | caa | gaa | cct | act | gct | aat | gcc | acc | act | acc | 2115 |
| Phe | Gln | Gln | Thr | Gln | Ile | Gln | Glu | Pro | Thr | Ala | Asn | Ala | Thr | Thr | Thr | |
| | | | 605 | | | | | 610 | | | | | 615 | | | |
| act | gcc | acc | act | gat | gaa | tta | aaa | aca | gtg | aca | aaa | gac | cgt | atg | gaa | 2163 |
| Thr | Ala | Thr | Thr | Asp | Glu | Leu | Lys | Thr | Val | Thr | Lys | Asp | Arg | Met | Glu | |
| | | 620 | | | | | 625 | | | | | 630 | | | | |
| gac | att | aaa | ata | ttg | att | gca | tct | cca | tct | cct | acc | cac | ata | cat | aaa | 2211 |
| Asp | Ile | Lys | Ile | Leu | Ile | Ala | Ser | Pro | Ser | Pro | Thr | His | Ile | His | Lys | |
| 635 | | | | | 640 | | | | | 645 | | | | | | |
| gaa | act | act | agt | gcc | aca | tca | tca | cca | tat | aga | gat | act | caa | agt | cgg | 2259 |
| Glu | Thr | Thr | Ser | Ala | Thr | Ser | Ser | Pro | Tyr | Arg | Asp | Thr | Gln | Ser | Arg | |
| 650 | | | | | 655 | | | | | 660 | | | | | 665 | |
| aca | gcc | tca | cca | aac | aga | gca | gga | aaa | gga | gtc | ata | gaa | cag | aca | gaa | 2307 |
| Thr | Ala | Ser | Pro | Asn | Arg | Ala | Gly | Lys | Gly | Val | Ile | Glu | Gln | Thr | Glu | |
| | | | | 670 | | | | | 675 | | | | | 680 | | |

```
aaa tct cat cca aga agc cct aac gtg tta tct gtc gct ttg agt caa    2355
Lys Ser His Pro Arg Ser Pro Asn Val Leu Ser Val Ala Leu Ser Gln
            685                 690                 695 aga act aca gtt cct gag gaa gaa cta aat cca aag ata cta gct ttg    2403
Arg Thr Thr Val Pro Glu Glu Glu Leu Asn Pro Lys Ile Leu Ala Leu
        700                 705                 710 cag aat gct cag aga aag cga aaa atg gaa cat gat ggt tca ctt ttt    2451
Gln Asn Ala Gln Arg Lys Arg Lys Met Glu His Asp Gly Ser Leu Phe
    715                 720                 725 caa gca gta gga att gga aca tta tta cag cag cca gac gat cat gca    2499
Gln Ala Val Gly Ile Gly Thr Leu Leu Gln Gln Pro Asp Asp His Ala
730                 735                 740                 745 gct act aca tca ctt tct tgg aaa cgt gta aaa gga tgc aaa tct agt    2547
Ala Thr Thr Ser Leu Ser Trp Lys Arg Val Lys Gly Cys Lys Ser Ser
                750                 755                 760 gaa cag aat gga atg gag caa aag aca att att tta ata ccc tct gat    2595
Glu Gln Asn Gly Met Glu Gln Lys Thr Ile Ile Leu Ile Pro Ser Asp
            765                 770                 775 tta gca tgt aga ctg ctg ggg caa tca atg gat gaa agt gga tta cca    2643
Leu Ala Cys Arg Leu Leu Gly Gln Ser Met Asp Glu Ser Gly Leu Pro
        780                 785                 790 cag ctg acc agt tat gat tgt gaa gtt aat gct cct ata caa ggc agc    2691
Gln Leu Thr Ser Tyr Asp Cys Glu Val Asn Ala Pro Ile Gln Gly Ser
    795                 800                 805 aga aac cta ctg cag ggt gaa gaa tta ctc aga gct ttg gat caa gtt    2739
Arg Asn Leu Leu Gln Gly Glu Glu Leu Leu Arg Ala Leu Asp Gln Val
810                 815                 820                 825 aac tga gcttttctt aatttcattc cttttttttgg acactggtgg ctcactacct    2795
Asn aaagcagtct atttatattt tctacatcta attttagaag cctggctaca atactgcaca    2855
aacttggtta gttcaatttt tgatcccctt tctacttaat ttacattaat gctcttttt     2915 agtatgttct ttaatgctgg atcacagaca gctcattttc tcagtttttt ggtatttaaa    2975
ccattgcatt gcagtagcat cattttaaaa aatgcacctt tttatttatt tattttttggc   3035 tagggagttt atccctttt cgaattattt ttaagaagat gccaatataa ttttttgtaag   3095 aaggcagtaa cctttcatca tgatcatagg cagttgaaaa attttttacac ctttttttttc  3155 acattttaca taaataataa tgctttgcca gcagtacgtg gtagccacaa ttgcacaata    3215
tattttctta aaaaatacca gcagttactc atggaatata ttctgcgttt ataaaactag    3275 ttttttaagaa gaaatttttt ttggcctatg aaattgttaa acctggaaca tgacattgtt   3335
aatcatataa taatgattct taaatgctgt atggtttatt atttaaatgg gtaaagccat    3395
ttacataata tagaaagata tgcatatatc tagaaggtat gtggcattta tttggataaa    3455
attctcaatt cagagaaatc atctgatgtt tctatagtca ctttgccagc tcaaaagaaa    3515 acaatacccct atgtagttgt ggaagtttat gctaatattg tgtaactgat attaaaccta   3575
aatgttctgc ctaccctgtt ggtataaaga tattttgagc agactgtaaa caagaaaaaa    3635
aaaatcatgc attcttagca aaattgccta gtatgttaat ttgctcaaaa tacaatgttt    3695
gattttatgc acttttgtcgc tattaacatc cttttttttca tgtagatttc aataattgag   3755
taattttaga agcattattt taggaatata tagttgtcac agtaaatatc ttgttttttc    3815
tatgtacatt gtacaaattt ttcattcctt ttgctctttg tggttggatc taacactaac    3875
tgtattgttt tgttacatca aataaacatc ttctgtggaa aaaaaaaaaa aaaaaaa       3933
```

<210> SEQ ID NO 5

```
<211> LENGTH: 23
<212> TYPE: DNA
<213> ORGANISM: Artificial Sequence
<220> FEATURE:
<223> OTHER INFORMATION: PCR Primer

<400> SEQUENCE: 5
ccagttacgt tccttcgatc agt                                              23

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
tttgaggact tgcgctttca                                                  20

<210> SEQ ID NO 7
<211> LENGTH: 28
<212> TYPE: DNA
<213> ORGANISM: Artificial Sequence
<220> FEATURE:
<223> OTHER INFORMATION: PCR Primer

<400> SEQUENCE: 7
tcaccattag aaagcagttc cgcaagcc                                         28

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                   19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                  20

<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
caagcttccc gttctcagcc                                                  20

<210> SEQ ID NO 11
<211> LENGTH: 57500
<212> TYPE: DNA
<213> ORGANISM: Homo sapiens
<220> FEATURE:
<221> NAME/KEY: misc_feature
<222> LOCATION: (1)..(57500)
<223> OTHER INFORMATION: positions 82000 to 139500 of the sequence with
      GenBank Accession No. AL137129.4
```

```
<300> PUBLICATION INFORMATION:
<308> DATABASE ACCESSION NUMBER: AL137129.4
<309> DATABASE ENTRY DATE: 2001-04-30
<313> RELEVANT RESIDUES: (1)..(57500)

<400> SEQUENCE: 11 taaaattta  tcctatatga  aattttcctt  tttggtgtct  gttatttaat  aggattgttt      60
gaattagggg  atactatttg  gtgcctttgt  aactatatga  aaattagttg  gttgaatatt     120
actgctttcc  atgttcatat  ttatatttgt  atagacatat  atatatatac  acatatacta    180
ctttcctttc  cattttcata  tttatatttg  tgtatacaca  tatacataaa  catatatttt    240 atacatttt  gaaaggaaa   attaacttaa  gggcatattt  aatgaatatt  caaaaatttt    300
tttgctgatc  aaattatcat  tctgctttaa  acttttgaaa  tgatccaaaa  aaattttaaa    360
tgacttagat  ttactgttac  aaaatgcttg  tcttttgatg  tcacaaacat  tatatactat    420
aatcactggc  cagagataat  tgctataagt  ataatgaaaa  gggaaatgat  ggaagatctc    480
tgcagctatc  ctcataaatg  agggtgggaa  cacgatgggc  agttccaaag  ttgaaaatag    540
agaatatatg  tggatttata  ttaacataat  tggtattctt  ggatagttaa  aaatggctaa    600
actgtaggag  aagcccgagt  aattactgtt  aacagaggaa  taaatttgag  ggcaataata    660
atgatgatag  gccaggcact  gtggctcatg  cctgtaatcc  cagcactttg  ggaacccgag    720
gcgagcggac  cacctgaggt  caggagttcg  agagcagcct  ggccaacatg  gtgaaacctc    780
gtctctacta  aaaatagaaa  aattatccga  gtgtggtggt  gcgtgcctgt  aatcccagct    840
acttgggagg  ctgaggcagg  agaatcactt  gtacctggga  ggcggagttg  cagtgagccg    900
aaatcgcgcc  actgcgctcc  agcctgtggg  ccagagcgag  actccgcctc  agaataataa    960
taatgataat  aataataacg  ccaccaacaa  tactaagagc  taacatttac  tgagtgctta   1020
ctatgcacca  gatattgttc  taagtataca  tttattatct  catttaacca  tccataatac   1080
tgtggtatag  acactttat   atccatttta  taaataagta  aactgagtta  tggagagatt   1140
aaacgacttg  ccagtaagat  tcaaagcctg  tgtacaagct  cacgcttgat  tctggagcca   1200
gtgttcttaa  cacagtatct  tgagaatgtt  aaactaaaaa  gttttaatt   tacagtattc   1260 tttccacaat  taaaaagaa   attatgagta  attattttta  gttctttctt  ctcttcaggc   1320
atttcccatg  gttcttttca  agacataata  catatcattt  agtgttgtag  atctgaaaaa   1380
acaaaagtag  cgtgaagatc  aaaaattttc  taaagagacg  gagtctcgct  acgttcccta   1440
ggctggaaca  cccaggcttc  tccagcctca  cacctctgag  tagctggaac  cacccctgtcc  1500 gctaaggtca  atgtttaatc  gtatctttgt  aggtctactg  accagttaaa  aagaggtgct   1560
gtatacattg  gttgttgtct  tgtcagagtt  tgatgcttct  atatagacca  ttgttttttac  1620 atgctaatac  aattgaaagc  cactacagat  atttatattt  acaacccaaa  gctaggtttt   1680
aacaagaaac  tcataaggca  aaggtgagaa  gtaaaataat  ttagcgccaa  gtggagatat   1740
atgtgcaatg  ctactttgtt  gggctcaaaa  catattttc   tttagaaga   ctgacaggct   1800 tgaagtttat  gcctccaaag  acaaaagtga  ttatgtttg   tttagtagct  tgcaaagttg   1860
ccaaaggcca  tttttctac   tctttccctg  aaattggttt  atatgcttat  taaagtcatt   1920
tatacctatt  tgcaaatgct  taacatagtt  tcagatttta  agatttccct  gcaacttat   1980 ttcccttgaa  gtttacagca  acaggagttc  atttttattt  ttaattgcat  ttattcagta   2040
agtaaactcc  gccacagaaa  aacttagtag  acaaggtgag  ttcccctgtg  ctccgtggca   2100
aagagtgcgg  tgggtgacat  tgaccccatgg ttaggtaatc  tggtaaggaa  agaccccgtt   2160
gtaacacatc  tgagcaacga  gaccaaagga  agggcttgct  gccacgaggc  gaagtctgct   2220
```

```
ttttttgaaca gagagcccag cagagttggg cggcaatcgt gcccagcact gaggccgagg   2280
agaaagagag caggagcatt acattactgc accaagagta ggaaaatatg atgcatgttt   2340
gggaccaggc aaccgaaatc ccttctcagc agcgcctccc aaagccgggc accgccttcc   2400
ttcggagaag gcgcagagtc cccagactcg ggctgagccg cacccccatc tcctttctct   2460
ttcctccgcc gctaaacaca gacgagcacg tgagcgtcgc agcccgtccc agctgtgcct   2520
cagctgaccg cctcctgatt ggctgagagc ggcgtgggct ggggtgggga cttgccgcct   2580
gcgtcgctcg ccattggatc tcgaggaacc cgcctccacc tcaggtgagg cgggcttgcg   2640
ggagcgcgcg ccggcctggg caggcgagcg ggcgcgctcc cgccccctct ccctccccg    2700 cgcgcccgag cgcgcctccg cccttgcccg cccctgacg ctgcctcagc tcctcagtgc    2760
acagtgctgc ctcgtctgag gggacaggag gatcaccctc ttcgtcgctt cggccagtgt   2820
gtcgggctgg gccctgacaa gccacctgag gagaggctcg gagccgggcc cggaccccgg   2880
cgattgccgc ccgcttctct ctagtctcac gaggggtttc ccgcctcgca cccccacctc   2940
tggacttgcc tttccttctc ttctccgcgt gtggagggag ccagcgctta ggccggagcg   3000
agcctggggg ccgcccgccg tgaagacatc gcggggaccg attcaccatg gagggcgccg   3060
gcggcgcgaa cgacaagaaa aagtaagccc attccctcgg cccgccgcct tctcccccgg   3120
cgaccccgcc cgcctgcccg cccctgggctc ctggccggc ctcggcgtta atgggattgg    3180 gggggggcagc cttttttgttt ctgctgctgc tcccctcccc tctcttcccc caacctcgcc   3240
ggccgggctc ccccgctgtc cacgtcgcca tcttgtcgtg ggggtggga gacgcctcga    3300 aagtgctttc aggggccggg gtctgagccc tgcttgccct cccgccggc cgtggggcc     3360 tcgcgccgcc cacctacccg cctcaaaaac ccagcctgct ctgtggcccc atccggaggg   3420
gactttaccc agcctgaaaa ccccgggaag agaaatgagc tgcagctcgg tagccgcggt   3480
ttgcacccgg agcttccgct ccttcccgcc cccatcctct ccagttccat gaaaactcg    3540 gccctggggc ggaccctgca cgctggtcct ggctttccag tggacttggg gccttgagtt   3600
cccgactgag ggactcgcgt ggtcggatgc gatcttgtcc tgtagttgtc cagccgtcgc   3660
gggtgtcttt gcctttgtgc attagggatt tgccgcgatg gccttaagat gcgaacttt    3720 tagtttgcac gtgcaggttt tgtttcgttt aatcgccttt gaaaaacttg cctagactga    3780
gagtcagagt aatgggaatt tagggaaatg gcaacatttt aaagagaact tcagaattgg   3840
atacttgagt tcatatcacc tgtcacgaga acgcagatat tataaatgaa tatatgcctc   3900
attcattctt caaataatga aaatgtaggg gctggttaaa tttaggcagt tttaatgata   3960
ctgaaaaaag tatatgatga gtgaatgaaa tgcggcacta aaatgttgca aaaattttcg   4020
aactctgtct cattttcctg aaattgaagt atattaaagg aaaccgtca acatatatct     4080 aaagtaagta atcactcggt tagaacttaa tgcaagtttt ataaatcacc ttgaagtttg   4140
agtctaaggg gtacattaga gattaagaat tgtgagttgg accagtggtg ttaagagcgg   4200
actcccccat cccccaacac acacacaatt ttgcccactt tggcatttta acttttaagg   4260
aaatcactta aggaattgaa gatttagagt aagagttttg gttagtagac tggctttgct   4320
gttaaatcct tccactcttc tggcagagag attaatttcc ctaatcagta tcagcagaag   4380
ataaacttgt ttatattcct gctgttttgt agatcccttc tcctggtcct tcttcaatag   4440
aatattaaat tcttagtttg tatacagcag agaaggtcac ttataaaatt caaaaagtga   4500
gcaaacaggt ctagattaat tccaagagtt accaggaatt aattgcagtt tattttgcgg   4560
aggtgattac agtgcttttg atgaaatgat aaagctgcta tattgtaaac ctaaggcaga   4620
```

```
ttacctctgt gtagtgccag ttttctatcc ttattatata ttgaatcata cttaatacaa    4680
tgcattaaat tatgtaccac ttttttttata tacagtatcg aactcattgt tttgccattc   4740
atccgttcag aatatcagaa gcagttttga aacgaattaa taaattagct actgttcatc   4800
agccccaatt ctaaataagc tcttagattt tcctcagccc atctgttact ttcaaaattt   4860
tctcatttga aaacttggca accttggatt ggatggattc atatttctta gtatagaagt   4920
tcttgatata actgaaaaat taagttaaac acttaataag tggtggttac tcagcacttt   4980
tagatgctgt ttataataga tgaccttttc taactaattt acagtttttt gaaagataac   5040
tgagaggttg agggacggag attttcttca agcaattttt ttttttcattt taaatgagct  5100 cccaatgtcg gagtttggaa aacaaatttg tcttttttaaa agaaggtcta ggaaactcaa  5160
aacctgaaga attggaagaa atcagaatag aaaatgggta tggttatgat actgtagatt   5220
taacgcagga catttcatgt tgttcctagt tatagggggct gaacttattt aatagcacgt  5280
gcattttgat ttttagattt ttaagggaat gtcaagagag taatgattct gtttcaggct   5340
tcaggccaga ctccttcaga gttttccaaa acaaataatt actgaatcat taaagtaaaa   5400
tttctgagaa tagatattcc ttaatttcct tcattaactt tggccattaa aagtcaagaa   5460
gctctctcat ttattagcaa acttttctcc ttatgattct attttgattg tccttttgtt   5520
tgaggaagca gcatatggtg gttaagagca taggatctag aggcagatac ctctgagtta  5580
agggtcccag cccttcactt gtgagcttga gcaagttact gaatgcctct gagcctcttt   5640
cctccttttg aaatgatgat aagaatagca gccatctgag cagttattgt aaaggttaaa  5700
tgagataatg cttgtgaagc acttagccca ttgcaggagt cttgatgaca ctgtgtactt   5760
gaaaatagat gttacctgtt aaaattcttg tttaaacttc cacaactctt aaaactcttt   5820
tttgctagtc cttccagctg tttcctttag tttcttttct gtgtcttcat gcatcttttc   5880
tatctcctga aagtgaaaag actaacattg gatccagagc ttgaaaagcg ttttttttcct 5940 gttacaatgg gcaaaagagt acatccttgg gttatattgg cacctagtat cagttatttt    6000
tcttgagcat ctgatctgct ctctactcta gtggaggcct cctgcttcac aattgctcac   6060
ccctgtgttt tctccccaaa tagaatactg agtttactct ggactctaga gtcaaacata   6120
cacagtattc tagtcttact gttcatttaa gcaagatatg tgcaagacac tgcattctta   6180
gtactggcag taagttaaaa cattttttcgt cttgatgcca aagtttagac aattttataa   6240 aaattaaccct ttgtaaaaga taatgagttg ataaaatatt ctcagtaaag cagctacgtg  6300
gtagaaaaac tgtcctttgc ttatgagttt ctccagagtt aagaccattg ggttccatct   6360
gaaggcaaga cttcaagctt gtcttactgg tctgttttgt ggctcaattt gtatgaagtc   6420
tatgcactct tccacacgtg tgtatttact gaactatcga gttatttag actgagaaag    6480 tattggagtt cattcctacg gtccactgca gagcaccttg tgcagtttgg agaatgtcaa   6540
cttttctacc tgttaacttc cattgtcttt acttttaacg ccattgtctg tgactctaat   6600
ggtgtcacgg ctcagggttt agattttgtg gttacattct attcttgtat gtcaagagtg   6660
gtgtatagaa agctgagggg gattatttag tctcttgact gatttttttt ttttttctga   6720
agaactcagt ttattatgtt tggtggtgaa ataaaaattg atgtgcatgg atgttaaaga   6780
tttgggttaa attgtgtgtt catagatgcc ttctcttagt atataatttt ttaaatttag   6840
atacttaaaa tactgtatcc ctttatctaa gattaacata agtctgtttc ttaaccagga   6900
taaaaaaatc taaatttaaa tgtgatgttg gatgagtttc caatcaagaa attgattttt   6960
taaactttgt gactagttat ccagtgggtg gattttaccc agtgtgtgta tgtgtttttct  7020
```

```
gcttaactct ggaaggttag aaagagaatt tgaaactaag acaagccaag cttcttgttg   7080
ctcagtattt ttggtaaaaa tatggtcaga ttgtttaaat taactatagg ctttggaatt   7140
ttaaaaataa ttatatctct tggtctcttg acacatcaag aattaactgt tttgtatatg   7200
cgttgagtat taatgttcat gttttctgca gtagaaattt ataaaccctt atttatttgc   7260
cagacatgat ccctttagag aaatctagta tctaaaacct gaattttaa aacaaaattt    7320 aaaattttg tttcataaaa acaaaaatgt gattacctca tggcttttt cttatagctt     7380 ttgattgttt tttaaaatcg tagttcaaaa acattaacct aaaatttacc atcttaacca   7440
tttctaagta ctgttcagta gtgttaagta tattcacatt gtgccactaa cttccagaac   7500
tttttcatct tgcaaagctg aaatcttacc cattaaacaa ctcccaattt cccctctcc   7560 tcagcctctg gcaaccacca ttttactttc tgtttctgca aatttaacta ctctagatgc   7620
ctcatataaa tagaattata gggttttaat atttttgtga tgggcttatt tcactttgtg   7680
taatgtcctc aaggttcatc catgttgtag catgtgtcag aatttccttc cttttgagt    7740 ctgagcaata ttccattata tgttccatat tttgtttctc cattcatcca gcaacggaca   7800
cttgggttgc ttccacatct tggttattgt gctgctctga acatgagtct gcaaatctct   7860
ctttgaagct ttcactttt ttggatacat atccagaaga gggatgctgg atcatatggt    7920 aaccctttt aattttcaag gaaccaccat attgttttct atagcagttg caccagttta    7980
cattcccacc aacagtgcac aagggttcct atttctccac atccttctaa acacttgttt   8040
tctttctttc cttccttctc ttctctttct ttccttagcca tctaatgtgg caaagtggta   8100
gccatctaat atgttgaagt gattgttttt aagggcttgt ttgtggataa ttaaccagct   8160
gaaagctaac tacagtttgc cagtggaagc tttaactgaa aggagagtaa gtacctctaa   8220
aaggagaatt caattttct agtgacttag atttgttatg ccagtacttt ttcacagaaa    8280 cacttttgg gtaaaatagt gtacacctgt tctattgttg ataaagccca atttaattag    8340
gaaatttgtt ctctaagatt taaaacaata attgaaataa tgtattttta ttaaaaactg   8400
ttcccaagat gttagctttt agctgttctg gtgatctcaa ctgttattta tgagtgtttc   8460 tttatttaa aatttcacct taaccggtta cagttttaac cataaagatt atttcaacat    8520
atgattttga aaatttatta tcttgtaaat gggaaaatgt agtgatggaa catagtttac   8580
tgtatgtagt tcttcacttg tttgaaaagt cacaatatat ttaggcaaat taatttaaaa   8640
gtgtctagta tttaatattg caattttcac tcattaagga caggtccccc gtgtttcccc   8700
cttttttttt tccaagtagt ttgggaggat ttgtttttcc agctgaaaaa tactatggtt   8760
aaaaataagg tttaaaggcg aaagttgaag tcttttgaggg ttgggatacg tttctgttct   8820
taagagtctt gtaaattcag atgctaagca aatttcttta aaatgatttc taccctcccc   8880
ctttccatta taaaactgga tatgtttcag tggaccaaat cccaagtagg ctgaatttga   8940
aatttgtggg ctgggcgcgg tggctcatgc ttgtaatccc agtactttgg gatgccgagg   9000
tgggtggatc acctgaggtc aggagttcga ccagcctg gccaacatgg tgaaaccccca   9060 tctctactaa aaataccaaa attagccagg cgtggtggcg ggtgcctgta atcccagcta   9120
cttaggaggc tgaggcagga gaattgcttg aacctgggag gcggaggttg cggtgagcca   9180
agatcgcccc attgcactcc agcctgggtg acagagcaag actgtgtttc aaaaaaatta   9240 aaaagaaat ctgtggtgtg aatactggta cgtggtgtac acagtgagct cttaataagt    9300
atttgaatta acaaatgaga caatgattga ataattggat gaacaaagag aatgcaggtt   9360
tttaaaaggt ttcttttagaa atattgtcgg cccggcacgg tggctcctgc ctgtaatccc   9420
```

```
accatttttgg gaggccgggg caggtgaatc acctgaggtc aggagttcaa gacaagcctg    9480
accaacttgg  agaaacccg  tctctactaa aaatacaaaa aaaaaaaaaa aaaaatagca    9540
ggatgtggtg  gcacatgcct gtaatcccag ctactcggag gctgaggcag gagaatcgct    9600
tgaacctggg  aagcagaggt tgcagtgagc caagatcgcg ccactgcact ccagcctgat    9660
gacagtgtga  gatgctgtct ccaaaaaaaa aaaaaaaaa  ttaaaagaa  tgttttaatt    9720
ctttagttcc  ctgtctgaga ttcactgatt ggtaagaaga aagttaaaga atctcctttg    9780
actttttttg  atatagatat ttaaattcta ttactttata gtaaggttgg ggtttatttt    9840
ctttgcttta  taatagaaga gcattgatta ttctctttgc tttataatag aataccattt    9900
aaataggagt  tccctgagtg tgtttacaat catttgatct ggctaaacta ttttaatgtt    9960
aatgaaattt  taaaattttg gaggaaaaaa tttaaaaact acacaggtgc acaaagaaat   10020
aaaaatcacc  tgcttttca  ctatgtagag accattgtct actatttctc aattctgtgt   10080
tacatctgta  tgttaataac tgtaggatta gggactgagt actgttttta acctgctttt   10140
aaaaaattta  catctacatt ttttcccatc taaatagtga ggaagagtat cagaattttg   10200
taggcttgtg  gtgatggtta aattagataa tattaatgtt gggtacttaa cataatatat   10260
ggctcttaat  actctccaga tttcagatat agtctgtttt accattactg ccttttatc   10320
aaacctattc  tcaaaaaagt gagaaaagtg ctgagattac aggcgtgagc caccatgccc   10380
ggcctcatgg  ttcttctta  ataataaatt agaagaagta gaattacagg gtcaaaaagt   10440
atccattta   aagctttcaa tgtaattgcc tgtttatctt ctagaaagtt tgacctagtt   10500
gtatttaga   gtgtcatttt cttgaacttt atcatcatta aagttttaaa tttggaacac   10560
tggcaattg   ataagtatat taggattctt cttattgcaa gtagcaaaat acaactcaat   10620
ctagtttaag  agggaaaat  gtagtcattg gctaacacaa tctaattttg gtttaagaga   10680
caaatctaga  gtctcaaatg atctcagagt gtaataatcc ctgactttg  tcttgatatt   10740
acttggcttg  tataccttg  ctctatttgc atgctggcct tactctgcca ctgacaggct   10800
gtctgtatgg  tgtggaagag gacggctagc atccccatac ctgcatccat acagtttgta   10860
atataaaaa   aaaaaaagta aaaaaaactc cctctctctt ctagtgtcta tatatcagtt   10920
tcctagaaga  aaacgttttg ccctacttgg ccatgtgaat ggagttccct gattacatga   10980
gtcaaatatg  tcttattgta gcatatttga tggtcttctt gtagaatatt atcttactat   11040
acacagaact  cttgaccagt aattaatggg ccatgagttt ttgttgcaag tcatttgaat   11100
tcatattcta  tagttttcta ccaagtgtag tcattctgca agctgttctt gtcatgactt   11160
ttgggaagtt  gagtatttct tctatggggtt agggttttca tctcaagaaa aagatgatcc   11220
ttttctctac  taaatatgtg ttaagatcac acattttct  agatcgttta gctctactgt   11280
gtgatcttac  acaaattgct ttattgggat gataagaata attgcctatt aggattgtta   11340
tgagaatgaa  atgatacatc aactcatatg aaacactcag aacagctctt ggcacaaagt   11400
aagggcttaa  ttaagtagaa actatccata tattcataat attatagtat tggttaagtt   11460
gttttcaaca  ttgtttagaa tcgctcaagc cttcttgtg  ataatctgac gaaggctatt   11520
caccaccagt  gagtaaataa tagtggcaga atagttactg atgctttcc  tttacttggt   11580
tttttttcca  taaacatctg gccttgcag  actaaatact ggtttatgta tagacatgtt   11640
attctaaaat  aattttccat agtggtaata ctaaaggaag aaaaatgttc tcaaagctat   11700
ttatttggga  tgttaaagga gggggaaatt aagaaagcct acatttccat gtcctttgtg   11760
tccagaatct  cattaaatgt cttttaactt gttagcagag gaaagtttgga tattgcctgc   11820
```

```
ctttgtagct aacatagtta aaatatttaa atggttatag tgtcaaacca gtagtcaaag    11880
ccttcactgt gaatggatga agggatattt tcttgaataa tttaagttga cttatttcag    11940
tggttcaaaa aatttcttca acgcttaacc atgactcagg cacctaacta ttatactatg    12000
tcctgtaaca gattgttgtg cattcattta ttcaacaggt atttgtgcag ctaatttatt    12060
gagtacagca ttgaatcgtt gatggcttag gccacagttg aacattccat tttttatgtt    12120
cattcattca ttcatagcat attccatttt taaattttca gttcattgca ctttaaagtt    12180
tgaggttctt gcgaagtaca gacttttggg tttaagtttt gttatttaat gtcaaccacc    12240
acaggcgcat tggccagtct gcttttagaa ttttcagaca tacatacaca aaacattctc    12300
acaagacaat ctacttattt tcttttttat tcctgtgttt cttaacacag gattaatgtt    12360
cagatctctt ttggagcaaa ataatcctct gaattttga gatgtaccca gtgacctcag     12420
tctgagtatg tatactgcat taaaaaatgt aaccttgttc cttttagtgg tcatttggta    12480
acagtttgat cataaacaaa tgcagcctca acacagaag gcttgaggca agtatacaga     12540
actatggaga gatcatttag atgatgtaga atatgccttt tctttttta caatgccacc     12600 aaaatgaaaa cacggtttta aaaattctca tagagtgtaa cttcaacact gctttaactc    12660
tattaaacaa agcactgcca tgttgtaatt cctatttatt actctctgga gttgtataaa    12720
ttaccaaatc cgccttttgt ttgatatcct tttcaaatat ctgagggtag ctatcatgtt    12780
tcttccttct attcttaaaa aatagtccca aatttcttga atctttaat ttaaaaatta     12840 tatattgagc atctgatttg tggaaaggca taggccatat taaaaatggg gcttcatatt    12900
aaaatgggga aagggtgga gattctcagg tggaatctga gatctgccac acactaatag     12960
tgttacctaa ccctttttaa agacaaagaa acaggatcag aagtcactt tggaaaattt     13020 atttggtaat attggatagg atggattagt atagttggaa aacagagact cttgctttag    13080
gagagctgct cctttgtcat ttccagaatc ttaatcatgg tcaaggttta gagctaaata    13140
tttaatagaa gaagtcttta gggtatgctt tctattgtac acccttattt caatacatgt    13200
gttttttcct gttatgtaag tactttatta ttatttatgc atcttctatt aaagttaagc    13260
aaataattat ttcaaggaca cattcttcta catacacaca aagtttaggg tcactgacct    13320
tcttaggttc tagtcttaga tctgttacca tctaagagca tataaataag ggaaacagaa    13380
agaaaaggat ttacaagctg agaaggaagc aatgcagaga aagaagagtg atagagtagg    13440
taatttgggg aaagtcagtg atacacagct cttaaccatg aacagtgatt cttcactctt    13500
gaatgtttgt gacattcatg aaggtattaa aagctgactt ttaaaaaatt gtttcagaga    13560
actggaaaaa aattcagttg ccacattctt ccttaggtca tctttgaact ctactcatgc    13620
acttacgtgt ttaaggcaaa gttttactaa acgcacactt gttcttgctg cttattgac    13680 ttttactgct agcttcttat tcttagcaat tataactcac attacatagt attgtgaaac    13740
tcactatatt cagtgttttg cctgacaaac atggtatgtt ataggatgtg tattcagtta    13800
tagctaaaaa taaattattc tcgttttttca aaattgctg gcctacctgt taagcttttg    13860
ctttaagacc tgctaatgtt tctcaaactt ctgtggttaa atcacctgag tgtctagttg    13920
ctctatggat tcccagggac ccattcgcca gagattctga tttggtaatt ttgggatgga    13980 actcaggat ctgtaaattt tacaagcact cagaaatgaa acatagactt taaacagcta     14040
agagtgctca tcaggattat gttgatatta tttttaaac agatgtgcca agcctttaat     14100
ttgaatttcc agggttggga tttggccttc tatatttggg ggaaaaaagt tctattgatg    14160
attgtggata tataccacag gtcaaccatt gaatagtcta gtcagtgtag ttagtgtatt    14220
```

```
ttataattac taagttctaa gtatgtggtg tattaatgtc ttaggagtg gatatatttc    14280
ctgtatttgt aaagcatttg ggtaggtttt ttaaagagaa aagtatgtaa caaactagtt   14340
ttgagcgttg ctcttttact tctttgggca ttttttgaaga acacgttaag tatcttctta  14400
gagcagaggg gctcagagtg gtccccagat tatcatcatt ggtaacacct agttggtgca   14460
ttactaactt gttagaaatg cacattctca ggcgccattc agacttcata aatcagaaac   14520
tctggaagta aggctcagca ttctgtgttt ttttttttctt tattatactt taagttttag  14580
ggtacatgtg cacaacgtgc aggttagtta catatgtata catgtgccat gttggtgtgc   14640
tgcacccagt aactcgtcat ttaacattag gtatatctcc taatgctatc cctcccgct    14700
cccccaccc cacaacaggc cccggcgtgt gatgttcccc ttcctgtgtc catgtgttct    14760
cattgttcag ttcctaccta tgagtgagaa cacgcggtgt ttggttttttt gtccttgcga  14820
tagtttgctg agaatgatgg tttccggctt catccatgtc cctacaaagg acatgaactc   14880
atccttttt atggctgaat agtattccat ggtgtatatg tgccacattt tcttaatcca    14940
gtctatcatt attggacatt tgggttggtt ccaagtcttt gctattgtga atagtgccac   15000
aataaacata cgtgtgcatg tgtctttata gcagcatgat ttataatcct ttgggtatat   15060
acccagtaat gggatggctg ggtcaaatgg tatttctagt tctagatccc tgaggaatcg   15120
ccacactgac ttccacaatg gttgaactag tttacagtcc cactaacagt gtaaagtgt    15180
tcctgtttct ccacatcctc tccagcacct gttgtttcct gacttttaa tgatcgccat    15240
tctaactggt gtgagatggt atctcattgt ggttttgatt tgcatttctc tgatggccag   15300
tgatgatgag cattttttca tgtgtctttt ggcagcataa atgtcgtctt tgagaagtg    15360
tctgttcata tcgtttgccc acttttgat ggggttgttt ttttcttgta aatttgtttg    15420
agttcattgt agattctgga tactagccct ttgtcagatg agtagattgc aaaaattttc   15480
tcccattctg taggttgcct gttcactctg atggtagttt cttttgctgt gcagaagctc   15540
tttagtttaa ttagatccta tttgtcaatt ttggcttctg ttgccatggc ttttggtgtt   15600
ttaaacatga agtccttgcc catgcctatg tcctgaatgg tattgcctag gttttattct   15660
acggttttta tggttttagg tctaacattt aagtctttaa tccatcttga attaattta    15720
gcataaggtg taaggaaggg atccagtttc agctttctgc atatggctag ccagttttcc   15780
cagcaccatt tattaaatag ggaatccttt ccccatttct tgtttttgtc aggtttgtca   15840
aagatcagat ggttgtagat aagcggcatt atttctgagg gctctgttct gttccattgg  15900
tctatatctc tgtttttggta ccagtaccat gctgttttgg ttactgcatc cttgtagtat  15960
agtttgaagt caggtagtgt gatgcctcca gctttgttct tttggcttag gattgacttg   16020
gcaagcattc tgtgtttttga gaattcttcc aggggactgt gatgaaaact gacgtttgag  16080
aaccttcatc ttagagtaaa aactttacat acacattttt gttgttttat ttatctagca   16140
caatacttct tttttttgaa atggagtttt gctcttgttg cccaggctgg agtgcaatgg   16200
tgtaatctca gctcaccaca acctccatct cccaggttca gttgattctc ctgcctcagc   16260
ctcccgagta gctgggtta caggcacgtg gcaacatgcc tagctaattt tgtatttta    16320
gtagagacgg ggtttctcca tgttggtcag gctggtctcg aactcccgac ctcaggtgat   16380
ccgcccacct cagcctccca aagtgctggg attacaggcg tgagccactg cacctggcac   16440
aataccttat atataatcag ggctcaaaga tttgttgaga ggctcaacac caattctgga   16500
ccaggaaaga ttttatttat atcactagtc aggaataatc taaaaacaaa aagcacattc   16560
ttcttacaag taatatttca atacacatta atgtaaacac atggaaaagt attagctact   16620
```

```
taataaatta acatgtaaat gaaaaattta cacattatgg ctatttcaga tgtgatatag   16680
atttcatttt cagaaggaac cctccaatgt aaaacagtga ttcttttccc cgtttatttt   16740
actgcattag aaaatcacat ttaaagtaag cattttggtg aggtttggaa ggtgaataaa   16800
tccatctttt ctttaattat ggatatttaa gagagatgtt gttgtgccgt ttagataata   16860
atgatctaaa ccaagaaatt tagttgcttt caaaaataaa ataagtgtat gcattctgaa   16920
cattttcttt tagaaacaaa ccatttcatc tgttttttg  aatttcaaat taattataca   16980
gaattttcaa aatttgaaaa ttaggttagc atgagaaact gaagatactg aattatattg   17040
cctgttcagt ctatactttt ctttaggata tacagtagga aagaaatatg atagttcaag   17100
ttagattact acttctttca gagttttttg acaaatgcag gtacagtgat agtgtcagtt   17160
catggtgaat ttttgttaaa ataaattaca aaaaatttgt gatcctggta tcttgaaact   17220
agttaatatt tgtaaacttt gctaacactg tatatcactg tattctggtt ttatctgtgc   17280
atctatgagt tatatgtgtg tatagctaca tatgttttata tttatacaca tacattacac   17340
acaggagtgg aatcatactc aattttttt  gtatagcctg ctctgttcat ataatactat   17400
attgtagcat ctagtataag caaagattaa tttttgtaga ctttgctttt atcctgaaat   17460
tttgtggtag ctggtttaat ggaaagacaa tttctgtgac gtgttttgtc agttagggat   17520
tgaccctggt aaaatattgc tggataacaa caagcaatgt aaaaatacat ttgttccata   17580
agataacctc cgtgaaggta gagacttggt ctgttttgtt tattgcaccg tgtcctgttc   17640
tgggaagagt gttagactca tagaagatga tcaagaaata ttttttgaat acatcaataa   17700
cattctctaa catgtgggta tcctaaaggt ttattttttaa agtttattga ttagaattca   17760
gaagatattt tcccagataa aataatagat tgctagctgt cttgaaaatg taatttatat   17820
ttaatttgaa atgtcaggtt tttgctattt tttccattaa gtagagatag ggttttttaaa   17880
aattacatgt gatgtttttaa gtattctggt tttgcaacaa ttactagata gaaaatgtaa   17940
caacagatcc tattaataat acttccaata atacatataa aatacttgtc taaaagtaac   18000
cctccttaaa aaaacaaagc tggccaggcg cggtggctca cgcctgtaat cccagcactt   18060
tgggaggctg aggcaggcgg atcaagaggt caggagttca agaccagcct ggccaacata   18120
gtgaaacccc atctctagta aaaatacaaa aaattagccg ggtgtggtgg caggcgcctg   18180
taacccccagc tactcaggaa aatcgcttga acctgggagg cggaggttgc agtgagcgga   18240
gatcgcacca ctgtacttca gccttgggca acagtgcgag actctgtctc aaaaaaaaaa   18300
aaaaaaaag  gcaataggat taggtatcaa cttaatgaaa acttcgtgac agcactttct   18360
tgaaaaagac tgtggaaacc aaagttagta aactcctgtt tctgcctggg ttcggaaaac   18420
ataaagatga taaagatgtt taagtattcc tttttttttt ttttttttt  tttgagacag   18480
tgtcttgctc tgtctggagt gcagtggcac aatcacagct cactgcagcc ttgaactcct   18540
gggctcaaat aatcctcctg cctcagcctc ctgagtatct ggaactacag gagtgcacca   18600
ttacactcgg ctagtaattt gattggttaa gaacattaac tataactcac acatttttcct   18660
gaccacattt gcttaggaca aaacagtaaa agacatgagt gtagatgaaa gcgataaggg   18720
aactaatctt aaacactgaa cctctttttca gcaaattggc tttctagttt ctcagctctc   18780
tctttacacc tctaaatctc tttcctggca agatcattta tttgccttgg tttatggtga   18840
tactcttcat tgttatactg gtgggtgatt gttttaattg atagctgttt ttttctactt   18900
caggaagatg acactgctgg ctctgctggc tctgatgttt accttgtggc taatgcctgt   18960
gtttgcctgt gttcacattt attccacgat tcatttgtta acatttacta agctgctttt   19020
```

```
ctgtgccagg aacttggcta gataaataaa tggttgtttt tgtacacaga attagctgtc   19080
ataatcagtt actgtagcat ttattcttgc aaaaatatat atttatactt caactagtga   19140
tcgaatctca acttattaat tcatacattc agccagcaca taattgaata cttcttatgt   19200
gtcagaaact gttctaggtg cttgggatgt tcattgaaca aaatagacaa aagtctccgc   19260
ctctatggaa cttactttcc agtgaaggtg tggattggtg ggatagaaaa taaaataatc   19320
aagtaagata tgtacttagg cttttcataaa aatacagcag ggcaagagga ccaagatgga   19380
ggcagtgatc agggaatctc aatgagggtg agactgcgac aaagacttga aaaggtgga    19440 gaagcaagcc ttgtgggtat ttagggtagc agtagtccag gcaaggggaa caactagtgc   19500
aaaggctcta ggaggcaatg tgtttgaagt gttttaagaa cagtaaggag gctagtatgg   19560
ttagaacaga atgagcaaag ggggcaaagt ggtagaaggt gagatcaaag aggtaatgag   19620
gccattgtgg aggcccatat ggactattgg aagggctttg gcttttactc taaatgaggc   19680
aaaaaccatt ttaagcagag aggagtgata tgacttgatt tcttgttaaa aggattattc   19740
tagttgctgt tacagaaaaa gattacaggg gtgcaaagaa acagggagac aaaagaatat   19800
aagattttca ctgtaactta tatctagtat gcttgcttat acttgaaaat gcatatccag   19860
ataattgtag taaattcaaa tattatgttt atttaatagt actaacattg atatgctggt   19920
taattatgat taggagcact aataaagcac aaatcaggga ttcccaaaaa gaatgttgaa   19980
agggcagtca gcttttcctg tgccagaaat caaagtcata gcagatttgg ggcaaatatg   20040
tcaaagtcaa acttacgcac atcactactg agaagacaaa gatgaatgtg tgacagtttc   20100
ctgcccccaa gaatctttaa gcattgtgaa ggaagattaa tatagccaaa taactagagt   20160
gatcagttct accagagagg accagttttg gaagccagag gaaaaaaaaa aaaaacagaa   20220
acaaaatgat gtttgaatta aatctttaaa agtttctctt ataaatttac caagccacat   20280
attgggaatg gtaccccagg cagaaggagt agagtaagca agccagaaag gaaatactat   20340
ggtgcttttg agtaactgca gtgtggctga agaatgtgga aaatgatgag gataaagagg   20400
tggacaggga actaggtaag ggagggcttc ctttttaaata attagaacctt gtcctgtgta   20460 catttaatgg gattttaatc aggccataat gccaaatttc tttacttcgg aaggatcttt   20520
atggtgatgt tttcagaaag aaattaaagc agagtaacag tggttagcaa taatgatcag   20580
ctagtggttc ccaaacttac gtatcatatg catcttggaa gtttttaaaa actcagattt   20640
tgggatcctg acttagatct actgaatcag aatttacaga ttcaaattcc cagtgaggcc   20700
taggaatttg aaatgttgaa tgtccttcac gatgcagcta gacaagcatt tgggaataaa   20760
gcattaggtg actatttcag tagactaagg agtgggaggc catttaagct caaaggctat   20820
tctacttctc actatatttc tagtacctag cacagtgcat ggtacttgat agatgcatcc   20880
tttctcccat acctcgccct acacatctct tcatgtgtat ccttattaat atcctctatt   20940
ataaactggt aaacatgttt ccctgagttc tgtgagctgc tccagcaaag atgggtttgt   21000
gagaatccca acttttgaag cctgtcagtc agaagttcct gaggccagac ttgcaactcc   21060
tgttgagggg gcagtcttgg ggactgagcc ctcaacctga cactgtctcc aggtagatag   21120
tgttagaatt gaattgaagg acacccagtt ggtgtccgct gcagaactga ttgctcacct   21180
ggtggtggag agaaccccctc ctctcccgat agggttgcag aagttgtctt ctgtgttgtt   21240
gattgctgtg gtgtgggagc agagggggga aaaagctgt tggagagttt tttccaaaac    21300
aataggagat tatttagatt tataaaaata gaatcaaagt agattaactg agcacattgt   21360
gaaatataga gtagagctgt gtgtaaggag tatatcttaa tgtcaagctg acaccaaatt   21420
```

```
gaatgtttgc tggaacgttc aaaaatctaa gcttcccaaa tctgtgaaaa cactcaggtt   21480
agtaaacagt cttatgcaaa cagcaagaca atgctcaaag ccatttaagg aaaaagaaca   21540
gtaactgaat tctcttatgg aaatgtgaga tgttgtttta gtaagtactg atggtgttat   21600 acttttgtt tattcgtttg ctggtatttc agttcctaaa attccttcaa atatgctgca    21660
aaatacaaac caagaacttg gtggattttc catttgtttt cctgtgggaa atgatggaat   21720
taaaaacctt gaggattaga ccttgagagt taccttccag tgtttatgcc accattatac   21780
aaaattctgg aggacaaaac ccttcccact taaaaaccag ttagtttcag aaaatcacct   21840
catgttagga gactgcatca ttatagtatg tgtgttagct ttaggtatag atctaaaata   21900
tttttaatat tttaaaaact taagcctttc ttcattaatt tggcctaata caagttagaa   21960
taactttaaa aatgagtaca aacaacaagg aagggccagg cgcagtggct caacgcctgt   22020
aatcccaaca ctttgggagg ccaaggtggg cagatcacct gaggtcagga gttccagacc   22080
agcctggcca acataatgaa accccatctc tactaagaat acaaaaatta gctgggcgtg   22140
gtggcacacg cctgtaatcc cagctactcg ggaggctgag gcaggagaat tgcttgaacc   22200
caggaggcag aggttgcagt gagccgagat cgcgccattg cactccagtc tgggcaacaa   22260
gggtgaaatg ccgtctcagg aaaaaaaaaa acagtttctg tgactgctag acaaatgttg   22320
agcaagtaaa acaccaacaa tgttgaactt agatattgaa atagctgctc tgtacaaata   22380
aagtctactg ggagtataga ctgaattacc atcttttgac tctttcgcca taatgattgg   22440
cattaccgga agggattacc ttgctttgaa gagctgctgg acagtagagc agagagcatc   22500
tattaccatt gtaggtgcct ttcagttagg attttggatt tataagcaaa ctccaagaaa   22560
gagcctggtt ctgagtttct ctgaatagct taggtcaagt cctaaattct gaagccaact   22620
cctataattc cttctttatg tctttggcat gtgaagtagg caaatttcga actttataat   22680
aatagcctag acttacaaat acttgccttg gtaatcagga tgagttttg agagacaaca    22740 tagtctagtg ttaatcgcgt ggacaccaga ctgcttgagt gaaatacagg ttctaccatt   22800
tattaacgga gtaatgttgg gtaagctatt tagccagggt ccttatctgt aacatggtga   22860
taataataaa gattaaataa taggtgaaaa atgtttagaa taccactgtg ttattagtaa   22920
gcaccatgca taggtgtttg gatttaaaaa tactggcaaa ggccaggttg ggtggctcac   22980
acctataatc ctcgcacttt gggaggccaa ggcagaagga tcgctttagc ccaggagttc   23040
aggaccagtc gaggcaacat agattccgtc tctgcaaaaa atttaacaga attagttggg   23100
catggtagcg tgtgcctgta gctacttggg aggctgaggt agggagggg aggattgctt    23160 gagcccacga tttcgaggct gcagtgagct tatgatcatg ccactgtact ccagcttggg   23220
tgacagagca agactctgtc tctaaaataa aatgaaaata aaactgcagg caaaaatgcc   23280
aactgaagag tgaacatgaa cttttcttg cattttct gggcctgaga ctttaagaag      23340
tgcagggcag ttaaaatgat gagatataat tctcacctat cagctcagca gaaattaata   23400
agattaaaaa gatgcgtaat atataatatt gcagagtgca tggggaatt gatatacaca    23460 ttcatgaact ggcagagaca aaaatgggca cagaaccatt tggaaagcta ttgtgtattt   23520
taaaaatttt cagtagcaca tttttatat catgaaattt cacttcagaa tgtcagtcct    23580
gtagaaatac tgacgcaagt gcaaaaacaa caaaaaccaa cttgtacctt caaggccaga   23640
aagagttatt tcaccaaata acataattga ggtacattaa ctttattaga agtaaatctg   23700
ataatctgct cacattttaa atagttatgg tttaacttca gttcttgaag tcacatattt   23760
ttacaattag gaatgctaac aggcttttg tgcaatacga aagatgact ttaaatgcct     23820
```

```
acaattattt tgtgtccttt tatttttttt taattttttac tgacctacta caaagcacta    23880
aatattttat gttcttaatc tgaagaacaa tagacattct ctataaaaca actcttgctt    23940
attcatgaac tttgtacaca agaagcttaa taagacgggc tcaaaattat ttttctaaat    24000
atatttccta tacaaaataa tttcaagata taattgttac ttttgtgtct aatactgtat    24060
gttaaataat aaaatggtaa gcatgtaaaa actacaatac cacaaagatt gagctatttt    24120
gccagtagta tactccaact ttagttctag aacagttgta gaaatgggta aacaaactgt    24180
tttaactgta ctcttaactg aaatatagta cctatgcag tagcagaaca tatcagcaga     24240
agaacttcac ttgacctgta cttaaaaaca aaacagatgc aatttataaa atttagagaa    24300
atatagtgac cttatttgca tgtgaaaat gtacttcttt ctgatctaca tatcttctgt     24360
tgtgcaatgt aagcagtaaa acaaatagta caggattcat ctctgtggga cctagacccc    24420
ctggtctaac aaataattct tggtcagtac tgtaattctg tggtataaaa ctgataaaat    24480
tagccttcct gtgactagac aagaagccgg gcagtttaaa tgctgaaact cacaagaact    24540
tcagaagctt tagcttttaag ctttaagctt acttagaaat gttataagac ctccagtagt   24600
cacatatgaa gaatatcatg aagattttc cattaaatct ttattataga tcccttgatt     24660
ggtttctgtc tagactcatt gtgtgataaa ggacataata attttatca ccttcatcta     24720 atataggttt gtcaactcta tattagttgt tttcttgaag gctggttttc ttccaaaatt    24780
cagtcttatt ttcagtctac actagctttt aaatatactg tcctttagat gctttatcta   24840
acctcaaatt tctaatggat ttgtcttaga cacttattgc cactccttag atagtcattg    24900
ctatctttga agttctggac gatacgtgta ttacagagga actggagaca ttccatcacc    24960
atagttagct tgattggata ccctttaaaa gcatatactc gcgcctgtaa tcccagcact    25020
ttgggaggcc gaggcgggtg gatcacttga ggtctggagt ttgagacaag cctggccaac    25080
atggtgaaac ctgtctgtac taaaaataca aaaattagcc tggcatggta ccacatgcct    25140
gtaatcccag ctactcagga ggctgaggca ggagaattgc ttgaacctgg gaagtggagg    25200
ttgcagtgaa ccaagatctt gccattgcac tccagcctgg gtgacaagag cagaactcca    25260
ttaaaaaaaa aaaaagcat atatagcaca tattataagg ttttcaattt tttcaccaag     25320
tgtttcattt gggtagtcat ttattggtag tttacatcag ttgagtggtt cagaaaaaat    25380
acagtaagtt gcttataaaa ttctgaacac tttggccagg cacaatggct caagcctgta    25440
atttgagccc tttgtgaggc tgaggcagga gaattgcttg agcttaggcg ttcaagacca    25500
gcctaggtaa caaagaacgc ctggaatgat tgtggcattt gaactaatat tcaggtttaa    25560
caagagataa ttgaccatca ctctatttta gaggctttat ttgaaccaga tagaaatcta    25620
tttcccacag ctatcactgc ctgtcaccta caacttaagg gggttgggga ggaagtgaga    25680
gattttctgt tagggccaat agggacctgc tagataccc cccatcctgg gaatggtgta     25740
tggaactcca gtgtatgctg gagttattat catcatactt gttttttat tttactcttc     25800 tgcttataca gatcaagtct tacgttttat ttttaagttt aaattgaaaa catttacaga    25860
gaacaatgca gtgaaatgaa aaaattacag actgctggca tttgcatttt catgtagcct    25920
cagtgactaa ttttttttta ttgtacagca ttgagaaaat cctagttcat ataactagtt    25980
atagttcata tagattcata taactagttt taagtgataa tagtttcttc cttttttcc     26040 tccaccatct aaccagatga agataatagt ttttaatagc tcaccgtaaa tttcaaggta    26100
ctcaagttaa attgatctag atgcttgagt tgaatttttt ctatcaaagt tcaataacat    26160
gcttacattc cttattaaag tataaaagtc ctataaacac acaaacttga gtaagtacta    26220
```

```
aaactagtat cagtattgtc acaatacaac atgttatatt gtaacaagag catttgctga   26280
gaactgtgct tgttactcca gaatgttgct tctatggttg tacctttcaa ctttgcagat   26340
catttggaag gaggagagat ttggggtgga gacaattcgg tacttcattc acaggatgta   26400
aggaggatta agtaaaataa tgctggctaa aagtccttat ttagcatact gcccaatgct   26460
cactaaatca taatagctgt ttttaacatt tggtgaagaa tctatttaac aggagtgagt   26520 tgagggcat aggagatcat gtgagtgttt aaagtagaag cagcattccc cattaagaag    26580
agaaatactg tggaagagca aagactttaa acacctggg ttcaaatcct atttgctaca    26640
taatggctac ttttaaccta ttgaacgcca gttccctcat ttgtaaaata gggacaatat   26700
ttaacctatt tacaggttgt gagagaacta ggcacctagt acagggtaat gttggcacat   26760 ggtaacctt aataaactgt tgctattcaa caagctatta gatgtcacta ggcagttaag    26820
caaaggaaga cagcttttgc ttggtgtgac aatgaaaatc tttctgattt ccttcttgga   26880
agagttccct gaagatatgt cattgtattg acacctttat ttttgctaac ctatccctct   26940
aaattctgga tattgtgtgt gccacagctt tttttcttcc atattcctgc atttatttgg   27000
cacctgttgt gccagtaata gataaggggc tgctaaggga ggaggcaacc tgcactggct   27060
tatagctgct aatgtcagtt cctatagctt atcgtcagtg ttattcatgt ggtaaaaggg   27120
tgagaaagta ctggagtcta aagaaacaag tagaaatcag tttgtagcta ttaccgttct   27180
acctgctaac aactcctgtt ttcaagttat tatgtacaac tttaggtagt ttctctagcc   27240
ttaatcgtgg tttctctgta ttgagactac ttttgaattc tatgaagtac agccttagat   27300
gtacaggcta cttaaatt ttgcctaaaa taaaaacatt ctctccaatt acatatgctg     27360
gggaggaaac acctgcttcc gacaggttta aagcttggtt ttggacttt tgtgagagtt    27420 ccttatgtgt gcagtaatcc aaaatttgta tagttgccct ttataaaagt acattaatct   27480
agtagacaaa tctccatgta acttaattac atggcatctt ctaatccttc tgtgataagc   27540
agaaatgtaa agttttattc aagttaaggc aaactaactt gtatacactt tccatctcgt   27600
gtttttcttg ttgttgttaa gtaggataag ttctgaacgt cgaaaagaaa agtctcgaga   27660
tgcagccaga tctcggcgaa gtaaagaatc tgaagttttt tatgagcttg ctcatcagtt   27720
gccacttcca cataatgtga gttcgcatct tgataaggcc tctgtgatga ggcttaccat   27780
cagctatttg cgtgtgagga aacttctgga tgctggtgag ttattttaca agggtataaa   27840
taggcctgaa aattgaagt tagaagtaaa tagaaattat ttttagaagg tggtcgcaat    27900
gttttgattt tgtatacctc tttatattgt gatatgtaca cgtttaaaaa tttttctgta   27960
attctcacta tttttatcaa gcttcatttt tttctcatca gttattcttt gaaataatca   28020
ttctttatgc acataatttg ttttgctta ttctcttaaa catactctca attcttttct    28080
aatataacat ccttttatt acctgctttt aaagctttag tcaggaataa gatactggct    28140 tttccctcc ccccttttc tcctgttcca tctacctttc ttcctttaaa aaacatgact     28200
caggccgggc gcggtggctc acgcctgtaa tcccagaact tgggatgct gaggcgggtg    28260 gatcatgagg tcaggagttc aagaccagcc tggccaagat ggtgaaaccc catatatacc   28320
aaaaatataa aaattagat gggcacgctg taggtgcct gtaatctcag ctactaggga    28380
ggctgaggca ggagaattgc ttaaactcag agggcggagc ttgcagtaag ccgagatcaa   28440
gccactgcac tccagcctgg gcggcagagt gagactccat ctcaaaaata ataaaataaa   28500
taaataaata aaaaacatta ctcttctttc ttcttctatg gtttgctttg ctgcattact   28560
ttaatcatga aaagcagctg gcacatctaa ttatagtttt tctagcttct ggcctgcact   28620
```

```
tttctgtgtt gaaatggctg tatatattaa ataaagtgtc tgcgagaaaa ctttgtaaaa    28680
acatctaaat attatatcat ttaagtacaa cttttaact aattatttc ctcttcttgt     28740 gcccttttta ggtgatttgg atattgaaga tgacatgaaa gcacagatga attgctttta   28800
tttgaaagcc ttggatggtt ttgttatggt tctcacagat gatggtgaca tgatttacat   28860
ttctgataat gtgaacaaat acatgggatt aactcaggta aaatgcacac atattaagag   28920
ctcttctata tgtttttatg attttatgat ctagccctaa tttttaaaaa tgtgtttaca   28980
gtttgaacta actggacaca gtgtgtttga ttttactcat ccatgtgacc atgaggaaat   29040
gagagaaatg cttacacaca gaaatggtaa gaaaagtctg ttgtttgatt taatgtgaca   29100
ggtggtttta cataataaga tactattgct aattattaaa ctttgctatt gtacttaccc   29160
aaggcaaaat gttatttcat gtttaataaa atgtctattc tttgttaaaa ctattatttt   29220 agttttagg aatttcattt tgaaagccca cctaattgca taaataattg tgtgggtgtg    29280 agaataaaa tggaaagta aaatcatgac caagagagt acaaataact tttttttt        29340 tttttaaga tggggtctcg ctcttttgcc catgctggag tgcagtggca caatcagctg    29400
actgcagcct tgaccgctgg gactcaagcg atcctcccac ctcagtctcc caagttagct   29460
gggaccacag acgcgtgcta ccatgcccag ctaaattttt aaaaattatt gtagagaca    29520 aagtctcact atgctgctca ggctggtctt gaactactgg gcttaagcca tcctctcacc   29580
tcggcctctc aaagtgttgg gattacaggc atgagccacc acgcccaggc tacctttttt   29640
ttccttttct ttttaaattg tgatagggt cttgctgta ttgcccaggc tggtcttaaa    29700
ctcctggact caagtgatcc tcctggctca gcctcccaaa gtgctaggat ataggcatg    29760 cgccaccaca cctggtggag ttaaaaatta aaatacacca ttaaggcaag agaaaattat   29820
aatacaaatg gcagataata ggactttaga cagtcattaa agttgaggtg ccagtttgag   29880
tctaaggccc aataaaaaaa gttcaccaga attttaagac aaacaactgc ttatttgact   29940
tctttggatg ttctcaataa ttcgagaccg tgtagttaga ttataaagta ttacattgtg   30000
gatgcccaca tattaacaaa aatagagagt aagacctcta attcttagga attaattgtt   30060
aaaaataatc aagtgttcca agatttttg gaaactacct cttgaattaa aaaattaaag    30120
tctttctaca tttttatctt gttaaacagt gtatactgat cataattatt taaaaaatca   30180
tgtgttctaa gattttgga agtacctct tgaattacaa aaacaagaaa gtctttccac     30240
atttgtgcct tcttaagcag tgtatactga tcataattga actttcttc atgatggaaa    30300 gttaccacaa ggaaaatttc ttatgttctg ctgttctttg ttgctctcca atttaagtgc   30360
atacgtttgt ttgcttctat attataaaac ctcaaattta cttttgtat aattttgag     30420 gttttctttt tcatctcatt tattataata atagctaacc tccattgaga gaatgctgtg   30480
tgccaggaca ctgttcttcc tattttatat gcttttaact cctttattcc tcacaacaac   30540
cctgtgaagt taactgttag acaatttcta ttttactagg aaactgaggt acagagttac   30600
taagtaactt tcccaacatt atttggttag taaatggcag agcttgggct gaacttcagt   30660
agactggctt cagagtccac gctcattagt cctttggagc gcttttcata ttcttgaatt   30720
ctcacattct gtcttttttc actctgtcag caggacctga ctcctgtttt taaatttcat   30780
attgtgtttt tactgttaat ttggaaaaca aatgcatact tttagaatt ctgtataaag    30840 gaggagtaaa tatgctgtga acaaggacct aagtgggttg tcaatgagtt taatatatga   30900
gttctaatgt gcagagttga ggtttatatt gactgctcag tgcttccctg gggctagact   30960
ataaatggat ggatattagg aagtcttgtt ctgatttggt aatgatgtta atgcattatt   31020
```

```
ctaaatcaga tagtcttaat atagtttaaa tgtatgtttc gaaccaaatg ttcttttta   31080
aagcacacaa acattttgaa atcattacta atgtggttaa tgaattattg atgttccatt   31140
gggaaactaa aatgcagatt tttctctttt agaaatcagg gactattgca aagcatcaca   31200
ttttagtgat acactgagag ccagtggtgt gtttatacaa atagtcctat tttccaaata   31260
aattctagaa aaatgcttta gaatttataa attatacaaa atatgactta tttttagaga   31320
gtttaaaatt taggttttt taatggtttg tttttgtttg tttgttttt gtttttttt     31380
tcctcattag gaaaacacta gtacttttca gttaccttga tttttaaatt aatctgcagg   31440
tccccattca aaggccttgg gttcctttca aaggtcagta taattcaagc ttagtttatg   31500
aaggactgaa catacccaaa ggattttgca tgtggatctt tactgccact accacaacca   31560
tcaacaccta cacacacacg acacacacac attctctctc tctctctctc tctctctctc   31620
tctcccctc cctcccgcac tccttccctt cccctcctt tgctctcatg gcatctttta    31680
aaaatatact cttaaatcct tccagggagg gcaaattcac ttcttaatct aagtaaaccc   31740
aaatggcatg catcagcacc aggactgccc atctttccta gttccattat tcatagagta   31800
taggctggaa ttcatcttgt tcctcaagag tccagcattt ctagttaacc atgcctacat   31860
ttaaacttac tctcatttct tttctacttt acagtgtttt ttcaatatac tagcattaca   31920
gtttccagat ttgatttctc tcctgtctta tttccatcag ttttcaagtc tattaagatt   31980
ctacctcttc atttgtcttt tgccaccatt cttttccctc atactctact ggctcagccc   32040
tctcattaca gtcacctaat tctaacatat atattgctgc taagttaatt ttccttaagt   32100
tactgattgt gctttttaa agccccttgt tgaatattta ggcaggactc catgtggaca   32160
tccacagccc tccgtggtac agccctaacc ttcccttcta gctttgcctt actactcttc   32220
tacgtgtact ctacattgtg gacaaactac tatatgctgt ttttcaaaca tgtcctattt   32280
ttcctacctc tgtgcttttc attctcttac ttctccttgg aatacccttc taacccatct   32340
ctacttactg acattctaat gtctcttttt ctaagcaaga cttcttgatt tcccttgact   32400
agaaattatc ttctaagctc tccctatcct tctttaaagc attttataa gtctcaagta   32460
ccaactctac attgtgtttt tgttgacctt actatatcta ctacattttt aacttcttca   32520
ggaaaggtgg cgtatcttac tcatctttgt attgcctaca atatctagtc caggttctga   32580
ataataaata tttttatatg tgttctgaag cacactgacc aatgaagata agaaatcaag   32640
aggctagttc cttatttttt ttaatttttt tttttgagac agtgtctcac tttgtcaccc   32700
aggctggagt gcagtggcac aatctcagtt cactacaacc tctgcctccc gggttcaagt   32760
gattctcacg cctcaacctc ccaagtagct gggattatag gcatgtgcca ccacacctag   32820
ctgatatta tatttttagt agagatgggg ttttgccatg atggccagca tggtctcaaa   32880
cttctgtcct caagtgatct tcctgcctca gcctcccaaa gtgctgggat tacaggcatg   32940
aggcataagc cactgcgccc agcaagatgc tcttttctca gtcacctaaa tataatctca   33000
ttttagtta tagaaggttt gaaattggag tgaatagact ttacttaatt ctgactttat   33060
ttctgtagct tttttttttt gagatggatt ctcgctctat atcccaggtt ggagtgcagt   33120
ggcacagtct cagctcactg caacctctgc ctcccacgtt cgagtgattc ccctgcctca   33180
gtctcccaag tagctgggat tacaggcacc cactatcaca cccagctaat ttttgtattt   33240
ttagtagaga cagggtttca ccatgttggc caggccggtt tcgaactcct gacctcaagt   33300
gatcctcttg cctcagcctc ccaaagtgct gggattacag gcatgagcca ccgtgccctg   33360
cctatttctg taacttttga taagtcattt gatctgttgt tgttgttttc tcatagtaac   33420
```

```
aaagtagaag taattttctg cctgctttac tagataaatt aaggggaaaa aaataagata  33480
cgtaaaaatg ttatttgtta ttaaaaagaa agttgttatt ttaaaggttc tataaagaca  33540
tagagtgctt attagaaatt gagctaacac attcaggaaa ggataggaag agtttgctga  33600
agttctttct ttagggattc ttgtgtaccg atagcacagt taaagagcaa actcatacca  33660
tttttatatt tctgtgtatt tgactaagct tactggcttc aatgattaac tgttatccca  33720
aatatggatt atctttcagc caactcaggg aatcacagct actgagtagt gtgtgtcaga  33780
tctcttgggt gtgctggagt gagtaaaagg ggaatgaatt actgtgttca tgctgagact  33840
taattgaacg ggtattcagt tgatctaggt gatgggcact ttgttacttt tattgtaaca  33900
aatttgtata tttagttgct ttaaaacttt atttcatgct ttcattaggc cttgtgaaaa  33960
agggtaaaga acaaaacaca cagcgaagct tttttctcag aatgaagtgt accctaacta  34020
gccgaggaag aactatgaac ataaagtctg caacatggaa ggtaagtgaa aattatttgt  34080
gattgattat acactttatt tatacataga cattgtagta ttaagataac tttagaattg  34140
tgagggaagg tttacagttc catggtgttt ggttatgtaa catttatatc ttcaactcat  34200
ttgcatgtga tctccaaaat gcagaaccgt gtagtaattt gccaatttga ggcacaaact  34260
taaattacgt gaattgtggc actggtgttc caggcttaat cagttggctt tgccagccac  34320
acaatatttg aatcctgata gggcttaatt ttctattaat catggtttta tatctttgtt  34380
caatgttgaa acatagtcat cagtgcaaga ataactatc aaacagccat gatgatgaga  34440
tgaatgaaaa agcagcctag actttatacg aggggaattt tttaaagagt aatgtatagg  34500
ccctgggcag gaagtaggtc ataggtggta tcataggaaa aatgttcatt gattttcaaa  34560
aacgtgatta atccactagt gacagtaaat tttatcaaag cttactggcc atgtcagact  34620
caactactta tctctgcttt ttttttccct agcattgtaa atatttttt taactgcttt  34680 gttcttcata cacaggtatt gcactgcaca ggccacattc acgtatatga taccaacagt  34740
aaccaacctc agtgtgggta taagaaacca cctatgacct gcttggtgct gatttgtgaa  34800
cccattcctc acccatcaaa tattgaaatt cctttagata gcaagacttt cctcagtcga  34860
cacagcctgg atatgaaatt ttcttattgt gatgaaaggt aaattagatc taaaatgtga  34920
atttgaaatt tttaattagt ctacagcatt actgaatatt caccatagca aagattcagc  34980
gctggccatg catggtggct cacacctgta atcccagcac tttggaaggc tgaggcaagc  35040
ggggggtgga tcatctgagg tcaggagatt gagaccagcc tggccaatgt ggtgaaaccc  35100
catctctact aaaaaataca aaaattagtg ggacgtggtg gcaggcacta ctcaggaggc  35160
tgaggcagga gaatcgcttg aacctgggag gtggatgttg tggtgagctg agctcacacc  35220
accacactgc aagcctggat gacagagcaa gactcccatt tcaaaaaaaa aaaaaaaaat  35280
tactcaatgt taaactatac tttccactaa attgaacaga atgatacatc ctataatatt  35340
agattaactt tgtaaattaa ttcagccaca tttattgaac atttactctg tactatgaac  35400
acttacttta ctaggtgcta tccagaagtt aagatgagtc ttttttttccc caatagggc  35460 tctacttact tagagaattt caaagatatg cagtgtgtat tttgagcaaa gatagattac  35520
cttaggttgg ggactagaaa gccaagtgtt tgtacatctc ttcatcctac atattttccc  35580
tgagaagctt caaccttgcc catggtttct attactattt cccacatttc ttcctgtaac  35640
taattctatt taattgccaa cttaatattt ctatctggat attcttctgt attgtaaact  35700
aagtattact gtaacaactg tactactact gcccccaaac aacatcatca tcaaaaactg  35760
cctttcttcc tataatgctt attgtggttt aatacaccac catacacaca tgactccagc  35820
```

```
aaaactttgg aagtcatctg taacttttct tttacattca ttggctacat acagttggtg   35880
tctaaatctt acagatttac tatctacata tatctcttga tccatttcct cctttccatc   35940
cttgcactcc tgccattgaa ttcattagct cattattact cttgacttga gttgttggca   36000
tagctgcctt tttgccaaca gatttgtacc cttataatct ttcatctaag ttgccagaaa   36060
gtgggtgtcc taatgtgaaa atcagatcat gtcattctgt tgttgaaaat gcctcaaatg   36120
cttccctcca tctttgcaca caaaaatatt ttgtttataa aaatactaga tgagggaagt   36180
aaatttttca tttatcaaaa gaagatgtgt attttagaag actgaaaaaa aatagaccta   36240
cacaatacaa tctaaactta gcatggcaaa caaagatatt tatgctctgg ccctaactct   36300
gtctttggaa tcagatgtta gattcactca tggcttgcag ctctgatact tacaatgtgg   36360
ccttggcctt ggtacttaac tgttgtaaaa ttcacattcc ttatctataa aataagaatc   36420
atggctgggt gggtggctc atgcctataa tcctagcact gtgggaggcc gaggtgggtg   36480
gatcacctga ggtcaggagt ttgaaaccag cctggccaac atggtaaaac cccatctcta   36540
ctaaaaatac aaaaattagc tgggtatggg ggcacatgtc cgtaatccca gctacttggg   36600
aggctgaggt aggagaattg cttgaatcca ggaggcggag gttgcagtga accaagcttg   36660
caccactgca ctccggcctg ggagacggag tgagactcca tctcaaaaaa caaaacaaa   36720 acaaaaaaaa gacctcagaa ggatgttgtc aggattaaag gagtccattg agtgcctagt   36780
acagatagtg aatgcttcac tactggtgtc aactttaaga aaatgaatat agaaaagcta   36840
agaattattt taaggtgttt actactagca tgtaaatgta tgatgggaca gagatttcca   36900
tcctattttg aggaattatt ttttattttt ttgaaaactt aaggtaacaa agtagagagg   36960
aggccaggga gaaaggaagg tagtggagca aaaatgagaa agggagtgac attcccctct   37020
agttatagca gaaaattagc aaaatgatca tgacaggagg taacagtaaa gacagccagc   37080
tcatatatca accaagacag ttttgagttt gaccagcaga ctgttatttt ctggtttaga   37140
gctctttcca ggaacttctt gcatctataa cccctgagaa ccaagctatg gaaaaatttt   37200
tgctcaattt taagaaaatc taacatatca agctcctcaa ctccaaaata ttccacaaat   37260
agctgctatt tactatactg agtaataatc atttaaaatt attcaacact ttatttgagc   37320
atctactatg ttcatggcac taaagtagaa atgaagatga acagttcctg cctcaaaata   37380
aatgagtagt atactgcttt agatcatggg tttcctagtc cattaaaaac acttttttggt  37440 catattttct ggacaccccg accctttttgg tatagaatat aacctatgta attctctaaa  37500
gttaaattaa cctcacttttt cttgctctaa tatgtgtaaa actgaccttc taggaaagca   37560
tatacagttt atattttttga cttcttggta tcttttagtg atagacatac ctcagattga   37620
gaagcactga ttgacattag attaaatcag agcttcctat gacaatataa acaataccttt  37680 cattaatctg atcccctac ctacttcttc agcatcatct catatctgtc tccactaatc   37740
atattataga atctttgtta cctgcaccat gttaagcatt tttaaaaatc ttttgtttat   37800
accatacctt tttcctgaaa gcggttttgc ctttcctttg tctctagtca taagtctcct   37860
ataagaggct gttcctcatt ctaccattcc tttgcatgga taggattcca tggaatagat   37920
tctcatcact gcatttatca cattatttcc taagtagtac agtacatcta ctggaagatt   37980
agccacgtat tgagttttgt ctttgcattt tcatgcctag aataatgccg ggcacacata   38040
ggcatattaa gatttgaata gtgaaaaagt ttttaattcc atggggattt tatttaaaca   38100
gaaaaatata agaccaatta gaattatttt taaagcataa tttcaagaaa tatgactgat   38160
tttgtttaaa aacatgtttt cctttataat gctgccacct ggtgttgctg tgtttagaga   38220
```

```
tgtcccttg taaagaattg agggtttgag ttgagtttgg tttggttttt ggcaaatcag    38280
cttttccttt gtatatttat tttgtaataa actatggaag atcttgcctt taagtgtgag    38340
aacacaagca atgttacttt tatacccttta tagaatatct tgcctatgtc cttcctgtag   38400
ttaggtaggg ttttttttt gacacacagc atgttatata aggtttgctt gcacctcggt    38460
aggaaagtcc tctgaaatct aaaggctgag aatctaaaag cttaactcat gttttgctcc   38520
tagaaagact tgagaagaga gtatttctgt tcagcatggt actaagaaga cagctttctc   38580
ttcctcatgt catggttgcc atttcatact gcttacagag aataagatct agtctctgtc   38640
ttaaataaag gtctactctc tgccagcgag ctagataggg taattggatt gttttccaat   38700 ctatttcat ttgaaatatt gttttatctg aaattactcc cataatttca tgtaatgcca    38760
aaaactaaac taagtacaag agcatcttca aaaaccaaca taattccttt agttcccatt   38820
tagtgtagat gctctttggt tgatgatatt agaattgtgt aatggctatt gatctctcaa   38880
agtgaggtgt tgcctagggg cttaaaagtt actacataaa gaatttggct ttatgaagaa   38940
atgttacaga ttttatctat attttaaaat aagtgtaagt gactaccttt ataacttta    39000 ccatgtagtt tagtagtatt tcttatctgt ttattaatac cctgccttgt taccaaaagt    39060
atgtataatg agatgtaata agaataggta acaagtaggc tgggcacgtt ggctcatgcc    39120
tgtaatccca gtactttggg aggccaaggc gggtgaatta cctgagttca ggagttcaag    39180
acgagcctga ccaacatgga gaaaccccat ccctactaaa aatacaaaat tagctgggca    39240
tggtggcaca tgcctgtaat cccagctact gggaggctg aggcagggga atcgcttgaa     39300
cctaggaggt ggaggttgcg gtgagccaag atcacacctc attgtgctct ccagcctgag    39360
caacacgagg gaaactcttg tctcaaaaaa aaagaccagg taacaagttt gggtgaacag    39420
gattaaagag ttaaataaca ggaggaatct agaggactta agaaatgtg tggtgttgga     39480 tttaataact gtagttgcca aaggtgaggt gtaaatttat tctaagcaaa ggaggatgct    39540 cattttgaa aattcacttg tccataagat taatgcctat cagttaactt gggaggagaa     39600 aaattttct ttatcagtgt ctccctttt tttcttaaat cttgtatttt ttactaacag      39660
aattaccgaa ttgatgggat atgagccaga agaactttta ggccgctcaa tttatgaata   39720
ttatcatgct ttggactctg atcatctgac caaaactcat catgatagta agtacaatgg    39780
aagaactcag agatattcta attacttaac tgttgcaacc tctgtacagt ttggctaccc   39840
atctaattct ctggttaaaa gttctagact aaatgtgtta acaggcctat tcagtagaga   39900
tcttgaccat tttgtgtttt gtatgtgttg caacaaatat cagtaaaaat agaatcattt   39960
aatcatagaa aaaacttcct ggcattttaa atacaaagac ttttgaaaat ccaaatatta   40020
tagagtattg aatagcataa ttttcagaat tcacataaat actcagaaca gtggttggta   40080
tgtaaaaggc actcagaaag tatttgtaca atcaatgaat gtgaaggtgg tgaacatcac   40140
ctttggtaat aagtaccatt ttaaaaaatg cttataagtg catagttagg tatttatatt    40200
tatgggttca tgaaatattt tgatataggc atgcagtgca taaggataaa tggagtacct   40260
atcacctcaa gcattatctt gtgtgacaaa caatccagtt atactctttt ggttatttt    40320 attttatttt attttatttt tttcttttga gacaggatct cactctcgcc caggctggag    40380
tgcagtggag caatctcagc tcactgcaac ccccgcctac cgggttcaag agattctcct   40440
gcctcatcct cccaagtagc tgggattata agcatgtacc accatgcctg gctaatttt    40500 gtattttag tatagacagg gttttgccat gttggccagg ctggtctcga actcctgacc     40560
tcaggttatc cacctgcctt ggcacccggc ctcttttagt ttcttttaaaa tgtacaatta   40620
```

```
aattattttt tactatagtc acccaaaaca agtacctttg acataagatt tgattctgaa    40680
ttttactcaa atgaatgtta agatccccaa gataagttaa actttggact atctcacctg    40740
tttaatctgt acctatgcat gacttcccac tgtgcttgag gatacctgaa tatcactgag    40800
tttgtgtgac tgatcagcct tgaactcaag agtaaatcca agtctgcagt caggacaccc    40860
caatcctcaa aataatacca tcattagcat ttatttagta cttttctccca aatcagtatt    40920 taatttaaat tgccaaaaga cttacaatgt ggtatcaatt tatatttaaa tatgctacat    40980
atagcttttt aaagcatctt tggttctctg gaaaccatag tcagaattta aggaagttat    41040
tgtggcacca ttttcttgaa aaaggctatt gattattctc taatctgaca ccaacctaag    41100
tcattaaagg aattttagtt actgaagatt gtatattcat gaactcttca cttagctcac    41160
tggcagcaaa ggagttttat ttaggggtt tgaaaaagga atgggtaca ttttcagcta     41220 ttctgggacg cactgtcaga atgtaagcag ttacaactga ttccactaaa taaacatttg    41280
ttttccaaaa caatgatgaa cattcagcat ctgttcattt aattgaaaat tcaaagttaa    41340 aatatttttct ctgcatgatt cttttctttt tcccccctag tgtttactaa aggacaagtc   41400
accacaggac agtacaggat gcttgccaaa agaggtggat atgtctgggt tgaaactcaa    41460
gcaactgtca tatataacac caagaattct caaccacagt gcattgtatg tgtgaattac    41520
gttgtgaggt aagtaagttt gagaaataaa cattttgggg gaacaaatag taattctttt    41580
tggatactct gttcatttat aggaagataa gataataaat attaactaaa ttttaattct    41640
tttacatcgc taccaaatta ttattttcta tactctgacc taggtttcca gtccagctat    41700
tccacagtga tgctgctaaa cactgtcagt agttgtctat ccccatacct tcactcctat    41760
ttttaaaaag accatgaaaa aaataccaga tccattgatt ggtttggtct aattatacag    41820
atatcggcat atactatctc aagacagctg tgttcttttt gtaggaagaa tcctggccta    41880
gatttgtatc atagctctac cactcattag ctccctgacc ttggggaagt ctcttcattt    41940
ttctgaattt catctatgta gataatcctt cagaaggtta taatgaaaat taaatgaaat    42000
tctatgagat tagggagggg ggagggatag cattaggaga tatacttaat gtgaatgatg    42060
agttaatgga tgtagcacac caacatggca catgtataca tatgtaacaa acctgcacgt    42120
tgtgcacatg caccctagaa cttaaagtat aatttaaaaa agaaaagaaa ttctatgaga    42180
ttaataagct atatgatgta atacatggct cttgtatatt catgaactct tcacttagct    42240
ctttggcttg tgaatattat gtacatcaaa atttaatttt tcatttgatc tattttacta    42300
gactcctgcc ccatctagtc tacctgtcca cattattacc acattctagt ccatcttgcc    42360
cattactacc aggctaagct ttctagtgtg gatatgtcat catcttattt tccttagaat    42420
tttagcgatc ttttttatcat ttccaagata aacacttgcc taggtgtaca gcatccttgt   42480
ttaccatcat actcacgcat tagagattta gccttccctt taaaatctag ggtcactcct    42540
cttaggaaga ctttgggcag ttttttatttt tgctacttct gacaccatcc tttaatgttt   42600
taatattagt gccacagagt tcttttgtga ctttaccatt atgtaagaat cttccacttg    42660
gaatgtcttt ctcttcctca cacccccagtc tgcctagcaa atgccacttg atcccaagta   42720
tcagcttgtt agcttctcag tgaagcaagc cttctctatt ttagcagtta tcacagtgta    42780
ttttaattgt ttacatatct actttcacaa tgggttataa atttcttaag gtcaagggtt    42840
ggctatttta atctttgcat tatcagttca tttcagatag tgaacattta atacgttaat    42900
taaaggaata atttacattt aagccaaacg tgaagataaa ctattgctca tcatccctct    42960
tcagccgtat cctgtaggtg gtatcacctt atattcttac caccaaagaa aatatggccc    43020
```

```
ctctcttaga aagatcttaa tcatttatct gtgtatcttt aggactatcc ttagatcatg    43080
cctcacatat tgatgccaaa gagttctttt gtgccaattt cataatgtgt gtcagcacaa    43140
caattctgaa gatttgttgg tgtctttcat gtacttgact acaaattgcc ttgccattac    43200
tactcttctc aaaggatatc tgaaattctt ttttctttt ttttttttga gatggagtct     43260
cactgtcacc caggctggag tgcagtggcg tgatcttggc tcactccatt tcccgagctc    43320
aagtgattct catgcctcag cctcccaagt agctgggact acaggtgtgc accaccacac    43380
cgggctaatt ttttgtattt ttagtagaga cagggttttg ccatgttggc caggctcttg    43440
aactcccagg ctcaagcgat ccacccgcct cagcctccca aagtcctggg attacaggca    43500
tgagccacca cgcccagcct ggatatctga aattcttaac tgaaattagt caaattatct    43560
tgtactgggg attttttttt taatttcaac ttttattttt gattcagggg atacatgcat    43620
aggtttgtta catgggtata tcatgtgatg ctgaggtttg gggtacaatt gatcctgtca    43680
cccaggtagt gagcataata cccaacagtt gttcaaccct tgcccctctc ccctagtagt    43740
cctcagtgtc tattgatgcc atctttatgt ccacaagtaa cccagtgttt agctcccact    43800
tacaagtgag aacatgcagc atttggtttt ctgttcctgg gttatctcac ttaggataat    43860
ggtctctgga tgcatccatg ttgctgcaaa ggacattatt tcattctttt ttatggttgc    43920
atactgtgga ttttattggg tctttatttt gtattagcat tttaaaaccc taaatgtgac    43980
acagtacgca tgagtgatca tgcatctcaa gaaatcttga aatgttcctg tccataaagc    44040
agaatttttt aagagaccat ttcacagtct cccttcccct cactgtatca agtgctcatt    44100
tgtgaattac caatttctct tgttttgaca gtggtattat tcagcacgac ttgattttct    44160
cccttcaaca aacagaatgt gtccttaaac cggttgaatc ttcagatatg aaaatgactc    44220
agctattcac caaagttgaa tcagaagata caagtagcct ctttgacaaa cttaagaagg    44280
aacctgatgc tttaactttg ctggcccag ccgctggaga cacaatcata tctttagatt     44340
ttggcagcaa cggtgagtag ttatttttgt taatcccta aattgtgtct gttgctacaa      44400
gccccatttc aactaaacat tactttacgg tttttgttgg taatcatttg gacattacaa    44460
gctaatatat gtttatagtt ttcttaaatg tatttgctta aatattttg cccccgtaat      44520 ttcttaccat tcttgctttt ttatactgtt ggaaattgtg cttcaaagtg tccttaaggt    44580
atttcttctt cccacataaa ttttcctgg ctactctatt tctgtatcct gctgtcagat     44640
tttctccaca gttagcaga gttatatgga agtaggcatt gttgcattaa aggataaaaa     44700
agtagtcata ctataacatc aagcattgaa gatgaaaact gcaattttaa agtagagaac    44760
attttaatgt ataaaaaggt tggtattgcc ttttgtcttt tatgccatag agattaagac    44820
gcggtatcaa tagtggattg taaaggtaac tcagacttat ggttatacta tactattgta    44880
tgtaaacttt ctgatgaagg aaaatttggt gacattttgt tgtttgatga attagacaaa    44940 cctttgtga aaaagaacat aaatttttta tatgtgaaaa tccttgtggc cgggcgcagt      45000
ggctcacgcc tgtaatccca gcactttggg aggccgaggc gggtggatca cttgaggtta    45060
ggagttcgag accagcctgg ccaccatggt gaaacccgt ctctaccaaa aatacaaaag     45120
ttagctgggc gtggtggtgt gcgcctgtaa tcccagctac ttgggaggct gaggcagggg    45180
aattgcttga acctgggagg cagaggttgc agtgagccaa gattgcgcca ttgcactcca    45240
gcctgggcaa cagagcaaga ctctgtcttg ggtaaaaaaa aaaaaaaatc cttctatact    45300
ttagattgac tcatattttt tccccacaga cacagaaact gatgaccagc aacttgagga    45360
agtaccatta tataatgatg taatgctccc ctcacccaac gaaaaattac agaatataaa    45420
```

```
tttggcaatg tctccattac ccaccgctga aacgccaaag ccacttcgaa gtagtgctga   45480
ccctgcactc aatcaagaag ttgcattaaa attagaacca aatccagagt cactggaact   45540
ttcttttacc atgccccaga ttcaggatca gacacctagt ccttccgatg gaagcactag   45600
acaaagttca cctgaggtag gtgtcatgat ataatcagaa agggacaact ttcagatttt   45660
aacattcaag aatgtattta taagtttgat tcaaacactt atttgaacca caaattacat   45720
ttgtgtgtgt gtttgaattt tagcacttta aaattattgc aagagctact gcctaaccta   45780
gacctgagca catgttttag gctcaaagat agtcaggaac atgggaagaa actagcttaa   45840
tataaaccaa aaggtgaaac gtacattgtt tctctattat ttatatcagt aggacaaaaa   45900
catcttgaat ttggacattt aaagagaata gtactaagtg tgctcaaggt agctacagcc   45960
tatacctgtt acccctttta gtttgtttta ttgtgttttg ttttgttttg agaaagagtc   46020
tcactatcac ccaggctgga gtgcagtggt gcaatcacag cctcaacctc ccaggctcaa   46080
atgattctcc cacctcagcc tcccaagtag ctgggactac aggcctgcat caccatgcct   46140
ggctaatttt ttaaccttttt tttgtgtgtg tgtgtggagt tggggttctc actatgttgc   46200
tcaggctggt tttaaactcc tgggctcaag cgatcctcct gccttggcct cccaaagtac   46260
taggattaca ggcgtgagct accatgcctg gcccattacc cctttgagtt ggagaactgt   46320
ctggtagcaa tagacttacg aggqtttaaa tgggaaagga ccttataaat tctttgccca   46380
atttagtcta atttccatca ctattttgaa attttgggta agtataatat gaaaataaca   46440
agtgttacat aaaataaata cttagtaact ggtcttttttt attctggatc tgtcttgata   46500
ttaattgtcc tatgaacaca aaaataatct ttaaaggcta ggctggccaa gacttagaga   46560
tatcacacag ggctctattt ctaaatctag aatgattcca ttttagggct tcctacatct   46620
aaaaatatgc tcaggagtag ggcaacttag atctgaacat tataacttga taaatgaggc   46680
ataaataagc tttaataagt ggtaaataat tctacattag gtatttgttg aataaaactg   46740
acaagctaag agtaggggat ttgacatctc acagccttgt gttgaatgaa tatatatcct   46800
atgctctggt tgcttaattt acccagaaaa aaaaatgttt gattcatctt ggtttttatc   46860
taacaaaagt aaatctaaca aaaacgttag aatgaggaaa gcaaaatttc ttgtttagaa   46920
tacacagcta tagttttttg ttaaacttct tgcccagaac tcttaaaata gtaataatgt   46980
acattcgttc aggtatatgc aggtaaaata acttaggttt ctactcccac ccccgacagt   47040
aacagtgaga ttttaggta gctcagtcac cacaggagtg tgccttctca gttcaaaggt   47100
aaattccagt gaatgtagca tctagttaat tggtcaatta ggtaccattg tgggatgtga   47160
attaccaaat aggttttatt ctttagaata aggtgtttct tttcatctca attttgtaaa   47220
tgatgttata ttacatagtc agaaatatat atattggcaa aattagttac cagtataagc   47280
ttcaaaatgt cactattttc acaaatttttt tttttttttt tttttttga catggagtct   47340 cactctgtcg ccaggctgga gtgcagtggc atgatcttgg ctcactgcaa cctctgcctc   47400
ccaggttcaa gtgattctcc tgcctcagcc tcctgagtag ctgggattac aggcgtttgc   47460
caccatgcct agctaatttt tgtattttta gtagagacga ggtttcacca tgttggccag   47520
gatggtctcg atctcttgac ctcattatcc ctccaccttg gcttcccaaa gtgctgggat   47580
tacaggcgtg agccactgag cccggcctag ttaaataaaa tttgataaac acgatggact   47640
tggttgtgtg ttttctggtt tttctgagat ctagtttgaa aattctgaca actagcaaag   47700
tatatggaag cttcttcagg aaatagtaaa catatttctt tttacagcct aatagtccca   47760
gtgaatattg tttttatgtg gatagtgata tggtcaatga attcaagttg gaattggtag   47820
```

```
aaaaactttt tgctgaagac acagaagcaa agaacccatt ttctactcag gtatatgaac   47880
ttatttgttt tatattaaat ttcattaatt tttagtctga agtgacttg agtttcactt   47940 gtttttatt tataaggtgt ggccattgta aaaactcatg tatttgctgt tttaaaggac   48000
acagatttag acttggagat gttagctccc tatatcccaa tggatgatga cttccagtta   48060
cgttccttcg atcagttgtc accattagaa agcagttccg caagccctga aagcgcaagt   48120
cctcaaagca cagttacagt attccagcag actcaaatac aagaacctac tgctaatgcc   48180
accactacca ctgccaccac tgatgaatta aaaacagtga caaagaccg tatgaaagac    48240 attaaaatat tgattgcatc tccatctcct acccacatac ataaagaaac tactagtgcc   48300
acatcatcac catatagaga tactcaaagt cggacagcct caccaaacag agcaggaaaa   48360
ggagtcatag aacagacaga aaaatctcat ccaagaagcc ctaacgtgtt atctgtcgct   48420
ttgagtcaaa ggtatttata tgtaacattc aagttatagt tcttttatta tttttgagat   48480
aaatgtatgt gatagtacat gattttaaa cttatagcaa actttctgat atatatgccc    48540
taacgcaaat tcttgagaac tcaaaaaact ttctaaatta acctcatata tttttctt     48600 ttctttcttt ttttttttt tgagacagag tctcgctttg tcgcccaggc tggagtgcaa    48660
tggcatggca ccatctcagc tcacggcaac ctctgcctcc tgggtgcaag agattctcct   48720
gcctcagcct cccgagtagc tgggattaca ggcatgcacc accacgcccg gctgattttt   48780
ttggtatttt tcatagagac agggtttctc cacgttggtc aggctggtct caaactcccg   48840
acttcaggtg atccgcctgc ctcagcctcc gaaagagctg ggattacagg tgtgagccac   48900
catgcccgct cctatttttt ctaaataat tataaattct aaaattaccct atctaaatgg    48960 aggagggtct tctgacacct ttaaaataaa atccagctca gtactgtaaa tgtgtttaca   49020
gaacttgttt aaagttctta cagttgttta aatcagacta gttaactacc ctcactactt   49080
agatgcttcc atttcttaga gctcttttt aagcttatct gaagaaaagc ccttccaatt    49140
taagggttat ttccaattgc acattccaaa ttgagccttc catcttcagc attcaatata   49200
gatatttaca ggcccctctt ttaaaatttt attatagtta acttgtatta aagttgctt    49260 tattttcat tacgtatttg tagaacatta gctatatata tattgcaggc tacataggtt    49320
ttcaaactgt acaacaggaa tctaagcatg aattgttact tctatggagc tagttcaaac   49380
aaacatatgg acatgaccca attttaagt tatactttct gtatataatt tgtaagggga    49440
tttcacatat tttaagttg aggctatagc tagaagaaat taagttttat ctaataagtg    49500
tgtggaaaag ggaaatgatt ccttctctac tatgtctaga ctaagccaga tatcaatagc   49560
aataggaaag aaccactgtc gtagccagaa cacatagctt ttttccctgc ctaacattcc   49620
caccttgacc tagagtgctg ggagaggtct ttttccctaag cttggaaaag acattgggc    49680 tttagatgaa ctcagaagta ctttacatta ctttatttac tgtgtcactt actcactttt   49740
gactctgagc tccacgaggg caatcacagt gtcttgggca tttagtgat actaatactt    49800 agctcatgac ctaatgtgta gtacttcctc aataaatggt tgttgaggca gggcgcagtg   49860
gctcatcact gtaatctcag cactttggga ggctgaagcg ggtggatcac ctgaggccaa   49920
gagtttcaga ccagcctggc caacatggtg aaacccggtc tactaaaaat gcaaaaatta   49980
gctgggcgtg gtggcacgtg cctgtaatcc cagctacttt gggaggttga ggcaggagaa   50040
ttgcttgaac cctggaggtg gaggctgcag tgagccgaga tcgtgccatt gcactccagc   50100
ctgggcgaga agagtgaaac tcggtttcaa aaaaaaaaa aaaaaaaaa gttgttggac     50160 tgacagatgc atgaatacag tagtaaaaat gacaatcact tataagttac agtttactat   50220
```

```
cagctacaga ggatgggata tccagttttc tgaacaactg ttctcttgta cttgtcaaag   50280
ccaaagtgta acaacacatc aagtcacttt agcaatttat ttttgagacg gagttttgct   50340
cttgttgccc aggctggagt gcaatggcgt gatctcggat cttggctcac cgcaactgcc   50400
gcctcgctgg ttcaagcaaa tctcgtgcct cagcctcccg agtagctggg attacaggca   50460
tgcaccacca cacccagcta attttgtatt tttagtagag acagtgtttc tccaggttga   50520
tcaggctggt ctcaaactcc cgacctcagg tgatccacct gcctcagcct cccaaagtgc   50580
tgggatgaca gttgtgagcc actgtgccca gctagcaact gtttttaaac attagttcca   50640
atgtagtgta cactgaaaac ttttatgaaa ggaatttcaa aaattaagat aaaccattaa   50700
aaacgtaatt actaagtact actactacta caatgatatt tacataatag actgagttac   50760
atttcataaa gacaatatat ctgtataaga attttttaaac ttccctgtct atataataga   50820
agttttagag aaattttttta aaaccaaag aaaactgcaa aataagatca cttacctatt   50880
tggcattctc aactgtctgg aacagcaagg agccattatg attatgcatt tggtttgtgg   50940
ggtgtcttga aaagtcaaaa taatgtaaca aagctgatgt actttactca ttagaacaat   51000
tcttcacaat ttaatattaa ttttagatat acatagttca tgtttgataa ccagatcaat   51060
actgagtgaa aaatagcata gtgggaagag caggggaggg gaggtaggga tctggagacc   51120
tagagtgtac ttccatattg caactagtga gcagtaggac tttgagaaag ttacccaata   51180
ggcctcaggg ttctaattta taaaatgggt atgatatgcc tgccttatct gtcttgggaa   51240
cttaagtaag gttaaaatga actaatgaac ttgaaatgtt ttataaactg aaaatgctat   51300
acgaatgtga gattgatctt gtatttcaat agtcccaaca atatcactgc attgttatat   51360
taggtggaat aaaaggacaa tatttaactg ttttgactct acaatagtgt caatttagtt   51420
gtgttcagct ctattttata aaatagggat acgcatactg tagaaaattt cctgttaaat   51480
taagctttga cggccaggtg ctcacgcctg taatcccagc actttgggag gccaaggtgg   51540
gcagatcact tgcgctcagg agtttgagac cagcctgagc aacatagtga atcctgtct   51600 ctacaaaaat atgtatatat aaattagtca taatcccagc tacttgagag gctgaggtgg   51660
gaggatcact tgattccaga ggcagggctt ggttgcagta agcagagatc acgtctctgc   51720
actccagcct ggctgacaga gtaagaccgt gtttcaccaa aaaaaaaaaa aaaaaattaa   51780
gcttttactt ttaagatgat aaactttagt gatcaggaaa gttatcttat gtatattata   51840
ttccttaata ttggagaact aaagaattat gtattttctt taaaagcgct cactggatat   51900
tttttttaaa aacgctatat tttcatttag aattttttc ttttcagaac tacagttcct   51960
gaggaagaac taaatccaaa gatactagct ttgcagaatg ctcagagaaa gcgaaaaatg   52020
gaacatgatg gttcactttt tcaagcagta ggaattgtaa gtatgagtag taggttttgc   52080
ttttctagct aatgtgctat ttcgtgtgtg tgtgtgtgtg tgtgtgtgtg tgtgtgtttc   52140
cacgtttctt ccaaatagta aagttatatt ttcagaagtt atacattggg tttttttact   52200
ctgtatgcac tggttttaa aaatacaaat gtttaataca tacattcttg gtataaaaat   52260
tccaaacaat tccagtgtat tttgagttaa aaagtgaagt tctcccctta ctccaccctg   52320
aatatcacca ccaatctcat tctcttccct ttaagttact ttgccttatt aaaagaactg   52380
ctattggcca ggcacagtgc ctcacgcctg taatcccagc actttgggag gccaagatga   52440
ggatcacttg aggtcaggag ttcgagacca gcctggccaa cttggtgaaa ccctgtctct   52500
actaaaaata caaaaattag ccaggcgtgt tggtgcacac ctataatccc agccactctg   52560
gaggctgagg caggagaata gcttgaaccc gggaggtgga ggttgcgatg agctgagatc   52620
```

```
aggccactgc actccagcct gggtaagaga gtgagagtcc atctcatatt taaaaaagaa   52680
ctgctatgtt ttggggtaag tcaatggtgg tataatacat tctgatattt tcaaactaaa   52740
ttaactggaa agtatttata gacagaatgg tcataatgga tgacaaataa cttaagaaag   52800
aattcaaaat aatttagggt agtatttaag aaactgccta taatgttatt aaatttacac   52860
caatttcaag gttttggtt gtttaaaaaa aaaattcaac aaactaaact tgaaataact   52920
ttactgttta tagggaacat tattacagca gccagacgat catgcagcta ctacatcact   52980
ttcttggaaa cgtgtaaaag gatgcaaatc tagtgaacag aatggaatgg agcaaaagac   53040 aattattta ataccctctg gttagtttat tctttttgac cttgaacatc acaaagacaa   53100
aatacatgaa acatttttat ttaggagctt aatctaagt gagaatgact ttggttcctt   53160
agcaagatta aaaagtaaag ttgtggctgg gcgcggtggc tcacacctgt aatcccagca   53220
ctttgggagg ccgaggcagc cagatcatct gaggtcagga gttggagacc agcctggcca   53280
ccatggtgaa accccgtctc tactaaaaat acaaaaatta gctgggcgtg gtggcgggcg   53340
cctgtaatcc cagctacttg ggaggctgag gcatgagaat tgcttgaacc cggaaggcag   53400
aggttgcagt gagccaagat ggcaccactg cactccagcc tgggcgacaa gggtgagact   53460
ctgcctcaaa aaaaaaaaa aaaaaagta cagttgtatt tcatgtgatg gtcttaatac   53520
agagattaac atttcaaggt ggagcttttc atttttagta attttctttg atttctctat   53580
gtccatgtgc tgtcaatatt gatagaagct gaaatttgtg aacttttatg acttcttttt   53640 ttttttttt ttttttgag acagggtctc gctctgttgc ccaggcctgg agtgcagtgg   53700
catgatcata gctcactgca gtctcaaact cctgtgctca agctcaagca atcatcctac   53760
ctcagcctcc tgagtagctc gcactacaga catgcctcac cacacccggt tgcttttgt   53820 agagatgggg tctcactatg ttgcctaggc tggtttcaaa ctcctggcct caagtgatcc   53880
tcctgcctca gcctgtgcta ggattacagg catcagcttt gatgcccacc atatttatgc   53940
ctttttccaa attgttattt ctttgtgcct ttattgtatc ctgtaaacat ttctgacaca   54000
gcaacagtat cactggatta tacttacttt ttaacatagt tgtggttttg ccaggtaaac   54060
taaaacccct tccagaattt tgctttattt tctatgatac ctaacacatt gtgggtgttt   54120
aataaatatt cattgactag atgaatgtat acttaggtat ctcttttgtt tttcagattt   54180
agcatgtaga ctgctggggc aatcaatgga tgaaagtgga ttaccacagc tgaccagtta   54240
tgattgtgaa gttaatgctc ctatacaagg cagcagaaac ctactgcagg gtgaagaatt   54300
actcagagct ttggatcaag ttaactgagc ttttttcttaa tttcattcct tttttggac   54360 actggtggct cattacctaa agcagtctat ttatattttc tacatctaat tttagaagcc   54420
tggctacaat actgcacaaa cttggttagt tcaattttga tccccttcct acttaattta   54480
cattaatgct cttttttagt atgttcttta atgctggatc acagacagct cattttctca   54540
gttttttggt atttaaacca ttgcattgca gtagcatcat tttaaaaaat gcaccttttt   54600
atttatttat ttttggctag ggagtttatc ccttttcga attattttta agaagatgcc   54660
aatataattt ttgtaagaag gcagtaacct ttcatcatga tcataggcag ttgaaaaatt   54720
tttacacctt ttttttcaca ttttacataa ataataatgc tttgccagca gtacgtggta   54780
gccacaattg cacaatatat tttcttaaaa aataccagca gttactcatg gaatatattc   54840 tgcgttata aaactagttt ttaagaagaa attttttttg gcctatgaaa ttgttaaacc   54900
tggaacatga cattgttaat catataataa tgattcttaa atgctgtatg gtttattatt   54960
taaatgggta aagccatta cataatatag aaagatatgc atatatctag aaggtatgtg   55020
```

```
gcatttattt ggataaaatt ctcaattcag agaaatcatc tgatgtttct atagtcactt   55080
tgccagctca aaagaaaaca atacccctatg tagttgtgga agtttatgct aatattgtgt   55140
aactgatatt aaacctaaat gttctgccta ccctgttggt ataaagatat tttgagcaga   55200
ctgtaaacaa gaaaaaaaaa atcatgcatt cttagcaaaa ttgcctagta tgttaatttg   55260
ctcaaaatac aatgtttgat tttatgcact tgtcgctat taacatcctt ttttcatgt     55320 agatttcaat aattgagtaa ttttagaagc attattttag gaatatatag ttgtcacagt   55380
aaatatcttg ttttttctat gtacattgta caaattttc attccttttg ctctttgtgg    55440
ttggatctaa cactaactgt attgtttttgt tacatcaaat aaacatcttc tgtggaccag  55500 gccccttttga tcagctttta tgttcaaata ttaataatat ttgcttcaac acctccaact  55560
cataaaattg tttaccaaca atttaagcac ttatgaaaat tacatggtac tggttatttc   55620
tacatttatc ttagtgccat caccttaatg tatgttgagt ccctaaatgt catgttaaat   55680
aataacaacc ataatatccc attgaaaaga gtatgttgtt agaaaagaaa catcattttt   55740
aagtttctga gcctattaaa atgctcaaac acaaatatt agtattttta aaatatgaat    55800
gggatgagtg aagcagttct cagcattata gtcacaatgt tacaaaggct agagcttctc   55860
tgaagatttc taatctgttc ccattaacag attaataaat ttagacttca aatgaataat   55920
ttgcccaagc tttaaaagta atagatggca gaccaaaaat gtaagcttaa gtttcctgac   55980
tctaaagtca aacttagaac aaatttggtt tgtttttgtt ttaatgatac tgcgttttaa   56040
aacaaagtag ctttatcctt tttctcctgt attttttcttt tacaaaatag ctgtatttct  56100
tttatactga taatctcatt tttaaaaatc agacagtgta gaaagatatt ttttaaaaca   56160
gaaaaatcac tatgaatccc tgcacctaca ggtacagaaa attattttta tgaacaaatt   56220
atgtaggaag tgccagagcc ttaggtcctt taccctgagg tatatatact gaacaaaagg   56280
aactgagcca cagatctctt aggtagctct ttttatctta caatggagga cagtgattac   56340
aattatatga aaattttgga acaaaagtta atactaagat tcagtgcaaa atttggggg    56400 gggggggca caggtatact taagcacaaa cactgtgacc caaagtgctt caacatttag    56460
ttacagatag tagtatacta gaagtggtat tttagaataa agtggttgct tagtattcac   56520
aggtcacaaa acaaaaaatt attcttgtat agcaaattag cttcagttga aaactatttg   56580
taaaagcaga ttatgtaatg accaggagtt caggaaaatg acttctgaaa gcattgagaa   56640
gggaaagcca cgttaaagga cagtacagct ggaaggaagc aagtacttac ccactgctca   56700
gtcactaaga caacaagctc cttggagtgc tttaagctac ggaatagcag aactggccct   56760
tcccaatttt atgcaccgtc acaaatttct tcataatggt tttgtccaag gcttataacc   56820
caaccctggc aactataatc cttactttat gaaacagctg tatttctttt atactcataa   56880
cccagaaaaa tgagaatgta tgttctgagt ataaaagaaa tgtagctatt ccataaaaat   56940
acaggagaaa aagaataaag ctattttaat tttttaatg cagtatcatt aaaaaacaaa    57000
ccaagtttgt tctaagtttg actttagagt caggagactt aagcttacat ttctggtctg   57060
ccatctatta ctttagagc ttgggtaaat cttcatttga gatctaaatg ctatatatag    57120
ttcattcata gcagtaccag ataagggagg agtatatcta tacagtatat agtcttgaag   57180
aagtgatcta aggctcggag cttttgaggt ggccatgagt gactccaaag tccatggagc   57240
taaccaccct gcagtgctag ccaatccagt tgaacatacc cttttctcca ttgttaactg   57300 tttgttaaa tagcaaacag aaggcggcaa tggaggtgtg gaaaactgag gatccgatgt   57360
cacttgaaag taatgagatc acataacatt gagggaatgt cctaagagga gtggcagggc  57420
```

-continued

| ataaatagaa atgaataaaa gtgttttcaa gtgccattta gtgggttctg aatttgaact | 57480 |
| agagattgag atatccagtt | 57500 |

<210> SEQ ID NO 12
<211> LENGTH: 754
<212> TYPE: DNA
<213> ORGANISM: Homo sapiens
<220> FEATURE:
<221> NAME/KEY: misc_feature
<222> LOCATION: (1)..(754)
<223> OTHER INFORMATION: n = a, c, g, or t
<300> PUBLICATION INFORMATION:
<308> DATABASE ACCESSION NUMBER: AU123241
<309> DATABASE ENTRY DATE: 2000-10-23
<313> RELEVANT RESIDUES: (1)..(754)

<400> SEQUENCE: 12

| ccctgacgct gcctcagctc ctcagtgcac agtgctgcct cgtctgaggg gacaggagga | 60 |
| tcaccctctt cgtcgcttcg gccagtgtgt cnggctgggc cctgacaagc cacctgagga | 120 |
| gaggctcgga gccgggcccg gaccccggcg attgccgccc gcttctctct agtctcacga | 180 |
| ngggtttccc gcctcgcacc cccacctctg gacttgcctt tccttctctt ctccgcgtgt | 240 |
| ggagggagcc agcgcttatg ccggagcgag cctgggggcc gcccgccgtg aagacatcgc | 300 |
| ggggaccgat tcaccatgga gggcgccggc ggcgcgaacg acaagaaaaa gataagttct | 360 |
| gaacgtcgaa aagaaaagtc tcgagatgca gccagatctc ggcgaagtaa agaatctgaa | 420 |
| gtttttatg agcttgctca tcagttgcca cttccacata atgtgagttc gcatcttgat | 480 |
| aaggcctctg tgatgaggct taccatcagc tatttgcgtg tgaggaaact tctggatgct | 540 |
| ggtgatttgg atattgaana tgacatgaaa gcacagatga attgctttta tttgaaaancc | 600 |
| ttgggatggt tttgttatgg ttctcccnca tgatggtgac atgattttac atttcttgat | 660 |
| aatgttgaaa caaatacntt gggattnact tcanttttga aacttaactg ggaaacantg | 720 |
| tgttttgatt tttactccat cccatgtnaa ccat | 754 |

<210> SEQ ID NO 13
<211> LENGTH: 3551
<212> TYPE: DNA
<213> ORGANISM: Homo sapiens
<220> FEATURE:
<221> NAME/KEY: CDS
<222> LOCATION: (29)..(2236)
<300> PUBLICATION INFORMATION:
<308> DATABASE ACCESSION NUMBER: AB073325.1
<309> DATABASE ENTRY DATE: 2001-10-23
<313> RELEVANT RESIDUES: (1)..(3551)

<400> SEQUENCE: 13

| gtgaagacat cgcggggacc gattcacc atg gag ggc gcc ggc ggc gcg aac | 52 |
|  | Met Glu Gly Ala Gly Gly Ala Asn |  |
|  | 1               5 |  |

| gac aag aaa aag ata agt tct gaa cgt cga aaa gaa aag tct cga gat | 100 |
| Asp Lys Lys Lys Ile Ser Ser Glu Arg Arg Lys Glu Lys Ser Arg Asp |  |
|     10              15                  20 |  |

| gca gcc aga tct cgg cga agt aaa gaa tct gaa gtt ttt tat gag ctt | 148 |
| Ala Ala Arg Ser Arg Arg Ser Lys Glu Ser Glu Val Phe Tyr Glu Leu |  |
| 25              30                  35                  40 |  |

| gct cat cag ttg cca ctt cca cat aat gtg agt tcg cat ctt gat aag | 196 |
| Ala His Gln Leu Pro Leu Pro His Asn Val Ser Ser His Leu Asp Lys |  |
|             45                  50                  55 |  |

| gcc tct gtg atg agg ctt acc atc agc tat ttg cgt gtg agg aaa ctt | 244 |
| Ala Ser Val Met Arg Leu Thr Ile Ser Tyr Leu Arg Val Arg Lys Leu |  |

```
                       60                  65                  70
ctg gat gct ggt gat ttg gat att gaa gat gac atg aaa gca cag atg      292
Leu Asp Ala Gly Asp Leu Asp Ile Glu Asp Asp Met Lys Ala Gln Met
         75                  80                  85 aat tgc ttt tat ttg aaa gcc ttg gat ggt ttt gtt atg gtt ctc aca      340
Asn Cys Phe Tyr Leu Lys Ala Leu Asp Gly Phe Val Met Val Leu Thr
     90                  95                 100 gat gat ggt gac atg att tac att tct gat aat gtg aac aaa tac atg      388
Asp Asp Gly Asp Met Ile Tyr Ile Ser Asp Asn Val Asn Lys Tyr Met
105                 110                 115                 120 gga tta act cag ttt gaa cta act gga cac agt gtg ttt gat ttt act      436
Gly Leu Thr Gln Phe Glu Leu Thr Gly His Ser Val Phe Asp Phe Thr
                125                 130                 135 cat cca tgt gac cat gag gaa atg aga gaa atg ctt aca cac aga aat      484
His Pro Cys Asp His Glu Glu Met Arg Glu Met Leu Thr His Arg Asn
            140                 145                 150 ggc ctt gtg aaa aag ggt aaa gaa caa aac aca cag cga agc ttt ttt      532
Gly Leu Val Lys Lys Gly Lys Glu Gln Asn Thr Gln Arg Ser Phe Phe
        155                 160                 165 ctc aga atg aag tgt acc cta act agc cga gga aga act atg aac ata      580
Leu Arg Met Lys Cys Thr Leu Thr Ser Arg Gly Arg Thr Met Asn Ile
    170                 175                 180 aag tct gca aca tgg aag gta ttg cac tgc aca ggc cac att cac gta      628
Lys Ser Ala Thr Trp Lys Val Leu His Cys Thr Gly His Ile His Val
185                 190                 195                 200 tat gat acc aac agt aac caa cct cag tgt ggg tat aag aaa cca cct      676
Tyr Asp Thr Asn Ser Asn Gln Pro Gln Cys Gly Tyr Lys Lys Pro Pro
                205                 210                 215 atg acc tgc ttg gtg ctg att tgt gaa ccc att cct cac cca tca aat      724
Met Thr Cys Leu Val Leu Ile Cys Glu Pro Ile Pro His Pro Ser Asn
            220                 225                 230 att gaa att cct tta gat agc aag act ttc ctc agt cga cac agc ctg      772
Ile Glu Ile Pro Leu Asp Ser Lys Thr Phe Leu Ser Arg His Ser Leu
        235                 240                 245 gat atg aaa ttt tct tat tgt gat gaa aga att acc gaa ttg atg gga      820
Asp Met Lys Phe Ser Tyr Cys Asp Glu Arg Ile Thr Glu Leu Met Gly
    250                 255                 260 tat gag cca gaa gaa ctt tta ggc cgc tca att tat gaa tat tat cat      868
Tyr Glu Pro Glu Glu Leu Leu Gly Arg Ser Ile Tyr Glu Tyr Tyr His
265                 270                 275                 280 gct ttg gac tct gat cat ctg acc aaa act cat cat gat atg ttt act      916
Ala Leu Asp Ser Asp His Leu Thr Lys Thr His His Asp Met Phe Thr
                285                 290                 295 aaa gga caa gtc acc aca gga cag tac agg atg ctt gcc aaa aga ggt      964
Lys Gly Gln Val Thr Thr Gly Gln Tyr Arg Met Leu Ala Lys Arg Gly
            300                 305                 310 gga tat gtc tgg gtt gaa act caa gca act gtc ata tat aac acc aag     1012
Gly Tyr Val Trp Val Glu Thr Gln Ala Thr Val Ile Tyr Asn Thr Lys
        315                 320                 325 aat tct caa cca cag tgc att gta tgt gtg aat tac gtt gtg agt ggt     1060
Asn Ser Gln Pro Gln Cys Ile Val Cys Val Asn Tyr Val Val Ser Gly
    330                 335                 340 att att cag cac gac ttg att ttc tcc ctt caa caa aca gaa tgt gtc     1108
Ile Ile Gln His Asp Leu Ile Phe Ser Leu Gln Gln Thr Glu Cys Val
345                 350                 355                 360 ctt aaa ccg gtt gaa tct tca gat atg aaa atg act cag cta ttc acc     1156
Leu Lys Pro Val Glu Ser Ser Asp Met Lys Met Thr Gln Leu Phe Thr
                365                 370                 375 aaa gtt gaa tca gaa gat aca agt agc ctc ttt gac aaa ctt aag aag     1204
Lys Val Glu Ser Glu Asp Thr Ser Ser Leu Phe Asp Lys Leu Lys Lys
```

```
                380                 385                 390
gaa cct gat gct tta act ttg ctg gcc cca gcc gct gga gac aca atc    1252
Glu Pro Asp Ala Leu Thr Leu Leu Ala Pro Ala Ala Gly Asp Thr Ile
    395                 400                 405 ata tct tta gat ttt ggc agc aac gac aca gaa act gat gac cag caa    1300
Ile Ser Leu Asp Phe Gly Ser Asn Asp Thr Glu Thr Asp Asp Gln Gln
410                 415                 420 ctt gag gaa gta cca tta tat aat gat gta atg ctc ccc tca ccc aac    1348
Leu Glu Glu Val Pro Leu Tyr Asn Asp Val Met Leu Pro Ser Pro Asn
425                 430                 435                 440 gaa aaa tta cag aat ata aat ttg gca atg tct cca tta ccc acc gct    1396
Glu Lys Leu Gln Asn Ile Asn Leu Ala Met Ser Pro Leu Pro Thr Ala
                445                 450                 455 gaa acg cca aag cca ctt cga agt agt gct gac cct gca ctc aat caa    1444
Glu Thr Pro Lys Pro Leu Arg Ser Ser Ala Asp Pro Ala Leu Asn Gln
                460                 465                 470 gaa gtt gca tta aaa tta gaa cca aat cca gag tca ctg gaa ctt tct    1492
Glu Val Ala Leu Lys Leu Glu Pro Asn Pro Glu Ser Leu Glu Leu Ser
            475                 480                 485 ttt acc atg ccc cag att cag gat cag aca cct agt cct tcc gat gga    1540
Phe Thr Met Pro Gln Ile Gln Asp Gln Thr Pro Ser Pro Ser Asp Gly
        490                 495                 500 agc act aga caa agt tca cct gag cct aat agt ccc agt gaa tat tgt    1588
Ser Thr Arg Gln Ser Ser Pro Glu Pro Asn Ser Pro Ser Glu Tyr Cys
505                 510                 515                 520 ttt tat gtg gat agt gat atg gtc aat gaa ttc aag ttg gaa ttg gta    1636
Phe Tyr Val Asp Ser Asp Met Val Asn Glu Phe Lys Leu Glu Leu Val
                525                 530                 535 gaa aaa ctt ttt gct gaa gac aca gaa gca aag aac cca ttt tct act    1684
Glu Lys Leu Phe Ala Glu Asp Thr Glu Ala Lys Asn Pro Phe Ser Thr
                540                 545                 550 cag gac aca gat tta gac ttg gag atg tta gct ccc tat atc cca atg    1732
Gln Asp Thr Asp Leu Asp Leu Glu Met Leu Ala Pro Tyr Ile Pro Met
            555                 560                 565 gat gat gac ttc cag tta cgt tcc ttc gat cag ttg tca cca tta gaa    1780
Asp Asp Asp Phe Gln Leu Arg Ser Phe Asp Gln Leu Ser Pro Leu Glu
        570                 575                 580 agc agt tcc gca agc cct gaa agc gca agt cct caa agc aca gtt aca    1828
Ser Ser Ser Ala Ser Pro Glu Ser Ala Ser Pro Gln Ser Thr Val Thr
585                 590                 595                 600 gta ttc cag cag act caa ata caa gaa cct act gct aat gcc acc act    1876
Val Phe Gln Gln Thr Gln Ile Gln Glu Pro Thr Ala Asn Ala Thr Thr
                605                 610                 615 acc act gcc acc act gat gaa tta aaa aca gtg aca aaa gac cgt atg    1924
Thr Thr Ala Thr Thr Asp Glu Leu Lys Thr Val Thr Lys Asp Arg Met
                620                 625                 630 gaa gac att aaa ata ttg att gca tct cca tct cct acc cac ata cat    1972
Glu Asp Ile Lys Ile Leu Ile Ala Ser Pro Ser Pro Thr His Ile His
            635                 640                 645 aaa gaa act act agt gcc aca tca tca cca tat aga gat act caa agt    2020
Lys Glu Thr Thr Ser Ala Thr Ser Ser Pro Tyr Arg Asp Thr Gln Ser
650                 655                 660 cgg aca gcc tca cca aac aga gca gga aaa gga gtc ata gaa cag aca    2068
Arg Thr Ala Ser Pro Asn Arg Ala Gly Lys Gly Val Ile Glu Gln Thr
665                 670                 675                 680 gaa aaa tct cat cca aga agc cct aac gtg tta tct gtc gct ttg agt    2116
Glu Lys Ser His Pro Arg Ser Pro Asn Val Leu Ser Val Ala Leu Ser
                685                 690                 695 caa aga act aca gtt cct gag gaa gaa cta aat cca aag ata cta gct    2164
Gln Arg Thr Thr Val Pro Glu Glu Glu Leu Asn Pro Lys Ile Leu Ala
```

|     |     |     |     |     |     |     |     |     |     |     |     |     |     |      |
|---|---|---|---|---|---|---|---|---|---|---|---|---|---|---|
| ttg | cag | aat | gct | cag | aga | aag | cga | aaa | atg | gaa | cat | gat | ggt | tca | ctt | 2212 |
| Leu | Gln | Asn | Ala | Gln | Arg | Lys | Arg | Lys | Met | Glu | His | Asp | Gly | Ser | Leu |      |
|     |     |     | 715 |     |     |     | 720 |     |     |     | 725 |     |     |     |     |      |

|     |     |     |     |     |     |     |     |      |
|---|---|---|---|---|---|---|---|---|
| ttt | caa | gca | gta | gga | att | att | tag catgtagact gctggggcaa tcaatggatg | 2266 |
| Phe | Gln | Ala | Val | Gly | Ile | Ile |      |      |
|     |     |     | 730 |     |     | 735 |      |      |

```
aaagtggatt accacagctg accagttatg attgtgaagt taatgctcct atacaaggca      2326
gcagaaacct actgcagggt gaagaattac tcagagcttt ggatcaagtt aactgagctt      2386
tttcttaatt tcattccttt ttttggacac tggtggctca ctacctaaag cagtctattt      2446
atattttcta catctaattt tagaagcctg gctacaatac tgcacaaact tggttagttc      2506
aattttgat ccccttctta cttaatttac attaatgctc ttttttagta tgttctttaa       2566
tgctggatca cagacagctc atttttctcag ttttttggta tttaaaccat tgcattgcag     2626
tagcatcatt ttaaaaatg cacctttta tttatttatt tttggctagg gagttttatcc      2686
cttttcgaa ttatttttaa gaagatgcca atataatttt tgtaagaagg cagtaacctt       2746
tcatcatgat cataggcagt tgaaaaattt ttacaccttt tttttcacat tttacataaa      2806
taataatgct tgccagcag tacgtggtag ccacaattgc acaatatatt ttcttaaaaa       2866
ataccagcag ttactcatgg aatatattct gcgtttataa aactagtttt taagaagaaa     2926
ttttttttgg cctatgaaat tgttaaacct ggaacatgac attgttaatc atataataat     2986
gattcttaaa tgctgtatgg tttattattt aaatgggtaa agccatttac ataaatataga    3046
aagatatgca tatatctaga aggtatgtgg catttatttg gataaaattc tcaattcaga     3106
gaaatcatct gatgtttcta tagtcacttt gccagctcaa aagaaaacaa tacccctatgt    3166
agttgtggaa gtttatgcta atattgtgta actgatatta aacctaaatg ttctgcctac     3226
cctgttggta taaagatatt ttgagcagac tgtaaacaag aaaaaaaaaa tcatgcattc     3286
ttagcaaaat tgcctagtat gttaatttgc tcaaaataca atgtttgatt ttatgcactt     3346
tgtcgctatt aacatccttt ttttcatgta gatttcaata attgagtaat tttagaagca    3406
ttatttagg aatatatagt tgtcacagta aatatcttgt ttttctatg tacattgtac       3466
aaattttca ttccttttgc tctttgtggt tggatctaac actaactgta ttgttttgtt      3526
acatcaaata aacatcttct gtgga                                            3551
```

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer
<400> SEQUENCE: 14
aaagtgatgt agtagctgca         20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer
<400> SEQUENCE: 15
ggtatcatat acgtgaatgt         20

<210> SEQ ID NO 16

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 16
taccacgtac tgctggcaaa                                              20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 17
tgtgctttga ggacttgcgc                                              20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 18
gaaatgtaaa tcatgtcacc                                              20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
tcaaagaggc tacttgtatc                                              20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
ttaatgcaac ttcttgattg                                              20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 21
atcattatta tatgattaac                                              20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 22
```
gaaaggcaag tccagaggtg                                              20

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
taaactccct agccaaaaat                                              20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 24
cattagcagt aggttcttgt                                              20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
gatcatgatg aaaggttact                                              20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
aaatttcata tccaggctgt                                              20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 27
agtttcctca cacgcaaata                                              20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 28
actgatcgaa ggaacgtaac                                              20

<210> SEQ ID NO 29
<211> LENGTH: 20
<212> TYPE: DNA
<213> ORGANISM: Artificial Sequence
<220> FEATURE:

<223> OTHER INFORMATION: Oligonucleotide primer

<400> SEQUENCE: 29
cgctttctct gagcattctg                                                   20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 30
aaatcaaaca cactgtgtcc                                                   20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 31
tcctttagta aacatatcat                                                   20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 32
caaagttaaa gcatcaggtt                                                   20

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 33
ctagtgcttc catcggaagg                                                   20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 34
aatgccacat accttctaga                                                   20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 35
tcgtgagact agagagaagc                                                   20

<210> SEQ ID NO 36

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 36
atgaaaggtt actgccttct                                                  20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 37
tcagcaccaa gcaggtcata                                                  20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 38
aagtttgtgc agtattgtag                                                  20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
ctgagcattc tgcaaagcta                                                  20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 40
ttcagattct ttacttcgcc                                                  20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 41
gataacacgt tagggcttct                                                  20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 42
```
tcaaagcgac agataacacg                                              20

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 43
caaagcatga taatattcat                                              20

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 44
ccatcatctg tgagaaccat                                              20

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 45
atatggtgat gatgtggcac                                              20

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 46
ctcctcaggt ggcttgtcag                                              20

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 47
tgagctgtct gtgatccagc                                              20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 48
agataacacg ttagggcttc                                              20

<210> SEQ ID NO 49
<211> LENGTH: 20
<212> TYPE: DNA
<213> ORGANISM: Artificial Sequence
<220> FEATURE:

<223> OTHER INFORMATION: Oligonucleotide primer

<400> SEQUENCE: 49
catggtgaat cggtccccgc                                               20

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 50
tgttatatat gacagttgct                                               20

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 51
ccttatcaag atgcgaactc                                               20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 52
ccaaatcacc agcatccaga                                               20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 53
aactgagtta atcccatgta                                               20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 54
ttagttcaaa ctgagttaat                                               20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 55
aggccatttc tgtgtgtaag                                               20

<210> SEQ ID NO 56

-continued

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 56
ctatctaaag gaatttcaat                                               20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 57
cccatcaatt cggtaattct                                               20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 58
tatcatgatg agttttggtc                                               20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 59
aataatacca ctcacaacgt                                               20

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 60
caactttggt gaatagctga                                               20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 61
agtgactctg gatttggttc                                               20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 62
```
catctccaag tctaaatctg                                          20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 63
ctaatggtga caactgatcg                                          20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 64
cactgttttt aattcatcag                                          20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 65
ataatgttcc aattcctact                                          20

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 66
agaaaaagct cagttaactt                                          20

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 67
attgtagcca ggcttctaaa                                          20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
atcttcttaa aaataattcg                                          20

<210> SEQ ID NO 69
<211> LENGTH: 20
<212> TYPE: DNA
<213> ORGANISM: Artificial Sequence
<220> FEATURE:

<223> OTHER INFORMATION: Oligonucleotide primer

<400> SEQUENCE: 69
tgtgcaattg tggctaccac                                           20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 70
aacaatgtca tgttccaggt                                           20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 71
gctggcaaag tgactataga                                           20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 72
ttccacagaa gatgtttatt                                           20

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 73
tttttccaca gaagatgttt                                           20

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 74
tagagctaaa cgatctagaa                                           20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 75
taactctttc tggccttgaa                                           20

<210> SEQ ID NO 76

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 76
attggcccta acagaaaatc                                               20

<210> SEQ ID NO 77
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 77
agaacttatc ctacttaaca                                               20

<210> SEQ ID NO 78
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 78
gtttccctcg tgttgctcag                                               20

<210> SEQ ID NO 79
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 79
ttgtacttac tatcatgatg                                               20

<210> SEQ ID NO 80
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 80
acttacttac ctcacaacgt                                               20

<210> SEQ ID NO 81
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 81
aatctgtgtc ctttaaaaca                                               20

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 82
```

-continued

```
tgtgcactga ggagctgagg                                                    20

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 83
acgttcagaa cttatctttt                                                    20

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 84
catgctaaat aattcctact                                                    20

<210> SEQ ID NO 85
<211> LENGTH: 20
<212> TYPE: DNA
<213> ORGANISM: Homo sapiens

<400> SEQUENCE: 85
tgcagctact acatcacttt                                                    20

<210> SEQ ID NO 86
<211> LENGTH: 20
<212> TYPE: DNA
<213> ORGANISM: Homo sapiens

<400> SEQUENCE: 86
acattcacgt atatgatacc                                                    20

<210> SEQ ID NO 87
<211> LENGTH: 20
<212> TYPE: DNA
<213> ORGANISM: Homo sapiens

<400> SEQUENCE: 87
gcgcaagtcc tcaaagcaca                                                    20

<210> SEQ ID NO 88
<211> LENGTH: 20
<212> TYPE: DNA
<213> ORGANISM: Homo sapiens

<400> SEQUENCE: 88
ggtgacatga tttacatttc                                                    20

<210> SEQ ID NO 89
<211> LENGTH: 20
<212> TYPE: DNA
<213> ORGANISM: Homo sapiens

<400> SEQUENCE: 89
gatacaagta gcctctttga                                                    20

<210> SEQ ID NO 90
<211> LENGTH: 20
<212> TYPE: DNA
```

```
<213> ORGANISM: Homo sapiens

<400> SEQUENCE: 90
caatcaagaa gttgcattaa                                                   20

<210> SEQ ID NO 91
<211> LENGTH: 20
<212> TYPE: DNA
<213> ORGANISM: Homo sapiens

<400> SEQUENCE: 91
gttaatcata taataatgat                                                   20

<210> SEQ ID NO 92
<211> LENGTH: 20
<212> TYPE: DNA
<213> ORGANISM: Homo sapiens

<400> SEQUENCE: 92
cacctctgga cttgcctttc                                                   20

<210> SEQ ID NO 93
<211> LENGTH: 20
<212> TYPE: DNA
<213> ORGANISM: Homo sapiens

<400> SEQUENCE: 93
atttttggct agggagttta                                                   20

<210> SEQ ID NO 94
<211> LENGTH: 20
<212> TYPE: DNA
<213> ORGANISM: Homo sapiens

<400> SEQUENCE: 94
acaagaacct actgctaatg                                                   20

<210> SEQ ID NO 95
<211> LENGTH: 20
<212> TYPE: DNA
<213> ORGANISM: Homo sapiens

<400> SEQUENCE: 95
agtaaccttt catcatgatc                                                   20

<210> SEQ ID NO 96
<211> LENGTH: 20
<212> TYPE: DNA
<213> ORGANISM: Homo sapiens

<400> SEQUENCE: 96
acagcctgga tatgaaattt                                                   20

<210> SEQ ID NO 97
<211> LENGTH: 20
<212> TYPE: DNA
<213> ORGANISM: Homo sapiens

<400> SEQUENCE: 97
gttacgttcc ttcgatcagt                                                   20

<210> SEQ ID NO 98
<211> LENGTH: 20
<212> TYPE: DNA
```

<213> ORGANISM: Homo sapiens

<400> SEQUENCE: 98
cagaatgctc agagaaagcg                                          20

<210> SEQ ID NO 99
<211> LENGTH: 20
<212> TYPE: DNA
<213> ORGANISM: Homo sapiens

<400> SEQUENCE: 99
ggacacagtg tgtttgattt                                          20

<210> SEQ ID NO 100
<211> LENGTH: 20
<212> TYPE: DNA
<213> ORGANISM: Homo sapiens

<400> SEQUENCE: 100
atgatatgtt tactaaagga                                          20

<210> SEQ ID NO 101
<211> LENGTH: 20
<212> TYPE: DNA
<213> ORGANISM: Homo sapiens

<400> SEQUENCE: 101
aacctgatgc tttaactttg                                          20

<210> SEQ ID NO 102
<211> LENGTH: 20
<212> TYPE: DNA
<213> ORGANISM: Homo sapiens

<400> SEQUENCE: 102
gcttctctct agtctcacga                                          20

<210> SEQ ID NO 103
<211> LENGTH: 20
<212> TYPE: DNA
<213> ORGANISM: Homo sapiens

<400> SEQUENCE: 103
agaaggcagt aacctttcat                                          20

<210> SEQ ID NO 104
<211> LENGTH: 20
<212> TYPE: DNA
<213> ORGANISM: Homo sapiens

<400> SEQUENCE: 104
ggcgaagtaa agaatctgaa                                          20

<210> SEQ ID NO 105
<211> LENGTH: 20
<212> TYPE: DNA
<213> ORGANISM: Homo sapiens

<400> SEQUENCE: 105
agaagcccta acgtgttatc                                          20

<210> SEQ ID NO 106
<211> LENGTH: 20
<212> TYPE: DNA

<213> ORGANISM: Homo sapiens

<400> SEQUENCE: 106
cgtgttatct gtcgctttga                                      20

<210> SEQ ID NO 107
<211> LENGTH: 20
<212> TYPE: DNA
<213> ORGANISM: Homo sapiens

<400> SEQUENCE: 107
atgaatatta tcatgctttg                                      20

<210> SEQ ID NO 108
<211> LENGTH: 20
<212> TYPE: DNA
<213> ORGANISM: Homo sapiens

<400> SEQUENCE: 108
atggttctca cagatgatgg                                      20

<210> SEQ ID NO 109
<211> LENGTH: 20
<212> TYPE: DNA
<213> ORGANISM: Homo sapiens

<400> SEQUENCE: 109
gtgccacatc atcaccatat                                      20

<210> SEQ ID NO 110
<211> LENGTH: 20
<212> TYPE: DNA
<213> ORGANISM: Homo sapiens

<400> SEQUENCE: 110
gctggatcac agacagctca                                      20

<210> SEQ ID NO 111
<211> LENGTH: 20
<212> TYPE: DNA
<213> ORGANISM: Homo sapiens

<400> SEQUENCE: 111
gaagccctaa cgtgttatct                                      20

<210> SEQ ID NO 112
<211> LENGTH: 20
<212> TYPE: DNA
<213> ORGANISM: Homo sapiens

<400> SEQUENCE: 112
gcggggaccg attcaccatg                                      20

<210> SEQ ID NO 113
<211> LENGTH: 20
<212> TYPE: DNA
<213> ORGANISM: Homo sapiens

<400> SEQUENCE: 113
agcaactgtc atatataaca                                      20

<210> SEQ ID NO 114
<211> LENGTH: 20
<212> TYPE: DNA

<213> ORGANISM: Homo sapiens

<400> SEQUENCE: 114
gagttcgcat cttgataagg      20

<210> SEQ ID NO 115
<211> LENGTH: 20
<212> TYPE: DNA
<213> ORGANISM: Homo sapiens

<400> SEQUENCE: 115
tacatgggat taactcagtt      20

<210> SEQ ID NO 116
<211> LENGTH: 20
<212> TYPE: DNA
<213> ORGANISM: Homo sapiens

<400> SEQUENCE: 116
cttacacaca gaaatggcct      20

<210> SEQ ID NO 117
<211> LENGTH: 20
<212> TYPE: DNA
<213> ORGANISM: Homo sapiens

<400> SEQUENCE: 117
agaattaccg aattgatggg      20

<210> SEQ ID NO 118
<211> LENGTH: 20
<212> TYPE: DNA
<213> ORGANISM: Homo sapiens

<400> SEQUENCE: 118
gaccaaaact catcatgata      20

<210> SEQ ID NO 119
<211> LENGTH: 20
<212> TYPE: DNA
<213> ORGANISM: Homo sapiens

<400> SEQUENCE: 119
acgttgtgag tggtattatt      20

<210> SEQ ID NO 120
<211> LENGTH: 20
<212> TYPE: DNA
<213> ORGANISM: Homo sapiens

<400> SEQUENCE: 120
tcagctattc accaaagttg      20

<210> SEQ ID NO 121
<211> LENGTH: 20
<212> TYPE: DNA
<213> ORGANISM: Homo sapiens

<400> SEQUENCE: 121
gaaccaaatc cagagtcact      20

<210> SEQ ID NO 122
<211> LENGTH: 20
<212> TYPE: DNA

<213> ORGANISM: Homo sapiens

<400> SEQUENCE: 122
cgatcagttg tcaccattag                                                    20

<210> SEQ ID NO 123
<211> LENGTH: 20
<212> TYPE: DNA
<213> ORGANISM: Homo sapiens

<400> SEQUENCE: 123
ctgatgaatt aaaaacagtg                                                    20

<210> SEQ ID NO 124
<211> LENGTH: 20
<212> TYPE: DNA
<213> ORGANISM: Homo sapiens

<400> SEQUENCE: 124
aagttaactg agctttttct                                                    20

<210> SEQ ID NO 125
<211> LENGTH: 20
<212> TYPE: DNA
<213> ORGANISM: Homo sapiens

<400> SEQUENCE: 125
tttagaagcc tggctacaat                                                    20

<210> SEQ ID NO 126
<211> LENGTH: 20
<212> TYPE: DNA
<213> ORGANISM: Homo sapiens

<400> SEQUENCE: 126
gtggtagcca caattgcaca                                                    20

<210> SEQ ID NO 127
<211> LENGTH: 20
<212> TYPE: DNA
<213> ORGANISM: Homo sapiens

<400> SEQUENCE: 127
acctggaaca tgacattgtt                                                    20

<210> SEQ ID NO 128
<211> LENGTH: 20
<212> TYPE: DNA
<213> ORGANISM: Homo sapiens

<400> SEQUENCE: 128
tctatagtca ctttgccagc                                                    20

<210> SEQ ID NO 129
<211> LENGTH: 20
<212> TYPE: DNA
<213> ORGANISM: Homo sapiens

<400> SEQUENCE: 129
ttctagatcg tttagctcta                                                    20

<210> SEQ ID NO 130
<211> LENGTH: 20
<212> TYPE: DNA

```
<213> ORGANISM: Homo sapiens

<400> SEQUENCE: 130
ttcaaggcca gaaagagtta                                              20

<210> SEQ ID NO 131
<211> LENGTH: 20
<212> TYPE: DNA
<213> ORGANISM: Homo sapiens

<400> SEQUENCE: 131
ctgagcaaca cgagggaaac                                              20

<210> SEQ ID NO 132
<211> LENGTH: 20
<212> TYPE: DNA
<213> ORGANISM: Homo sapiens

<400> SEQUENCE: 132
aaaagataag ttctgaacgt                                              20

<210> SEQ ID NO 133
<211> LENGTH: 3933
<212> TYPE: DNA
<213> ORGANISM: Homo Sapiens
<220> FEATURE:
<221> NAME/KEY: CDS
<222> LOCATION: (265)..(2745)
<300> PUBLICATION INFORMATION:
<301> AUTHORS: Hogenesch, et al.
<302> TITLE: Characterization Of A Subset Of The Basic-Helix-Loop-
      Helix-PAS Superfamily That Interacts With Components Of The
      Dioxin Signaling
<303> JOURNAL: J. Biol. Chem.
<304> VOLUME: 272
<305> ISSUE: 13
<306> PAGES: 8581-8593
<307> DATE: 1997
<308> DATABASE ACCESSION NUMBER: U29165.1
<309> DATABASE ENTRY DATE: 1997-04-11
<313> RELEVANT RESIDUES: (1)..(3933)

<400> SEQUENCE: 133
cacgaggcag cactctcttc gtcgcttcgg ccagtgtgtc gggctgggcc ctgacaagcc     60
acctgaggag aggctcggag ccgggcccgg accccggcga ttgccgcccg cttctctcta    120
gtctcacgag gggtttcccg cctcgcaccc ccacctctgg acttgccttt ccttctcttc    180
tccgcgtgtg gagggagcca gcgcttaggc cggagcgagc ctgggggccg cccgccgtga    240
agacatcgcg gggaccgatt cacc atg gag ggc gcc ggc ggc gcg aac gac       291
                            Met Glu Gly Ala Gly Gly Ala Asn Asp
                             1               5 aag aaa aag ata agt tct gaa cgt cga aaa gaa aag tct cga gat gca      339
Lys Lys Lys Ile Ser Ser Glu Arg Arg Lys Glu Lys Ser Arg Asp Ala
 10              15                  20                  25 gcc aga tct cgg cga agt aaa gaa tct gaa gtt ttt tat gag ctt gct      387
Ala Arg Ser Arg Arg Ser Lys Glu Ser Glu Val Phe Tyr Glu Leu Ala
                 30                  35                  40 cat cag ttg cca ctt cca cat aat gtg agt tcg cat ctt gat aag gcc      435
His Gln Leu Pro Leu Pro His Asn Val Ser Ser His Leu Asp Lys Ala
             45                  50                  55 tct gtg atg agg ctt acc atc agc tat ttg cgt gtg agg aaa ctt ctg      483
Ser Val Met Arg Leu Thr Ile Ser Tyr Leu Arg Val Arg Lys Leu Leu
         60                  65                  70 gat gct ggt gat ttg gat att gaa gat gac atg aaa gca cag atg aat      531
Asp Ala Gly Asp Leu Asp Ile Glu Asp Asp Met Lys Ala Gln Met Asn
```

```
                 75                  80                  85
tgc ttt tat ttg aaa gcc ttg gat ggt ttt gtt atg gtt ctc aca gat      579
Cys Phe Tyr Leu Lys Ala Leu Asp Gly Phe Val Met Val Leu Thr Asp
 90                  95                 100                 105 gat ggt gac atg att tac att tct gat aat gtg aac aaa tac atg gga      627
Asp Gly Asp Met Ile Tyr Ile Ser Asp Asn Val Asn Lys Tyr Met Gly
                    110                 115                 120 tta act cag ttt gaa cta act gga cac agt gtg ttt gat ttt act cat      675
Leu Thr Gln Phe Glu Leu Thr Gly His Ser Val Phe Asp Phe Thr His
                125                 130                 135 cca tgt gac cat gag gaa atg aga gaa atg ctt aca cac aga aat ggc      723
Pro Cys Asp His Glu Glu Met Arg Glu Met Leu Thr His Arg Asn Gly
            140                 145                 150 ctt gtg aaa aag ggt aaa gaa caa aac aca cag cga agc ttt ttt ctc      771
Leu Val Lys Lys Gly Lys Glu Gln Asn Thr Gln Arg Ser Phe Phe Leu
        155                 160                 165 aga atg aag tgt acc cta act agc cga gga aga act atg aac ata aag      819
Arg Met Lys Cys Thr Leu Thr Ser Arg Gly Arg Thr Met Asn Ile Lys
170                 175                 180                 185 tct gca aca tgg aag gta ttg cac tgc aca ggc cac att cac gta tat      867
Ser Ala Thr Trp Lys Val Leu His Cys Thr Gly His Ile His Val Tyr
                    190                 195                 200 gat acc aac agt aac caa cct cag tgt ggg tat aag aaa cca cct atg      915
Asp Thr Asn Ser Asn Gln Pro Gln Cys Gly Tyr Lys Lys Pro Pro Met
                205                 210                 215 acc tgc ttg gtg ctg att tgt gaa ccc att cct cac cca tca aat att      963
Thr Cys Leu Val Leu Ile Cys Glu Pro Ile Pro His Pro Ser Asn Ile
            220                 225                 230 gaa att cct tta gat agc aag act ttc ctc agt cga cac agc ctg gat     1011
Glu Ile Pro Leu Asp Ser Lys Thr Phe Leu Ser Arg His Ser Leu Asp
        235                 240                 245 atg aaa ttt tct tat tgt gat gaa aga att acc gaa ttg atg gga tat     1059
Met Lys Phe Ser Tyr Cys Asp Glu Arg Ile Thr Glu Leu Met Gly Tyr
250                 255                 260                 265 gag cca gaa gaa ctt tta ggc cgc tca att tat gaa tat tat cat gct     1107
Glu Pro Glu Glu Leu Leu Gly Arg Ser Ile Tyr Glu Tyr Tyr His Ala
                    270                 275                 280 ttg gac tct gat cat ctg acc aaa act cat cat gat atg ttt act aaa     1155
Leu Asp Ser Asp His Leu Thr Lys Thr His His Asp Met Phe Thr Lys
                285                 290                 295 gga caa gtc acc aca gga cag tac agg atg ctt gcc aaa aga ggt gga     1203
Gly Gln Val Thr Thr Gly Gln Tyr Arg Met Leu Ala Lys Arg Gly Gly
            300                 305                 310 tat gtc tgg gtt gaa act caa gca act gtc ata tat aac acc aag aat     1251
Tyr Val Trp Val Glu Thr Gln Ala Thr Val Ile Tyr Asn Thr Lys Asn
        315                 320                 325 tct caa cca cag tgc att gta tgt gtg aat tac gtt gtg agt ggt att     1299
Ser Gln Pro Gln Cys Ile Val Cys Val Asn Tyr Val Val Ser Gly Ile
330                 335                 340                 345 att cag cac gac ttg att ttc tcc ctt caa caa aca gaa tgt gtc ctt     1347
Ile Gln His Asp Leu Ile Phe Ser Leu Gln Gln Thr Glu Cys Val Leu
                    350                 355                 360 aaa ccg gtt gaa tct tca gat atg aaa atg act cag cta ttc acc aaa     1395
Lys Pro Val Glu Ser Ser Asp Met Lys Met Thr Gln Leu Phe Thr Lys
                365                 370                 375 gtt gaa tca gaa gat aca agt agc ctc ttt gac aaa ctt aag aag gaa     1443
Val Glu Ser Glu Asp Thr Ser Ser Leu Phe Asp Lys Leu Lys Lys Glu
            380                 385                 390 cct gat gct tta act ttg ctg gcc cca gcc gct gga gac aca atc ata     1491
Pro Asp Ala Leu Thr Leu Leu Ala Pro Ala Ala Gly Asp Thr Ile Ile
```

```
                395                 400                 405
tct tta gat ttt ggc agc aac gac aca gaa act gat gac cag caa ctt     1539
Ser Leu Asp Phe Gly Ser Asn Asp Thr Glu Thr Asp Asp Gln Gln Leu
410                 415                 420                 425 gag gaa gta cca tta tat aat gat gta atg ctc ccc tca ccc aac gaa     1587
Glu Glu Val Pro Leu Tyr Asn Asp Val Met Leu Pro Ser Pro Asn Glu
                430                 435                 440 aaa tta cag aat ata aat ttg gca atg tct cca tta ccc acc gct gaa     1635
Lys Leu Gln Asn Ile Asn Leu Ala Met Ser Pro Leu Pro Thr Ala Glu
                445                 450                 455 acg cca aag cca ctt cga agt agt gct gac cct gca ctc aat caa gaa     1683
Thr Pro Lys Pro Leu Arg Ser Ser Ala Asp Pro Ala Leu Asn Gln Glu
        460                 465                 470 gtt gca tta aaa tta gaa cca aat cca gag tca ctg gaa ctt tct ttt     1731
Val Ala Leu Lys Leu Glu Pro Asn Pro Glu Ser Leu Glu Leu Ser Phe
        475                 480                 485 acc atg ccc cag att cag gat cag aca cct agt cct tcc gat gga agc     1779
Thr Met Pro Gln Ile Gln Asp Gln Thr Pro Ser Pro Ser Asp Gly Ser
490                 495                 500                 505 act aga caa agt tca cct gag cct aat agt ccc agt gaa tat tgt ttt     1827
Thr Arg Gln Ser Ser Pro Glu Pro Asn Ser Pro Ser Glu Tyr Cys Phe
                510                 515                 520 tat gtg gat agt gat atg gtc aat gaa ttc aag ttg gaa ttg gta gaa     1875
Tyr Val Asp Ser Asp Met Val Asn Glu Phe Lys Leu Glu Leu Val Glu
                525                 530                 535 aaa ctt ttt gct gaa gac aca gaa gca aag aac cca ttt tct act cag     1923
Lys Leu Phe Ala Glu Asp Thr Glu Ala Lys Asn Pro Phe Ser Thr Gln
        540                 545                 550 gac aca gat tta gac ttg gag atg tta gct ccc tat atc cca atg gat     1971
Asp Thr Asp Leu Asp Leu Glu Met Leu Ala Pro Tyr Ile Pro Met Asp
555                 560                 565 gat gac ttc cag tta cgt tcc ttc gat cag ttg tca cca tta gaa agc     2019
Asp Asp Phe Gln Leu Arg Ser Phe Asp Gln Leu Ser Pro Leu Glu Ser
570                 575                 580                 585 agt tcc gca agc cct gaa agc gca agt cct caa agc aca gtt aca gta     2067
Ser Ser Ala Ser Pro Glu Ser Ala Ser Pro Gln Ser Thr Val Thr Val
                590                 595                 600 ttc cag cag act caa ata caa gaa cct act gct aat gcc acc act acc     2115
Phe Gln Gln Thr Gln Ile Gln Glu Pro Thr Ala Asn Ala Thr Thr Thr
                605                 610                 615 act gcc acc act gat gaa tta aaa aca gtg aca aaa gac cgt atg gaa     2163
Thr Ala Thr Thr Asp Glu Leu Lys Thr Val Thr Lys Asp Arg Met Glu
        620                 625                 630 gac att aaa ata ttg att gca tct cca tct cct acc cac ata cat aaa     2211
Asp Ile Lys Ile Leu Ile Ala Ser Pro Ser Pro Thr His Ile His Lys
635                 640                 645 gaa act act agt gcc aca tca tca cca tat aga gat act caa agt cgg     2259
Glu Thr Thr Ser Ala Thr Ser Ser Pro Tyr Arg Asp Thr Gln Ser Arg
650                 655                 660                 665 aca gcc tca cca aac aga gca gga aaa gga gtc ata gaa cag aca gaa     2307
Thr Ala Ser Pro Asn Arg Ala Gly Lys Gly Val Ile Glu Gln Thr Glu
                670                 675                 680 aaa tct cat cca aga agc cct aac gtg tta tct gtc gct ttg agt caa     2355
Lys Ser His Pro Arg Ser Pro Asn Val Leu Ser Val Ala Leu Ser Gln
                685                 690                 695 aga act aca gtt cct gag gaa gaa cta aat cca aag ata cta gct ttg     2403
Arg Thr Thr Val Pro Glu Glu Glu Leu Asn Pro Lys Ile Leu Ala Leu
        700                 705                 710 cag aat gct cag aga aag cga aaa atg gaa cat gat ggt tca ctt ttt     2451
Gln Asn Ala Gln Arg Lys Arg Lys Met Glu His Asp Gly Ser Leu Phe
```

```
                              715                 720                 725
caa gca gta gga att gga aca tta tta cag cag cca gac gat cat gca       2499
Gln Ala Val Gly Ile Gly Thr Leu Leu Gln Gln Pro Asp Asp His Ala
730                 735                 740                 745 gct act aca tca ctt tct tgg aaa cgt gta aaa gga tgc aaa tct agt       2547
Ala Thr Thr Ser Leu Ser Trp Lys Arg Val Lys Gly Cys Lys Ser Ser
                750                 755                 760 gaa cag aat gga atg gag caa aag aca att att tta ata ccc tct gat       2595
Glu Gln Asn Gly Met Glu Gln Lys Thr Ile Ile Leu Ile Pro Ser Asp
            765                 770                 775 tta gca tgt aga ctg ctg ggg caa tca atg gat gaa agt gga tta cca       2643
Leu Ala Cys Arg Leu Leu Gly Gln Ser Met Asp Glu Ser Gly Leu Pro
        780                 785                 790 cag ctg acc agt tat gat tgt gaa gtt aat gct cct ata caa ggc agc       2691
Gln Leu Thr Ser Tyr Asp Cys Glu Val Asn Ala Pro Ile Gln Gly Ser
    795                 800                 805 aga aac cta ctg cag ggt gaa gaa tta ctc aga gct ttg gat caa gtt       2739
Arg Asn Leu Leu Gln Gly Glu Glu Leu Leu Arg Ala Leu Asp Gln Val
810                 815                 820                 825 aac tga gcttttctt aatttcattc cttttttgg acactggtgg ctcactacct          2795
Asn aaagcagtct atttatattt tctacatcta attttagaag cctggctaca atactgcaca     2855
aacttggtta gttcaatttt tgatccccct tctacttaat ttacattaat gctctttttt     2915
agtatgttct ttaatgctgg atcacagaca gctcattttc tcagtttttt ggtatttaaa     2975
ccattgcatt gcagtagcat catttttaaaa aatgcacctt tttatttatt tattttttggc   3035 tagggagttt atcccttttt cgaattattt ttaagaagat gccaatataa ttttttgtaag    3095 aaggcagtaa cctttcatca tgatcatagg cagttgaaaa attttttacac cttttttttc    3155 acattttaca taaataataa tgctttgcca gcagtacgtg gtagccacaa ttgcacaata     3215
tattttctta aaaaatacca gcagttactc atggaatata ttctgcgttt ataaaactag     3275
tttttaagaa gaaattttt ttggcctatg aaattgttaa acctggaaca tgacattgtt      3335
aatcatataa taatgattct taaatgctgt atggtttatt atttaaatgg gtaaagccat     3395
ttacataata tagaaagata tgcatatatc tagaaggtat gtggcattta tttggataaa     3455
attctcaatt cagagaaatc atctgatgtt tctatagtca ctttgccagc tcaaaagaaa     3515 acaatacct atgtagttgt ggaagtttat gctaatattg tgtaactgat attaaaccta      3575
aatgttctgc ctaccctgtt ggtataaaga tatttttgagc agactgtaaa caagaaaaaa    3635
aaaatcatgc attcttagca aaattgccta gtatgttaat ttgctcaaaa tacaatgttt     3695
gattttatgc actttgtcgc tattaacatc cttttttttca tgtagatttc aataattgag    3755 taatttaga agcattattt taggaatata tagttgtcac agtaaatatc ttgttttttc      3815
tatgtacatt gtacaaattt ttcattcctt ttgctctttg tggttggatc taacactaac     3875
tgtattgttt tgttacatca aataaacatc ttctgtggaa aaaaaaaaa aaaaaaa        3933

<210> SEQ ID NO 134
<211> LENGTH: 20
<212> TYPE: DNA
<213> ORGANISM: Artificial Sequence
<220> FEATURE:
<223> OTHER INFORMATION: Synthetic Construct

<400> SEQUENCE: 134
tgatgagcaa gctcataaaa                                                   20
```

```
<210> SEQ ID NO 135
<211> LENGTH: 20
<212> TYPE: DNA
<213> ORGANISM: Artificial Sequence
<220> FEATURE:
<223> OTHER INFORMATION: Synthetic Construct

<400> SEQUENCE: 135
gcaactgatg agcaagctca                                         20

<210> SEQ ID NO 136
<211> LENGTH: 20
<212> TYPE: DNA
<213> ORGANISM: Artificial Sequence
<220> FEATURE:
<223> OTHER INFORMATION: Synthetic Construct

<400> SEQUENCE: 136
ggaagtggca actgatgagc                                         20

<210> SEQ ID NO 137
<211> LENGTH: 20
<212> TYPE: DNA
<213> ORGANISM: Artificial Sequence
<220> FEATURE:
<223> OTHER INFORMATION: Synthetic Construct

<400> SEQUENCE: 137
ccagttagtt caaactgagt                                         20

<210> SEQ ID NO 138
<211> LENGTH: 20
<212> TYPE: DNA
<213> ORGANISM: Artificial Sequence
<220> FEATURE:
<223> OTHER INFORMATION: Synthetic Construct

<400> SEQUENCE: 138
tgtgtccagt tagttcaaac                                         20

<210> SEQ ID NO 139
<211> LENGTH: 20
<212> TYPE: DNA
<213> ORGANISM: Artificial Sequence
<220> FEATURE:
<223> OTHER INFORMATION: Synthetic Construct

<400> SEQUENCE: 139
cacactgtgt ccagttagtt                                         20

<210> SEQ ID NO 140
<211> LENGTH: 20
<212> TYPE: DNA
<213> ORGANISM: Artificial Sequence
<220> FEATURE:
<223> OTHER INFORMATION: Synthetic Construct

<400> SEQUENCE: 140
cacatggatg agtaaaatca                                         20

<210> SEQ ID NO 141
<211> LENGTH: 20
<212> TYPE: DNA
<213> ORGANISM: Artificial Sequence
<220> FEATURE:
<223> OTHER INFORMATION: Synthetic Construct

<400> SEQUENCE: 141
```
tcctcatggt cacatggatg                                                20

<210> SEQ ID NO 142
<211> LENGTH: 20
<212> TYPE: DNA
<213> ORGANISM: Artificial Sequence
<220> FEATURE:
<223> OTHER INFORMATION: Synthetic Construct

<400> SEQUENCE: 142
tctctcattt cctcatggtc                                                20

<210> SEQ ID NO 143
<211> LENGTH: 20
<212> TYPE: DNA
<213> ORGANISM: Artificial Sequence
<220> FEATURE:
<223> OTHER INFORMATION: Synthetic Construct

<400> SEQUENCE: 143
gcatttctct catttcctca                                                20

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct

<400> SEQUENCE: 144
gtgtgtaagc atttctctca                                                20

<210> SEQ ID NO 145
<211> LENGTH: 20
<212> TYPE: DNA
<213> ORGANISM: Artificial Sequence
<220> FEATURE:
<223> OTHER INFORMATION: Synthetic Construct

<400> SEQUENCE: 145
ggccatttct gtgtgtaagc                                                20

<210> SEQ ID NO 146
<211> LENGTH: 20
<212> TYPE: DNA
<213> ORGANISM: Artificial Sequence
<220> FEATURE:
<223> OTHER INFORMATION: Synthetic Construct

<400> SEQUENCE: 146
tggttactgt tggtatcata                                                20

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct

<400> SEQUENCE: 147
tcacaaatca gcaccaagca                                                20

<210> SEQ ID NO 148
<211> LENGTH: 20
<212> TYPE: DNA
<213> ORGANISM: Artificial Sequence
<220> FEATURE:
<223> OTHER INFORMATION: Synthetic Construct

<400> SEQUENCE: 148
tgggttcaca aatcagcacc                                                   20

<210> SEQ ID NO 149
<211> LENGTH: 20
<212> TYPE: DNA
<213> ORGANISM: Artificial Sequence
<220> FEATURE:
<223> OTHER INFORMATION: Synthetic Construct

<400> SEQUENCE: 149
tgaggaatgg gttcacaaat                                                   20

<210> SEQ ID NO 150
<211> LENGTH: 20
<212> TYPE: DNA
<213> ORGANISM: Artificial Sequence
<220> FEATURE:
<223> OTHER INFORMATION: Synthetic Construct

<400> SEQUENCE: 150
gtcttgctat ctaaaggaat                                                   20

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct

<400> SEQUENCE: 151
tattcataaa ttgagcggcc                                                   20

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct

<400> SEQUENCE: 152
tgataatatt cataaattga                                                   20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct

<400> SEQUENCE: 153
tgagttttgg tcagatgatc                                                   20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct

<400> SEQUENCE: 154
acttgtcctt tagtaaacat                                                   20

```
<210> SEQ ID NO 155
<211> LENGTH: 20
<212> TYPE: DNA
<213> ORGANISM: Artificial Sequence
<220> FEATURE:
<223> OTHER INFORMATION: Synthetic Construct

<400> SEQUENCE: 155
tggtgacttg tcctttagta                                               20

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct

<400> SEQUENCE: 156
tcctgtggtg acttgtcctt                                               20

<210> SEQ ID NO 157
<211> LENGTH: 20
<212> TYPE: DNA
<213> ORGANISM: Artificial Sequence
<220> FEATURE:
<223> OTHER INFORMATION: Synthetic Construct

<400> SEQUENCE: 157
tactgtcctg tggtgacttg                                               20

<210> SEQ ID NO 158
<211> LENGTH: 20
<212> TYPE: DNA
<213> ORGANISM: Artificial Sequence
<220> FEATURE:
<223> OTHER INFORMATION: Synthetic Construct

<400> SEQUENCE: 158
tcctgtactg tcctgtggtg                                               20

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct

<400> SEQUENCE: 159
gcaagcatcc tgtactgtcc                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic Construct

<400> SEQUENCE: 160
cagacatatc cacctctttt                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic Construct

<400> SEQUENCE: 161
```
tcaacccaga catatccacc                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic Construct

<400> SEQUENCE: 162
tatgacagtt gcttgagttt                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic Construct

<400> SEQUENCE: 163
ttatatatga cagttgcttg                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic Construct

<400> SEQUENCE: 164
gaagggagaa aatcaagtcg                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic Construct

<400> SEQUENCE: 165
attctgtttg ttgaagggag                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic Construct

<400> SEQUENCE: 166
ttcatatctg aagattcaac                                               20

<210> SEQ ID NO 167
<211> LENGTH: 20
<212> TYPE: DNA
<213> ORGANISM: Artificial Sequence
<220> FEATURE:
<223> OTHER INFORMATION: Synthetic Construct

<400> SEQUENCE: 167
tctgattcaa ctttggtgaa                                               20

<210> SEQ ID NO 168
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 168
attacatcat tatataatgg                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic Construct

<400> SEQUENCE: 169
ctacttcgaa gtggctttgg                                              20

<210> SEQ ID NO 170
<211> LENGTH: 20
<212> TYPE: DNA
<213> ORGANISM: Artificial Sequence
<220> FEATURE:
<223> OTHER INFORMATION: Synthetic Construct

<400> SEQUENCE: 170
tcagcactac ttcgaagtgg                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Construct

<400> SEQUENCE: 171
ctttgtctag tgcttccatc                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic Construct

<400> SEQUENCE: 172
atcatccatt gggatatagg                                              20

<210> SEQ ID NO 173
<211> LENGTH: 20
<212> TYPE: DNA
<213> ORGANISM: Artificial Sequence
<220> FEATURE:
<223> OTHER INFORMATION: Synthetic Construct

<400> SEQUENCE: 173
tctaatggtg acaactgatc                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic Construct

<400> SEQUENCE: 174
catcatgttc catttttcgc                                              20
```

```
<210> SEQ ID NO 175
<211> LENGTH: 20
<212> TYPE: DNA
<213> ORGANISM: Artificial Sequence
<220> FEATURE:
<223> OTHER INFORMATION: Synthetic Construct

<400> SEQUENCE: 175
gtcagctgtg gtaatccact                                                 20

<210> SEQ ID NO 176
<211> LENGTH: 20
<212> TYPE: DNA
<213> ORGANISM: Artificial Sequence
<220> FEATURE:
<223> OTHER INFORMATION: Synthetic Construct

<400> SEQUENCE: 176
taactggtca gctgtggtaa                                                 20

<210> SEQ ID NO 177
<211> LENGTH: 20
<212> TYPE: DNA
<213> ORGANISM: Artificial Sequence
<220> FEATURE:
<223> OTHER INFORMATION: Synthetic Construct

<400> SEQUENCE: 177
ggagcattaa cttcacaatc                                                 20

<210> SEQ ID NO 178
<211> LENGTH: 20
<212> TYPE: DNA
<213> ORGANISM: Artificial Sequence
<220> FEATURE:
<223> OTHER INFORMATION: Synthetic Construct

<400> SEQUENCE: 178
aggtttctgc tgccttgtat                                                 20

<210> SEQ ID NO 179
<211> LENGTH: 20
<212> TYPE: DNA
<213> ORGANISM: Artificial Sequence
<220> FEATURE:
<223> OTHER INFORMATION: Synthetic Construct

<400> SEQUENCE: 179
ccctgcagta ggtttctgct                                                 20

<210> SEQ ID NO 180
<211> LENGTH: 20
<212> TYPE: DNA
<213> ORGANISM: Artificial Sequence
<220> FEATURE:
<223> OTHER INFORMATION: Synthetic Construct

<400> SEQUENCE: 180
cttcaccctg cagtaggttt                                                 20

<210> SEQ ID NO 181
<211> LENGTH: 20
<212> TYPE: DNA
<213> ORGANISM: Artificial Sequence
<220> FEATURE:
<223> OTHER INFORMATION: Synthetic Construct

<400> SEQUENCE: 181
```

```
taattcttca ccctgcagta                                          20

<210> SEQ ID NO 182
<211> LENGTH: 20
<212> TYPE: DNA
<213> ORGANISM: Artificial Sequence
<220> FEATURE:
<223> OTHER INFORMATION: Synthetic Construct

<400> SEQUENCE: 182
ctgagtaatt cttcaccctg                                          20

<210> SEQ ID NO 183
<211> LENGTH: 20
<212> TYPE: DNA
<213> ORGANISM: Artificial Sequence
<220> FEATURE:
<223> OTHER INFORMATION: Synthetic Construct

<400> SEQUENCE: 183
aagctctgag taattcttca                                          20

<210> SEQ ID NO 184
<211> LENGTH: 20
<212> TYPE: DNA
<213> ORGANISM: Artificial Sequence
<220> FEATURE:
<223> OTHER INFORMATION: Synthetic Construct

<400> SEQUENCE: 184
atccaaagct ctgagtaatt                                          20

<210> SEQ ID NO 185
<211> LENGTH: 20
<212> TYPE: DNA
<213> ORGANISM: Artificial Sequence
<220> FEATURE:
<223> OTHER INFORMATION: Synthetic Construct

<400> SEQUENCE: 185
acttgatcca aagctctgag                                          20

<210> SEQ ID NO 186
<211> LENGTH: 20
<212> TYPE: DNA
<213> ORGANISM: Artificial Sequence
<220> FEATURE:
<223> OTHER INFORMATION: Synthetic Construct

<400> SEQUENCE: 186
gctcagttaa cttgatccaa                                          20

<210> SEQ ID NO 187
<211> LENGTH: 20
<212> TYPE: DNA
<213> ORGANISM: Artificial Sequence
<220> FEATURE:
<223> OTHER INFORMATION: Synthetic Construct

<400> SEQUENCE: 187
tgagccacca gtgtccaaaa                                          20

<210> SEQ ID NO 188
<211> LENGTH: 20
<212> TYPE: DNA
<213> ORGANISM: Artificial Sequence
```

<220> FEATURE:
<223> OTHER INFORMATION: Synthetic Construct

<400> SEQUENCE: 188
ccaggcttct aaaattagat                    20

<210> SEQ ID NO 189
<211> LENGTH: 20
<212> TYPE: DNA
<213> ORGANISM: Artificial Sequence
<220> FEATURE:
<223> OTHER INFORMATION: Synthetic Construct

<400> SEQUENCE: 189
gtgcagtatt gtagccaggc                    20

<210> SEQ ID NO 190
<211> LENGTH: 20
<212> TYPE: DNA
<213> ORGANISM: Artificial Sequence
<220> FEATURE:
<223> OTHER INFORMATION: Synthetic Construct

<400> SEQUENCE: 190
agtttgtgca gtattgtagc                    20

<210> SEQ ID NO 191
<211> LENGTH: 20
<212> TYPE: DNA
<213> ORGANISM: Artificial Sequence
<220> FEATURE:
<223> OTHER INFORMATION: Synthetic Construct

<400> SEQUENCE: 191
taaataaaaa ggtgcatttt                    20

<210> SEQ ID NO 192
<211> LENGTH: 20
<212> TYPE: DNA
<213> ORGANISM: Artificial Sequence
<220> FEATURE:
<223> OTHER INFORMATION: Synthetic Construct

<400> SEQUENCE: 192
actgcctatg atcatgatga                    20

<210> SEQ ID NO 193
<211> LENGTH: 20
<212> TYPE: DNA
<213> ORGANISM: Artificial Sequence
<220> FEATURE:
<223> OTHER INFORMATION: Synthetic Construct

<400> SEQUENCE: 193
ttgtgcaatt gtggctacca                    20

<210> SEQ ID NO 194
<211> LENGTH: 20
<212> TYPE: DNA
<213> ORGANISM: Artificial Sequence
<220> FEATURE:
<223> OTHER INFORMATION: Synthetic Construct

<400> SEQUENCE: 194
atatattgtg caattgtggc                    20

```
<210> SEQ ID NO 195
<211> LENGTH: 20
<212> TYPE: DNA
<213> ORGANISM: Artificial Sequence
<220> FEATURE:
<223> OTHER INFORMATION: Synthetic Construct

<400> SEQUENCE: 195
agaaaatata ttgtgcaatt                                               20

<210> SEQ ID NO 196
<211> LENGTH: 20
<212> TYPE: DNA
<213> ORGANISM: Artificial Sequence
<220> FEATURE:
<223> OTHER INFORMATION: Synthetic Construct

<400> SEQUENCE: 196
cttaaaaact agttttataa                                               20

<210> SEQ ID NO 197
<211> LENGTH: 20
<212> TYPE: DNA
<213> ORGANISM: Artificial Sequence
<220> FEATURE:
<223> OTHER INFORMATION: Synthetic Construct

<400> SEQUENCE: 197
atgtaaatgg ctttacccat                                               20

<210> SEQ ID NO 198
<211> LENGTH: 20
<212> TYPE: DNA
<213> ORGANISM: Artificial Sequence
<220> FEATURE:
<223> OTHER INFORMATION: Synthetic Construct

<400> SEQUENCE: 198
ttttatccaa ataaatgcca                                               20

<210> SEQ ID NO 199
<211> LENGTH: 20
<212> TYPE: DNA
<213> ORGANISM: Artificial Sequence
<220> FEATURE:
<223> OTHER INFORMATION: Synthetic Construct

<400> SEQUENCE: 199
tgagaatttt atccaaataa                                               20

<210> SEQ ID NO 200
<211> LENGTH: 20
<212> TYPE: DNA
<213> ORGANISM: Artificial Sequence
<220> FEATURE:
<223> OTHER INFORMATION: Synthetic Construct

<400> SEQUENCE: 200
taatagcgac aaagtgcata                                               20

<210> SEQ ID NO 201
<211> LENGTH: 20
<212> TYPE: DNA
<213> ORGANISM: Artificial Sequence
<220> FEATURE:
<223> OTHER INFORMATION: Synthetic Construct

<400> SEQUENCE: 201
```

```
gatgttaata gcgacaaagt                                                    20

<210> SEQ ID NO 202
<211> LENGTH: 20
<212> TYPE: DNA
<213> ORGANISM: Artificial Sequence
<220> FEATURE:
<223> OTHER INFORMATION: Synthetic Construct

<400> SEQUENCE: 202
aaaaggatgt taatagcgac                                                    20

<210> SEQ ID NO 203
<211> LENGTH: 20
<212> TYPE: DNA
<213> ORGANISM: Artificial Sequence
<220> FEATURE:
<223> OTHER INFORMATION: Synthetic Construct

<400> SEQUENCE: 203
aatgcttcta aaattactca                                                    20

<210> SEQ ID NO 204
<211> LENGTH: 20
<212> TYPE: DNA
<213> ORGANISM: Artificial Sequence
<220> FEATURE:
<223> OTHER INFORMATION: Synthetic Construct

<400> SEQUENCE: 204
tatattccta aaataatgct                                                    20

<210> SEQ ID NO 205
<211> LENGTH: 20
<212> TYPE: DNA
<213> ORGANISM: Artificial Sequence
<220> FEATURE:
<223> OTHER INFORMATION: Synthetic Construct

<400> SEQUENCE: 205
acagaagatg tttatttgat                                                    20

<210> SEQ ID NO 206
<211> LENGTH: 3973
<212> TYPE: DNA
<213> ORGANISM: Mus musculus
<220> FEATURE:
<221> NAME/KEY: CDS
<222> LOCATION: (258)..(2768)
<300> PUBLICATION INFORMATION:
<308> DATABASE ACCESSION NUMBER: NM_010431.1
<309> DATABASE ENTRY DATE: 2003-12-20
<313> RELEVANT RESIDUES: (1)..(3973)

<400> SEQUENCE: 206
cgcgaggact gtcctcgccg ccgtcgcggg cagtgtctag ccaggccttg acaagctagc         60
cggaggagcg cctaggaacc cgagccggag ctcagcgagc gcagcctgca cgcccgcctc        120
gcgtcccggg ggggtcccgc ctcccacccc gcctctggac ttgtctcttt cccgcgcgcg        180
gcggacagag ccggcgttta ggcccagcgc agcccggggg ccgccggccg ggaagacaac        240
gcgggcaccg attcgcc atg gag ggc gcc ggc ggc gag aac gag aag aaa          290
                   Met Glu Gly Ala Gly Gly Glu Asn Glu Lys Lys
                    1               5                   10 aag atg agt tct gaa cgt cga aaa gaa aag tct aga gat gca gca aga          338
Lys Met Ser Ser Glu Arg Arg Lys Glu Lys Ser Arg Asp Ala Ala Arg
```

|  |  |  |  |  |  |  |  |  |  |  |  |  |  |  |  |
|---|---|---|---|---|---|---|---|---|---|---|---|---|---|---|---|
|  |  | 15 |  |  |  | 20 |  |  |  | 25 |  |  |  |  |  |
| tct | cgg | cga | agc | aaa | gag | tct | gaa | gtt | ttt | tat | gag | ctt | gct | cat | cag | 386 |
| Ser | Arg | Arg | Ser | Lys | Glu | Ser | Glu | Val | Phe | Tyr | Glu | Leu | Ala | His | Gln |  |
|  |  | 30 |  |  |  | 35 |  |  |  | 40 |  |  |  |  |  |
| ttg | cca | ctt | ccc | cac | aat | gtg | agc | tca | cat | ctt | gat | aaa | gct | tct | gtt | 434 |
| Leu | Pro | Leu | Pro | His | Asn | Val | Ser | Ser | His | Leu | Asp | Lys | Ala | Ser | Val |  |
| 45 |  |  |  |  | 50 |  |  |  |  | 55 |  |  |  |  |  |
| atg | agg | ctc | acc | atc | agt | tat | tta | cgt | gtg | aga | aaa | ctt | ctg | gat | gcc | 482 |
| Met | Arg | Leu | Thr | Ile | Ser | Tyr | Leu | Arg | Val | Arg | Lys | Leu | Leu | Asp | Ala |  |
| 60 |  |  |  |  | 65 |  |  |  |  | 70 |  |  |  |  | 75 |
| ggt | ggt | cta | gac | agt | gaa | gat | gag | atg | aag | gca | cag | atg | gac | tgt | ttt | 530 |
| Gly | Gly | Leu | Asp | Ser | Glu | Asp | Glu | Met | Lys | Ala | Gln | Met | Asp | Cys | Phe |  |
|  |  |  |  | 80 |  |  |  |  | 85 |  |  |  |  | 90 |  |
| tat | ctg | aaa | gcc | cta | gat | ggc | ttt | gtg | atg | gtg | cta | aca | gat | gac | ggc | 578 |
| Tyr | Leu | Lys | Ala | Leu | Asp | Gly | Phe | Val | Met | Val | Leu | Thr | Asp | Asp | Gly |  |
|  |  | 95 |  |  |  | 100 |  |  |  | 105 |  |  |  |  |  |
| gac | atg | gtt | tac | att | tct | gat | aac | gtg | aac | aaa | tac | atg | ggg | tta | act | 626 |
| Asp | Met | Val | Tyr | Ile | Ser | Asp | Asn | Val | Asn | Lys | Tyr | Met | Gly | Leu | Thr |  |
| 110 |  |  |  |  | 115 |  |  |  |  | 120 |  |  |  |  |  |
| cag | ttt | gaa | cta | act | gga | cac | agt | gtg | ttt | gat | ttt | act | cat | cca | tgt | 674 |
| Gln | Phe | Glu | Leu | Thr | Gly | His | Ser | Val | Phe | Asp | Phe | Thr | His | Pro | Cys |  |
| 125 |  |  |  |  | 130 |  |  |  |  | 135 |  |  |  |  |  |
| gac | cat | gag | gaa | atg | aga | gaa | atg | ctt | aca | cac | aga | aat | ggc | cca | gtg | 722 |
| Asp | His | Glu | Glu | Met | Arg | Glu | Met | Leu | Thr | His | Arg | Asn | Gly | Pro | Val |  |
| 140 |  |  |  |  | 145 |  |  |  |  | 150 |  |  |  |  | 155 |
| aga | aaa | ggg | aaa | gaa | cta | aac | aca | cag | cgg | agc | ttt | ttt | ctc | aga | atg | 770 |
| Arg | Lys | Gly | Lys | Glu | Leu | Asn | Thr | Gln | Arg | Ser | Phe | Phe | Leu | Arg | Met |  |
|  |  |  |  | 160 |  |  |  |  | 165 |  |  |  |  | 170 |  |
| aag | tgc | acc | cta | aca | agc | cgg | ggg | agg | acg | atg | aac | atc | aag | tca | gca | 818 |
| Lys | Cys | Thr | Leu | Thr | Ser | Arg | Gly | Arg | Thr | Met | Asn | Ile | Lys | Ser | Ala |  |
|  |  | 175 |  |  |  | 180 |  |  |  | 185 |  |  |  |  |  |
| acg | tgg | aag | gtg | ctt | cac | tgc | acg | ggc | cat | att | cat | gtc | tat | gat | acc | 866 |
| Thr | Trp | Lys | Val | Leu | His | Cys | Thr | Gly | His | Ile | His | Val | Tyr | Asp | Thr |  |
| 190 |  |  |  |  | 195 |  |  |  |  | 200 |  |  |  |  |  |
| aac | agt | aac | caa | cct | cag | tgt | ggg | tac | aag | aaa | cca | ccc | atg | acg | tgc | 914 |
| Asn | Ser | Asn | Gln | Pro | Gln | Cys | Gly | Tyr | Lys | Lys | Pro | Pro | Met | Thr | Cys |  |
| 205 |  |  |  |  | 210 |  |  |  |  | 215 |  |  |  |  |  |
| ttg | gtg | ctg | att | tgt | gaa | ccc | att | cct | cat | ccg | tca | aat | att | gaa | att | 962 |
| Leu | Val | Leu | Ile | Cys | Glu | Pro | Ile | Pro | His | Pro | Ser | Asn | Ile | Glu | Ile |  |
| 220 |  |  |  |  | 225 |  |  |  |  | 230 |  |  |  |  | 235 |
| cct | tta | gat | agc | aag | aca | ttt | ctc | agt | cga | cac | agc | ctc | gat | atg | aaa | 1010 |
| Pro | Leu | Asp | Ser | Lys | Thr | Phe | Leu | Ser | Arg | His | Ser | Leu | Asp | Met | Lys |  |
|  |  |  |  | 240 |  |  |  |  | 245 |  |  |  |  | 250 |  |
| ttt | tct | tac | tgt | gat | gaa | aga | att | act | gag | ttg | atg | ggt | tat | gag | ccg | 1058 |
| Phe | Ser | Tyr | Cys | Asp | Glu | Arg | Ile | Thr | Glu | Leu | Met | Gly | Tyr | Glu | Pro |  |
|  |  | 255 |  |  |  | 260 |  |  |  | 265 |  |  |  |  |  |
| gaa | gaa | ctt | ttg | ggc | cgc | tca | att | tat | gaa | tat | tat | cat | gct | ttg | gat | 1106 |
| Glu | Glu | Leu | Leu | Gly | Arg | Ser | Ile | Tyr | Glu | Tyr | Tyr | His | Ala | Leu | Asp |  |
|  |  | 270 |  |  |  | 275 |  |  |  | 280 |  |  |  |  |  |
| tct | gat | cat | ctg | acc | aaa | act | cac | cat | gat | atg | ttt | act | aaa | gga | caa | 1154 |
| Ser | Asp | His | Leu | Thr | Lys | Thr | His | His | Asp | Met | Phe | Thr | Lys | Gly | Gln |  |
| 285 |  |  |  |  | 290 |  |  |  |  | 295 |  |  |  |  |  |
| gtc | acc | aca | gga | cag | tac | agg | atg | ctt | gcc | aaa | aga | ggt | gga | tat | gtc | 1202 |
| Val | Thr | Thr | Gly | Gln | Tyr | Arg | Met | Leu | Ala | Lys | Arg | Gly | Gly | Tyr | Val |  |
| 300 |  |  |  |  | 305 |  |  |  |  | 310 |  |  |  |  | 315 |
| tgg | gtt | gaa | act | caa | gca | act | gtc | ata | tat | aat | acg | aag | aac | tcc | cag | 1250 |
| Trp | Val | Glu | Thr | Gln | Ala | Thr | Val | Ile | Tyr | Asn | Thr | Lys | Asn | Ser | Gln |  |
|  |  |  |  | 320 |  |  |  |  | 325 |  |  |  |  | 330 |  |
| cca | cag | tgc | att | gtg | tgt | gtg | aat | tat | gtt | gta | agt | ggt | att | att | cag | 1298 |
| Pro | Gln | Cys | Ile | Val | Cys | Val | Asn | Tyr | Val | Val | Ser | Gly | Ile | Ile | Gln |  |

-continued

```
                   335                 340                 345
cac gac ttg att ttc tcc ctt caa caa aca gaa tct gtg ctc aaa cca      1346
His Asp Leu Ile Phe Ser Leu Gln Gln Thr Glu Ser Val Leu Lys Pro
                350                 355                 360 gtt gaa tct tca gat atg aag atg act cag ctg ttc acc aaa gtt gaa      1394
Val Glu Ser Ser Asp Met Lys Met Thr Gln Leu Phe Thr Lys Val Glu
            365                 370                 375 tca gag gat aca agc tgc ctt ttt gat aag ctt aag aag gag cct gat      1442
Ser Glu Asp Thr Ser Cys Leu Phe Asp Lys Leu Lys Lys Glu Pro Asp
380                 385                 390                 395 gct ctc act ctg ctg gct cca gct gcc ggc gac acc atc atc tct ctg      1490
Ala Leu Thr Leu Leu Ala Pro Ala Ala Gly Asp Thr Ile Ile Ser Leu
                400                 405                 410 gat ttt ggc agc gat gac aca gaa act gaa gat caa caa ctt gaa gat      1538
Asp Phe Gly Ser Asp Asp Thr Glu Thr Glu Asp Gln Gln Leu Glu Asp
            415                 420                 425 gtt cca tta tat aat gat gta atg ttt ccc tct tct aat gaa aaa tta      1586
Val Pro Leu Tyr Asn Asp Val Met Phe Pro Ser Ser Asn Glu Lys Leu
        430                 435                 440 aat ata aac ctg gca atg tct cct tta cct tca tcg gaa act cca aag      1634
Asn Ile Asn Leu Ala Met Ser Pro Leu Pro Ser Ser Glu Thr Pro Lys
    445                 450                 455 cca ctt cga agt agt gct gat cct gca ctg aat caa gag gtt gca tta      1682
Pro Leu Arg Ser Ser Ala Asp Pro Ala Leu Asn Gln Glu Val Ala Leu
460                 465                 470                 475 aaa tta gaa tca agt cca gag tca ctg gga ctt tct ttt acc atg ccc      1730
Lys Leu Glu Ser Ser Pro Glu Ser Leu Gly Leu Ser Phe Thr Met Pro
                480                 485                 490 cag att caa gat cag cca gca agt cct tct gat gga agc act aga caa      1778
Gln Ile Gln Asp Gln Pro Ala Ser Pro Ser Asp Gly Ser Thr Arg Gln
            495                 500                 505 agt tca cct gag aga ctt ctt cag gaa aac gta aac act cct aac ttt      1826
Ser Ser Pro Glu Arg Leu Leu Gln Glu Asn Val Asn Thr Pro Asn Phe
        510                 515                 520 tcc cag cct aac agt ccc agt gaa tat tgc ttt gat gtg gat agc gat      1874
Ser Gln Pro Asn Ser Pro Ser Glu Tyr Cys Phe Asp Val Asp Ser Asp
    525                 530                 535 atg gtc aat gta ttc aag ttg gaa ctg gtg gaa aaa ctg ttt gct gaa      1922
Met Val Asn Val Phe Lys Leu Glu Leu Val Glu Lys Leu Phe Ala Glu
540                 545                 550                 555 gac aca gag gca aag aat cca ttt tca act cag gac act gat tta gat      1970
Asp Thr Glu Ala Lys Asn Pro Phe Ser Thr Gln Asp Thr Asp Leu Asp
                560                 565                 570 ttg gag atg ctg gct ccc tat atc cca atg gat gat gat ttc cag tta      2018
Leu Glu Met Leu Ala Pro Tyr Ile Pro Met Asp Asp Asp Phe Gln Leu
            575                 580                 585 cgt tcc ttt gat cag ttg tca cca tta gag agc aat tct cca agc cct      2066
Arg Ser Phe Asp Gln Leu Ser Pro Leu Glu Ser Asn Ser Pro Ser Pro
        590                 595                 600 cca agt atg agc aca gtt act ggg ttc cag cag acc cag tta cag aaa      2114
Pro Ser Met Ser Thr Val Thr Gly Phe Gln Gln Thr Gln Leu Gln Lys
    605                 610                 615 cct acc atc act gcc act gcc acc aca act gcc acc act gat gaa tca      2162
Pro Thr Ile Thr Ala Thr Ala Thr Thr Thr Ala Thr Thr Asp Glu Ser
620                 625                 630                 635 aaa aca gag acg aag gac aat aaa gaa gat att aaa ata ctg att gca      2210
Lys Thr Glu Thr Lys Asp Asn Lys Glu Asp Ile Lys Ile Leu Ile Ala
                640                 645                 650 tct cca tct tct acc caa gta cct caa gaa acg acc act gct aag gca      2258
Ser Pro Ser Ser Thr Gln Val Pro Gln Glu Thr Thr Thr Ala Lys Ala
```

```
                       655                 660                 665
tca gca tac agt ggc act cac agt cgg aca gcc tca cca gac aga gca    2306
Ser Ala Tyr Ser Gly Thr His Ser Arg Thr Ala Ser Pro Asp Arg Ala
        670                 675                 680 gga aag aga gtc ata gaa cag aca gac aaa gct cat cca agg agc ctt    2354
Gly Lys Arg Val Ile Glu Gln Thr Asp Lys Ala His Pro Arg Ser Leu
685                 690                 695 aag ctg tct gcc act ttg aat caa aga aat act gtt cct gag gaa gaa    2402
Lys Leu Ser Ala Thr Leu Asn Gln Arg Asn Thr Val Pro Glu Glu Glu
700                 705                 710                 715 tta aac cca aag aca ata gct tcg cag aat gct cag agg aag cga aaa    2450
Leu Asn Pro Lys Thr Ile Ala Ser Gln Asn Ala Gln Arg Lys Arg Lys
            720                 725                 730 atg gaa cat gat ggc tcc ctt ttt caa gca gca gga att gga aca tta    2498
Met Glu His Asp Gly Ser Leu Phe Gln Ala Ala Gly Ile Gly Thr Leu
                735                 740                 745 ttg cag caa cca ggt gac tgt gca cct act atg tca ctt tcc tgg aaa    2546
Leu Gln Gln Pro Gly Asp Cys Ala Pro Thr Met Ser Leu Ser Trp Lys
                    750                 755                 760 cga gtg aaa gga ttc ata tct agt gaa cag aat gga acg gag caa aag    2594
Arg Val Lys Gly Phe Ile Ser Ser Glu Gln Asn Gly Thr Glu Gln Lys
765                 770                 775 act att att tta ata ccc tcc gat tta gca tgc aga ctg ctg ggg cag    2642
Thr Ile Ile Leu Ile Pro Ser Asp Leu Ala Cys Arg Leu Leu Gly Gln
780                 785                 790                 795 tca atg gat gag agt gga tta cca cag ctg acc agt tac gat tgt gaa    2690
Ser Met Asp Glu Ser Gly Leu Pro Gln Leu Thr Ser Tyr Asp Cys Glu
                    800                 805                 810 gtt aat gct ccc ata caa ggc agc aga aac cta ctg cag ggt gaa gaa    2738
Val Asn Ala Pro Ile Gln Gly Ser Arg Asn Leu Leu Gln Gly Glu Glu
                        815                 820                 825 tta ctc aga gct ttg gat caa gtt aac tga gcgtttccta atctcattcc      2788
Leu Leu Arg Ala Leu Asp Gln Val Asn
                830                 835 ttttgattgt taatgttttt gttcagttgt tgttgtttgt tgggtttttg tttctgttgg  2848
ttattttgg acactggtgg ctcagcagtc tatttatatt ttctatatct aattttagaa   2908
gcctggctac aatactgcac aaactcagat agtttagttt tcatcccctt tctacttaat  2968
tttcattaat gctcttttta atatgttctt ttaatgccag atcacagcac attcacagct  3028
cctcagcatt tcaccattgc attgctgtag tgtcatttaa aatgcacctt tttatttatt  3088
tatttttggt gagggagttt gtcccttatt gaattatttt taatgaaatg ccaatataat  3148
tttttaagaa agcagtaaat tctcatcatg atcataggca gttgaaaact ttttactcat  3208
ttttttcatg ttttacatga aaataatgct ttgtcagcag tacatggtag ccacaattgc  3268
acaatatatt ttctttaaaa accagcagt tactcatgca atatattctg catttataaa   3328
actagttttt aagaaatttt ttttggccta tggaattgtt aagcctggat catgaagcgt  3388
tgatcttata atgattctta aactgtatgg tttctttata tgggtaaagc catttacatg  3448
atataaagaa atatgcttat atctggaagg tatgtggcat ttatttggat aaaattctca  3508
attcagagaa gttatctggt gtttcttgac tttaccaact caaaacagtc cctctgtagt  3568
tgtggaagct tatgctaata ttgtgtaatt gattatgaaa cataaatgtt ctgcccaccc  3628
tgttggtata aagacatttt gagcatactg taaacaaaca aacaaaaaat catgctttgt  3688
tagtaaaatt gcctagtatg ttgatttgtt gaaaatatga tgtttggttt tatgcacttt  3748
gtcgctatta acatcctttt ttcatataga tttcaataag tgagtaattt tagaagcatt  3808
```

-continued

```
atttaggaa tatagagttg tcatagtaaa catcttgttt tttctatgta cactgtataa    3868 attttcgtt cccttgctct ttgtggttgg gtctaacact aactgtactg ttttgttata    3928
tcaaataaac atcttctgtg gaccaggaaa aaaaaaaaaa aaaaa                   3973

<210> SEQ ID NO 207
<211> LENGTH: 20
<212> TYPE: DNA
<213> ORGANISM: Artificial Sequence
<220> FEATURE:
<223> OTHER INFORMATION: Synthetic Construct

<400> SEQUENCE: 207
gatcatgatg agaatttact                                                20

<210> SEQ ID NO 208
<211> LENGTH: 2818
<212> TYPE: DNA
<213> ORGANISM: Homo sapiens
<220> FEATURE:
<221> NAME/KEY: CDS
<222> LOCATION: (150)..(2762)
<300> PUBLICATION INFORMATION:
<301> AUTHORS: Sang et al.
<302> TITLE: MAPK Signaling Up-Regulates The Activity Of Hypoxia-
       Inducible Factors By Its Effect on P300
<303> JOURNAL: J. Biol. Chem.
<304> VOLUME: 278
<305> ISSUE: 16
<306> PAGES: 14013-14019
<307> DATE: 2003
<308> DATABASE ACCESSION NUMBER: NM_001430.1
<309> DATABASE ENTRY DATE: 2003-10-06
<313> RELEVANT RESIDUES: (1)..(2818)

<400> SEQUENCE: 208
cctgactgcg cggggcgctc gggacctgcg cgcacctcgg accttcacca cccgcccggg   60
ccgcggggag cggacgaggg ccacagcccc ccacccgcca gggagcccag gtgctcggcg  120
tctgaacgtc tcaaagggcc acagcgaca atg aca gct gac aag gag aag aaa   173
                                 Met Thr Ala Asp Lys Glu Lys Lys
                                  1               5 agg agt agc tcg gag agg agg aag gag aag tcc cgg gat gct gcg cgg   221
Arg Ser Ser Ser Glu Arg Arg Lys Glu Lys Ser Arg Asp Ala Ala Arg
        10                  15                  20 tgc cgg cgg agc aag gag acg gag gtg ttc tat gag ctg gcc cat gag   269
Cys Arg Arg Ser Lys Glu Thr Glu Val Phe Tyr Glu Leu Ala His Glu
 25                  30                  35                  40 ctg cct ctg ccc cac agt gtg agc tcc cat ctg gac aag gcc tcc atc   317
Leu Pro Leu Pro His Ser Val Ser Ser His Leu Asp Lys Ala Ser Ile
                 45                  50                  55 atg cga ctg gaa atc agc ttc ctg cga aca cac aag ctc ctc tcc tca   365
Met Arg Leu Glu Ile Ser Phe Leu Arg Thr His Lys Leu Leu Ser Ser
             60                  65                  70 gtt tgc tct gaa aac gag tcc gaa gcc gaa gct gac cag cag atg gac   413
Val Cys Ser Glu Asn Glu Ser Glu Ala Glu Ala Asp Gln Gln Met Asp
         75                  80                  85 aac ttg tac ctg aaa gcc ttg gag ggt ttc att gcc gtg gtg acc caa   461
Asn Leu Tyr Leu Lys Ala Leu Glu Gly Phe Ile Ala Val Val Thr Gln
     90                  95                 100 gat ggc gac atg atc ttt ctg tca gaa aac atc agc aag ttc atg gga   509
Asp Gly Asp Met Ile Phe Leu Ser Glu Asn Ile Ser Lys Phe Met Gly
105                 110                 115                 120 ctt aca cag gtg gag cta aca gga cat agt atc ttt gac ttc act cat   557
Leu Thr Gln Val Glu Leu Thr Gly His Ser Ile Phe Asp Phe Thr His
                125                 130                 135
```

```
ccc tgc gac cat gag gag att cgt gag aac ctg agt ctc aaa aat ggc    605
Pro Cys Asp His Glu Glu Ile Arg Glu Asn Leu Ser Leu Lys Asn Gly
            140                 145                 150 tct ggt ttt ggg aaa aaa agc aaa gac atg tcc aca gag cgg gac ttc    653
Ser Gly Phe Gly Lys Lys Ser Lys Asp Met Ser Thr Glu Arg Asp Phe
        155                 160                 165 ttc atg agg atg aag tgc acg gtc acc aac aga ggc cgt act gtc aac    701
Phe Met Arg Met Lys Cys Thr Val Thr Asn Arg Gly Arg Thr Val Asn
    170                 175                 180 ctc aag tca gcc acc tgg aag gtc ttg cac tgc acg ggc cag gtg aaa    749
Leu Lys Ser Ala Thr Trp Lys Val Leu His Cys Thr Gly Gln Val Lys
185                 190                 195                 200 gtc tac aac aac tgc cct cct cac aat agt ctg tgt ggc tac aag gag    797
Val Tyr Asn Asn Cys Pro Pro His Asn Ser Leu Cys Gly Tyr Lys Glu
            205                 210                 215 ccc ctg ctg tcc tgc ctc atc atc atg tgt gaa cca atc cag cac cca    845
Pro Leu Leu Ser Cys Leu Ile Ile Met Cys Glu Pro Ile Gln His Pro
        220                 225                 230 tcc cac atg gac atc ccc ctg gat agc aag acc ttc ctg agc cgc cac    893
Ser His Met Asp Ile Pro Leu Asp Ser Lys Thr Phe Leu Ser Arg His
    235                 240                 245 agc atg gac atg aag ttc acc tac tgt gat gac aga atc aca gaa ctg    941
Ser Met Asp Met Lys Phe Thr Tyr Cys Asp Asp Arg Ile Thr Glu Leu
250                 255                 260 att ggt tac cac cct gag gag ctg ctt ggc cgc tca gcc tat gaa ttc    989
Ile Gly Tyr His Pro Glu Glu Leu Leu Gly Arg Ser Ala Tyr Glu Phe
265                 270                 275                 280 tac cat gcg cta gac tcc gag aac atg acc aag agt cac cag aac ttg   1037
Tyr His Ala Leu Asp Ser Glu Asn Met Thr Lys Ser His Gln Asn Leu
            285                 290                 295 tgc acc aag ggt cag gta gta agt ggc cag tac cgg atg ctc gca aag   1085
Cys Thr Lys Gly Gln Val Val Ser Gly Gln Tyr Arg Met Leu Ala Lys
        300                 305                 310 cat ggg ggc tac gtg tgg ctg gag acc cag ggg acg gtc atc tac aac   1133
His Gly Gly Tyr Val Trp Leu Glu Thr Gln Gly Thr Val Ile Tyr Asn
    315                 320                 325 cct cgc aac ctg cag ccc cag tgc atc atg tgt gtc aac tac gtc ctg   1181
Pro Arg Asn Leu Gln Pro Gln Cys Ile Met Cys Val Asn Tyr Val Leu
330                 335                 340 agt gag att gag aag aat gac gtg gtg ttc tcc atg gac cag act gaa   1229
Ser Glu Ile Glu Lys Asn Asp Val Val Phe Ser Met Asp Gln Thr Glu
345                 350                 355                 360 tcc ctg ttc aag ccc cac ctg atg gcc atg aac agc atc ttt gat agc   1277
Ser Leu Phe Lys Pro His Leu Met Ala Met Asn Ser Ile Phe Asp Ser
            365                 370                 375 agt ggc aag ggg gct gtg tct gag aag agt aac ttc cta ttc acc aag   1325
Ser Gly Lys Gly Ala Val Ser Glu Lys Ser Asn Phe Leu Phe Thr Lys
        380                 385                 390 cta aag gag gag ccc gag gag ctg gcc cag ctg gct ccc acc cca gga   1373
Leu Lys Glu Glu Pro Glu Glu Leu Ala Gln Leu Ala Pro Thr Pro Gly
    395                 400                 405 gac gcc atc atc tct ctg gat ttc ggg aat cag aac ttc gag gag tcc   1421
Asp Ala Ile Ile Ser Leu Asp Phe Gly Asn Gln Asn Phe Glu Glu Ser
410                 415                 420 tca gcc tat ggc aag gcc atc ctg ccc ccg agc cag cca tgg gcc acg   1469
Ser Ala Tyr Gly Lys Ala Ile Leu Pro Pro Ser Gln Pro Trp Ala Thr
425                 430                 435                 440 gag ttg agg agc cac agc acc cag agc gag gct ggg agc ctg cct gcc   1517
Glu Leu Arg Ser His Ser Thr Gln Ser Glu Ala Gly Ser Leu Pro Ala
            445                 450                 455
```

-continued

| | |
|---|---|
| ttc acc gtg ccc cag gca gct gcc ccg ggc agc acc acc ccc agt gcc<br>Phe Thr Val Pro Gln Ala Ala Ala Pro Gly Ser Thr Thr Pro Ser Ala<br>460                             465                     470 | 1565 |
| acc agc agc agc agc agc tgc tcc acg ccc aat agc cct gaa gac tat<br>Thr Ser Ser Ser Ser Ser Cys Ser Thr Pro Asn Ser Pro Glu Asp Tyr<br>    475                         480                       485 | 1613 |
| tac aca tct ttg gat aac gac ctg aag att gaa gtg att gag aag ctc<br>Tyr Thr Ser Leu Asp Asn Asp Leu Lys Ile Glu Val Ile Glu Lys Leu<br>490                             495                     500 | 1661 |
| ttc gcc atg gac aca gag gcc aag gac caa tgc agt acc cag acg gat<br>Phe Ala Met Asp Thr Glu Ala Lys Asp Gln Cys Ser Thr Gln Thr Asp<br>505                         510                     515                     520 | 1709 |
| ttc aat gag ctg gac ttg gag aca ctg gca ccc tat atc ccc atg gac<br>Phe Asn Glu Leu Asp Leu Glu Thr Leu Ala Pro Tyr Ile Pro Met Asp<br>                   525                     530                     535 | 1757 |
| ggg gaa gac ttc cag cta agc ccc atc tgc ccc gag gag cgg ctc ttg<br>Gly Glu Asp Phe Gln Leu Ser Pro Ile Cys Pro Glu Glu Arg Leu Leu<br>540                           545                     550 | 1805 |
| gcg gag aac cca cag tcc acc ccc cag cac tgc ttc agt gcc atg aca<br>Ala Glu Asn Pro Gln Ser Thr Pro Gln His Cys Phe Ser Ala Met Thr<br>    555                         560                       565 | 1853 |
| aac atc ttc cag cca ctg gcc cct gta gcc ccg cac agt ccc ttc ctc<br>Asn Ile Phe Gln Pro Leu Ala Pro Val Ala Pro His Ser Pro Phe Leu<br>570                           575                     580 | 1901 |
| ctg gac aag ttt cag cag cag ctg gag agc aag aag aca gag ccc gag<br>Leu Asp Lys Phe Gln Gln Gln Leu Glu Ser Lys Lys Thr Glu Pro Glu<br>585                         590                     595                     600 | 1949 |
| cac cgg ccc atg tcc tcc atc ttc ttt gat gcc gga agc aaa gca tcc<br>His Arg Pro Met Ser Ser Ile Phe Phe Asp Ala Gly Ser Lys Ala Ser<br>                   605                     610                     615 | 1997 |
| ctg cca ccg tgc tgt ggc cag gcc agc acc cct ctc tct tcc atg ggg<br>Leu Pro Pro Cys Cys Gly Gln Ala Ser Thr Pro Leu Ser Ser Met Gly<br>620                           625                     630 | 2045 |
| ggc aga tcc aat acc cag tgg ccc cca gat cca cca tta cat ttt ggg<br>Gly Arg Ser Asn Thr Gln Trp Pro Pro Asp Pro Pro Leu His Phe Gly<br>    635                         640                       645 | 2093 |
| ccc aca aag tgg gcc gtc ggg gat cag cgc aca gag ttc ttg gga gca<br>Pro Thr Lys Trp Ala Val Gly Asp Gln Arg Thr Glu Phe Leu Gly Ala<br>650                         655                     660 | 2141 |
| gcg ccg ttg ggg ccc cct gtc tct cca ccc cat gtc tcc acc ttc aag<br>Ala Pro Leu Gly Pro Pro Val Ser Pro Pro His Val Ser Thr Phe Lys<br>665                         670                     675                     680 | 2189 |
| aca agg tct gca aag ggt ttt ggg gct cga ggc cca gac gtg ctg agt<br>Thr Arg Ser Ala Lys Gly Phe Gly Ala Arg Gly Pro Asp Val Leu Ser<br>                   685                     690                     695 | 2237 |
| ccg gcc atg gta gcc ctc tcc aac aag ctg aag ctg aag cga cag ctg<br>Pro Ala Met Val Ala Leu Ser Asn Lys Leu Lys Leu Lys Arg Gln Leu<br>700                           705                     710 | 2285 |
| gag tat gaa gag caa gcc ttc cag gac ctg agc ggg ggg gac cca cct<br>Glu Tyr Glu Glu Gln Ala Phe Gln Asp Leu Ser Gly Gly Asp Pro Pro<br>    715                         720                     725 | 2333 |
| ggt ggc agc acc tca cat ttg atg tgg aaa cgg atg aag aac ctc agg<br>Gly Gly Ser Thr Ser His Leu Met Trp Lys Arg Met Lys Asn Leu Arg<br>730                           735                     740 | 2381 |
| ggt ggg agc tgc cct ttg atg ccg gac aag cca ctg agc gca aat gta<br>Gly Gly Ser Cys Pro Leu Met Pro Asp Lys Pro Leu Ser Ala Asn Val<br>745                         750                     755                     760 | 2429 |
| ccc aat gat aag ttc acc caa aac ccc atg agg ggc ctg ggc cat ccc<br>Pro Asn Asp Lys Phe Thr Gln Asn Pro Met Arg Gly Leu Gly His Pro<br>                   765                     770                     775 | 2477 |

-continued

| | | | | | | | | | | | | | | | | |
|---|---|---|---|---|---|---|---|---|---|---|---|---|---|---|---|---|
| ctg | aga | cat | ctg | ccg | ctg | cca | cag | cct | cca | tct | gcc | atc | agt | ccc | ggg | 2525 |
| Leu | Arg | His | Leu | Pro | Leu | Pro | Gln | Pro | Pro | Ser | Ala | Ile | Ser | Pro | Gly | |
| | | | 780 | | | | 785 | | | | | 790 | | | | |

| | | | | | | | | | | | | | | | | |
|---|---|---|---|---|---|---|---|---|---|---|---|---|---|---|---|---|
| gag | aac | agc | aag | agc | agg | ttc | ccc | cca | cag | tgc | tac | gcc | acc | cag | tac | 2573 |
| Glu | Asn | Ser | Lys | Ser | Arg | Phe | Pro | Pro | Gln | Cys | Tyr | Ala | Thr | Gln | Tyr | |
| | | | | 795 | | | | 800 | | | | | 805 | | | |

| | | | | | | | | | | | | | | | | |
|---|---|---|---|---|---|---|---|---|---|---|---|---|---|---|---|---|
| cag | gac | tac | agc | ctg | tcg | tca | gcc | cac | aag | gtg | tca | ggc | atg | gca | agc | 2621 |
| Gln | Asp | Tyr | Ser | Leu | Ser | Ser | Ala | His | Lys | Val | Ser | Gly | Met | Ala | Ser | |
| | 810 | | | | | 815 | | | | | 820 | | | | | |

| | | | | | | | | | | | | | | | | |
|---|---|---|---|---|---|---|---|---|---|---|---|---|---|---|---|---|
| cgg | ctg | ctc | ggg | ccc | tca | ttt | gag | tcc | tac | ctg | ctg | ccc | gaa | ctg | acc | 2669 |
| Arg | Leu | Leu | Gly | Pro | Ser | Phe | Glu | Ser | Tyr | Leu | Leu | Pro | Glu | Leu | Thr | |
| 825 | | | | | 830 | | | | | 835 | | | | | 840 | |

| | | | | | | | | | | | | | | | | |
|---|---|---|---|---|---|---|---|---|---|---|---|---|---|---|---|---|
| aga | tat | gac | tgt | gag | gtg | aac | gtg | ccc | gtg | ctg | gga | agc | tcc | acg | ctc | 2717 |
| Arg | Tyr | Asp | Cys | Glu | Val | Asn | Val | Pro | Val | Leu | Gly | Ser | Ser | Thr | Leu | |
| | | | | 845 | | | | | 850 | | | | | 855 | | |

| | | | | | | | | | | | | |
|---|---|---|---|---|---|---|---|---|---|---|---|---|
| ctg | caa | gga | ggg | gac | ctc | ctc | aga | gcc | ctg | gac | cag | gcc | acc | tga | 2762 |
| Leu | Gln | Gly | Gly | Asp | Leu | Leu | Arg | Ala | Leu | Asp | Gln | Ala | Thr | | |
| | | | 860 | | | | 865 | | | | | 870 | | | | gccaggcctt ctacctgggc agcacctctg ccgacgccgt cccaccagct tcaccc        2818

<210> SEQ ID NO 209
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 209
aagccttgga gggtttcatt g                                              21

<210> SEQ ID NO 210
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 210
tgctgatgtt ttctgacaga aagat                                          25

<210> SEQ ID NO 211
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 211
cgtggtgacc caagatggcg aca                                            23

<210> SEQ ID NO 212
<211> LENGTH: 3415
<212> TYPE: DNA
<213> ORGANISM: Mus musculus
<220> FEATURE:
<221> NAME/KEY: CDS
<222> LOCATION: (184)..(2808)
<220> FEATURE:
<221> NAME/KEY: misc_feature
<222> LOCATION: (1)..(3415)
<223> OTHER INFORMATION: n = a, c, g, or t
<300> PUBLICATION INFORMATION:
<301> AUTHORS: Compernolle et al.
<302> TITLE: Loss of HIF-2 Alpha And Inhibition of VEGF Impair Fetal
       Lung Maturation, Whereas Treatment With VEGF Prevents Fatal
       Respiratory Distress In Premature Mice

```
<303> JOURNAL: Nat. Med.
<304> VOLUME: 8
<305> ISSUE: 7
<306> PAGES: 702-710
<307> DATE: 2002
<308> DATABASE ACCESSION NUMBER: NM_010137.1
<309> DATABASE ENTRY DATE: 2003-04-07
<313> RELEVANT RESIDUES: (1)..(3415)

<400> SEQUENCE: 212
ctagccagcc ctctgcaaac ttccacctga ttgagcggga ctctcggacc tgcgagcact      60
aaagaccttt cacacctgcc cgggcgacag agagctgcgg agggccacag caaagagagc     120
ggctgcagcc cctacggggt taaggaaccc aggtgctccg ggtctcggag ggccacggcg     180 aca atg aca gct gac aag gag aaa aaa agg agc agc tca gag ctg agg       228
    Met Thr Ala Asp Lys Glu Lys Lys Arg Ser Ser Ser Glu Leu Arg
    1               5                  10                  15 aag gag aaa tcc cgt gat gcc gcg agg tgc cgg cgc agc aag gag acg       276
Lys Glu Lys Ser Arg Asp Ala Ala Arg Cys Arg Arg Ser Lys Glu Thr
                20                  25                  30 gag gtc ttc tat gag ttg gct cat gag ttg ccc ctg cct cac agt gtg       324
Glu Val Phe Tyr Glu Leu Ala His Glu Leu Pro Leu Pro His Ser Val
            35                  40                  45 agc tcc cac ctg gac aaa gcc tcc atc atg cgc ctg gcc atc agc ttc       372
Ser Ser His Leu Asp Lys Ala Ser Ile Met Arg Leu Ala Ile Ser Phe
        50                  55                  60 ctt cgg aca cat aag ctc ctg tcc tca gtc tgc tct gaa aat gaa tct       420
Leu Arg Thr His Lys Leu Leu Ser Ser Val Cys Ser Glu Asn Glu Ser
65                  70                  75 gaa gct gag gcc gac cag caa atg gat aac ttg tac ctg aaa gcc ttg       468
Glu Ala Glu Ala Asp Gln Gln Met Asp Asn Leu Tyr Leu Lys Ala Leu
 80                  85                  90                  95 gag ggt ttc att gct gtg gtg acc caa gac ggt gac atg atc ttt ctg       516
Glu Gly Phe Ile Ala Val Val Thr Gln Asp Gly Asp Met Ile Phe Leu
                100                 105                 110 tcg gaa aac atc agc aag ttc atg gga ctt acc cag gta gaa cta aca       564
Ser Glu Asn Ile Ser Lys Phe Met Gly Leu Thr Gln Val Glu Leu Thr
            115                 120                 125 gga cac agc atc ttt gac ttc act cat cct tgc gac cat gag gag atc       612
Gly His Ser Ile Phe Asp Phe Thr His Pro Cys Asp His Glu Glu Ile
        130                 135                 140 cgt gag aac ctg act ctc aaa aac ggc tct ggt ttt ggg aag aag agc       660
Arg Glu Asn Leu Thr Leu Lys Asn Gly Ser Gly Phe Gly Lys Lys Ser
145                 150                 155 aaa gac gtg tcc acc gag cgt gac ttc ttc atg agg atg aag tgc aca       708
Lys Asp Val Ser Thr Glu Arg Asp Phe Phe Met Arg Met Lys Cys Thr
160                 165                 170                 175 gtc acc aac aga ggc cgg act gtc aac ctc aag tcg gcc acc tgg aag       756
Val Thr Asn Arg Gly Arg Thr Val Asn Leu Lys Ser Ala Thr Trp Lys
                180                 185                 190 gtc ctg cac tgc acc ggg caa gtg aga gtc tac aac aac tgc ccc cct       804
Val Leu His Cys Thr Gly Gln Val Arg Val Tyr Asn Asn Cys Pro Pro
            195                 200                 205 cac agt agt ctc tgt ggc tcc aag gag ccc ctg ctg tcc tgc ctt atc       852
His Ser Ser Leu Cys Gly Ser Lys Glu Pro Leu Leu Ser Cys Leu Ile
        210                 215                 220 atc atg tgt gag cca atc cag cac cca tcc cac atg gac atc ccc ctg       900
Ile Met Cys Glu Pro Ile Gln His Pro Ser His Met Asp Ile Pro Leu
225                 230                 235 gac agc aag act ttc ctg agc cgc cac agc atg gac atg aag ttc acc       948
Asp Ser Lys Thr Phe Leu Ser Arg His Ser Met Asp Met Lys Phe Thr
240                 245                 250                 255
```

|                   |      |
|-------------------|------|
| tac tgt gac gac aga atc ttg gaa ctg att ggt tac cac ccc gag gag<br>Tyr Cys Asp Asp Arg Ile Leu Glu Leu Ile Gly Tyr His Pro Glu Glu<br>                260                 265                 270 | 996 |
| cta ctt gga cgc tct gcc tat gag ttc tac cat gcc ctg gat tcg gag<br>Leu Leu Gly Arg Ser Ala Tyr Glu Phe Tyr His Ala Leu Asp Ser Glu<br>            275                 280                 285 | 1044 |
| aac atg acc aaa agt cac cag aac ttg tgc acc aag ggg cag gtg gta<br>Asn Met Thr Lys Ser His Gln Asn Leu Cys Thr Lys Gly Gln Val Val<br>        290                 295                 300 | 1092 |
| tct ggc cag tac cgg atg cta gcc aaa cac gga gga tat gtg tgg ctg<br>Ser Gly Gln Tyr Arg Met Leu Ala Lys His Gly Gly Tyr Val Trp Leu<br>    305                 310                 315 | 1140 |
| gag acc cag ggg acg gtc atc tac aac ccc cgc aac ctg cag cct cag<br>Glu Thr Gln Gly Thr Val Ile Tyr Asn Pro Arg Asn Leu Gln Pro Gln<br>320                 325                 330                 335 | 1188 |
| tgt atc atg tgt gtc aac tat gtg ctg agt gag atc gag aag aac gac<br>Cys Ile Met Cys Val Asn Tyr Val Leu Ser Glu Ile Glu Lys Asn Asp<br>                340                 345                 350 | 1236 |
| gtg gtg ttc tcc atg gac cag acc gaa tcc ctg ttc aag cca cac ctg<br>Val Val Phe Ser Met Asp Gln Thr Glu Ser Leu Phe Lys Pro His Leu<br>            355                 360                 365 | 1284 |
| atg gcc atg aac agc atc ttt gac agc agt gac gat gtg gct gta act<br>Met Ala Met Asn Ser Ile Phe Asp Ser Ser Asp Asp Val Ala Val Thr<br>        370                 375                 380 | 1332 |
| gag aag agc aac tac ctg ttc acc aaa ctg aag gag gag ccc gag gag<br>Glu Lys Ser Asn Tyr Leu Phe Thr Lys Leu Lys Glu Glu Pro Glu Glu<br>    385                 390                 395 | 1380 |
| ctg gcc cag ttg gcc ccc acc cca gga gat gcc att att tct ctc gat<br>Leu Ala Gln Leu Ala Pro Thr Pro Gly Asp Ala Ile Ile Ser Leu Asp<br>400                 405                 410                 415 | 1428 |
| ttc gga agc cag aac ttc gat gaa ccc tca gcc tat ggc aag gcc atc<br>Phe Gly Ser Gln Asn Phe Asp Glu Pro Ser Ala Tyr Gly Lys Ala Ile<br>                420                 425                 430 | 1476 |
| ctt ccc ccg ggc cag cca tgg gcc gcg ggg ctg agg agc cac agt gcc<br>Leu Pro Pro Gly Gln Pro Trp Ala Ala Gly Leu Arg Ser His Ser Ala<br>            435                 440                 445 | 1524 |
| cag agc gag tcc ggg agc ctg cca gcc ttc act gtg ccc cag gca ggc<br>Gln Ser Glu Ser Gly Ser Leu Pro Ala Phe Thr Val Pro Gln Ala Gly<br>        450                 455                 460 | 1572 |
| acc cca ggg aac act aca ccc agt gct tca agc agc agt agc tgc tcc<br>Thr Pro Gly Asn Thr Thr Pro Ser Ala Ser Ser Ser Ser Cys Ser<br>    465                 470                 475 | 1620 |
| acg ccc agc agc cct gag gac tac tat tca tcc ttg gag aat ccc ttg<br>Thr Pro Ser Ser Pro Glu Asp Tyr Tyr Ser Ser Leu Glu Asn Pro Leu<br>480                 485                 490                 495 | 1668 |
| aag atc gaa gtg att gag aag ctt ttc gcc atg gac acg gag ccg agg<br>Lys Ile Glu Val Ile Glu Lys Leu Phe Ala Met Asp Thr Glu Pro Arg<br>                500                 505                 510 | 1716 |
| gac ccg ggc agt acc cag acg gac ttc agt gaa ctg gat ttg gag acc<br>Asp Pro Gly Ser Thr Gln Thr Asp Phe Ser Glu Leu Asp Leu Glu Thr<br>            515                 520                 525 | 1764 |
| ttg gca ccc tac atc cct atg gac ggc gag gac ttc cag ctg agc ccc<br>Leu Ala Pro Tyr Ile Pro Met Asp Gly Glu Asp Phe Gln Leu Ser Pro<br>        530                 535                 540 | 1812 |
| atc tgc cca gag gag ccg ctc atg cca gag agc ccc cag ccc acc ccc<br>Ile Cys Pro Glu Glu Pro Leu Met Pro Glu Ser Pro Gln Pro Thr Pro<br>    545                 550                 555 | 1860 |
| cag cac tgc ttc agt acc atg acc agc atc ttc cag ccg ctc acc ccg<br>Gln His Cys Phe Ser Thr Met Thr Ser Ile Phe Gln Pro Leu Thr Pro<br>560                 565                 570                 575 | 1908 |

```
ggg gcc acc cac ggc ccc ttc ttc ctc gat aag tac ccg cag cag ttg    1956
Gly Ala Thr His Gly Pro Phe Phe Leu Asp Lys Tyr Pro Gln Gln Leu
                580                 585                 590 gaa agc agg aag aca gag tct gag cac tgg ccc atg tct tcc atc ttc    2004
Glu Ser Arg Lys Thr Glu Ser Glu His Trp Pro Met Ser Ser Ile Phe
            595                 600                 605 ttt gat gct ggg agc aaa ggg tcc ctg tct cca tgc tgt ggc cag gcc    2052
Phe Asp Ala Gly Ser Lys Gly Ser Leu Ser Pro Cys Cys Gly Gln Ala
        610                 615                 620 agc acc cct ctc tct tct atg ggg ggc aga tcc aac acg cag tgg ccc    2100
Ser Thr Pro Leu Ser Ser Met Gly Gly Arg Ser Asn Thr Gln Trp Pro
    625                 630                 635 ccg gat cca cca tta cat ttc ggc cct act aag tgg cct gtg ggt gat    2148
Pro Asp Pro Pro Leu His Phe Gly Pro Thr Lys Trp Pro Val Gly Asp
640                 645                 650                 655 cag agt gct gaa tcc ctg gga gcc ctg ccg gtg ggg tca tcg cag ttg    2196
Gln Ser Ala Glu Ser Leu Gly Ala Leu Pro Val Gly Ser Ser Gln Leu
                660                 665                 670 gaa cct ccg agc gcc ccg cct cat gtc tcc atg ttc aag atg agg tct    2244
Glu Pro Pro Ser Ala Pro Pro His Val Ser Met Phe Lys Met Arg Ser
            675                 680                 685 gca aag gac ttc ggg gcc cga ggt cca tac atg atg agc cca gcc atg    2292
Ala Lys Asp Phe Gly Ala Arg Gly Pro Tyr Met Met Ser Pro Ala Met
        690                 695                 700 atc gcc ctg tcc aac aag ctg aag cta aag cgg cag ctg gag tat gag    2340
Ile Ala Leu Ser Asn Lys Leu Lys Leu Lys Arg Gln Leu Glu Tyr Glu
    705                 710                 715 gag caa gct ttc caa gaa aca agc ggg ggg gac ctt cca ggc acc agc    2388
Glu Gln Ala Phe Gln Glu Thr Ser Gly Gly Asp Leu Pro Gly Thr Ser
720                 725                 730                 735 agt tca cac ttg atg tgg aaa cgt atg aag agc ctc atg ggc ggg acc    2436
Ser Ser His Leu Met Trp Lys Arg Met Lys Ser Leu Met Gly Gly Thr
                740                 745                 750 tgt cct ttg atg cct gac aag acc atc agt ggg aac atg gcc ccg gat    2484
Cys Pro Leu Met Pro Asp Lys Thr Ile Ser Gly Asn Met Ala Pro Asp
            755                 760                 765 gaa ttc acc caa aaa tct atg aga ggc ttg ggc cag cca ttg aga cac    2532
Glu Phe Thr Gln Lys Ser Met Arg Gly Leu Gly Gln Pro Leu Arg His
        770                 775                 780 ttg cca ctt ccc cag cca cca ttt acc agg aac tca ggg gag aac gcc    2580
Leu Pro Leu Pro Gln Pro Pro Phe Thr Arg Asn Ser Gly Glu Asn Ala
    785                 790                 795 aag act ggg ttc ccg cca cag tgc tat gcc tcc cag ttc cag gac tac    2628
Lys Thr Gly Phe Pro Pro Gln Cys Tyr Ala Ser Gln Phe Gln Asp Tyr
800                 805                 810                 815 ggt cct cca gga gct caa aag gtg tca ggc gtg gcc agt cga ctg ctg    2676
Gly Pro Pro Gly Ala Gln Lys Val Ser Gly Val Ala Ser Arg Leu Leu
                820                 825                 830 ggg cca tcg ttc gag cct tac ctg ttg ccg gaa ctg acc aga tat gac    2724
Gly Pro Ser Phe Glu Pro Tyr Leu Leu Pro Glu Leu Thr Arg Tyr Asp
            835                 840                 845 tgt gag gtg aac gtg ccc gtg cct gga agc tcc aca ctc ctg cag ggg    2772
Cys Glu Val Asn Val Pro Val Pro Gly Ser Ser Thr Leu Leu Gln Gly
        850                 855                 860 aga gac ctt ctc aga gct ctg gac cag gcc acc tga gccagggcct         2818
Arg Asp Leu Leu Arg Ala Leu Asp Gln Ala Thr
    865                 870 ctggccgggc atgcccctgc ctgccccgcc gtcttgacct gccagcttca cttccatctg  2878
tgttgctatt aggtatctct aacaccagca cacttcttac gagatgtact caacctggcc  2938
```

-continued

```
tactggccag gtcaccaagc agtggcnttt ntctgacatg ctcactttat tatccatgtt    2998
ttaaaaatac atagttgttg tacntgctat gttttaccgt tgatgaaagt gttctgaaat    3058
tttataagat ttccccntcc ttccttccct tgaattactt ctaatttata ttccccaaag    3118 gttttttctct ctctcattca tatccatact aacaagcatg gtggctggtg cctctcccta   3178
ggaaagcttt ggcgtcattc aactcaagtg ttcttgttct tgttgccaaa gagaaaagga    3238
ttttcctcca ctgtggattt tccctctccc ccaccccac atacacacac acacacacac     3298
acacacccct acacacatat acacacatgc acgtatgcgt gcacacacac acacacacat    3358
atacacacac acacacacac acacacacac ccctacacac atatacacac atgcacc      3415
```

<210> SEQ ID NO 213
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 213
ggccatcgtt cgagcctta                                                   19

<210> SEQ ID NO 214
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 214
ggcacgggca cgttca                                                      16

<210> SEQ ID NO 215
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 215
ctgttgccgg aactgaccag atatgactg                                        29

<210> SEQ ID NO 216
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 216
ggcaaattca acggcacagt                                                  20

<210> SEQ ID NO 217
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 217
gggtctcgct cctggaagat                                                  20

<210> SEQ ID NO 218
<211> LENGTH: 27

```
<212> TYPE: DNA
<213> ORGANISM: Artificial Sequence
<220> FEATURE:
<223> OTHER INFORMATION: Oligonucleotide primer

<400> SEQUENCE: 218
aaggccgaga atgggaagct tgtcatc                                       27

<210> SEQ ID NO 219
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 219
gtcagctgtc attgtcgctg                                               20

<210> SEQ ID NO 220
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 220
ggcctggctc aggtggcctg                                               20

<210> SEQ ID NO 221
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 221
ggtcatgttc tcggagtcta                                               20

<210> SEQ ID NO 222
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 222
gtggagcagc tgctgctgct                                               20

<210> SEQ ID NO 223
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 223
ggtacatttg cgctcagtgg                                               20

<210> SEQ ID NO 224
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 224
tgggcctcga gccccaaaac                                               20
```

<210> SEQ ID NO 225
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 225
gaataggaag ttactcttct                                              20

<210> SEQ ID NO 226
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 226
tggaagtctt ccccgtccat                                              20

<210> SEQ ID NO 227
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 227
gcagctcctc agggtggtaa                                              20

<210> SEQ ID NO 228
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 228
catggtagaa ttcataggct                                              20

<210> SEQ ID NO 229
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 229
tcacttcaat cttcaggtcg                                              20

<210> SEQ ID NO 230
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 230
gagcttccca gcacgggcac                                              20

<210> SEQ ID NO 231
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 231
tgaaggcagg caggctccca                                         20

<210> SEQ ID NO 232
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 232
ggtgctggcc tggccacagc                                         20

<210> SEQ ID NO 233
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 233
cgaatctcct catggtcgca                                         20

<210> SEQ ID NO 234
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 234
tgctgttcat ggccatcagg                                         20

<210> SEQ ID NO 235
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 235
tactgcattg gtccttggcc                                         20

<210> SEQ ID NO 236
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 236
ctcccagcct cgctctgggt                                         20

<210> SEQ ID NO 237
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 237
aggagcgtgg agcttcccag                                         20

<210> SEQ ID NO 238
<211> LENGTH: 20

```
<212> TYPE: DNA
<213> ORGANISM: Artificial Sequence
<220> FEATURE:
<223> OTHER INFORMATION: Oligonucleotide primer

<400> SEQUENCE: 238
ctgtggacat gtctttgctt                                               20

<210> SEQ ID NO 239
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 239
agtgtctcca agtccagctc                                               20

<210> SEQ ID NO 240
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 240
ctattgtgag gagggcagtt                                               20

<210> SEQ ID NO 241
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 241
tcatagaaca cctccgtctc                                               20

<210> SEQ ID NO 242
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 242
aaatgtgagg tgctgccacc                                               20

<210> SEQ ID NO 243
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 243
ttgggcgtgg agcagctgct                                               20

<210> SEQ ID NO 244
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 244
gcgctgctcc caagaactct                                               20
```

<210> SEQ ID NO 245
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 245
gcagcaggta ggactcaaat                                               20

<210> SEQ ID NO 246
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 246
gtgctgccac caggtgggtc                                               20

<210> SEQ ID NO 247
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 247
tggtcatgtt ctcggagtct                                               20

<210> SEQ ID NO 248
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 248
tcagtctggt ccatggagaa                                               20

<210> SEQ ID NO 249
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 249
tctcacgaat ctcctcatgg                                               20

<210> SEQ ID NO 250
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 250
tcttcaggtc gttatccaaa                                               20

<210> SEQ ID NO 251
<211> LENGTH: 20
<212> TYPE: DNA
<213> ORGANISM: Artificial Sequence
<220> FEATURE:
<223> OTHER INFORMATION: Oligonucleotide primer -continued

<400> SEQUENCE: 251
aggtcccctc cttgcaggag                                               20

<210> SEQ ID NO 252
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 252
tgggccagct catagaacac                                               20

<210> SEQ ID NO 253
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 253
tcaaatgtga ggtgctgcca                                               20

<210> SEQ ID NO 254
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 254
catctgctgg tcagcttcgg                                               20

<210> SEQ ID NO 255
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 255
acagggattc agtctggtcc                                               20

<210> SEQ ID NO 256

<400> SEQUENCE: 256

000

<210> SEQ ID NO 257
<211> LENGTH: 78695
<212> TYPE: DNA
<213> ORGANISM: Mus musculus

<400> SEQUENCE: 257
aacaagtcgc agttctgcgg aaggaggagg aagggcaggc gggcgcccga ggagcgcagc     60
tccagagaaa ggggagggac ggggtcaggg cagaggctgt ggccgcgcct ccctattggc    120
cgggacacgg tgggaagtcg gggcaggcag ccagcgtgcg gggcggggct tctctggagc    180 cccgccccg gcccgccccc agcccgatgt cccactcccg cgcccctcgc gccctcccgc    240
gggcgggccg tccgagtttt taaagtgggc tgacagccga ggaggccgga cattcgagag    300
cggccggtgt acagctccgg agtccgcagc gctccgctcc agtctcctg aggcggccgt    360

-continued

```
acaatcctcg gcagtgtcct gagactgtat ggtcatctca gcggccgcac tcgcttgccc    420
ccggattttt ttccaacttg ctctcttcga gccattttt tttctttttt tcttttttctt    480 tttttcttt tctttttgg ttggttggtt ttgatttgtc agatcccaga aaagtgactc     540
ctgttcgggg ctaaacggaa ctccaggtcc cttgtcgctg ctctctctct cttttggcgt    600
cttacaacct cctcccactc ctttccccgg ccccgcctcc tcctgcaggt tcctccccgt    660
cacccccctc ctccctcctc ctcctccgca cctagccagc cctctgcaaa cttccacctg    720
attgagcggg actctcggac ctgcgagcac taaagacctt tcacacctgc ccgggcgaca    780
gagagctgcg gagggccaca gcaaagagag cggctcagc ccctacgggg ttaaggaacc     840
caggtgctcc gggtctcgga gggccacggc gacaatgaca gctgacaagg agaaaaaaag    900
gtaagcggga gtcaaagctg gcgaccgact tggtcccagg cattggcgga actgcgcgtg    960
gcgggcgcga cccggggcag tcgggagagg ggtgcgagag ttctcggagg ctggaggacc   1020
gctgttgagg ggcttttgagt aagcgagtcg gtgatgcctt tagggacaag gagctgcggt   1080
gtcgcagtag agttgcaaag cggatagttc cgagaccttg agacacggag agatggccct   1140
ggaggtcagg ggtgcttccg cggcgccttc caaagtctgt cgtccctgga gcaccaagct   1200
tccctagcga gtgttttgaa atgtttctgg gctgatgccc tcgactctta gggtttccat   1260
gctggagcag tagacacgcc tttcttttcc taagaccctc taggtctttc cgagagcgtt   1320
cctatgcggg ctttgcgccc caaactagca tggaacagag ggcaaagcgc aactctgggg   1380
tgcgccctga ccgagaagcc ggaacactgt caagggtcct gctccagacg gcacccaagt   1440
ttgttcaacc cccttaacct taccctacac ctagactccg gcagagagtg gggagtgagt   1500
gacctggatt gccctgcggg ggcaggtgct ctagtgtgca gagagaagac cgtgacaccc   1560
ggcggctccg agtgtctgat tcttaagacg aagggcagcc acgaaggttt gtcctcgcga   1620
acctttcggc actgggtgag aggcaactcg ggcaactcg cgctgccctc gagcctcctt    1680
caatccgccc cgcatctggt gacttgacac ccagctctag gagctgaggt gggaacacac   1740
tgtgaccccg ccgcagacct gggtacattc tcgtcgcctg caaaagttta tagctggccg   1800
cctggcactt tgctcctgtt tcgatcggtg cgtgccgtgg gttagagctt ccagcactgc   1860
gctccgtggc gacttagctg gggtgtccgg aatggtacgc gtgaccgcag aatggcgcga   1920
gctgccagag atccgtggcc agactggaaa agactggcgg tgaggaccca gccccgagca   1980
aacgggcttt tgtttgggc ttccacttag ggacatgagc caggaactgt gtatcctctg    2040
gtcgaaagct gcagctccca cctcagggca ccgataagga gttgataaac tccagcgaat   2100
cgcacccgtc ctggcccggc gcccgcgccc tgcgctggcg gatctctaga gggggaaggt   2160
attgagtccg gttctagatt ccccattatc gcccaccaaa caactctgag gttctgtgta   2220
ctttgagggt agagaaggag aagcaagaga gagagagaga aaaaaaaga ctaagattct    2280 agctcaaact gtaaaccag ccagagggta atcacaaacc atcaaaaccg cgaagttgga    2340
cagcagagta gccaggagca cttattgaac actttattac tgccttgtct atgggtgact   2400
gtcgcgtttg tccagagatga gacctgacag taatcagtgt caagtgtcat cttgctctta   2460
ggtctatcaa tccttgggag agtcagggat cagtggggaa agctatttcc atacccagct   2520
tgcagagact ctttgccgag ggctggcagg gagtatagtc agagcctaga gaacgttgc    2580 ataatgacac tacaaattat ccacaacagc ggccacttta agaaccagtg tgacacagac   2640
tgtgaacctc ctaggaatct tcggcctgta gtgcagtgcc ccagtggtag ccaggcccgc   2700
agggtgtgtg tgtgtgtgtg tgtccaaaaa acagggcaag cagtgtaggt tcagtgtagg   2760
```

```
ttcagacttc caaagcctgt taggatagtg gttttgagat tctggttaaa ttgactgact    2820
tcttgggggc atcaatatgt agttgaaaat tgtgaagcag ggcatcaaaa gttaatgtcc    2880
cttaaatggc tgcccagagc tttccagagc gcttcaggaa atcaatgtga gcagcaaggg    2940
ttcccggatt ggtgatacca cccactagtg gttcaagggc cggttcttct ccagggcata    3000
actgagcatt tgtatggttc cttctggaaa cagcccttcc agaggccaga aggcttgttt    3060
tagtcccaaa catccttgtg tgggtggata tattccttca tgatagtcag gagccagtct    3120
tttatttgtt ggctggttag cagactgggg gagccacagc aagctctctt ggagttctca    3180
tcaacccagc aggattcctg attctaggaa gagccaagtg tggatgctct caagtgggga    3240
tttgtagaac aattaagata aatggaagtg aggtctttgg gtggccagga atccaagtcc    3300
aggcacaaag ctagactctg gtccaagta cctttcagga gtgcttctgg tatttggtgc     3360
cagggcaaag atgggcaagg aattggagat agctggacct tcaagttttc taactgtggc    3420
tggcttctga tggcagcaga tttaattgtt cctctgttaa aataaaccca aggtccatca    3480
gttttcccag ccgaggagac aatgctggct gggcttcttg agtgaagctt atctcctaac    3540
tagtgttcct tcaacatttg acaacagtct aacctggtag agcagtgctg tacgacacta    3600
tcagcctggc atttaaactg tactaaagat gactttctta gagttttggt ttttttgttt    3660
tgttttgttt tttgggtttt tttttttttt tttggttttt tgttgttgtt ttggtttttt    3720
gttgttgttg ttttttttcag ttttattgtg aggcttgaag attattttat aagcaagtat   3780
gaaagccata acatattttt ctctttctgg ataaggctca aggaaggtaa ataatccct     3840 ctcggtacaa ggaaaattag tgctgataag aatcagaaag ttggttcatt acaatcagtt    3900
agcatgtgaa cagcagagcc tcccacccca tccccccac ccccccaccc cccccacccc    3960
cgccatggca tgcctcttgc cactgaggat ttccaaagga ttagtgcagc tcaccatcac    4020
catacctcca ccaccaccac caccagaccc ctgaaccttc aagacagagg tttactttcc    4080
tagataattg caagagcctt gttctgagct gaggcaggag agatgtcaac cagtcagtgg    4140
cgctgctctt ggtagttaaa aactttgggg aatcggaatc cattggttga gtaccttttcc   4200 tttatttcag ttaggggaaa acaaaaaaca aaaccaaac aaacaacaac aacaacaaaa    4260
gaccccaaca aaccctacta ctcgaggtat aaaataaaac caatgcaagc accctcctgg    4320
ttcctggatg tagcaagttg cttttgtgaag tagaggacat tccacagcta ctagattgtt    4380
gcctggtgtg attaggcaat tttgcaggga tgaaagcctg aactgaaaac aggctacttt    4440
gtttacgttg tcaacaaagc ctctctgctg ctgtttctct gcctctgtgc atgtgtgtgt    4500
ttacatggcc ctgcccaggg ttctaggaat ctatgttgtt tagagagaga aggaaccaag    4560
tagttaattc ctagtgctgt agggcttcag cccctgggt ttgaaagtgc ctccttcaag    4620
gctgagcctt ttccatcttt gaggaaatct tttctgtgca gcatttactt gctttaaaaa    4680
ctgcaacaac aaagcaaaaa cggtcctgtc ctatctcaag ataatagggt cctccttcgt    4740
tttatcttga tgaatctttc cttagtccta aggaaagttt tgtggtacac aaactaccga    4800 gcttttacc aagttactga gtaagttctg ttttctccca gggccttatt attcagctttc    4860 gcacactcca gaaacatgct ggtgagtctc acaatgacat ctataccaag atactaacca    4920
gtgggtctgg aaaaacagtg ctgaaaacta agaaatgggg catctgttca ttactcccaa    4980
ttgcttggtc tgatgggggt cagggtgggg ggacaggacc acccaagaaa ccgttggggt    5040
atcagccact catgggtgtt ttctttggta gggttcaaat atttgaagct aaagaaaaga    5100
aattctgaat ggtatttcag ttggtaaccg tacaccatta ttgaaatgca ttcgtcattg    5160
```

-continued

```
aggaagctgg ctctgtgtcc ctgagataat aaacggtaga tgctggacac cagcataaac    5220
tggatctcag agagagtgtg gtggtagacg ttagaacttg gagatgatga acataaaaat    5280
acggatgctc cacaggcgtt ctgcaccatg aactttgaca catggacaaa atgactacca    5340
gttggttggt tttttttttt ttttaaagat ttatttatta ttatacctaa gttcactgta    5400
gctgacttca gacacaccag aagagggtgt cagatctcat tatgggtggt tgtgagccac    5460
catgtggttg ctgggatttg aactcaggac cttcggaaga gcagtcagtg cccttttacct   5520
gcccagccat ctcaccagcc cggctaccga gtttaactgc ttgatgtaca cacttgtttt    5580
gggtggagaa tttgcaggga ggacacttac tggcctccac agtgacaacc aaaggtttct    5640
gtttccactg aggacaacgg tggccttgac tgactccgtg aaggccgaga agggagggga    5700
gtacttttcc gggagccttg taaatgagct tccggggtag taatagatct ctaaaattct    5760
atagagtgta tgttttgttc tctgggtttt tttttttta atgttaatct caatctcccc     5820
tcttcatgaa gagtgaaccc agagctttgc acgggctggg atagcattct ctaccactga    5880
gctggatcgc caccctttgt tcagctccta gtcgcctttc aaaggtggtg tgaagagaaa    5940
ataccttctt cctgcttgtc tgtctagcac ccaagagctc ccctccctga gttctaggct    6000
acaggctgcc tgttcctaca tttcaatgcc agcgtcttgt cttgtcctag ggagtgtcta    6060
taagacatgt tttccactat ccctgctat ctggagattc ttttgaacct tagaaatgga     6120
tgtgctcttg ggagaaatga gctacatagg cagaaggaca agatggaaag ctgagcgctc    6180
aatcttcccg tgccagcgct gtcctcagaa cttttccggat taactttgtt aatccttgta   6240
acaaccctgt gagataagcc ctgttattat ctccagttca ctgatgggaa ctcaggtgca    6300
gcaaggttgc tgcccgttgt cacaggcagt atatcttgga gctgagactc tccagagtcc    6360
acactctcac ccaccgttcc ttgcctcctg gccttaccta aaaggcctat aaagcattta    6420
ataccatgtc tgaatgtggt aagcactcta taaatgataa cttcttttgt tgctgtgttt    6480
ataattatta taatgactt tctcgtgact catcccttgt atcaaacctc acacacacag      6540
gcaggaactg aagacccaaa ggctattcct gaattcctgg aattacttat ttttttaat     6600
atatatatag atatttcctc agctaaagca ggggacagtt ctccactgcc cctggaagtt    6660
caaagctttc ttcccaccct ttgctggtgg caagacttca agaaccgttc agtcttcaga    6720
ctccattgtg cggagggacc tgttaggagc tcttcctctg tggctccttt gatcttttga    6780
aattgcaagc ataggaagga aaagatggat ggggggaggg gataaatagt agtttatgat    6840
tgtcgtgatc atattttat agagtccttt ctctggtgag caccccaggc catataccaa     6900
gagccttgag atcttcttga gtttcctcgc ctcaaaccat gattgctttg gaacagttgt    6960
gggttgtggt atgggtttgg ggtggggcgg ggtgggatgg ggtggggtag ggtgggtgg     7020
ggtggggtgg ggtggggcat gtatgaatat atgcagctag caacacacag ttttttcaagt   7080
agagtctatg tgcaattcac tgacattttt ctggtcctgt tactcaaaga cacagaacca    7140
atctgaacgt ccgagactga gagaaatgtg gaggttattt gagatcccca gaatcagaga    7200
taagcgtggc cgagaccaga gtgttatgtg cgtctgagtg gcctttcttt ccctaatagc    7260
tcaagaaata ctggtttgct tatggccttg ggctgtttcc agaggccacc agtacatcct    7320
ccaggctcct gggataaaga gtgttgcctg ccgagaagca caggattctt taagttagg     7380
agtggtctgt atgccagacc ctaggaagca gatactttct catacagaat gagatttcat    7440
gatgaatggc ttgttggtaa gtaaaacaaa cacatgaaaa cgtgtgtgtg tgtgtgtgtg    7500
tgtgtgtgtg tgtgtgtgtg tgatggctct gcacgtaaga gcatttgctg atcttataga    7560
```

```
agccctgagt ttgactccag cacccatgtg ctcataacta ccctcagta tagttcctag    7620 ggatctgaca cccagttccc acagccacgc agtcacatgt cacacactta aaataacac    7680 acacacacac acacacacac acacacatgt atgtatgtat atccgtgtat acatctgaca    7740
tgttttaatt ccacaacatc atggaaatag acctttagaa ttttcctata tcccccccag    7800
tggctcacta cattcaccat tctagtggca acttccgatg tcataggtaa gaatcagatg    7860
attcatgttt ttcatctggt tagactatgt acccaaacat gtatacacat acacacacac    7920
acacacacac acacacacac acacacggat ctactgtgct gccctattga ccatgatagt    7980
ctagagactg acccatgctg ttatattggc tacccccccc ccctaaatgg caggctacag    8040
ccactggcaa ttttagatgt taatgagtag tgttagtggc ctcttttggt ctgcccttgg    8100
tttgaagtgc acagttagtt ggcctcttaa ctggaaagtc agtagtttgc taagaataag    8160
aggatacata ggctccatct aagaaagtta cgaatgcttt ataaatcatt taaaatacac    8220
cagctacagt atatggtttg gaactggcaa taatttaaag cactatgttg tgtgtctagc    8280
catgaagggt tctgtgtctt tggatggcat atcactgtta acaaacacac atgttactca    8340
taattgaaag cgctcagcct cttgtcacca tgtaaggttt gtcctgacct gcctgcctcc    8400
tggaggggcg ggaactggag gggctaaaga accaaacctc ttcatctgaa gccaaaccta    8460
ggcgtggaga ggctgggccc agaacaccat cttgggctcc tggtcttgtg ttgtgttgta    8520
ggaaggggcc atagccagga acctaaagga gcaacttagc tgcagcacta accccgctca    8580
ttactaatga gtaattacag caaatattta caggtctcct tcctaccttt atgacttcct    8640
gttgctgaag cactttggag tgttgagaaa gattgttctg gaacatacgt catacatggt    8700
tgtaggaaaa gagtgcctct aagcgcacac acacacacac acacacacac acacacgctt    8760
ggttttgttt atgaattcca tgtgggaata acaaaattac accttctaga agctgagaat    8820
tttacttttc aaaacaaggt ttaaaaatca attctcaact gctggtttta aagcaccaat    8880
aaggctattc atgttcataa agtaaaactt gaggttaaat cataggcatt gcctaaatac    8940
tttttaaagc actacaatgt tttatgaaac tgtgacccct cacagtgcct tctgagtgaa    9000
aacagaaaaa cctagtagaa taaatcaagg tctataaaac aagccatgtg ggcaattctc    9060
tgagttccag aagccctggt aatgtattta gggtttgttg ttgttgttgt tgtttgtttg    9120
tttgtttgtt tgttttttaa aatcggtcca gtgagtggct ttctcagtct gctcctgtga    9180
gccactgtgc cctgtgtttc tctctggtgt gtccagcagt tcccaggtgc tatttagaa    9240 tggcagcctt cgctccagcg ctggctgagg ttgatggagc taattttggt gtctagggta    9300
aagggagcga gaaagcctgt gcaggagtca aaaaggcttt cttgtcccgg gctgagagca    9360
gcgtggtgtt accagacaca ctacatttca cctttagaac ctttgtttgt gtacttgcac    9420
aacaaatgtt tacctagata ttaagataaa ggaaatatga aggtcccatt tcactggtga    9480
caagggagcg tctataattg taactgtatc accgtgtagc aagcaggagt cccttttact    9540
ctatagccag gtcttaaggg aattaatggt gggtgtggtg tacaagccaa ggcccttctc    9600
agtttctgtt tctggctttta ttgctgctac tatgttttct tggctcagcc aatgttttgc    9660
cccacccatt tggtgaaggc ctttgtggtg gtcaaggatt cagagggaat tctaaagcac    9720
tctgtggccc cactctggag tcatccgctg ttctatggaa accagttagc agaccctggc    9780
accatcactc ttttcctagg ctctcagaaa acgtttacat ggtaccaata cgaccttgtt    9840
tcaggccttc acgttgtctt ggaagcacag caaattttcc ttgtggcaag agggttccat    9900
gaggacttgg gggtttcttt gaagatcccc caaggattag ctaaatactc agtctgaaga    9960
```

```
tctaagaacc tcactcaagg gccttcccat agggaagcta cgaagcaggt gactgctgga    10020
aatgagggtc cccacactcc agctctctca tctgccccac tcagtcactt acggcacctc    10080
ctgagctccc cacaagccta ttcctctgcc acacaggtat tgtcacagta ctcgttcgtc    10140
tctggttctt agtccatgct tgaatgcttt ttccctcttt ctgcccaaat atctcacact    10200
ttgtcttatc atgaatgagc ctaagctctc tgcctttaac agaaacccat agcattccca    10260
ccctgccttt ccctccattt gctgttttat acttctttgt tgtctaaaga cattttattt    10320
gttcttgcct ttccacgttc gttcttgcac atggcacaag agcagggatg tctgattttc    10380
tgatgtggcc aataaatgct gatccttttc attttctct gaaatcatgg ccattagaaa     10440
aataaataca gaatgacttt ggttttttgt tttgttttgt ttttcgaga cagggtttct     10500 ctgtatagcc cctggctgtc ctggaactca ctctgtagac caggctggcc tcgaactcag    10560
aaatctgcct gcctctgcct cccgagtgct gggattaaag gcgtgtgcca ccactgcccg    10620
gcttcgaatg actttgttga tgtcccactt tctcgggctc agctgtctcc atccacacga    10680
cttcccttca cctgtttctg tgaacaagaa aataattggg gttgggggag gggcaaggca    10740
cgggccaggt gagcattatt tgccatcaga tgcaaggatc aggcaggtag tatgccaatg    10800
ctgttgtgca tcaagaatgc atggtagtct aggtaaactc cccagcttaa ctccggagtt    10860
aacagctttc caggtgggaa attatgcaaa tgcatccgta tcagctgtcc caaagggtct    10920
ccctggaaag cagacctcct tcagtcagca gggcattgtg tagccctgta tccatctgat    10980
cttctgtctg aattttaaa tttgcataat aagtttaaag cttgctttct atttccattt      11040
taggtgttct gtagttgtct gtaggtggaa ttcaggaata tggggacctt agttcaaagg    11100
gatggaaacc acaggcagaa acactgcctc agatcagctt acccatcctt atttgataat    11160
caccacgcag gtcagaagag gtttgtggta ctgctggcct cgagtataca tgcttacagg    11220
ttatttgctg atttggggac tgtgctgcac agagagatca caccaaggca tttgatgact    11280
ctggtctctt caaatgactc gtttaaacca gtatgtggca gtgtgtggca ccaaggcacc    11340
tggctgcatc tttaggatgt tgccatcttg gtgtggagta aaaactaggc cagatacagc    11400
acagagccag gagcagaaaa tggataggaa tcgagagctc tgagttgtat aaagttaaaa    11460
aggactgggc tggagaagac cagagctttg agagaagagc attaaataag acttcggtct    11520
tgaagattag aatttgggtt tgcacaggca gcaactgcag gctacgctgg ggatgggcga    11580
ggcagtgcag accgcgagac ggaaagaagc agagtgcgca ggacagggct tgggggtgc      11640 tcctttcttt caactcggaa tcagtagatc ttatattagc agagatggag cctgggcctg    11700
gactggagaa tctagggaca ggccctcttc gagcatgttt gatggaattc tcagcctgcc    11760 tttttttggag acattagaag ctatttagag caatttatt gtccttctcc cacaaactta     11820
gctagagtgt gcacacctag gagtgattgg cagaagccat gatggcctcc aaaacaatga    11880
cctcaaagcg ctgaacccat agatcttagg aaacccactg tcattccgtc aggtatgtat    11940
ttctttgtgg cttgcatagc tgcttgggag tgataaatac tagagttcta tcagaatggg    12000
aacctgaagg gggacggctt gctgttaccc taaaattgcc ttgcccttca ttcccatgtt    12060
ctcactagga ggccaaagcc tttgtcccct tggggacttg gtaaggtcat tgtcatatc     12120 ctttcttgcc atttctcctt agagaaggat aaggcttctt tcggcaccta gcacgtggag    12180
ggagttacac agccaaggct gagtcaaatc tttagtctct actggtagct cttcatccaa    12240
acccagccca gagcactccg gccaagccgt tctgtgacct tctctttaag acccagatct    12300
ggttgatgtt ctgagtctga ccatgccaga agagtggggg aaaaaaagaa tcctctttcg    12360
```

```
gagtcacctg ggtaggacag tcagagccct ttcctctcca caagcaggtg tgaccttttc    12420
cctggaggaa tttagaagca ctaaggtcac agttggtcaa agtgggccag agttggtca     12480 aagatcccaa atccctggac aagagcccac atcagggaca gcagaggcca gcaactgatc    12540
ctagttacat gagtttaccc tgcccagtgg tacttcaagg gagggaacgg ctcctagatg    12600
gttttgtgtt aaactttaac ctcacaatga caactgtcat gtctcaactg ttagttctgt    12660
cccctgtggt tgtaggacgg aggaaccact gctcagttct ggcaggctgg ttaggccagt    12720
ggtttgctca ggttaaagcc tgagcccaga aagagtctt ctggagccaa ggagccgtaa     12780
tcgcctgcca gaaccacata gggacagggg acagtggagc tttgcagcac agtacagact    12840
ggcccttatc caggagctaa ctgagacctc gggccatccc ttctggaagc ctcagggaag    12900
ctctaagaaa agccagaaac caagaccaga cctgaccaca catactcaga tctctccaca    12960
ttataaatgc gagtgtagca tctacattcc gatagcttct tacaggggtc aggaagggaa    13020
aaggaagatg tcttagccaa gtttgcctgt gactaaacac cagatagcta gctccatgtc    13080
tatgtatctg tgttttcttt cctaagtgtg tttcttaagg tttaaaaaga tgcatgtgta    13140
tgcccgggtg tttgtatgtg taacacatgt ctcaggtacc tgcagagacc agaagagggc    13200
gctggatctc ctgaagctgg aattacaagt ggttgtgagc catggatcat gggtacttgg    13260
aactgggcct gggccctctg tgctcttagc tgctaagcta tctacccac cagcgtctgt      13320 gttcatgttc ttttccaaag taaaaggtcc ttaaaaaaac aacaaacgag caaacaaaca    13380
aacaaacaag caagccttg cttctcctga actcatagca ggttcttcct ggccttggtc      13440 agtgagggc taggcccggg catagctcaa gccagtgtgg ttctcatgtt ctctagctca      13500
ttccaggcta tggggagatc cagaggacta gcgcgctcct agtgagtgca ctctccatcc    13560
tgagccatct ctcaagcaca ttagattctt ttctctaaat cagtgggtgc attttagttc    13620
tggccacctg tagttgcttg tgtggggaca agggtggtga catcacctta attttcctgg    13680
ccttgggtcc ccggagccct tgtttatttc ggggagtgac aagctttcac ccacttgaat    13740
tccttcgcct ccaaatagcg tcagaatgac cacaagcctc ctgtgtttct tcgctttctc    13800
gggttttgcc agattctaaa tgccgtcagg gccactggct cttgttttat gtccctggca    13860
aagctggcct tcccatgaag ttcaaagccg cttttcaggca tcttgggagt ctgggagact    13920
gctttcgctt gctctctgct ttgtgcggac ctaggttgga gatgtcacct ctgtctgctg    13980
ctctctgaat acgaaccagg gaatgttcta gtaataccac gtgctttaaa tgtatatttt    14040
aaaagcacac tttgtgagta ttatcttaat ggaaagaact ttgaaaagta taagtgcaa     14100 accttctagg cattgtcatt aaggagcaga gcaatatact cattaggtgt gttattacct    14160
cttaaaagtg aaccgcctgc agacaggagg aagccttgag agaggctaac aggagactct    14220
ggtctccagg ctcctaccgg tgggtccctc cgcctgggct tttgggtcct gtggattctt    14280
gccaatcgtg gcatttagtg gatacccaa gactgaggaa atctgaagaa agtcctgaca     14340
agcaccagat cccaacaccc ttctgcttgc tttgtttccc ctcacctgtg aagcaggaga    14400
gggcacagcc cagcactcac gtcaaggacg acacatcctt ccgtgtcgca caggaaccag    14460
ggctgcccag gccatagctg ctcgcctctt cctcgttcca ctattttatg ccaaagagag    14520
gcattgacaa cctagaaaca ggtgctactc taaagagacc ttggtctcct tgaatgcaga    14580
ggcctggctg tgcttatacc ctaaccagga gacttgaccg gtcactcagc tctggcctca    14640
gacctatcat caactgtaac acatctggac ttcttacctc tgagctctct cttccctcag    14700
ccccacccgg gagactggcc agctgacttc aagcggtcct tctcagctta aatatcacct    14760
```

```
cctcagggaa gcctttctcg acgtccttcc attgacctct aatcctgttc catttgtctt   14820
ctaaacattt tccacgtgta atttacatgt ttacttatgt ctaccatgcc cctcccctgc   14880
cagggtgaaa ctgaaggtat ggactccaca cgtgccttgt ttaccactga gggctcagcc   14940
tttagaatgg agcctgcatg cactgctgct ttttacagat gcgttcagcg aactcgttgc   15000
tccgatattg ctgggctcta cattaccacg gtttacaatt gtccagtgtt ttcctaaagc   15060
tgattttgtt tttgttttct gaggtagggt cccaggggct aggatttaca tgaatgcccc   15120
catacttgtt ctttccaaag ctcttggtgc taacaccaag gaattgtcac tttttagcat   15180
atggatgagg cagttgagac actagagtat aatgaccatg ccagggtctg gcagtaccta   15240
cctgaacacg ttcccagccc cagactattt gcaaagatcc acgctgcctc tcttggcccc   15300
atagttttct gttgtggcga tgttattgtt tgtcatattt ggcaatgttt accccagaga   15360
agtagggcca ttgtgtgctg gtagcgtctg ggaatgcaca gccaagtccc aggggaatgg   15420
ccactgctgt tcttaccaca attagaaatt gtcaagccag gagcagaagc agggtgggtg   15480
ctgccataca ctgctggttc tgcctctcca tggggctggg gtgagggtcc tagctccgca   15540
gccccgtgtg tctccttgtc ctggctctcc cactcacatc gaagtgtgga ccttctcctg   15600
cagggcgatg tgctatgctt agtgaatttc ctgagaagag gtaggcatta gctggctaga   15660
tgaccacctc tggcctcaat tattcaatta ttctaccctc tccaaaatga accagtagat   15720
gggaaccaga ccaggtaacc ccaaaactct ccaggttcta gctccgctct gaagggaatt   15780
tccagggggtc tggcctcctg tttgcagatg ctgactctgg aaagagcagg ggaagttgga   15840
ggttgttggc aggggctggc ggacctcttt ccatctcttt gtaactcttc ctctccaaaa   15900
agatattcca tcccatcagg agttgctgtt gggcctggtt cagtgcagca ggatgaacaa   15960
ccgcccccaa aagtcagctg aggtctgata tgtgatatgg tagaaagctc ccaaaaggag   16020
gccatgcctc catctccctg atgcaggctt ctggggtgtt ctgatgccat taacggacag   16080
gggtcagaca ccaagtgcct ctgtctaggc cttcgttttc atgtctggca ggtgactgtt   16140
ctgtgccctt caattgaaca aggctgcaca gatgtaaact gccacagagg aagggcacat   16200
tgctgctatg attcctgtgt acgaatgttt ctggcgtgct cacacctggt agtgacatga   16260
actgattgac acttgcagcc tgcaaatacg gtcctgcaac ctgaggcacc aagggagaag   16320
tcagctagga agcccgtgag gccttaagtt gttgaatgaa gtcatgctgc acagggtggg   16380
gggtgggggt gaccgtgctg caggatagag gtgagtcaca gtgcaagact gttggggagt   16440
caccttgaat ctgagccaaa aaagcagaaa tattgggact cgtttatcag ccttctatca   16500
ggtacatcaa gttctggatg ccacccact ggccagcgac atgatgtgga cggctctgct   16560
ctaccgccct gggaaggctc tctgctggct cttgccccgc tgagcaaagt ccgcttgttc   16620
gctggagttc acacagactc cttgccaggc ctgcccagaa tcctgtctcc tctgacttcc   16680
tgtgttcttg cataatattt ccttgcctct tgaatggctg gccccagtgc gggggcagct   16740
cactggctct gctggattga gagtaggatg tggagggagg atgggtgata tttggatcta   16800
atccgtgggt gctccgcgtc ctggtggcag agccctcaa acttttttgat ggaagctttc   16860
agccagaagg gagtgagaga gcattgcaga ctgtatacac acactcgctc gtgcacatgc   16920
tccctggctt cttatattca tgaatcatct ccctgggaaa attgttgaag tagttcaatt   16980
gttttcttct ggtcataaaa atatgaatta ttcccatata gtcactgtat aagaagccta   17040
aaagtaaaat aaatatatat atatatataa ataaaaaaca aaaaaatgta ttattgaaag   17100
ataagttcca ttaacagtga atatagtttc tcctacgtca gaaaggctga tcccatggc   17160
```

```
tatgggatac cagcaatatt agctgtatta agttctgctt actgatgcat cttcatgaga   17220
ctcccattca ctaccgtcc aggctcaaaa agcaagtggt aactggccca acaattattt    17280
ccaaacctga aaagcaatgt ctcccctgaa gttctgacca gtatgctctg gagtcccaga   17340
aataactgca aaatcaaagg ctggtgcctg tgtgagcctt tctgtaggct tagagtaatt   17400
cccatgatta cacaggagaa ggctgcttcg atgacagctc tgagggctgg gcctggtctc   17460
actttgggga aaaaaaactc catctatcca cagggccgtg tgtgagttaa gccaggagcc   17520
cactggctgg cagagcaagt ttaactttgg cttttccagtg ctcaagattt cagggaggct   17580
ctatttaaat tttacttggc tgtcacccct ctgaaaattt gtagcactat ccgtatcttt   17640
aaggaagtga cctttccccg tccttgtcct tgttagcatg acatgagaac ttggaagcgt   17700
ccatggtgac ctgcttccag tttgattatt gaaaacaaaa caaaaccatg catagatccg   17760
gggtttctga cttacctctg gaaactgtac tttctacagg gtggccatga gagtttgcag   17820
gccacctgct aaaagttgac aacctgagag tctgcagtag acaacacaca cagcatgctt   17880
ctgtgttgga tctgagtgtc tcctgcatct gtctgttttc tttgcttctc ctttaaactg   17940
ggttaaccat cctccatatt ggtactgggg atagatagca cccagggcct cacagattgc   18000
tagaaaagtg ctctaccaat gagcaacgtc ctctgctcaa tgagtgtgtg tgtgtgtgtg   18060
tgtgtgtgtg tgtgtgtgtg tgtgtgtgta aatatcagaa acttggttaa ataaatatat   18120
gtaacataca atatacttat ataatatatg tgtatatatt atatatctcc atcccaaagt   18180
tctctgtttg agactggact taatacttcc cgttgggaat tgcttataag gttttacttt   18240
ttagtaaaga aaagttgttt gtttcctaaa ctctctggct taaacttttt acttaagtca   18300
aaaagcaaga gaatacctct cggcttgaat acctttattt ttaaagctca agagtctttt   18360
ttaaaacaaa aacttgctac agaacttggc accagggggac tgcaaggatt taccttattt   18420
tgatgatagc tgcctgcaaa cgatctatta gaataatctg cataattgca gtctcccctt   18480
cagtttattc agcctgcact ccctagtcta gatttactgg ccagactgtt attacatcaa   18540
attccttgat gctgtattcc tgaggactga tggaactaag agttacagag aggaatcagc   18600
gacctttgtc tgcttttcag aattcttcag aacatactga tttagccagg ggcttttgcg   18660
attgctctcc ttactgggtc agtacctgat tttgctgggt ttctggccac acatgtgcgt   18720 tgggaagca ggatagatag ggcgagaaac ctgaattggc agtcagagtt atgaaacagg    18780
actttgttac aattgatagg tctgtacagt ggacgcacag cagctgttgg catggtaact   18840
cctacgtggc agagtgcatg gagcccgcag atgactttag cagcgctccg tgttaatttg   18900
ataaatggct tttttaatag tagtttgtgg gctaatggaa agattgaagc gaaccctcgt   18960
taatggaagg gaggatggag attttgaagc cactgggtga agtcggagag tcccagccaa   19020
gtctccattt tcagctcagt gtctcttttc atgtgcctga agtgtggcaa accaaagtac   19080
agtagggagc ctgccttgag agtaggcatc ggccctgggc tccggcttac gagtgaagag   19140
gcttcagggt ccttattcaa tacagttgct ttgtgcaggg gcttagctta gggccactgt   19200
aagaagtcta cattgtgttt tcttttcct tagtggtaat ggggcagggg ttatggtggc    19260
cgacaggtct ggcatattta gccgtttggt tggttgtatt gtggttattt gggttctcag   19320
aggggttgtt tattttgtc tctggttgt ttgttgacat agggtctcgt aacccaggct     19380
ggcctcagat gccctacata tatatatctc tgaggatgac cctggacctc tgatccttct   19440
actgccagct ccagggtgct ggggtcatag gcgtgaacca ccttgcctag ctaatgtggt   19500
atcggggatt gaacacagag cttctgcctg ctagatgaca ctctatcaat taacggcatc   19560
```

```
tcctcctggt tcggccatc tttcattgtg tgagaataca taatcacacc acactgctgg    19620
cccactcaag gagcctctct gcaacccaca ctgaagctct gcgttcctta tatagcgctc    19680
gacaaacacc tctgggggat ggatctcctc actgtgttgc caaagcaaaa cctggggttt    19740
tttgcctttc tggcaagttc ccaggagacg cggacattac cggttctcag tccacatgct    19800
gagaacttgg tgctttacac taatgcggag aaaattggga acaagacata aagaggccaa    19860
atgacttgca ccttaatggc taaggatgat ggagcttgaa cttgaacgtg ctagggcct     19920
ctaaggcacc tgctgtctct gtcttatcag caatggcaga agtgcagtgg ctggagcatc    19980
ccaagggtac cttctgccat cccaagggta cacggtgtat taatctgtca cagtcaagtt    20040
cagaggtggc ctcggaagcc tgctgctcac agccttctct gcgtgcgcat tggagttggt    20100
tttcccctgg gctaacctac aatggagaca gtaccaacaa acccaccaat gcagctgaaa    20160
caaaacaaga ctttatccgg gcattagtct aggccgccta ggagagaagt ggtttgtggc    20220
ttagatttgt aagggacgtg gcatctccag ttgttctagg ccagaacaga tcatcacagc    20280
tggagtcttt gttcagatct caggcaaccc agggtacttg agaagtttaa gacagatagc    20340
attactagag aggtttgttt ggttggcttg cttttacat tttcatactt tttctcctta    20400
actcatactc caaacattcc attacatggc gctaggtgta gtgacggata ttaagatggt    20460
ggccagtgaa tacttgctaa gaaaagtagg ccaaaggcat ctgtgtccaa atatgctgaa    20520
ccgctcagcc caagagcggg agggatgatc aagacagaag gacaggtaac acctgggatt    20580
cacacaacac attggctctt aaagtcacat tttcaatgtc cttaaaaaac aaaatgcaca    20640
gacacagaca caattaaaat aagtcttaaa agaaaaaatt taaaaatgca aaaattatag    20700
tggctactgc tactgttctg tccccaggat gtcttccaca aagagggaat ggaagccaaa    20760
gcagggtttt gtgtgcgtcc ggagcctcct gaccaatagc tgtgattctt ctggctttag    20820
aaataaccca atgccatctc tccagtggct ttgccaaccc acatgatacc tatttctcat    20880
tacccccaat aacgaatatt tagtctgtga ctgttgtgta tacagggtga tctcgtctca    20940
ataactattt ataagcaact taaaagcaag ggtgggatta ggaggtatat atagctcgat    21000
ggtaaagtgt tctttagcat acccaaggcc ctgagtttga tccttagcat aggatcagag    21060
tgaaaggggc aagggcaagc aagatgtttg tggtggtgga ggtggtggtg gtggtagtgt    21120
gtgttactgt gtgttactgt gtgtgtgtgt ttctctctct ccatcatgtg tataatatgg    21180
catgtgtata gtaaatatta catgtaaata ttcaccatat taaaagctat ctgtaaatgc    21240
aaatttaatt tgtgaagaga taaagcttcc aggtccattg aagaggagag gtggctctaa    21300
ataggctgtt gcagacaaaa cagacaccgt caggagcaca gatgctctac tttggctgtg    21360
acacaccctg tggcagagaa gactggggtg agaatgaaaa atggacatcc ttgggcaact    21420
cccagatgcc atgggttttc cacatcacat ttgatcttat aggtaaaatt gtctttaatg    21480
ctggggatcc agtgcaaggc ctcacatata gtaagcaagg cttcttccac tgaccacatc    21540
catgacactc gctttttttg tttgtttgtt ttgttttgtt tttcaagaca gggtttctct    21600
gtgtagccct ggctgtcctg gaacacactt tgtagaccag cctggcctcg aactcagaaa    21660
tccgcctgcc tctgcctcct gagtgctggg attaaaggtg tgcgccacca caactggcga    21720
cactagcttt taaagtcata ttctaaaaac tactacataa gtgggtatct gcgcacagct    21780
tgtaacagac ttcacaagag gggcagagtc cgtgattcgg agttgttttg ttaaatgtca    21840
agaatacaga aacatagaac tggttaatat ttctgctttc gatgcaaatg ggttaggtta    21900
gagccaggct catggccttc cccggtctta ctctgcctca tgtagcttgg ctacaggcct    21960
```

```
tgggcatagt gttggattaa gcagagaggg tccctaatag gtatgttcag gaaataggta    22020
tgttaaataa aggaaatggg gtttggggtg ggctgaactt tcctgaagga gcaggaagat    22080
tttctctagt cagatctttg taagagcctc cttcttactt acaattaacc ccccccccac    22140
acacacacac catggaagat gtcctgacac cctatggact cagggttcac tgcttagggc    22200
tctctgttct atatgcttaa gtcaggatct tagagataag ggttgtggaa accaattcct    22260
gagttacatc acaatactaa tatcctttgg aagtttttag gtcattacct taggaaggga    22320
agctattttg ctattcattg gagatgggag gaggaacata aagcaaaaat tctgctgat     22380 gtgggtgttt gcttggggcc aaggtactgg gaggggcacc aagggtgtgc ttcctttatg    22440
tttgtaaaag ccctactagc ctctgtttaa gacggtcctg taggtaggtg caggagggca    22500
tgaatcattt tgtgctgcct tcctcttggt tcagcagagc ccagcaagtc agatgggtag    22560
aggtgaccta tctggcctgg tcaggctttc cattggtcag cagcaaaact gtgctctggg    22620
cactgatgat gccaggcccg tgctggggcc catgctggag gatgaggtcc acaagccagt    22680
tcctctgtac ctccaaggct tacaaaaccc cagccactgg gctgtgcaat ctcacttcaa    22740
atgagtgtta tgtccaccca tggccgtcac acatgagcat ttcagtggaa agagactgaa    22800
attctattgc catggacttt cagaactcat gctcgatgga gatagaaccc accagtgtat    22860
taggttcttg aaagctacct cctgcgcatc atttaaatcc taaaaagata atttccaatg    22920
aagagaaact gattattttt tgctagggac aggttggctt aaggtgggtg ctattcgaga    22980
tgtctgagac ctgagggatg accaggatga aaggaaatg gtcctacact gggctaggtc     23040
ctccaggcaa ccccctaca gagagcagtc tcctgcccgg ggtggatttg ggaccttctg     23100
aaatctttgt ggtccaccag tagggaatca acttcttact acggagagca gctggagacg    23160
taagcataac gcctttccat tgtcccggcg tgtattctca agtgggtccc ggcttcctgg    23220
aacggcttcc cttgagtgtg agggctgaga tgagtctgcc gggtgatgaa tgggttcagg    23280
aaggagtggc tgcatcacct gcctggggga tgagcaccca cgtgacttca tggttgtgca    23340
agaattgggc aacgtttggc cagggtggag aggtcttggc aaaggcagtt tcactcctaa    23400
cagattccta tctcctccat gggggaaaaa caactatcag gagatccatc tgtacagcat    23460
tggaggacgt tgatcgcttc ttcagctgtc tgtggccttt tatttgctaa gaactcatgg    23520
attgaagacc tcagaagatt aaggaagata ggcatcccct tccttcctgt ggcagctctg    23580
gagaagggga gggtgggtaa aaggaagaca aggtgggagg ccatcaatgg caggacgggg    23640
agaaatggtt ttagagcgtc tgcagagtag tcgcagagca gagtggtagg cttgcaggtt    23700
caagttgtgg atctacctct tagctgaggt atcttgataa agtactttaa accctctgta    23760
cctatgtgtt taaagtacaa gatggaaatc attgtagtat tgaatcagag ggtagggctt    23820
agtcatcatg aaggttggtc ctagttccaa gacactagac acaagtggaa gggctgaact    23880
aaacttgggt ttttgactta ccactcttca ggtctcaatt tcttcatctg tacagtaaag    23940
agactagagc agattaatgc taaggttttg tgtattctaa atgatatgat tccatggttg    24000
aataactatt aagtgtctgc tgtatgttcc agcactgtac ggggcatgcg tgaataggga    24060
tctctttgtc cttaagatct tgtcttactg gggaatgttc actaatacac aggagaacat    24120
ttaattcaca aatcaactca caaattaaaa aacattagaa gccagacatg gtgacgcacg    24180
cctttaatcc cagcacttgg gaggcagagg caggtggatt tctgagtttg aggccagcgt    24240
ggtctacaga gtgagttcca ggacagctag ggctacacag agaaacctg tctgaaaaa     24300 caaaaacaaa aacaaagcaa aacaaaaaaa aaacaaaaca aaaaattag aaattgaaaa     24360
```

```
cttggagcat tttggctgga tagatggttc atctgtcaaa ggcacttggc tgctctttcg   24420
gaggacaggc atttaattcc cagcacccac atggctggtc acagttgcct gtaactccaa   24480
tttcaaggaa tctggtgccc ttttatggcc tccatgagca ccagttaggc atgtgatgca   24540
tatatatgca gacaaaagat ctatacagaa gtcaaaagta aataaattaa aaacccaaat   24600
gccgagtaat ggatctgaag aacattggaa taagaaattt cactgtggac cagagtaggg   24660
agacttgaca gcagctatgc accttgtcac atcccaggaa cactagcatt aatactgaag   24720
ctggagaaaa cagcctccta tttgaggctt agaccaaatt ttataagaag agtatagact   24780
gaaagtatga tgtggtccaa actggtttct catatattct tggatgttca tcctatcaga   24840
acaacgtatc tggcacacgt gagaattcac tttccaaagg ctgggaagat ctagggctct   24900
gcattgttag cttcagcagc acgtagtgtt ctcagccctg cctctagagg gtagcgcaca   24960 ggcaatacccc atcacacaat acccatctta cctatagctt ggagaagagc tttgagtggc   25020
cttatgcttc ctgagccaga ttcttctaag ataaattctt ccagtgccta aactttgacg   25080
acattgtggg aggggaatat cgatacacac ccctgaagtc tctgcatcta catttggagg   25140
aaacttagca acccccttcaa aggtgtttca taataaccaa accatagttc ctcatgcaaa   25200
ttggctgatc caggcaacaa gggaatattc ctaatggcca aagtagtgga gttcaggtca   25260
tctcagtgat agagctggga agaggcttac gcaggtcttg aaaagtaaga agaggccatt   25320
ttgggagata agatgggtaa ggcctcagct acctaccagt ttccaggcca cctctcccaa   25380
tgcacacatg cgcgcgcaca cacacacaca cacacacaca cacacacaca cgcactcttt   25440
ctcacacact cttttacaca tacattcttt cacacacaca ctcttacaca cacattcttt   25500
cacatacaca cacactcttt ctcacactct cttttacaca cacattcttt cacacacaca   25560
ctctttctca cacactcttt tacacacatt cttttcacaca cacactctct ttctcaaaca   25620
cactctttta cacacatatt cttttcacaca cacactcttt tacacacaca ttctttcaca   25680 cacactttt ctcacacaca ctctttttgca cacacattct ttcacacaca cactctcttt   25740
tacacacaca ttctttcaca cacacacaca gacacacaca cagacacaca gacacacaca   25800
cacacacaca cacacacaca caccacattg caggtagtca gtgcatttgg atgtggttct   25860
ttatttccag acaggaagtg agatgtaaat gacagatgag gtgcatgaac tctctggcct   25920
cacccagaca ctgataattt cccatcatct cttgagcagt cagtgatggc ctggctcgat   25980
agggcggttc atgacaccct agcttcagat cagcagattg cagcttgttg ctgagactcc   26040
ttcctgttac agaccacaga aatcctggtg acatgcggcc catttacct tgtgtaaagg   26100 cacaaggaca tgtcacgctt gccatgagaa cacccgttca cacaggcacc aaagcagtag   26160
gcaggccaga tggagtcaca gggttcagag aaggactgtg acataatgct gaagcccgt   26220 gttggggaca gatgtctctc tgccttccag gaggcggcag taagcgcttc ttttccaaac   26280
cctcctctca tcccggtccc ctccccttt cgttcataaa aaagttattt tcttccaaat   26340
aagcaattcc aaaatatatg aaataaacgt tagttctaat gagcctctgg gaaagtgctc   26400 accctttgaac tcggccaagg attatgggga aagaaaaag tcgtaggaac ttgatagagc   26460
gttagagctt cctgggttt taagctgggt tatgtattgc atttctttgc cttaataagg   26520
acggttccag aactctgccc tggataattg ggccatgtct gatagtagag acccaggatt   26580
ggttactgga ttagggatta ttatctgggt gctaggcaac aattgggtag gaggccctgt   26640
ttctagaatg ttcttttcttt ccaaggactc agaaccttt ttttttttg atggtccctg   26700 tggggagtct gagacctagg aagaaacaag aggatgttta taggaggccg actgctaaag   26760
```

```
gggagtaaca ctcaggaact gtcctgctga gacaagctta cccccccccac ttccccgaga    26820 cattgctgct tcaaataaca gaaatcattt tctgaaagac aggctttcag tctgggtcgc    26880
ctctggctgc ttgtatggac tcttcacatc tgaatttccc caccctcctc ccccagataa    26940
gaagtttact tccagccatt ggcacaaatc atccctaggg tgacttgaac ctgactaagg    27000
acagctctcg aaaatcctga taaggtctcc aaacttctat gccctgtagc agtaactaac    27060
cattcccctt tctttaaact cgtccatctt gctttcattg tagtgttttt cctcatgcct    27120
aagtcaaatg agctctgtgt ctcatccta ccactctcga gggctgagca tcaccagtgg    27180
gctcctccta gggaccagag atctagaaac acagaggacc ttagctgagc tggaggtacc    27240
acttcacggc atgagctgtt tttcctcaat tttccttcct aggcctgcac agatttcttt    27300
actggatgga taggccccca tgcataccca gcctacctcc agcccagcac ctgctcagta    27360
cacttagcct gtaaatacag tcatcccaca aaggacattt tctctggtgg ctttaaggtt    27420
tgacggagag ttctctagac ttggcagctt agctgtgacc tcaggaatct cggtgctggc    27480
aaggctaggt ctttgcacta acgtggctca gtgcccatgg agataatctc ctcttgtaat    27540
gggtgcacaa tcattttatt gttgaagcaa taggaacgca aaaacagaag gaatcccaca    27600
acagagcttg cccgtggctc agtgagcctc tctgctcctg gctgagggca cctgggaca    27660 cctcaagttc aatcccaacc gccaccctga aggtcagctg attcataagg tgtgggctta    27720
tggaggagcc tacacccaca gcctgagcct ccccaggcct ggcactgccc tgtgttctgg    27780
ctaacacctc ctgtttattg tttgaaactc aaaagacaaa accctccagc aacctcctcc    27840 cttctactc tgagataggt accccctttt gtccctatta ccactgactt ctgcagtagc    27900
agcatttggc tccaacactt gagtgctcgg taggcatcag acacagttct gagcacgtta    27960
caagcgtttc ttccttccaa gtgctccatg gaacagagac ctgtaatgaa aactaaagta    28020
ggttgtccta gatcagagca tgcaagtgcc caggccctca ggcccaggct gcctgcttgt    28080
ctggctccca cactggcttc ctcacagagg cagtgttccc acctagtagg tctgcacttg    28140
tagtaagtac ctattcagta agtgaaggct tatggctcac aaaatacctga tgggatttaa    28200 attccaaaga gctgtgcagc ttacaaagtt acataaatgc acaggaccac tgactttta    28260 ttttagcaaa gtaagggtga tgcttatctg ttgttgttga tttttttta actctgtgga    28320 gagagatgga gagagagtac accacagtgc acgcatggga gccagaagat aagccaaggg    28380
agccagtttt ctccttccat cctctgggtc cctgggatca aacgcctcac ggcttcagat    28440
tggcagcagg tgccttcacc tgcccaggga tgctctatga ctccagttgc tttggaacgg    28500 ttttttcta ggtagcatag tcagagctgt gagatttggc agactgccac aggggaaagg    28560
acagtgtgtt tgtcagaata ctggcggcct ttagaagcga tttccatgaa gctgaagttg    28620
caactgacat tttaaaaata attaaggaaa gagagcaacc gaagtctgtc ccgggcggtt    28680
ccaaagaggt tgtgtgtctg ctctccagcc atcagcaggg ctgggatatc cgagactaag    28740
tgacaactca ggcaagcctc cagggtcaca caacacagcc cctccactca ggtctcccca    28800
tgctggtaga atgtagcatg caagcctctg gggctgtagg gtctgagtgg gccttttggca    28860 gcctttctct gtggctctcc acacagtaga acgagagatc cggcctgaag gctacacagc    28920
tgtgtctgag gcagagctga gttgctaata tctcttcctg atggccaagg cagggatttt    28980
tacaggccta gaaatctagc cctgcttcgg tagctctggg aggaggtcct gggtgctcca    29040
actgcttggc caggggacag atggagcatt gagcctttca ccaggatctc atggaaagcc    29100
agtgtcctgt cacctgtcac ctgtcacctg tcacctgtca ccattaatag gcacaaagag    29160
```

-continued

```
tgttgcacag aaaaaaagta ccaacttgtt ttcttttcaa ctgctgggct gggtaatgat   29220
gtaaaaacga cattatccct aataaacgtg atttgcagag atcgttgaca accccagtag   29280
cagagacttg cattagcagg taaacagata agagaaacag ccggcttcac cagctcctgg   29340
cgtggcacgt gtgtctaggt ctggtatgaa ctgaaggttg ggggtggagt gtggagtttt   29400
aaaggcgaat cgggtgatgg agagagtttg tcttaaggtt ggccatccca taaatctact   29460
tctcgatttt taggttgtgg tttcagttgt atacatgttt gttttggtgg tattttttt    29520 tcttaaggga tgggggcgtg cttatggggt gtgtggcttg tcctagtttc tcacctccat   29580
attacctcac caaaggaggt gggagccctg gtcaggccct agcaccgtcc ctgccaagtg   29640
actaaagagg gcagccacat ctgtggcata cagtctatgg gcctgcagcg agtggtagat   29700
tgctcgatta tgtcaaggag ttgggatcaa gacaggaact tccgcaggtg gggagagagt   29760
ggcttctgtc tggacctgtt cccctagtga gggctgactg gcagctggct ccctaaaaca   29820
cctgaatgta gtagcaggc acaggtaccc atgtctgtgt gagaatagct tcaggatatg    29880
tgggtaagtt agttgaaccc ttgggtgtta aataacctgg atacagtcac cgttatttct   29940
ctttaccatt tttttttctt tgccagaaag cactaaagca ttaggactct ggcttcctgc   30000
tcctgaggct ggaggagtgt ggcttgtcta accttctcag cagctggcca cgtcacatct   30060
gaaagagcta cctgatgctg ttgttgcctc tgtgcgtgtg tgtgtgcgtg tgtgtgtgtg   30120
tgtgtgtgtg taattcataa gcttgccttc cacctgtccc tcagaggaga ccccccaag    30180 ataaggaata actgaaaggc cagaacctca cagctgagga tcaatcaagt ctcagtgctc   30240
aggcctgggc cggggaggag gcatccacat ggactgcgga gagtggctga gggagcctct   30300
gcagggtggc aggttatgct ggaccttaaa gcttggaagg tcagaaggaa gaagaccctc   30360
tactaaggca caactactag gacctcgctg gatggccggc aggatgtggc atgtggatct   30420
acatgtatgg ggggggggcg caaagggaca cagctggaag acaggggcaa acatctggaa   30480
ataaatgaaa tacccatgca gtctgccaag gggtatagcc tggttaagga attgttttca   30540
tcctgtgggt aacgtgtgac ctgtgcttca gcaagaagac cttgacaagg tctctgagga   30600
cccagccgga atacggccca cagcagccca gccgacacgg ctgtacttgg agcttttaac   30660
aaagacattc atttctcttg cctatggtgt caaagagag attctcatat gtactgtcca    30720
gtgtggccaa agcttggcca acagaatggg ccgaatctaa ctggctgctg tgctgcctcc   30780
gatcacttgt ggggcagtgt gcacacttag tcaccccact ctgccttgcc acctttctcc   30840
tgcgctttgc tgtctcctga tcactggccc ctgtccttcc ctcagaggta tttgtgtcct   30900
ggcttcctgg cttccttccc tccacccact ctcccttcca attacctctc caagtctttc   30960
tgactttctc ctctcacact ctggtgttga ctggggagta aaccagtcct ccagaacaga   31020
acttctctgc aggctccctg aggtcagggg agccatctcc acttgtcact cttgctggaa   31080
gaccacacat ggaagaaggg aatcatgtct gtgcaatgag tgcagcgagt aagccctgc    31140 tggggaagac agcctgatgt cctaggttgc tcagggttac catctgagag gaagcctttg   31200
gcatttcccg tggcttcgga tgacttcttt gcaaaggaat ggagtaaagc ttcctaaata   31260
tgcacagata ctcaattctc acagggacga agaagggaca aatttgggag aaaacaagag   31320
cctgccctgt ggccgtgaat cagacccaga aagccagaca tgtgaccatg taaacggggc   31380
acatatcggt gttcttgcag tagaaccagc aagattctct cagttggttc cttttctaaa   31440
aacagggtct catgctgccc aggctagact tggatttgct atataacggc gggtggcctt   31500
gggctcctgg tcatccttct gggtgcagag attactgtcc tgcgtcccca tgcatggctg   31560
```

```
ctgcaggaca ctcatctcgg gcttgaacat taggcgagca ctctaccaag gcgagctaac   31620
tcctcccaga gatcctgcag ggtttccccc ttgtctgtac gtgttcccaa acccgtgcca   31680
cagctctgac cctgaattgg attagaagag cacatcctga ggttcttcat cttaacttgt   31740
gaccaagcgc cagtcctgac gaaaagacca aaacactttc tgttcttctt aaaattaaag   31800
tgtctgaagt agagagaggc tcagcccttta taattatgag aagtttccct cgcccaacac   31860
ccatctgctt aggatggctc cccacacctt tcctccttgt cctcttcctc ctcttccttt   31920
tctacatcct aatgtgtaac ccttgtaggg gactttctgc ccccttcttc ctgcgtatac   31980
ccagtgctgg ccgcagaggc agcccagctc tgttttctca tgatgcagtg attattttg    32040 gcactgcgca tattttctct aatgttatta ttgcctcctc cacccttctg ggtgccttct   32100
gaggagcact cagttttttgg caattccaca caaaatcaga gggttaattt tagttcagtg   32160
gtgaagacga ggcaaggaga gaggggggatg ccttctcctt tcgccccact gcagcatcct   32220
atgcccaccc caaagggat gcgtttcccc atgcctactc ataaaagagc ttgcttgctt   32280
ccctggctct gtgttagcca ttcatccact gctgggcctg gggttgaggg taccgctctc   32340
cagaggtgac gtccttcggg ggctgcacct cagggctggc atcttaatga cttgacttgg   32400
cgggcttaga acagcctcat tcagaccgag ttcactccct gcgcagttgg cccactcagc   32460
ttctgtccat agagttctct tgttcaagct gcaggaggaa atggagattt ccaagtggga   32520
agcagccttc ccaatgcctt aactcttccc tgcagggaag aggagctaca gagagagagc   32580
aaaagaaaac ccaagaggca cagctgcagt tccctgggag aggggacag gggcggggtg    32640 gggagcagtg tggctggggg ctgaggctgg agccagcaca gctgggatca ctttccttcc   32700
tggggaggtg ggaaggaaga aagtggaggg cgcatttgaa ttgccctaca tcaattagca   32760
gatatttttc agtttgtcca gagctgaggc cctgagaaga acatgcaaaa gtagagaatg   32820
cagtgtctct gctgccacag tccttaaagc agtaggaaca tcacacagga aagccggtaa   32880 gatgggggaca ttctctaata atgaatggcg ttagtaatgt gggcagaagt gccagaggga  32940
gccgggacca ggcatggcaa gaaatataca agtgaagctg attcttcctg acagaggaag   33000
tggtctgatc cgttacgtag taagtaccct tgaccaaaca tggcgttggg tagtggacac   33060
actgcacact gtctttggct tcaagatctt aaaggtcctg gaattctttc tgttgaaagt   33120
gtgaggtcat agaccagcag catcagcatc agcatctagg atggtgctag aaatgtagac   33180
cctcatgccc cggcccagcc ccgaacttaa aagtacagtg gatcaagttc cctaatgctc   33240
tgtgcactcg gaacagtgta ggtgatgtca tagactagat gatagcccag tgtttattca   33300
gagggatgga tcacatgctt gtgtgcacgt gggagcaaac acacacacac acttttacct   33360
atgagtgtca ctgtattaag aactgttccc gggtagaaac ttcttggtct aatcacgtgc   33420
tgggttagaa ttcttaggga agattcaaac agtgagcagc attgaggaat ttacgcccca   33480
gaagtcactg aggtggtttt taatgccttc ctctggtact gcttgtgcct cagaggaagg   33540
actctgaggg aaccaagggt gggggccttc ccagaagaac atgtctgcat ggggtgaaat   33600
gaaagggaga acagcatgag gctgactctg cagcgtggaa tctctggagc aatgtgaaga   33660
ggtcagaaca ggcagggcct tcccggggaa aatggacacc tctggaggtg aacagaggag   33720
ctgtggaaca gagatagact aagatggtca agaggaacat tctggaaggc cgtgggggagt  33780 gtcagtgcct agagctaaat cttccaggct acgtgggact ggtcagctgt tctccacacc   33840
tcggagcctt gcttcatgct agggagttca tgtcacacac cgatcagcct cttcttcctt   33900
ttttctgctg tgcgattttg ctagctctct ctgctgaaaa agaagtgctg tagggacggc   33960
```

```
ttgcacatgt gctgtggctt gagccaaatc acagatttgt gttgttgggt gcttgtgggg   34020
tccaaaagaa ggtgtctgag aggacacagg agccctaagg agaaacccca gaggccttca   34080
ggcaacagct taggcatggg gcttacgccc agacccaggg gaaaggcccg aaagaaacgg   34140
accagggaga aagacgcgct caccggagac atccattaca cctgcccacc acagtaagca   34200
tgctgtcccc aagtcactct atctctgctc aacccctgtg attctctcca ccagcccttt   34260
ctccatccct ccctccctcc tttcttttt tctcccttta acttcttgtc tttagatctc    34320
caaacaaaga tgatctcccc cttccctctg gcaagtttgc cccttgaagc aatggcctag   34380
agtagaaggt gatcctgctg tccctctct tgccacttcc ttgatcaaga gagtgttttc    34440
aatggcttca aattcagtat tcttagaggg ctataccctc cgtgtgccca gttcagcgaa   34500
gccttctgag ctgcaagagg ggcctgttta ttggcatttg gagaaaattg cccaattaca   34560
acccaatgtg gcatgtgggc tgcgttgaca cagatgtgag agctaagcat gccaacttcc   34620
tccatctctg ggggctgctt cctcaggca cgtgacctgt cgccatactc tttccatgag    34680
atttgaggat taagtcaggc agtaggaatg gataagtgat ccttgttaag tgcaaagcac   34740
tgcccgtggt tatttgctag tttcagcagc ggcagcagca gcatttcaat ttgctgatac   34800
taattaaccc cttagctaga gtctgcacat tggcagaggt caggcagtaa agaacatcgg   34860
aggccagcaa agaacaacac ttagacagac aaatggccac tgctgcttgt tggcccttca   34920
ttacacgtaa acgtctacaa gtcttctcta gacctccatg tgtgaggaga gggacaacgg   34980
agagagagct agcttagagt gagggaagag gaattgttga cctgcaagat ggccatcatc   35040
ccggcactgg cttagagcca aaggcagcct cttcagatgc ttcaaaaaga tctaaggaaa   35100
agaggaaggc tgagaggaag gaagcctggg ggcggggcat gtagagccca ggaccaggca   35160
gaacatgagt ggttggtttt ccttccttct gcagactccc ctgcctcagg agtgaggcta   35220
cggatgttgc cactcaggtg aggggatgta agatggcagg gagttagata catgttacaa   35280
agcagtatgc agtgcagagg cctacatcat ggcactgttc acaacagcta agcgttgggg   35340
accccaactg agcaacatat ggggatcgcc aaatgcattg gggtctctgt tcacacaata   35400
cgctgtgact ggcttttagg aatattaaga agaaatctg agcattatac gtaatgttaa    35460
gtaagaaagt caaggggaaa agccgtacgt tccgtgagag tcctttctgt aagcatctgt   35520
gtatttccca ggttacccctt gccgagtagg atttgggctg attctcggtt gcatgatgaa  35580
aggcctcctt ccaagcctag agctgcttgc cagcacactc ctcacgagtc cttgaaaata   35640
catccgagga gttccatcta cttccaccta tccctatttt ctaagcctca gttttcctca   35700
tctctaaaat ggacaactgg cagcagctgt tccttcgtgc tgtgaagtga gatttactta   35760
ctcttaaagt gccttataag gtgttgtgtg tgactcaaat gtaaagtagt attcactaat   35820
atgctagtgt ttacctattg ccacgggcca ttcagaatgc tgaagcaaaa gccataggcc   35880
gggaaacttt caaacagcag ggagtcattg cttgtgtgtt tgaagtctgg gcagcaaaga   35940
tcaaggtttg agcctgatct gttttgttta ttgaggatcc acattctgct tcacacagtg   36000
gggctggtgg aaggtgccag ggatccaact gggccttatc ttacccagag agagggctcc   36060
accctcactt tggaggcaag gatttcaaca ttaactttgg agacataaaa ctcagacctg   36120
ggcccttgct agaataaggc taggccaagg acagtttgtc acagctactc ctgtgcgtgg   36180
ccagctttcc tagcaggctg gggactccac atgtcctaag gtgatagaag ggtctgggtt   36240
cccagatgga ctgcttggta attaaatctg ttactgtctt ctgggaggct gcctgggca    36300 ggaggctcgt ccgataagca tctccagtcg gcccctgtgc agaattgacc attaaagggg   36360
```

```
caagtggagt gagccccaga cattacttac tgtcagctct gaacgtagtc caggcctgct    36420
gctctgggga tactgaccct cagagagggt cagcagctgg gggctaaact ccccatgaag    36480
gacggctggg ctgaaaggcc attataagga cttctcattg agacggggca tgagagccta    36540
gccctcattt cagccactcc tccctctgct actctgttgc tggcctcccc ttccaggaca    36600
gagaccacac tcttcataaa ctgtctgttt gtctgagtgc actgctgcct ctctgcctcg    36660
tccaggtctc agttcttcct gagttcttaa ctccgggtct tccattttga ctgacagctt    36720
ttccttccct ttgttttgca tgccctgact gaccactact gccttgggtc agaatgcttc    36780
cagaaagtgg ctcatcagaa cattgtctcc atagaccacg ttctcgctag cctttagaaa    36840
ttaccctctg agaaattctt gtgagttgtc ttgttctttt gagtgcctcc agttgtggca    36900 aaaaaaaaa atatatcagt tgagagcaca ttttattctt tccaagaact atgagctgtc    36960
catagcctgg cctagtgact aaaagggtgg gtaagttggg gaacatacat agtcagttgg    37020
aatgatgtca ttgccattaa atgttgtaac tggtattctt ttgtggttcc aacattaatt    37080
cctaaatcac ctaccaaaat gttagagtag cagccgcctc agcaggataa gcctcagcct    37140
tctcctgaag tgactcttgt aatggccatc accttttgt gatactcggt ataaatctct    37200
atgccattgt ttgggtccct tcctgtagct atagcatctg tagagcaatg gccccaccag    37260
ccctaacagt atctgttcag cctatgatag tgactttaaa tctgcttgac atgatggcca    37320
tgacaccgtg tgagggagag ggggagtgca tggtcagatc tcagaggtat ccgaggactt    37380
cctgcttttt gtgatgtata ataatgggtc ctgatgtctg tatcaataag aacgcaagtg    37440
attttgatat gagccaacat tgaaaatggc tgttttgcta aaatgacatc agtaacaata    37500
attccaatgt aaacatgggc caaaaaccaa aaacactcac tgaggaaaag ccctgcgccc    37560
caagctccat aaacgcaggt tttctttatt cctgagtgtt tgagaaaagg ggtaattgta    37620
tttccaacac atccttaatt ccagattaca tacatagtac accccaaaa tcaacaaaag    37680 ggcccttaa aatcagacag ctttgtccag gtgtggtggc acacagacct ttaattccag    37740
ctcggaggca aagccaggtg gatctctgat tttgaggcta gcctggtcta cgaagcaagt    37800
tccaggatgg ccaggactat attacagaga aactctgtct cagaaagaaa aaaaattga    37860 cagctgtgta acaatggtta gccctgggca cataagaaca gaattgggca ggagtcatgg    37920
tgtcctcaga taaatcaaat ctaaggtcag tccgagctgg gaccccagga tccattttt    37980 gggggggtcg agacagggtt tctctgtgta gccctggctg tcctggaact cactctctag    38040
accaggctgc ctggccttga actcagaaat ccacctgcct ctgcgtccca agtgctggga    38100
ttaaaggcat gtgccaccac tgcccggccc caggatctac ttttaaggct tttccagtga    38160
gcaatcaaga tcaagaactc tgcagaggca tgggttctgc tgtgatttca tcagttgcgc    38220
aaacaactgc taagcttggg gtccagggac tcttgatttt ctccgggacc ctgagtaatt    38280
tttcttttta aaatatttat gtattttat gttggatttt gtgttggctg tttcgctggc    38340
ctctgtgacc atgtaccatg tccacgcagc acccacaaag gaagaagata tcagaatcct    38400
taggactgga gttacagaca gttgtgagcc accatgtggg tgctgggaat tgaacccag    38460 gtatggaaga acagtgtgtg ctcttaacca ctgagccatt tctagcctga agctgctatt    38520
tctttcacca ggcagctgtt gtctggcagc tccacaagct cactgaagag cccacctcct    38580
tcctgcttgc cttcacagtg ccctgtgatt tagcgtacgt ttagatccaa ccaacaggtt    38640
ggcccaagct ggtttagtga gcctcgcttg acctctcagc cacttaacct tatacggtag    38700
cagacatctg acttagatac ctgatgactg cagtcacagt aaaagttgag tctgctggag    38760
```

```
acagctaggc ttggacactc gcagatgaga aacaaggatt gggccgagag taggtcactg    38820
tgaatgagag catcgggacc cactgccaca cttacagtat cacgtgctct ggccaagctt    38880
tgcctgggtg agttttacct catagtctag gcttctggat cctttgattc tactaattag    38940
atctaaaata tttggaaaga aattatgaat gtggtgaata tatacagtct ttttttctta    39000
ttatcggccc ctaaataata cagcataata gctacttata gtgctcacat tctaggacgc    39060
attgtaagta atcaagtggt ttaaagtata gatgcagatg tgtgcaggtt ccacacaaac    39120
actacccctt aaggactgga gcatctttga cttttgtcttt gaggggtagc cagtcgtagc    39180
tgagcgagga acgttaccc ctggattgat gcttctggac agtcagttct gttttacctt    39240
```

```
tagctctgcc actaattagg taattgctct aagcacagaa cttaaccaaa ttgggtctca   41220
gtttccaagt ctctgaaatg gagacaatgg ttgcaaggat aaaattagtc agcctgtctg   41280
ctccctgact ggaagggcct atgtagctcc tggttgtaag accttgggaa acggcatgg    41340 tatgttctgg gcctcagtgt tcctatctgt aaattgcaca atgtctaccg agccgtgtca   41400
gtaagaagag tataacgggg tgatatgtag ttgtcggcgc agtgactgaa cgtgtctgta   41460
tcagtaagtg tttatgtagc tgaaggagct tagccaaacc cagagctctt atgccaaaga   41520
gaacccagac tttagctagc ctgttcccca caactcagcc acggggtag  ggggcgcgga   41580 cgggagagct tgttcttggt atcgttgctg atacacggcc tgtggtgact gcttcacggc   41640
atagctgctc tggatgttaa caacgacggg atcaggcgct gaccctgctg ctgtccggaa   41700
gcgtgagggc tggtgctgag gagggaatt caggatctcc tacttggacc tcaggagcca    41760
gagctgtggt actccagtgc agccattcct cctgtgagcc cttaaggtat cccaccctaa   41820
ggagctcagg attgagatat aaaatccagg gaccaataat ggcccttaaa gtctggtaga   41880
agatgcaaat tctcccaggg gtcaggttct gagggggtgag aagggtggga tagaaataga  41940
gaggtgtggg gtttctgaga gctgaaaggc agggaagggg gagaaaggga gacaaggaaa   42000
gccaagggga gagggacaa  gaaaacccat ttccctcttt cacaacttct cacaaggttc   42060
tgcctgacca tccatgttat gtggctcttc ctgcagtctg gtatccaatg gctaatccat   42120
ctgggggcct agatggcctg caaatgaagt gagctctgac gtcgaaaacg tcgaaacagg   42180
gcctctgcct caaatccgca cggggatgag aggcatgcca gcattccagg aatccccaag   42240
tagtgatgtt ctgtccagat aacgacatgc tcaaagacag gcagaaagga gagcaacccc   42300
taggactggc aacctcagag ggtaaggtgg catgagccag cctggagcta attggaagaa   42360
ggccttgaaa gccacaaagc acactggaca tctacagaag caaataccaa gttagtttct   42420
ttattaaaca agcaatatat gttatttata gaaaacacag gaaaatatcg ataaccactt   42480
ggtaggccag ggagggcgag ctccctaact aaccccatta ctctgcaact cttactaatg   42540
gctaagtgcc tagactctgg ggttgccctg ccaggggcag agttcaccta ccagctggca   42600
gtcacgggtg aattacttag cctccgtggg cctgttttct tatctgtata ttggagatgc   42660
taacagcagc tactctcaca acaatttgtg aaatttaaag atgctaacac tgtactgtct   42720
gaaagagtag ctgaactgta tcaaaaaacc tgtcaccatg acgctgtgac catcgtaaaa   42780
atgtttgcta cttaactgca ctccctgtgt agcacacagg aagtgctgtg tgggacctgc   42840
acagtgtttt gaggacatga ttgccctctg ttgcggatag gttgtctttt catgacagga   42900
ttgttgctaa tgtttctttta tagtggaatg tgcccaggac taaaagtttc acataaataa   42960
atggtcacag tatgtcctca cagttactgg ttactgatgc gacacttagg cagcttcatg   43020
gtagaatctg acgagttagc aggcagatac tctgactttt aaacttaccc gtgttagtac   43080
gtgatatgga ctttgtacga agaccgtgtt tctttaggat ctctggaaag aggcaggttt   43140
gggtgtcagt ttgtcctttc cttcccattc tgcaacaaag aagagtcagt ctggcacctc   43200
aggctggcaa ggatggcacc cactgcagct accaccttg  gaggtctttg cttctggatt   43260
gcaaatggag gcgtgttgtc cgcctcatgt tctcttggcc tttactgatg tctccagact   43320
ctaacctgtc gtctctcaga tcagaaacag ggtcttaggt aagccagggc tggtctgacc   43380
gtagcttctt cgcccttctc tttccattgg tgcccttttga ccctgtcctc aaactttgtt  43440
cattagttta attaaatctt tgctaacgct acccacgtga agcccagttc tggctcctgc   43500
aagaatacag aagaaagcaa tttgagaaga caccaatgcg caaaagcaga gtcaatacca   43560
```

```
aaaggtggct tgctcatagc tccccgggc tgagccagat gggttcagtg ggagaattga    43620
ctcactgtgg gggtgagtgg gtcactaccg agagtgtgaa tggatgacgt ccacattcca    43680
ggactaaccc ctcgtttctt catgtaggag cagctcagag ctgaggaagg agaaatcccg    43740
tgatgccgcg aggtgccggc gcagcaagga gacggaggtc ttctatgagt tggctcatga    43800
gttgcccctg cctcacagtg tgagctccca cctggacaaa gcctccatca tgcgcctggc    43860
catcagcttc cttcggacac ataagctcct gtcctcaggt aaggcttgac aggtcctgcc    43920
ccaagctggc atctacctag gcctcgctcc aagacacatc tacaaatatc cactcacaga    43980
agctggcaca tggcctttag tgttacattt atttagttgc gtgtgagggt atgcatgtgg    44040
gtcagaggac agcctttggg agtccattct gttctcttct tccatcatct gggatctggg    44100
acttgaactt gggtcctcag gcttagcagc aaatgcctct agccactgga ccttcttgct    44160
ggccctgttc cttcatttta gcatctcccc tctggcaatg atcttctcat gagttcaccc    44220
agggaagaga ccaaggacag actcaagtga gagtgtgagg tgctcccaga gagtgtgagg    44280
tgctcccaga gagtgtgagg tgctccaagg ggttggagag ccgagagcag cttctcctgg    44340
aagcccatcc agtacctctg gacctctggc gagagtcccg ctccacactg tgttgactct    44400
gcaggaagcc tttatccttt gtcttccagc tacatctcta ggacatcaga aatggtgatg    44460
tcccttgtga tctatctctc agaaccttgg tttccttgcc tacaaactgg aattagccag    44520
gcatactgcc tgggaggata ggggtaggaa atgggggggg gggattatta gggcactata    44580
ggaatgagtg gagacagcgg ctcagctgta ttcgttcttg ctgggctagc ccccgccata    44640
gaggacagcc tcgggcacct ctccctgctc agccgatgcg ttcttctttc ccgcatatct    44700
cttcaccaac aaacagttca taacgaatgc tttctttcct ttgtcagagt tacatccctc    44760
aaaaatcatt tcctgttagg cctcaccagg aagaggcagc ctgggtttc cacttcaca    44820 tcctatgtgc agtcttgtca gacttatcag ttctgtaagg aaactgggca gcatatagct    44880
gccaggctgg cactacagca gggcagtgtc cgaggcatga gcaagggagg caggcaggca    44940 aggggggaaag agatcccgtg gctcatttg agttttcctg agtgagtgtg tcactctgga    45000
gatgactcct tacatggcta ttctgggaaa gagcccctg cacagagggg tccagaatga    45060
ggcggggaag ccagactagc ctgtgctatt ctgggccct gtgcacagga aggatatatg    45120
ggaaagacct tcgagggtta gaatggctgc tcatcccatc gtcctcctct aacccccagg    45180
ctggaggcta agcctgggct gcaaggctga ggtgaccgtg ctgttacaga aatgagcaga    45240
gagtggagaa agcaagggcg gagccgctgc acacacagca gggcaacagc aattactcag    45300
atttagacgg tgaaaatggt tgagggaagc tcaggctaag gacttgtaaa gcctggactg    45360
ctaaataaaa aggcagactc ggaggtgtct cacccatgcc ccatgcatgc cttcatttta    45420
cagaggattg tcctcttgga gaaatgagga cgacagttcg gtgatttgta ggattttgca    45480
aagcctgtca ggcaaaaaaa aaaaaaaaa aaaaaaaaa aaaaagaaa tgtagataag    45540 gggcagggag ccaatgtcca agtgaagcag ctagagcctg accaggacta gccaggagca    45600
gtgggtggcc aggaggttct gagagctgtg tcttgctgcc gtagcaggga cacattgtct    45660
gtgctcgccc acacagaagc ctgtgtgtct tcctcgatgg gtcgaggttg atttgcagag    45720
ggcttggcta gggttggatc ttccgagctt atctgccctc atgtgtcctg gtgcaacccc    45780
tcccgcactc cacgtactac acaaagccac agatacaaga gcagacacca cacggagcag    45840
acatctcagg agctctgagc cttgagaaca aggactgcct actctctaga cagcataagc    45900
acggacagac cagaaccctt ggcgcgtcag ctatggggct cccaggcctg aagaaagaaa    45960
```

```
agttagagat tgataaacaa gttttggtca tctggtcctg gtgaccttaa agaagtgctc   46020
ctgagtccag ccacggaagg agatgtggct tagttctcct tctctgccat ttctccaggc   46080
tcctaccagg cactctcggg actggttatt ccagaaatg gaatgtaaaa tgagccttt    46140 cctccccacc caccctttgt tttagtgtgt gcatgcgtgc tctggagagg ttagggaaga   46200
gcgtcgaagt cttgcttaaa gacttcaacc tcccttcttt tagacaggac ctctcgctcg   46260
actcgaagct cacgatttta gctaggttgg ctggctggca aactcacagg atcctgactg   46320
tgcaggtcaa cattggggtt ccgggcacac acagccaacc tgtcaatgcc gaggactcga   46380
actcacatct tcatgcctgg gcagccagtg ctcttatgca cttagccacc caagtggctc   46440
attgttttaa attttcacct attatatgca tgtgtttgtg gaggggagga aaggacaact   46500
tttgggagtt gattctccct ccccaccatg gatagggttc caaccaagtt gtcaggtctg   46560
aatagaaggc ctttttacct gctaagccat cgtttcaacc ctgaaccata ggtctttatg   46620
ttttgttttt gttggttagt tggtttgggg gttgtgtttg tttgtttgtt tgtttgttgt   46680
ttgttttttg agacagggtt tctctgtata gccctggctg tcctggaact cactctgtag   46740
accaggctgg cctcgaactc agaaatctgc ctgtctctgc ctcgcaagtg ctgtgggttt   46800
tttgtttgtt tgtttgtttg tttgttttat gtgacaaaaa gtttagagga tctttgagca   46860
gatatcctcc tgcactttgc ttattggtgt tgctgccatc tctctcagaa acattgtaca   46920
cagctctatc tcattggacc gcagagtcca tgaaacattg ttggatgata tgaaagtcta   46980
gcctgttgta caagttatag ctttgaagta agtctaacaa agaaacgat gtaagagaaa    47040 aatcagagcg aactctaatg tctttggacc caccttttag cagttacgtg ttacagtgtt   47100
acaacatata ctttcccaac tcaaaacaaa ctacagactc attacttagg caagtggagt   47160
tttgtatacc tcagagttca aacgcctaaa aaataccagg cttagcgtta gggccagttt   47220 cttcttact tagcagcaca cttccttga ttttcacagt aggctgcagt gtgtgggaat     47280
gttggggagg aagcctccgc gctgagaact ccaggctgag tcgggccaca gttgagattc   47340
atatcacagg aaacaaaccg aaacaatagc tttacgatac ttgcttccac actggcccag   47400
gaggacagaa cacactgtgg cgggaacatg ggtggaaata tcacttgatt gtcttaaatc   47460
cagatgaacc ctgcgctctg gggctgaagt ggagtcgctt ctgcgtccca agagctttag   47520
accgcagtaa atgtatagaa tgtgcattcg ccccaattct gatttgaggc ttcccagact   47580
catatgtaaa aaaatcaaat tctcattact gcagagttgg agatcagcac aaagccaggt   47640
ttctagacat aaatgtcaag tttatttttg attattttga tttgaatttg tttatgtttt   47700
attcctggca tttgcctagt gaagtcacac agtctgctca ggatatgatt ctccgatccc   47760
tgagacatta aaatccagga catggtttta aagctttcac catgacttct caggaaaagt   47820
gggacaaagg ggacagaatt acagcagcag atgtgatttc tgtgccctcc tatgccttgt   47880
ggtaagacct gttttccctg gttttcagcc caattgtttt actgtcccac ctcccccggc   47940
cccacctata ctcaaaatca aggccttttc tgtcctgttt ggaaggaggc cagtaagatg   48000
attcatgcca ggatgttact ggctgagagc agccagcggt cccttcaaga aagtctaacc   48060
ttgcttatag cattctctta aagcaaagag tctggccagt cagcgacagt cactgactgt   48120
agcgccccat agcatttat gaaggctagc gcagcaagca agggtgggg agcaggtgtg     48180 aaaagaacaa aataaaaatc tccaatgctg gacttgtggg gcacaccagg agagcagcag   48240
caaggccagc tgagatctat cactctgcag aaagtgtgag atagcccag cctgctcaca    48300 gtgcggcata aggcacagta agtggcccac actctttatg tttgccgtca gtatgcccgg   48360
```

```
aagacgcgtg cacagccttt gaaaggaaag accctgcgga gataactaag tagcaagcac   48420
cagggaagta ggaaacctgt atcggagctt gttaggaaca aggagtttct tgaagatgga   48480
aacatctaga aggatcatcc gggtgaagta agaaagcagc agccttacgg ctggcacagc   48540
caggcctcaa agacccagtt agaagccacc tgctctgcca cctgctagtt cacacaaggc   48600
aagtggctct accatactgg tgtgccaccc aacatgggcg gtgctgccta aggaaatga   48660 gcagtgctcc ggaaaaggcc ctccacagcc ttctcagcgg cacatatcct ggcggtggga   48720
gccatcaaag cctgtttact ggggctattt ttagcattaa agaatttcgt ggtccttctc   48780
aaaggagaca gttcgtctat accagttctt tgagattcga accctgacag attctgggaa   48840
gcaaatggcc aggatgtaga acctgagcta tttagaccac ccagcccagt tccttagcaa   48900
gcacctactt tattttgtac caatggtttg ctctccgttg ttatcagcat ccccaggagg   48960
ggcttaggct cttcgacaga tgtcttcctg gcagtttgtt ggttcctgaa ttgcacccttt  49020 ccttgcagta tccccagctc tccctgagac aggactgagt gtgtaatgag tgctgtgagc   49080
cagggaagcc atggaggaaa agccttagta actgcaggga gggagggagg tctggtgtgc   49140
gcagccgcca ggcatagcag ttttttagcag aattgtgaca ggaggctcag ggctctgggt   49200
gcagcagggg gatgtctgcc tccctcttgg ctgggagtga cctagccaag ttccttcaga   49260
gactcccagg aggacaagca ggtgctaaaa gagcaaatag ttccactgaa ggaaggggcc   49320
acacccaagc tgggctgctc tagggtcgca gggaaggggt ggggagggt gctattggcc   49380 attgtgactt cagtctcaag atgttccatg tctgtggccc cagacaccct tctccctcct   49440
ctctaaaggg cagtccacct gccactgtag ccaatttcgc cacctcctgg aagtaagcgt   49500
gctggacagt tcggaaaggc cgcttggctg tgccgggcct gttaaaaaca ggaaacttta   49560
agcagaacta ttttctctgg gtctagttaa ccccgatagg ttgtcttggg attactccag   49620
attttgaagt cagtgttgcc actgagatca aagaagctga agtgaaaata aattctcagt   49680
aggcctcagc actagcctct gtctgtctgg agaaagtagc cacctcgccc tataacccaa   49740
atgcagctga aaccttctcc gggcatgttt ccggggtcag gcacccttttg cccagactgg   49800 ctggttttcc tgacgtgggg gatagtcttc agcacgtggt ctctggagcg acagctttga   49860
caccctctga acactttttg ttgatgttgt tgttgttgtt aaaggaagaa aaggcacttt   49920
ttcagcttcc ctgaattagg aaggaagcct gggaggaggt agaaccttcc agcaccaccc   49980
tgggtggggt gcggcctcct cgtactagcc aggtcttggg ctctgagctc agcttaaatt   50040
ttcagcagag ggttccacgt ttttatttta ctttgcacaa atcccgcaag ttgcatagca   50100
gtcctgggcc cgccagaggt cctggcccac ccactcagcc ttggctagac ttgaactcac   50160
tatgtagacc aagatggcct ggaattcaca gagatctacc tgcctctgcc tcctgatagc   50220
tgggattaaa gacctgctct aacacacctg gttaaatcca gatttctaaa gcacacacat   50280
atttgacatt aaataatgaa caagaagagg gcatagcctg tggtctgagg ataacagcca   50340
ggagccggaa caagagctga gcttagattg cagaggtgga cttggtagtc caggacacac   50400
agagtgcatg gttggggta gagttccccc acaacgcccc ctagtgtctg cctcttgtcc    50460
ctcacggctt tgtgcctcta agttccattc tctttcgact attctatgtg ctatctatcc   50520
ccggacttat gtccccaaag tggtgctctg agaagccacc tctctgcccc ttgactgaaa   50580
gagaagcttt gggacactgg gctcccttat tgtcccagtc tctgatattg ggccatggat   50640
cttctgcctc tagctggcct cttgtctgtc ctggggaggaa ggctgtctgt gtgtcctgca   50700
gtggtggccc aatcctgtcc agttgcctga cagacctctc tttccatact catgtgaact   50760
```

```
cacattccag gtgaattagc aaattgctct ttctaactct atgaagaatg gagctggaat    50820
tttgctgggg attgtgttga atctgtagaa tgcttcggc aagatggcca ttctcactat    50880
cttaatcctg ccaatccatg agtgtgggag atatttcatg tttcctctcc atcctatgtc    50940
ttctttttta gagtcatctc tcctctgact gctggagctt gtgctctctg tacccttct    51000 ttggtacccc atggtaatgt gcgtgagggc ttatttagct ttgtgaggtt gtgagccacg    51060
aactcgccac cttggctctg atttgagata gtaatggtgt cttagaggag ggagcagatg    51120
aggtagagct tgtagtcgtt gatatcactt taagcagtta atttacttaa ccttacaatt    51180
catgaagatg ggaatcgcta tcctggtttg ctggtggagg actccagcgt tcaatcgtta    51240
cccaaagtca taagcaagtg ggaagcagat gtaggaatag atacaacatt tgactccgaa    51300
gcttgtgagg tggttgaacg tggccctgca cttagctcct ggggcttcct aacattctag    51360
acatcatagc ctttggaaaa atggcttgac tcagaagtct tgcactataa aatgagactg    51420
caaatggtac atgccttgtg cgttattgaa aagccaatgt agagtgttta atgctgggtc    51480
tgtctgtggt tgatgttcca cttacgttag cagctaaaat aactgctgct gctgctgcga    51540
ggtctagcat tctatctgta gcctctaccc ccagccttcc tattggtaca gcaaattctg    51600
ctaccacaga aaccacgctg tcccacagtc attgtcaatg tggcctgggt gttccaccag    51660
gcatgtggca aatgttagat ggttggtagt gtgccttttcc ctgtgccctg gagccatgcc    51720
tgtcccctcg gtcatgtctg ttttaacact cgtgcccctg ttgttcattc ccctctctct    51780
ccagtctgct ctgaaaatga atctgaagct gaggccgacc agcaaatgga taacttgtac    51840
ctgaaagcct tggagggttt cattgctgtg gtgacccaag acggtgacat gatctttctg    51900
tcggaaaaca tcagcaagtt catgggactt actcaggtga caccctctgc ctcgttcagt    51960
aggaaaaaca tgtctttatt tggggataga cactaacggg gggtcctagg catagtctta    52020
cttgactttt ccttatgcat tcccatatga tgatgacagt ccttaggact tcccaatgtc    52080
atggggcttg acattccttg tggctgccct gacaggtctc ttctagctag attaacttgg    52140
caaaagtata aatcaagccc ttgttgccat caacattgct ctgatacgtc tgtaagtcca    52200
tagacccaat attgactgga gactattgat aaccactcag ttcatccccc tgcctgtctc    52260
tgaatgcaga cattatccta gcttcctctt ggagtccgaa tgacttcatc actaggagta    52320
acagcatctg gccttgcttt tgaaacaggt agaactaaca ggacacagca tctttgactt    52380
cactcatcct tgcgaccatg aggagatccg tgagaacctg actctcaaaa acggtaaagt    52440
gttcttcttt gtttgcattc ttctcatgac ccccaaagcc tgcacaaata gcccaaatgg    52500
attatgttcc atagatacag ttggactagc ttctgggtga gtatgcagct gttgagatga    52560
ggcccagcac atagaatagc tcctaatggc ccatccatga tgcctgatgt cacactacga    52620
ggtcagggtg ccatctctag gacatttcat catcacctga gatcaatcat ctccgccaag    52680
cgacaccacc caaaccaata gcttcatcta gcctgatta tttatgggag ctacaggtgc    52740
cttttgtcgt gtatcaagcc acccaacaca caggcttaag caatctccca catttctggg    52800
gattctgtgg gcaggtctct agctcaatgt gacatcagct ggattgcagc catcagggc    52860 taaactaggt tgaagtgatt aagatggctc acctggtgtg ctgctgggac agtgaccaca    52920
gctctcagtc tatggagcct cccggtagcc ttcttcatat gaagactcca gagcaaccat    52980
cttgtatgac agctcaggcc atgcatcttc cttctcccct gtaaagtgca gctgcagaag    53040
cctacagacc atcctaggcc ctagccctga aataggcatg tcaccacttc taaccctatt    53100
cggctggcga gggaaaggtt caggcttgcc ctgtgtctca ggtccgtgtc aagaggcatg    53160
```

```
gcccttagga ttaccactga agagcagcta tgacgggaat gtggagattt tcagaagaac    53220
taaaactttg gtgctggaga gctggctctg tggttaagaa tactggctat tcttctgagg    53280
acctaagttg acctcccagg ttctttgact ggtggtaggt cacaactcca gcttcaggga    53340
gatccagggt cctcccctaa cctctgcagg tatctgcaca aatatgccca taaacacaaa    53400
ggtacaaact tcagcaaatc tttccaaacc acacgaaagg agccatcgct gtaggcagca    53460
gtggcttcca atgactggtg agatcctctt gaacttgaga atctatcacc agtctggaca    53520
gactgcccac atcaacatct tgtaaatctg tcacctgtca ctactatggg gtgtgtgctc    53580
atccaacctg aatagcaaag gcagtgatgc cacgcctgcg aggcgtgttc tcgttgcctt    53640
gtgtgctgca aaaggggagg ctttgttggc tcacctctcc tgttggtaca gagtactgta    53700
atccacactc agacttacaa agctttgtaa aattataacc acctcccttt ccaatgctgc    53760
cccagcctct catctgcatt gctgcttcct atccaaagac cttggtcaac tggcttccag    53820
agtacatagg ctggggacca ccatgagttt atttgtcttg cctgtggtgc caagaaaccc    53880
taggctaagc cacccaacac atagaatgat tggttcttga tggtgaaggg gctattgatc    53940
acagacctgc gccaccatac ttggctttca gaagcacttc ctaaatcggt gtctctcgtt    54000
gcttctcttc tagagaacac tgctccctgg gttctttgtc tcaactcaac tgctgaccaa    54060
aacctttgtt tgagcatctg tgagctgaac taagaatctc actcctgtgc tgttcaaagt    54120 cttcttttc aaatcgatgg caaaagatga ggccaaatct aggatctttt tgcttttagg     54180
tttctctgac tcatagctga gtgtcctcca cttatctgag gaaaactcag gtctttagat    54240
tcatgaatgg ggatttgaga tcaagcagac tcagccaatc agcaagtcct tgctgaaggt    54300
ttcaggctgc atagactcat ggtctaaaag caagggtcc gtgtggattc ctggaagaag     54360
aaaaggttgg gagacgggct gtggaatgct ttgatggtga gtggaaagcc tcaaactggg    54420
tcctgcaaac agtcaaggc tgttaagat gtttaagctg aggtgatact atcagatgtc      54480
agaatgggga gactccagtg attagcaagt taggagccca caattacaac ccagactatt    54540
aatcacaaat gaatattgag ctccctcatt cctaaatcct gggggggct ctctcagtac     54600 agttataact catcatatac aaactccacc taataactaa aattataaga agcctaatta    54660
tgggagagac agtttataag aacaacattc aagctgtcac ttaatgggtt ctgcagaaga    54720
tgtttaaatc cagttcaagg atgccagttc ttttgataca cagctgtttt agactgtgtc    54780
ggtcaaatca atgttcctta gaggtgtggg tgcagaggtt ggcagcttct cttagagcag    54840
tgtgactact tgttggaaag ttctgaattg ctctgtgatg ctgggcctgt ggaggccaag    54900
gatgaagatg gcggtgtagc cacagtttag acaccgttgg actcatgttt tctgttctgc    54960
ataacaagaa gcagaaaacc tggacaggct ttggagattt gtactaaagg aaagaagccg    55020
tatgttcctt gtctcggtga tttatttaat cctaaatgaa aggtcatcta attgatcttt    55080
atcaagaaca tcgttaagat agacttgtct acccagttcc agttaaaaac aagggggtgtg    55140 tgtgtgtgtg tgtgtgtgtg tgtgtgtgtg agtgtgtatg tgtgagtgtg tgagtgtgtg    55200
tgtgtgttca ttcccctccc ctcccctcct tgacatgtgt cacctttagga ggaaactgat    55260 gaatggtaca ttatccaaag catagtcatt cgaggattca ggtaggatat tggttgctca    55320
cattcctgag agacaggcta gcgagagcag agaggagtgt ccaaggataa ttctaactag    55380
acagacttat gtccttggag caaccatggt cactctcagg tttcctgcta gagacccaag    55440
gcctgactgg ggagagacat ctaaaactgt ggtgtagcct cacagctctc aggtgacaaa    55500
caggtacagt gtgtagcaaa catggcacag ctcctgcctt ccaggccttc ctgctcctgg    55560
```

```
gaatgcagtc acacaggagc ttctactcag ccatcctcca agaaatctaa cttctgcagg    55620
ggagcagctt tctcccagga gtccctccac tgtgagtctc caccaacctg gtgttagctc    55680
atagtccctg ggtgggactg gccatcacta gaagttttgt aaaaaacctt ccttgacata    55740
tttctgtcct ctagttctga ccacaattga gccaggactc aaggcacagc aacaaaggga    55800
caccattagt atttaagcca tgagggcctc tctgcccatg gcaggctaca cgcactctac    55860
tacaaaccac aggagacaca aatacaagtt gcccagaaac attgtaattt ggattaattt    55920
aactggctcc cacgcccttc cccactcagg ctctggtttt gggaagaaga gcaaagacgt    55980
gtccaccgag cgtgacttct tcatgaggat gaagtgcacg gtcaccaaca gaggccggac    56040
tgtcaacctc aagtcggcca cctggaaggt aggattcgtg gagtctcaag aaagagccag    56100
gagcaggagg tgcctgaggc ctctccctct tctcggccgt ctcggccttg tcttacttct    56160
gtgctttgac cccaggtcct gcactgcacc gggcaagtga gagtctacaa caactgcccc    56220
cctcacagta gcctctgtgg ctccaaggag cccctgctgt cctgccttat catcatgtgt    56280
gagccaatcc agcacccatc ccacatggac atcccctgg acagcaagac tttcctgagc    56340
cgccacagca tggacatgaa gttcacctac tgtgacgaca ggtggggtgt tgggacaggg    56400
tgggtcttac cagtgtgcat ctgtgagagt gtgacagcgc agggacggga ctaggacatg    56460
gtgtgggact gctggctgca agtttgtaga aggtagcctc cttccatgtg aagactttaa    56520
aatgaagaga gctaggttag actctaaccc tcagttccaa agcaactgga cgttctcttg    56580
ggagtggggg gcacagaaac aataaagact gtggacttgg actagagaac ctagcagagt    56640
catctgtggt cagtgtaggc tgctgttctt accttcatta aaggggagac cacagagggt    56700
gcacaggaag gcatgctgtg tggttgtcag tacatgcaag gtttgtatag actacaccac    56760
agttcctatc cacttgtgct gctgctgttg ggatggagat gtggaggaca acggtgagaa    56820
cgagttgtga tgtgcagtgg cttgcaccag ggtgagggaa gccaggtgag aggctgcact    56880
gggcgtgcat gcctagcctg agtgaaaggc atcactcact gtgcctgact acttcaccca    56940
tcgtaagctc agctctgccg tgtctctctg agcagaagat agatcggagg tacgccctct    57000
gcagttttca gagagacccc gaaagtcccg gtgccagatc catgacaccg gctttgaggt    57060
gcagtggcac ttgggatgct tgtgcagaaa cccaggagtg gtcagggatg tgggtgacag    57120
gagggagttg ctctgaagca ggaaaaccaa accctcacct gccatctcct gaaagcagaa    57180
aagagactgt aaaaggagc tggcaggtga gggaactatc tcccagaaag gttcatttgc    57240
tgttaatttc cattcattat tgtggtttga gtgggtttca ggtaaaaggg ctagccttgg    57300
gttaagggca aaggggaca gtcacaagaa atgggcagcc taaagggaca aagatgccat    57360
gtgcacgcac acagaggtac catggtgacg tccttaggtt ggctcagtac ggcgggtggg    57420
gtggggttca tactcacagg aaggatcctg ggatttagag atgtggctcg tcgtgcacag    57480
ggagatgccg cttagggtgg cttaggacac acagtatttt cagcatactc ttgccttcca    57540
aggaagctga ttgcatggcc ggcccaacgt gaattctgtt ctgctaggga gccgactgca    57600
gagggatgca aacacagagt gccccacgga gcgtttaacc gattagcaga ttagttaacc    57660
agggtacaga taggacagtt agtgaagggg ctattttaag tgtttaatcc cttggtgtta    57720
tttctcgatt gctttgggtt gggggagagg cttgttctgt ttgcatgtgt tgagatgtgg    57780
agcagtgtgt gtgtgtgtgt gtgtgtgtgt gtgtgtgtgt aagagggaa gggagagaga    57840 gagagagaga gagagagaga gagagagaga atacatacac taacatgacc ttctgagaga    57900
tgtgctctaa atccagagcc tacatgtgag agccagtgta gagcagggct cccccatttt    57960
```

```
actcagtgaa ttatttggtt tggtgacatc tgacacaaag gggattgtgt ccctaacag    58020 aagcagggaa agaatctgaa gagaggaatt ttgagtccac aatcagattt gagcgagttt    58080
gatactttcc tctgattatg cttgtatgtg tgtgatatgt ttctatatat gaatatatgt    58140
atatatgtat atgtatttga ttattaatta tgagtcagtg aatactttaa accctccaat    58200
agtgtctgtc attttcatat atgtataggg cacagttatg gcttagacag tattgcttat    58260
ctgaaaatct tggaactaaa ctcgtttctc attttcgagt ttgggggaaa ttttgcgtaa    58320
actgtcctca agtgaatcta gaaattcaac atccaaactg ctctagaatc tgaagttttt    58380
aagtgtaatg taggcacact ttgggcatca gattttcaga tgaagagtgc ccgcctgtgg    58440
actgctgtgg ctctggcaac aggagtcttc acttgcttgg ccaggcaaaa gaaaaatctc    58500
gtcttcctct agcccccacc ctctcaaggc tgcccatga tttgcagcaa tcctcctgcc    58560
ccagcatcct gagtgctgag gatgtcttta ttgtccgagt aattaatgtc ctcctctgct    58620
gtgcactcaa acataaaagt tgcagtctgt ctgtttccta acattcttag ggactaatcc    58680
atgagctgtc actggggaac agctgccata aactgttgtg tcacggggga aagaaacaag    58740
tcctggtgcc tgagggtttg ggcttgagat ccgagcagct tagtgaaacc acagggaatt    58800
tgtaggacag aacagaacgt gccattcatc ctggaggaag acccaagcca ttctgaaatc    58860
cttttaaagg gttgggtttt taaattcacg tgagatgcca tctagtggcc aaatagaata    58920
actgtgaagg aagccaactc atcaagatga ggttttctta gaaaaatcac atgtaatctc    58980 agtgtgatttt tgtgagtctt ctgtaacttt gaaagatgta tgaaaattat agtaagcatt    59040
taaaactcat aagtaaaacc atttaaagaa taaaccacac aaaaagaatt tgagagcacc    59100
atgttccatc aaaacaatac aggacatagc caagagttag gtttgtaagt taggaagact    59160
tgtgtataat gctcctgcag agaccccacc ccatacacat aattacagct acctgtagct    59220
ctacttacag ggacttgggc ctctggcctc tgagggcaca cgtacacggg cacaaacacg    59280
tgcgcctata tgcatacatg cacacacgtg ttatcacgca cacgtactta aatctttggg    59340
gaaaaagatg tatggtggat tcattcaaag aacttaggaa cagtaagaca gcttgagtga    59400
gagaaggctt gagggccatg gaaagaatgt ccgtgaagtc ctgggctgct gagatggctc    59460
agcaaataga ggaacttgcc gccaagcctg ggaaaccgag tttgacccc agaaccagta    59520 tggacagagc tgatttgctg acttcacaag tagtcctctg accacacaca cacacacaca    59580
cacacacaca ctatggcatg tacactcaca caaataaatg cattttttaa gaggaaatta    59640
taaagaacca taaagtgtga ggccaggcgt gtgtgaagac agctagaagg tgtgtcaagt    59700
ccaagagtaa agcagactgg tttaagcaaa ttcgttgtaa aataatatgt tccctttgc    59760 acattggaga tgattaataa actttgctgc tttttgtaat gggtggtatc gccttaattt    59820
cagggtgatc ttttgcaagc accgtgaatg tattttggtc tcatatataa ttgattccaa    59880
gtgctttagc aggcctgtac attgccttc tccagacatc tcagttaggg gttatccaat    59940
gcttctttag atcctgaagt tagactctaa cgtgctctgc gtgtccttat gtccgctcag    60000
ctgacagtat tctggaatca gcccctagcca tgtttgaatg tgtaataaca actactcaca    60060
tgttgtcctg aaacacctgg tctgttggaa atgctctgca gactccctgt agtttatatc    60120
agagtttatt gcatgatggg gttcctacca cggattagtc acttctcaca ttccttctca    60180
ctgttggggg ttttgtcgac ggagctggtg gcatgcagga tagcactggt ccaggctacc    60240
ttctggtgta taacttcacc ctaccaacaa cacatctcac agagaccata gatcccatag    60300
agaactgtta accatagagc tggggtatag acttcatata actgggcagt attcggggtg    60360
```

```
tgtgtgcaag acttaagggc tgttgcttga agcaagtctg gcccagataa aaatatatta   60420
aaatgattag gtcttgaaat ctgagtagtg aataatctag atatcattaa agaaatgcac   60480
tgccagtgct tataaatata cagaaaataa aaccaagtg tctgggggtc gttaaagcac     60540
acaaggaaag agccagtgag aatacacatt gattaatgat agcgttcttg ggaaggcaag   60600
tacgtggcta aaaagtgctc agtactttca tcttcacgca gagttcagat actccctaga   60660
cactgtgttt acatgattaa ctcagcaaac cctgggcctc tgaagggagg gagcagcgat   60720
agaattggca ctaggggggct gcagcctggg agggatggca tgtggctgat tctgctgtct   60780
ctagagggga cagcatgcag aagaccattt ccttcctgac cattccatat aacacaccta   60840
cacgtgtctt taacatgcca cacttcattc tgtgtgtgtt tgtatataca tgcgtatatg   60900
ggctcccttg gtctgcctgc atgcttctga aggtcagata tcagcactgg gtgtcttcct   60960
cttccattct ctactttgtt tttttgagac aggctcttgc aatgagctca gaacttactg   61020
ttttggctaa agtaactgat cagcaagctc ttgggatctg cctgctatgc cactgccatc   61080
cactggcccc acccactggc tccacccact ggccccaccc actggccccc agcatttgcc   61140
ccacccactg gcccagcact gggcttgcag acatcttctg ccatgcagca ggctgaggct   61200
ggggatctga actcagatct ttatgcttgg atagtgagca ctttgagcca tttcctcact   61260
cgtgcttgta gactatctcc agaacaaaga gcagttgtgg acagtgaata aatcacctca   61320
gattttacct tcacgcctca ctctgaaggc caaagccaga gtctggtctg acttcagaac   61380
aaagataccc ttcttccatt cattgtctgt ttcctctctt tcttcctctc ctgcctcctc   61440
ataggcttgc tccgtcctct ttggagtctc acttctttat ctgcttgtta ttaaagcatg   61500
cactcggtcc ccagctttga aatccgacag atctttttac gtttccccct cctctcgtgc   61560
agtctcgagt tgactttaa gtttacgggt gaccccaaat gattcttctt ccagcgagtc    61620
aaggatctct aattatgaag agcaaagtgg tccctctccc ctgatggaga gcacggatgg   61680
cactcttatc tgccgcagcc agggaaatga gcagggaagg ccccgggggc cataacagcg   61740
agtctataaa caagttcggt tccttaacct ccctatggcg tcggtgtgcc tgcggatggg   61800
ggcaaacggt cattagctgt aacttggggc ttcctggctt tgtgaagtct tgagaacccg   61860
catggtctgc gattgtgttc gggccgtgcg catttcccag ttttttactg tagtctgttt   61920
aaaggaatga agagggaaac attaaatatt tattttggct gacaagataa ctgaaagctg   61980
ctagcgggaa gataactggc aagtctgaaa tctgggtttg tttgtcttct agaacatgcc   62040
cattgtgtgt ctttgaaagg atgatacggt cattaggcaa aaacatctta ttatgaggtt   62100
gattataata tttactcgaa gccttttgat ggcaagatcc taatcgtgaa aggaaatggg   62160
atttcttcag gaaagatgat cacatccttc ctagaaggcc agtggtaaaa gtttgtagaa   62220
aattttgcat cggctcagtc cggctggcaa gtgagcaacc ctgtgagtgg ctctgctgtc   62280
cctggttctg gttctgattc ccagggagtt tgaggtgcag ttggcttctc gggaatgctg   62340
tatggctagg tacaggcatt gctccactcc tcattccccc cagctttata tcagcgggag   62400
tgtctgtggg taccagctcc agggtccgaa atcaagtggg gacaaatcct cttgtggtaa   62460
ggatggccag ctggcactag tgctctgcca gcctcacagg actgaattag ccatacttag   62520
aggttatgtc agtgggccta acctttgctc tgcaaagact tgggcctcca gcatcgcgtc   62580
tggtcagaaa acttgccttt tctctgctaa cataagagca ggtagtatac agaatggaag   62640
ggcagactga agactgtgat gagctgctag aggtgctcct gtgggtacac acatgtgcac   62700
gtacgtgtaa acacatgtga acacgtgtgc actgagatgg ttaatcatgc ttaaggaaag   62760
```

```
tagatcgtga cccgggttcc taagtggggc tggattgtca gcatgacttc cctcactgtg   62820
gggaggcagg aggagaaggc ccacggtgta agagtccagt acatccttcc tagggcccgg   62880
gcacatggcc tttaggcctc tgcaagagaa gaaggaattg aggggggttc ggtggagaag   62940
gagaggcctg cggtgactct gggagagaaa ctggttgcag atggctggtg gggagagtac   63000
atgacaccct gcaagttagc tgaaaatcag atttcttaca agcaaagact ggattctggg   63060
gagatctaga accagggcag tttgccccag ccaagagagt agctggccta agacgagtag   63120
ctggcttgag aaggactggg tctaacagcc acatgccatt acgattggat ggaatgaata   63180
cagagacagt cactcgagca agcagagctt tttattttcc ttgtccttag cctctgtcca   63240
gagggcacag aacacagctg tgccccaagg cagtgtgctc caaggaggat ggtcataccg   63300
agctgctccc gtcagctctg gcttgtgatg agcaaagtgt gaggcatcta cgatagagga   63360
ctcgtgggac tcacagcaga atgacatgcg actcacaagg tggccggtgc agtgattcta   63420
gggcaggctt ttgttcactt aaatgtctcc acacagaaag cttccatgcg tcttcgtggc   63480
tctctccata ttggcttttt cctgtccagt tctcaaccaa aactagacca tccagaggga   63540
acacatctac acgcggcgca ctcatgccat tttctggctt cgctgcttgt ttacctgcca   63600
ggactgattt ttatgttgct tccccttagc agcctctgtc cttctccctc atggagatgg   63660
gaagagacaa gctgctggag acacatctag ggtcatagat ggcagctgag cagcatccag   63720
gggtgacacc ggagagaaaa cttcctccct ggctcttcct cgccttccct tctgggacac   63780
aggatttcca tctaaacatt cctcagcttc aactagaatg agcttgagat gctagctagg   63840
aggcctcagc gcttgttcct gtctgaactg ggcacttgtg tggccatcaa gccaattctg   63900
tcctctctca gatctccact tacacagatg aactgggagg tggagccatg tgacccctcc   63960
tgaccccagg acctcttaga tactaggcag tagagtcctc tgagatagaa cttcaggaag   64020
ggcaggagag tggggacgg gggcagatcc acagttgcag ctgagtctga tgggtttttt   64080
ttaaattagg tatttatttc atttacattt ccaatgttat cccaaaagtc ccccacacgc   64140
tcccacttct tggccctggc attccctgt actgaggcat ataaagtttg cacaatcaat   64200
gggcctctct ttccagtgat ggccgactag gccatcttct gattcatatg cagctagaga   64260
catgagctcc ggggttactg gttagttcat attgttgttc cacctatagg gttgcagatc   64320
cctttagctc cttgggtact ttctctagct cctccattgg gggggccctg tgatccatcc   64380
aatagctgac tgtgagcatc cacttctgtg tttgttaggc cccagcatag tctcacaaga   64440
gacagctata tctgggtcct ttcagcaaaa tcttgctagt gtatgcaatg gtgtcagcgt   64500
ttggaagctt attatgggat ggatccctgg ctatggcagt ctctagatgg cccatccttt   64560
cgtctcagct ccaaactttg tctctgtaac tccttccttg ggtgttttgt tcccaattct   64620 aagaagggc aaagtgtcca cactttggtc tttattcttc ttgagtttca tgtgtttagc   64680
aaattgtatc ttatatcttg ggtattctaa gttcctgggc taatatccac ttatcagtga   64740
gtacatattg tgtgagttcg tttgtgattg ggttacctca ctcaggatga tgccctcctg   64800
atggggtttt gcttgagtaa agaaatggtg tgatgaggtg tgacgatact tgatacattc   64860
accttagatc ctgaagtctc tgatcgcatg ctgtgccaag gctgtttggt cttttgtcct   64920
cacctgctgc ttcctttta attcagaatc ttggaactga ttggttacca ccccgaggag   64980
ctacttggac gctctgccta tgagttctac catgcccctgg attcggagaa catgaccaaa   65040
agtcaccaga actgtgagtt cctagatacc ctgtgtcctc gacgtctgcc cttgagggta   65100
tgattgacaa gacacggcct tggttacttc ctcccagagt taccatcttg ggtggcagat   65160
```

-continued

```
aaggtagata ccttcaagat ggtcagagac tcaccgatgc caccagcccc taaatggcgt   65220
ttatgcaaat taagaaaaag actcttgagt cctcgcagat ggttaacatt ctatgcaacc   65280
ctcaggggca gtcttgaaga gcagctaaaa gtgggtgtgt aaccagcttg gggctgcact   65340
agatcggcaa gcacctcggc atagaagagg gcctgggaag gttccaacga gagttggctt   65400
gcactgaatc agtttccatg gtagagagga tggggctaac cagaggaaga ggtaagagag   65460
ggggctgcct gtgcagcagc acactgtgtg catgcgggag agcctgcaca gcgaaggagt   65520
tcaggaacag agctgtccag tagtagagcc tctatcacag aaacatcctg tgccttcata   65580
ggccacacaa gacctaggta gtacttgcag tgtgtctggt gcattgagaa atgtctttaa   65640
acttaagttt taaatgattt aagtagcttt tcttggcact tggctacctt attggactga   65700
gtggttctgt ggtgttccct tggccacgtt tccaattcgg tctttccatt tatgatgct   65760 ccagggtaat tttgaatacg taaaacccat caacatgtaa gaaactggac ttggtcctct   65820
gaggactagg gattggtaga cttgatctct accctaagga gtctttgttt tggaagaaaa   65880
gggagcctgg ctcccagaaa ctgggtgacc tttaacctta gcatctctca tagcatcgtg   65940
gtaatacaaa cagcaggtga atgataatct cataaacaga ctatatttag gaaagagatc   66000
atccaagcag gacactggta cagacagggc tgccgagggg ataggctagg agtcttcaaa   66060
taggaaaccc tgagaagcca cctagcagcc atactggcaa tgtaggaaac agaagtgtag   66120 cttttctgttc caagtctgat tctgcccgac actcctctgt ttacagtcgg gagagctcga   66180
gctcagcttc actaactgtg cagcaactcc acaagctgtg cacagcatgg ggggggggga   66240
gggagagaga gagagagaga gagagggagg gagggaggga gggagggagg gagggaatat   66300
gagaattcaa actcaccccct ctgtttcctc cctgggagct ttgggtttca tctgatctaa   66360
taatacagca ggggccatta tggcatctca gacaagtctc ttactgtctc tctgcataa   66420 aaacaaaaat atccaaatag actacccccag gggtggcagg acactccctg atgctctcag   66480
ggagatgacc cagccagaga ctccaaggta tggtgtcagc cttctcttgg agggccccca   66540
atgcttttgt gctccctagg ggttccccac ccccaaggcc gattggtaga gacacacaac   66600
tgtattctgc tcagctctgg cctagctcac cagctagtgt ctctgggtct ggcttccttt   66660
tttttcttgg ccttctaagc caatgggtc tgtcaacaca gccgggaaaa tatcttcatt   66720
ttaagtacct gggaattctt ggagggtagt gttatacttt gtctcctggg gagggccgtt   66780
agagagctca gtggccatgt ggaaagaaga cggctccctg tttagagctc cctcatctat   66840 aaaagagggat agcaaggaag ctggtcctac cggtttgcag ctgactcctg ggggaaatac   66900
gttggaaaaa cgttttggtt ggatattgtt tttacttaat ccatatattt aacccccccag   66960 cacacctaag gataactcac agtccaaata gaaagtacag actcttgatt ttctgggttt   67020
tgtttatttt tttcccccag tggagttagg aaaagctgcc ctgagcacag aggcctgtat   67080
ttaaccaaga ggcctgcatc aagcaaagtc tttccgccct atcccctac aagtacagtt   67140 ccattctaga tccctgcca gtgtgtgggg tctctgattc accatgtgtg tcacagcttg   67200
tgtgtgtttc ccatccaaac gcctggagaa gctccgtcct cagccagatt tagataattg   67260
aaagtcatca tttccaaatg ggctaataat ctatacactg tcactctcag aggggaagag   67320
ttgggctggt ttctctttgt tgtgctctta ggaaaacaag attaaaggcc ataaaaagcc   67380
tccctctctc tcctggagtg gcaggccctt caccaaggct ggcattaatg agaggaatgg   67440
gagtggtgtg acttagaggt gactgataca gcaggcccgc gcctgcactt aacagaagtg   67500
cagctcaaac ctccgctcag cgaacttctt cgtgaaaaag actaagaaca ctgaatgtgg   67560
```

```
caagcaataa gaactatgta aatgagctaa ttccaggctt gatgtcatgc aagaattgcg    67620
tcactgcagc caggtggcct ccatgtcacc cagaaagcga cagcagaaaa gataaaggtt    67680
ccttctctgg ccaaggagtc catgatggtt aacaacatgg ccttagcccg tttttttttt    67740
tttttttctt ctcacttctt tctggctcaa cataatgtag tcagagagga tccatggccc    67800
ctggaatcaa aagaccgatg atctaaacac tatgactgtt attctgtgca aagtgaagca    67860
aacacagcct tcctaggctg cgtttccttg tgttagaggg tgctgtctct cctccctcct    67920
gcacaggagt ccatttaaaa gattagatga agataagaca atcaaagtgg caaaacaatc    67980
tgactacttc tgataataaa aacatggtct tcagcagata atctagaagt ttcttacctt    68040
gttacacccc catgaaaaag aaagccacgt tcttttggat gtggatttgg atacagatgt    68100
ctattgcact tttattcaca acgggaaact caaacatcca ggtcaaagga ataaactggc    68160
catggtacac ccagggagac acttctctcc cacgaatcac agaaacaccc acaacctcag    68220
gaacacgatg ctcaaggata atgaagccaa actcaagaaa gtctactccc atagacgtct    68280
agaaaggaca ggagacggtg ccggggaaag atcggtgatc gtctggaatc agaagtcaga    68340
actaggagga ggagttaggc acgtgggcca tggggcaggt tcagatgaag ttttggtcc     68400 ctctgctgtg gtgatggcta cttaggtgtt tacgtttgtc aaaactcact gtactatatg    68460
cgtgaaatag ttacctctcc atgggattaa ttaaaattaa ttaattaaaa ttaaaattaa    68520
ttaaaataca ataaagcttg ttgtagagag gaaaatgtgt ctaatctaga ctctcaagcc    68580
tgagactgtg caagctggca atcatgttta gccaaaggac tctttcaagg gctgcagtcg    68640
ctgtcgatgg gaagcaggag tttcacacac tggtaaccca caccaagcaa ggcagccatg    68700
acactgaact ccacaggtgc actatgtaat gactgtcaca gggacttgaa tttacctctc    68760
aaggcagcgg tggctctgct gagcaatgcg cacatgtaat tctccatcat tcctgctcct    68820
cgctgctgtg tgttaagata tccaagaggg taagatgtgc caaggcagaa ggactgtgac    68880
tggtgtgact atgaacaagg ccatccctca tcagaccatg caggactgat gaggtggccc    68940
acgagctgac tggtagatcc aaggagactg cctacaggga acatagctgt tctctcctag    69000
aaccccagga caattgccgt aaacaattcc tagtaacata actggcacag tacctaagca    69060
ctaggcattg atagcttgtg gaagaggaaa ttcctaaaca gtgtttgtgt agccgatgag    69120
gcaggcaagt ccatttgatc tgcaaacagc agtagccttc tggacagtta gaaatgacag    69180
tgatggacat gagaggaaac cacaccagga ttgttactta cccaaagtcc ccaagccagc    69240
aagacttcct gagcctccca tcattcctct tcagttctct gtgacctggg cacttctggg    69300
ctggagctct gaacaatcat ttggagggggg gggggggtga aagtcagtgg acagtttaag    69360
aagctaacag acatttctaa aatcagcaga catgactgaa aaggagccct tgagagctct    69420
ttcacaaaaa taaaaatgca tttgaaaatg gggaagaaga caaactagtg tgtgggacac    69480
cccttggtgt ttttagactg tgaaattgac tacttagaat ggcctaggag aggaaagaaa    69540
ctctaagctg gcagtctcac ggggcagttg gcaagtttaa agaccttcca gtggctgagg    69600
ccctgaatta acagtacagg cctttcccta ctccagataa atagagcagt agtttctctc    69660
aaattgtatc tggctcctaa ggtagcagaa agttcaaggg acacaaagtt taaaaaacaa    69720
acttcagctg gtcttgtgga cacagctctt gagttgagtc ccagttattc agggggctaa    69780
ggcagaagaa tggtttaagg cccgcctaga cttcagaggg agttcaagga caacctgact    69840
aatgcatcaa ataacagaa aggactgggg ctggagctcc gtggacgagc acttgccccag    69900 ccctgttctg tcctccacag tcagggaatg ggacggggct gcagccctgc ggtccacctt    69960
```

```
ccagatgtgg tctgctacct tcaggaggtg aagtcagtag ggtgctgctc cctggttgac    70020
tgggagtcac tcctgcactg ggcaggcaaa catctgcttt ccttcagaac tcctattccc    70080
attttttgaa acgaagagtt ggctgaaatg atctcccccct cccccaaccc tctcactgtt   70140
cctggccttg gcatccatct ggcagctctg tccatccccc tccccgggca ggtgacactt    70200
cctgtggggt tagagtgtgt gctgcacacc actcctgcac ctctcttacc tctggctcct    70260
ttcttcacta gtgtgcacca aggggcaggt ggtatctggc cagtaccgga tgctagccaa    70320
acacggagga tatgtgtggc tggagaccca ggggacggtc atctacaacc cccgcaacct    70380
gcagcctcag tgtatcatgt gtgtcaacta tgtgctgagg tgagtcgagg agggagcagc    70440
cagcctctcg ggaccctggg cagtacctcc acatgctggc tgtggtgtgg atccttctaa    70500
ctgggagggc tctatattga ggtcttagga acagagctct agcgtgtttc tttttcattt    70560
gtcagctatg gtatcatgtc tctgacttgt gctgaggggg gagaagatgg catagagtaa    70620
tgcttgatgt tgtgtgaatg ggagacagtg ctctcctggg taagctgttt tgggaagatg    70680
tggatgttat accctctccc ctccaccccct ggaaagacta tgagcggctg ccattgataa    70740
tatgaaggaa actaacatag gaatccagga cttttgtgtg cctacagctt gagcacaggg    70800
agcgagcgaa cagcccacag gttgaggcta acctcaccgt ctctgcttct gtggctcaca    70860
gaattggatt gtttgtgttt ctgcctaaca cttctctgag aggtttatct accaggcttc    70920
tgacatgtct ggggcgggag agccaaaggc ttttgctaaa agatgcagat actctgagcc    70980
gctctctctt cccatcagtg agatcgagaa gaacgacgtg gtgttctcca tggaccagac    71040
cgaatccctg ttcaagccac acctgatggc catgaacagc atctttgaca gcagtgacga    71100
tgtggctgta actgagaaga gcaactacct gttcaccaaa ctgaaggagg agcccgagga    71160 actgcccag ttggccccca ccccaggaga tgccattatt tctctcgatt tcggtgcgta    71220
cttcctagcc ctggttgaac ccacagaacc ctcatggact ggcggacagt tcttgttatg    71280
acaagcctcc ctgccacag cttccctaaa ccacagatgc actcgggcct tgctgatcac    71340
tgtgcgtggt caggttctgc taggtagaga agaagcacag actcatggcc actgagttat    71400
aagtcctcat gaagggtaaa gaggtaggca aggagagggc tccctctcga ggggcccatc    71460
ctctacctgg cttgagagtc tgagttgagg cgtgtgtctc agggagtgtc ctctaactta    71520
agcgaaaggc tgagtcagaa cagcgccaga accagtagcc gagaggagac tgagggcgag    71580
gatgaagccc tcggtggctg cctgcgttag aatgtctgcc catcttcctg gaagagaagt    71640
ccttttggtc ctgagctctc ctctgacacc cggaactgtc cagggagagg cctcttccgg    71700
tctgcaccct ctccagccca gctctgactg ctccccttttg caatcaaatc cccctttgat   71760
aatgtgcatc tgagaggcca caggaaaatg gacacctcag agaaccagaa agggcaatga    71820
gccctcttgc acgagataac cttgtaaccc cccagctcca tgttggtact gaggcaaatg    71880
gcccaattct cctctgataa cttcctcagc tctgttctgg aaggctctgc aggaaacaac    71940
tgcttctatc tagtaagctc ggtctctgaa tgccaaatgc tgctggagat tgctctcttt    72000
ataggaagtc cccagattga atcatagttc tggtcctatc taggctccac agtactgagg    72060
gtgtcaactt caggccctct tttaggacct tttgtgaact ttctgggctt atccaccctg    72120
gggtgagccc agatctcacg aatgctcctc aagcaagcct tgtctttaca ggaagccaga    72180
acttcgatga accctcagcc tatggcaagg ccatccttcc cccgggccag ccatgggtct    72240
cggggctgag gagccacagt gcccagagcg agtccgggag cctgccagcc ttcactgtgc    72300
cccaggcaga caccccaggg aacactacac ccagtgcttc aagcagcagt agctgctcca    72360
```

```
cggtgagccc ccaccctcca ggagagcaca cagggctcat ggcccctca  agctctgctg  72420
ccagatgact ggacagaccc cctgagaagt actgcctccc ttgggtgtta cagtgccct   72480
aaggatggct cagatactcc gagagacact agagctgact accggctctt agcatctgtc  72540
ttccacccct atccacgtcg tgactcttga aatcacagca agaacctagg caggtctctg  72600
caaaccaaag gcttcaacca cagagccctg ctggccacag cctctatcca gtttgcacat  72660
caagacacac aggacaagta gctcacaacc cgtggtacac aaatccctct atttgacggg  72720
agaaatcgaa caagcctttc acagggtcac ctagatcatc agaaaacaca gaaattcact  72780
ttataattca taactgtagc caaattactg ttttgaggtt ggggtcagc  acagcatgag  72840
gaactggagg gctgcagcat caggaaagtt aaggaccact gatctaggaa gtgatccaag  72900
cctctcctta gagggagacg aaggttcaga gaggttgatg agctgagctg cttcacacag  72960
cttgtaaata gtagtcccct tcacagatgc ttggtagaac ggggcagagt gcagaaccat  73020
gcttgtctgt tctcaatgga ctcctggcga gacaggcccc gtgttcttac ttggtctcgt  73080
ccttcctggt ctccagccca gcagccctga ggactactat tcatccttgg agaatccctt  73140
gaagatcgaa gtgattgaga agcttttcgc catggacacg gagccgaggg acccgggcag  73200
tacccaggtg ggccccgcgc gtgggtgaca gagggctcct ttgcagagac ccccggtgtg  73260
ctgcgcaaag cttcggggtc aggaagcttg tgagtggcgc gctcccttcc tactgtgtcc  73320
ctgctcagcc ccacactcct gtctaactgt tgaccccatc tctgtcttgc acaaatggtg  73380
taagtggtgg tggtggaggt gggcgagggt ggtgatgaga atctccaggg gcgatcctca  73440
cacctccctt tgattgtctc agcctgagtt ctccacccca gcttccacat tgttctttag  73500
tgtgtggcct tatcctatcc tgcagaacct cttgttgttt ctgtgcatgt cttttcctc   73560
tgtgtgtgtg tgtgtgtacg cgcgcgcgtg tgcctgtgac acttcttagc acaagcaggc  73620
acacttcctt cagtaccagt cttgggtaca aagatctatc tgtagtgagg ggtcattggc  73680
tgaccgaccg cggctgaagc ttgtgtcttt gcttatgagt attctgttgt gaccatgggt  73740
gtccctgagt atctactggt gagtgagaac agcagtccct gtgggggaga tgaagattag  73800
ctggtacaaa taggataaag gagcagtgca acagaggcca gaagttggcc tggctaaaag  73860
agaaagagaa ggctgcaggt caaaagtgga gaaagctcac tgaacctgta caggatgaag  73920
ggacagatgc aggttatatc ccaacagcaa tccttgtacc ctcaatggca aatctgagca  73980
gttccagcag aggtatttga atggaggact gacagtttca aaaggcctag gcagggcagg  74040
gctgggccag ccactatgta ccctttgctc tgtgtctcct cagacggact tcagtgaact  74100
ggatttggag accttggcac cctacatccc tatggacggc gaggacttcc agctgagccc  74160
catctgccca gaggagccgc tcatgccaga gagccccag  cccaccccc  agcactgctt  74220
cagtaccatg accagcatct tccagccgct caccccgggg gccacccacg gccccttctt  74280
cctcgataag tacccgcagc agttggaaag caggaagaca gagtctgagc actggcccat  74340
gtcttccatc ttctttgatg ctgggagcaa agggtccctg tctccatgct gtggccaggc  74400
cagcaccccct ctctcttcta tgggaggcag atccaacacg cagtggcccc cggatccacc  74460
attacatttc ggccctacta agtggcctgt gggtgatcag agtgctgaat ccctgggagc  74520
cctgccggtg gggtcatcgc agttggaacc tccgagcgcc ccgcctcatg tctccatgtt  74580
caagatgagg ttagtgacag atgtctggct ggagggaca  tactgggcag ggcgagtaca  74640
tgtacacacc tgcttatgaa ggctctagag ggtcacatca gcttcccgct gaccatatcc  74700
cctcactgta tgtgtaggca gctggcactt ttcctagtcc tcctctgata tgtgagagcc  74760
```

```
agacccagc agatagaaga aggggctttt ttaagtgatg tctgtctacc tttggacaca   74820
gataggtatt atggtatttc ctccatagtc ctgtactttc catctgcctg gagcctctgt   74880
ggggtgcaca caggcaccag cattttcctg tcttcccagt aggctgcagt cccataagct   74940
gatgtgtctt gtctatagta cgtacccttt atagagcacc ccagatggtc ctctggaagg   75000
aaggcattca gcagaaatcc ttctagagac tgttgtcatc tagctgggca ggaccctga    75060 gggcaggact gaggtggaca ggtgtgcgga gagaggcgca ggtgacagaa ctcttgagca   75120
tcttacagaa ggaagagctg agctgccgcc gctcaagccc tttagcattc tgccctccat   75180
agatcgcctg agtcataagt gttagattct gatgaagaca ccaggcagcg ggaggctgta   75240
gatgcctcac acccaccact gtcttctctt ggcattggca ggtctgcaaa ggacttcggg   75300
gcccgaggtc catacatgat gagcccagcc atgatcgccc tgtccaacaa gctgaagcta   75360
aagcggcagc tggagtatga ggagcaagcc ttccaagaca caagcggggt aagccatgtc   75420
tgtgaacgaa cagcctactg gacaggaagg agatgaggct agggtagaga tgcagacagc   75480
tagatctggt agtgagcacc tgcccctgct gggtctgtgt gctacccacc ctactccacc   75540
ctggcccact tcctccaact acacatcacc tctgcagggg gaccctccag gcaccagcag   75600
ttcacacttg atgtggaaac gtatgaagag cctcatgggc gggacctgtc ctttgatgcc   75660
tgacaagacc atcagtgcga acatggcccc cggtaagcag gcctggccca ggggtctggt   75720
ggagggttga aggctcagag cacattccct gagccttgtt agaatgggtt atatccatgc   75780
catgagcagg atcccggttc agaggtctct acatgacttc tgaaaaagaa agcaggctga   75840
gagcgctatt gtctgcccta atgacagcac cacagttcac tctctggctt ggatcctcca   75900
gatgaattca cccaaaaatc tatgagaggc ctgggccagc cactgagaca cctgccacct   75960
ccccagccac catctaccag gagctcaggg gagaacgcca agactgggtt cccgccacag   76020
tgctatgcct cccagttcca ggactacggt cctccaggag ctcaaaaggt gtcaggtgag   76080
tgctttggaa ctcccaccat agccagggtc tgatgcaaac aggtggcctg gctggccaga   76140
gagctgagag gcagccactt gcaggaagca actctgcgtt tggacaagac tgccttcaga   76200 gccctgctc aggtctgatg cgactgctta cagtccatag ggctcttcat cagccaagct    76260
gcatgagatg gtttaggcag gaccaagtct cctctttatt ccagagcctg catggtacca   76320
ggcccagaaa ggatttgaca atgacttgtt caaagtacaa ggaaggccca ggagggtgca   76380
ggctcctcat tgatgagctg agattgtgtg agaaagtaag aaaggcctct ttggctgttg   76440
tccctgagaa agggcagagc cacggttact tctggccaag caggctcccc agaaggtggg   76500
tctcaggctg gggaagcttt ggtagaagga agcggctggt atggcaaggg ccccagggct   76560
gtggtggact tctgagcaag acaagctcgc tgccctggaa aggcaggctg gaagattgtg   76620
cacggctctg gaagggatcg tccagtaatc agtcagatca catccgggct cttggccccg   76680
caagaccaag agtctacatc tttcctcagc tgctcattgc ctgaagtgta tacacatacc   76740
gtaacaagct ttctctgaaa ggttgcacag gggactcact gatgggaggg tagcctggtg   76800
atccagtaag ttcagctatt gccactgaaa cacacaagtg ttcccataga cgcctttgct   76860
cggcacaaac aatctgtggt ttgagaaaga aaattccaga gccttgtcta cagtagcaga   76920 gttgggaaa atttatagtt gtgttcttag aattccatct gaagaaccca aaagccctgg    76980
gctgatattt cagttctgtt gtttaccagc aggtgggctt gcaagccaga agtcttaaaa   77040
gagaaagttt aaagtttaaa gagaggacca cacatcactc accccggta tacacatctg    77100 ggcagctgta gtcagcaaat gacaggtttc cccagctgtt gaatgcgaag caaaactaat   77160
```

```
ttcaacatag atcgtttctg cccatagacc gaaaggaggt gaatttaaga agggcagggc    77220
atctgttggt aggagtgcag gcaacgggaa gtgtggaccc cagaagggag agcacactgg    77280
gacccagctc tgtctctaaa ctgagagagc tctgctctcg ctccagccat ctttggatct    77340
caccactgct gtggcatgtc ctcttctggc tccgtcctct gaacagggga tggagcccca    77400
gggccagagt gctgctgcat cggaagttgc tggaagctgg agacacagtt gtttgcatgc    77460
atgccctttc ctctggtcat ctacagccag cggagcaggt gtgtgccagt cctctaaaac    77520
accctcctct ccctcctctc aggcgtggcc agtcgactgc tggggccatc gttcgagcct    77580
tacctgttgc cggaactgac cagatatgac tgtgaggtga acgtgcccgt gcctggaagc    77640
tccacactcc tgcaggggag agaccttctc agagctctgg accaggccac ctgagccagg    77700
gcctctggcc gggcatgccc ctgcctgccc cgccgtcttg acctgccagc ttcacttcca    77760
tctgtgttgc tattaggtat ctctaacacc agcacacttc ttacgagatg tactcaacct    77820
ggcctactgg ccaggtcacc aagcagtggc ctttatctga catgctcact ttattatcca    77880
tgttttaaaa atacatagtt gttgtacctg ctatgtttta ccgttgatga aagtgttctg    77940
aaattttata agatttcccc ctccctccct cccttgaatt acttctaatt tatattcccc    78000
aaaggttttt ctctctctca ttcatatcca tactaacaag catggtggct ggtgcctctc    78060
cctaggaaag ctttggcgtc attcaactca agtgttcttg ttcttgttgc caaagagaaa    78120
aggattttcc tccactgtgg attctccctc tcccccaccc ccacatacac acacacacac    78180
acacacccct acacacatat acacacatgc acgtatgcgt gcacacacac acacacacac    78240
acacacacac acacaccccc ctacacacac acacacacac acacatatac acacacacac    78300
acacacacac acacacccct acacacatat acacacatgc acgtatgcgt gcacacacac    78360
acacacacac acacaccccc ctacacacat atacacacat gcacgtatgc gtgcacacac    78420
acacacacac acacacatct aatcaccata ttgtaaaatt ttgtgttttt aaagccaact    78480
ctttgctccg gttttttcat acgacttagt atggggcaaa aaagcaatgt gaagaatcaa    78540
ctctagggtt acctgtgaag ccacgcggtg gtgttcgaag ctgtctggta atgccccat    78600 ctctccccgg gtccagtgga ttttttaac tattattcaa aagcaaaact gagttttgtt    78660
ttgtttggtt ttttaagaag aatttatatc cgggt                              78695
```

<210> SEQ ID NO 258
<211> LENGTH: 379
<212> TYPE: DNA
<213> ORGANISM: mus musculus
<220> FEATURE:
<221> NAME/KEY: misc_feature
<222> LOCATION: (345)..(345)
<223> OTHER INFORMATION: n = a, c, g, or t
<220> FEATURE:
<221> NAME/KEY: misc_feature
<222> LOCATION: (367)..(367)
<223> OTHER INFORMATION: n = a, c, g, or t
<300> PUBLICATION INFORMATION:
<301> AUTHORS: Aizawa et al.
<302> TITLE: Computational Analysis Of Full-Length Mouse cDNAs Compared
      With Human Genome Sequences
<303> JOURNAL: Mamm. Genome.
<304> VOLUME: 12
<306> PAGES: 673-677
<307> DATE: 2001
<308> DATABASE ACCESSION NUMBER: BY229956.1
<309> DATABASE ENTRY DATE: 2002-12-10
<313> RELEVANT RESIDUES: (1)..(379)

<400> SEQUENCE: 258

```
gattcgagag cggccggtgt acagctccgg agtccgcagc gctccgctcc agctctcctg    60
```

```
aggcggccgt acaatcctcg gcagtgtcct gagactgtat ggtcatctca gcggccgcac    120
tcgcttgccc ccggattttt ttccaacttg ctctcttcga gccatttttt tttcttttt     180 tcttttctt ttttctttt tcttttgg tgggttggtt tggatttgtc agatcccaga        240
aaagtgactc ctgttcgggg ctaaacggaa ctccaggtcc cttgtgctgc tctctctctc    300
tttgggcgtc ttacaacctc ctcccactcc tttccccggc ccgnctcct cctgcaggtt     360 cctcccngtc atccccta                                                  379
```

<210> SEQ ID NO 259
<211> LENGTH: 2730
<212> TYPE: DNA
<213> ORGANISM: mus musculus
<300> PUBLICATION INFORMATION:
<301> AUTHORS: Carninci et al.
<302> TITLE: High-Efficiency Full-Length cDNA Cloning
<303> JOURNAL: Meth. Enzymol.
<304> VOLUME: 303
<306> PAGES: 19-44
<307> DATE: 1999
<308> DATABASE ACCESSION NUMBER: AK087208.01
<309> DATABASE ENTRY DATE: 2004-04-03
<313> RELEVANT RESIDUES: (1)..(2730)

<400> SEQUENCE: 259

```
gaccatcgta aaatgtttg ctacttaact gcactccctg tgtagcacac aggaagtgct     60
gtgtgggacc tgcacagtgt tttgaggaca tgattgccct ctgttgcgga taggttgtct    120
tttcatggac agattgttgc taatgtttct ttatagtgga atgtgcccag gactaaaagt    180
ttcacataaa taaatggtca cagtatgtcc tcacagttac tggttactga tgcgacactt    240
aggcagcttc atggtagaat ctgacgagtt agcaggcaga tactctgact tttaaactta    300
cccgtgttag tacgtgatat ggactttgta cgaagaccgt gtttctttag gatctctgga    360
aagaggcagg tttgggtgtc agtttgtcct ttccttccca ttctgcaaca agaagagtc     420 agtctggcac ctcaggctgg caaggatggc acccactgca gctaccaccc ttggaggtct    480
ttgcttctgg attgcaaatg gaggcgtgtt gtccgcctca tgttctcttg gcctttactg    540
atgtctccag actctaacct gtcgtctctc agatcagaaa cagggtctta ggtaagccag    600
ggcctggtct gaccgtagct tcttcgcccct tctctttcca ttggtgccct ttgaccctgt    660
cctcaaactt tgttcattag tttaattaaa tctttgctaa cgctacccac gtgaagccca    720
gttctggctc ctgcaagaat acagaagaaa gcaatttgag aagacaccaa tgcgcaaaag    780
cagagtcaat accaaaaggt ggcttgctca tagctcccct gggctgagcc agatgggttc    840
agtgggagaa ttgactcact gtgggggtga gtgggtcact accgagagtg tgaatggatg    900
acgtccacat tccaggacta acccctcgtt tcttcatgta ggagcagctc agagctgagg    960
aaggagaaat cccgtgatgc cgcgaggtgc cggcgcagca aggagacgga ggtcttctat    1020
gagttggctc atgagttgcc cctgcctcac agtgtgagct cccacctgga caaagcctcc    1080
atcatgcgcc tggccatcag cttccttcgg acacataagc tcctgtcctc aggtaaggct    1140
tgacaggtcc tgcccccaag ctggcatcta cctaggcctc gctccaagac acatctacca    1200
atatccactc acagaagctg gcacatggcc tttagtgtta catttattta gttgcgtgtg    1260
agggtatgca tgtgggtcag aggacagcct ttggagtcc attctgttct cttcttccat     1320
catctgggat ctgggacttg aacttgggtc ctcaggctta gcagcaaatg cctctagcca    1380
ctggaccttc ttgctggccc tgttccttca ttttagcatc tccctctgg caatgatctt     1440 ctcatgagtt cacccaggga agagaccaag gacagactca agtgagagtg tgaggtgctc    1500
```

-continued

```
ccagagagtg tgaggtgctc ccagagagtg tgaggtgctc caaggggttg gagagccgag    1560
agcagcttct cctggaagcc catccagtac ctctggacct ctggcgagag tcccgctcca    1620
cactgtgttg actctgcagg aagcctttta tccttgtctt ccagctacat ctctaggaca    1680
tcagaaatgg tgatgtccct tgtgatctat ctctcagaac cttggtttcc ttgcctacaa    1740
actggaatta gccaggcata ctgcctggga ggataagggg taggaaatgg gggggggga    1800 ttattagggc actataggaa tgagtggaga ccgcgggtca gctgtattcg ttcttgctgg    1860
ggctagcccc ccccatagag gacagcctcg ggcacctctc cctgggtcag ccgatgcgtt    1920
cttctttccc gcatatctct tcacccacca accgttcata acgaatgctt tctttccttt    1980
gtcagagtta catccctcaa aaatcatttc ctgttaggcc tcaccaggaa gaggcagcct    2040
gggggttcca ctttcacatc ctatgtgcag tcttgtcaga cttatcagtt ctgtaaggaa    2100
actgggcagc atatagctgc caggctggca ctacagcagg gcagtgtccg aggcatgagc    2160
aagggaggca ggcaggcaag ggggaaagag atcccctggc tcattttgag ttttcctgag    2220
tgagtgtgtc actctggaga tgactcctta catggctatt ctgggaaaga gccccctgca    2280 cagagggtc cagaatgagg cggggaagcc agactagcct gtgctattct gggcccctgt     2340
gcacaggaag gatatatggg aaagaccttc ggaggttaga atggctgctc atcccatcgt    2400
cctcctctaa cccccaggct ggaggctaag cctgggctgc aaggctgagg tgaccgtgct    2460
gttacagaaa tgagcagaga gtggagaaag caagggcgga gccgctgcac acacagcagg    2520
gcaacagcaa ttactcagat ttagacggtg aaaatggttg agggaagctc aggctaagga    2580
cttgtaaagc ctggactgct aaataaaaag gcagactcgg aggtgtctca cccatgcccc    2640
atgcatgcct tcattttaca gaggattgtc ctcttggaga aatgaggacg acagttcggt    2700
gatttgtagg attttgcaaa gcctgtcagg                                    2730

<210> SEQ ID NO 260
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 260
ggttccttaa ccccgtaggg                                                20

<210> SEQ ID NO 261
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 261
acctgggttc cttaaccccg                                                20

<210> SEQ ID NO 262
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 262
ggagcacctg ggttccttaa                                                20
```

```
<210> SEQ ID NO 263
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 263
ttgtcagctg tcattgtcgc                                               20

<210> SEQ ID NO 264
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 264
tctccttgtc agctgtcatt                                               20

<210> SEQ ID NO 265
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 265
gaagacctcc gtctccttgc                                               20

<210> SEQ ID NO 266
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 266
caggtgggag ctcacactgt                                               20

<210> SEQ ID NO 267
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 267
aagctgatgg ccaggcgcat                                               20

<210> SEQ ID NO 268
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 268
ttcaggtaca agttatccat                                               20

<210> SEQ ID NO 269
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 269
```
aaggctttca ggtacaagtt                                                    20

<210> SEQ ID NO 270
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 270
aatgaaaccc tccaaggctt                                                    20

<210> SEQ ID NO 271
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 271
atgaacttgc tgatgttttc                                                    20

<210> SEQ ID NO 272
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 272
gtcccatgaa cttgctgatg                                                    20

<210> SEQ ID NO 273
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 273
acctgggtaa gtcccatgaa                                                    20

<210> SEQ ID NO 274
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 274
tgttagttct acctgggtaa                                                    20

<210> SEQ ID NO 275
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 275
gtcaaagatg ctgtgtcctg                                                    20

<210> SEQ ID NO 276
<211> LENGTH: 20
<212> TYPE: DNA
<213> ORGANISM: Artificial Sequence

```
<220> FEATURE:
<223> OTHER INFORMATION: Oligonucleotide primer

<400> SEQUENCE: 276
ggatgagtga agtcaaagat                                               20

<210> SEQ ID NO 277
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 277
atgaagaagt cacgctcggt                                               20

<210> SEQ ID NO 278
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 278
ttcatcctca tgaagaagtc                                               20

<210> SEQ ID NO 279
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 279
tgcacttcat cctcatgaag                                               20

<210> SEQ ID NO 280
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 280
tgacagtccg gcctctgttg                                               20

<210> SEQ ID NO 281
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 281
actctcactt gcccggtgca                                               20

<210> SEQ ID NO 282
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 282
gttgttgtag actctcactt                                               20
```

```
<210> SEQ ID NO 283
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 283
attggctcac acatgatgat                                               20

<210> SEQ ID NO 284
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 284
tgggtgctgg attggctcac                                               20

<210> SEQ ID NO 285
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 285
atgctgtggc ggctcaggaa                                               20

<210> SEQ ID NO 286
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 286
gggtggtaac caatcagttc                                               20

<210> SEQ ID NO 287
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 287
gtgcacaagt tctggtgact                                               20

<210> SEQ ID NO 288
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 288
ccttggtgca caagttctgg                                               20

<210> SEQ ID NO 289
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 289
```

```
gtccccugggg tctccagcca                                          20

<210> SEQ ID NO 290
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 290
tgaccgtccc ctgggtctcc                                           20

<210> SEQ ID NO 291
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 291
gtagatgacc gtccccctggg                                          20

<210> SEQ ID NO 292
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 292
gggttgtaga tgaccgtccc                                           20

<210> SEQ ID NO 293
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 293
catagttgac acacatgata                                           20

<210> SEQ ID NO 294
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 294
tccatggaga acaccacgtc                                           20

<210> SEQ ID NO 295
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 295
tctggtccat ggagaacacc                                           20

<210> SEQ ID NO 296
<211> LENGTH: 20
<212> TYPE: DNA
<213> ORGANISM: Artificial Sequence
```

```
<220> FEATURE:
<223> OTHER INFORMATION: Oligonucleotide primer

<400> SEQUENCE: 296
aaagatgctg ttcatggcca                                              20

<210> SEQ ID NO 297
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 297
tggtgaacag gtagttgctc                                              20

<210> SEQ ID NO 298
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 298
agctcctcgg gctcctcctt                                              20

<210> SEQ ID NO 299
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 299
ggccttgcca taggctgagg                                              20

<210> SEQ ID NO 300
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 300
aggatggcct tgccataggc                                              20

<210> SEQ ID NO 301
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 301
ctgctgggcg tggagcagct                                              20

<210> SEQ ID NO 302
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 302
tgaagtccgt ctgggtactg                                              20
```

```
<210> SEQ ID NO 303
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 303
tccaactgct gcgggtactt                                          20

<210> SEQ ID NO 304
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 304
ttgctcccag catcaaagaa                                          20

<210> SEQ ID NO 305
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 305
cagggaccct ttgctcccag                                          20

<210> SEQ ID NO 306
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 306
gtgctggcct ggccacagca                                          20

<210> SEQ ID NO 307
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 307
cttgaacatg gagacatgag                                          20

<210> SEQ ID NO 308
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 308
cagacctcat cttgaacatg                                          20

<210> SEQ ID NO 309
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 309
```
ctttgcagac ctcatcttga                                           20

<210> SEQ ID NO 310
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 310
ttcagcttgt tggacagggc                                           20

<210> SEQ ID NO 311
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 311
gtgaactgct ggtgcctgga                                           20

<210> SEQ ID NO 312
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 312
cacatcaagt gtgaactgct                                           20

<210> SEQ ID NO 313
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 313
ccgcccatga ggctcttcat                                           20

<210> SEQ ID NO 314
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 314
aggacaggtc ccgcccatga                                           20

<210> SEQ ID NO 315
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 315
caggcatcaa aggacaggtc                                           20

<210> SEQ ID NO 316
<211> LENGTH: 20
<212> TYPE: DNA
<213> ORGANISM: Artificial Sequence

```
<220> FEATURE:
<223> OTHER INFORMATION: Oligonucleotide primer

<400> SEQUENCE: 316
gatttttggg tgaattcatc                                              20

<210> SEQ ID NO 317
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 317
ctggccacgc ctgacacctt                                              20

<210> SEQ ID NO 318
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 318
gatggcccca gcagtcgact                                              20

<210> SEQ ID NO 319
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 319
cgaacgatgg ccccagcagt                                              20

<210> SEQ ID NO 320
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 320
aggtaaggct cgaacgatgg                                              20

<210> SEQ ID NO 321
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 321
cagtcatatc tggtcagttc                                              20

<210> SEQ ID NO 322
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 322
cctcacagtc atatctggtc                                              20
```

```
<210> SEQ ID NO 323
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 323
gttcacctca cagtcatatc                                               20

<210> SEQ ID NO 324
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 324
ggcacgttca cctcacagtc                                               20

<210> SEQ ID NO 325
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 325
gcacgggcac gttcacctca                                               20

<210> SEQ ID NO 326
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 326
tctctcccct gcaggagtgt                                               20

<210> SEQ ID NO 327
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 327
tctgagaagg tctctcccct                                               20

<210> SEQ ID NO 328
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 328
ggtccagagc tctgagaagg                                               20

<210> SEQ ID NO 329
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 329
```
gctcaggtgg cctggtccag                                              20

<210> SEQ ID NO 330
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 330
ggccctggct caggtggcct                                              20

<210> SEQ ID NO 331
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 331
agaacaagaa cacttgagtt                                              20

<210> SEQ ID NO 332
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 332
aacagttgag acatgacagt                                              20

<210> SEQ ID NO 333
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 333
tgtcactaac ctcatcttga                                              20

<210> SEQ ID NO 334
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 334
acaggagtca cttttctggg                                              20

<210> SEQ ID NO 335
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 335
catacagtct caggacactg                                              20

<210> SEQ ID NO 336
<211> LENGTH: 20
<212> TYPE: DNA
<213> ORGANISM: Artificial Sequence -continued

```
<220> FEATURE:
<223> OTHER INFORMATION: Oligonucleotide primer

<400> SEQUENCE: 336
aatctgtcca tgaaaagaca                                               20

<210> SEQ ID NO 337
<211> LENGTH: 20
<212> TYPE: DNA
<213> ORGANISM: Homo sapiens

<400> SEQUENCE: 337
cagcgacaat gacagctgac                                               20

<210> SEQ ID NO 338
<211> LENGTH: 20
<212> TYPE: DNA
<213> ORGANISM: Homo sapiens

<400> SEQUENCE: 338
caggccacct gagccaggcc                                               20

<210> SEQ ID NO 339
<211> LENGTH: 20
<212> TYPE: DNA
<213> ORGANISM: Homo sapiens

<400> SEQUENCE: 339
tagactccga gaacatgacc                                               20

<210> SEQ ID NO 340
<211> LENGTH: 20
<212> TYPE: DNA
<213> ORGANISM: Homo sapiens

<400> SEQUENCE: 340
agcagcagca gctgctccac                                               20

<210> SEQ ID NO 341
<211> LENGTH: 20
<212> TYPE: DNA
<213> ORGANISM: Homo sapiens

<400> SEQUENCE: 341
ccactgagcg caaatgtacc                                               20

<210> SEQ ID NO 342
<211> LENGTH: 20
<212> TYPE: DNA
<213> ORGANISM: Homo sapiens

<400> SEQUENCE: 342
agaagagtaa cttcctattc                                               20

<210> SEQ ID NO 343
<211> LENGTH: 20
<212> TYPE: DNA
<213> ORGANISM: Homo sapiens

<400> SEQUENCE: 343
atggacgggg aagacttcca                                               20

<210> SEQ ID NO 344
<211> LENGTH: 20
```

```
<212> TYPE: DNA
<213> ORGANISM: Homo sapiens

<400> SEQUENCE: 344
ttaccaccct gaggagctgc                                          20

<210> SEQ ID NO 345
<211> LENGTH: 20
<212> TYPE: DNA
<213> ORGANISM: Homo sapiens

<400> SEQUENCE: 345
agcctatgaa ttctaccatg                                          20

<210> SEQ ID NO 346
<211> LENGTH: 20
<212> TYPE: DNA
<213> ORGANISM: Homo sapiens

<400> SEQUENCE: 346
cgacctgaag attgaagtga                                          20

<210> SEQ ID NO 347
<211> LENGTH: 20
<212> TYPE: DNA
<213> ORGANISM: Homo sapiens

<400> SEQUENCE: 347
gtgcccgtgc tgggaagctc                                          20

<210> SEQ ID NO 348
<211> LENGTH: 20
<212> TYPE: DNA
<213> ORGANISM: Homo sapiens

<400> SEQUENCE: 348
tgggagcctg cctgccttca                                          20

<210> SEQ ID NO 349
<211> LENGTH: 20
<212> TYPE: DNA
<213> ORGANISM: Homo sapiens

<400> SEQUENCE: 349
gctgtggcca ggccagcacc                                          20

<210> SEQ ID NO 350
<211> LENGTH: 20
<212> TYPE: DNA
<213> ORGANISM: Homo sapiens

<400> SEQUENCE: 350
tgcgaccatg aggagattcg                                          20

<210> SEQ ID NO 351
<211> LENGTH: 20
<212> TYPE: DNA
<213> ORGANISM: Homo sapiens

<400> SEQUENCE: 351
cctgatggcc atgaacagca                                          20

<210> SEQ ID NO 352
<211> LENGTH: 20
```

```
<212> TYPE: DNA
<213> ORGANISM: Homo sapiens

<400> SEQUENCE: 352
ggccaaggac caatgcagta                                           20

<210> SEQ ID NO 353
<211> LENGTH: 20
<212> TYPE: DNA
<213> ORGANISM: Homo sapiens

<400> SEQUENCE: 353
acccagagcg aggctgggag                                           20

<210> SEQ ID NO 354
<211> LENGTH: 20
<212> TYPE: DNA
<213> ORGANISM: Homo sapiens

<400> SEQUENCE: 354
ctgggaagct ccacgctcct                                           20

<210> SEQ ID NO 355
<211> LENGTH: 20
<212> TYPE: DNA
<213> ORGANISM: Homo sapiens

<400> SEQUENCE: 355
aagcaaagac atgtccacag                                           20

<210> SEQ ID NO 356
<211> LENGTH: 20
<212> TYPE: DNA
<213> ORGANISM: Homo sapiens

<400> SEQUENCE: 356
gagctggact tggagacact                                           20

<210> SEQ ID NO 357
<211> LENGTH: 20
<212> TYPE: DNA
<213> ORGANISM: Homo sapiens

<400> SEQUENCE: 357
aactgccctc ctcacaatag                                           20

<210> SEQ ID NO 358
<211> LENGTH: 20
<212> TYPE: DNA
<213> ORGANISM: Homo sapiens

<400> SEQUENCE: 358
ggtggcagca cctcacattt                                           20

<210> SEQ ID NO 359
<211> LENGTH: 20
<212> TYPE: DNA
<213> ORGANISM: Homo sapiens

<400> SEQUENCE: 359
agcagctgct ccacgcccaa                                           20

<210> SEQ ID NO 360
<211> LENGTH: 20
```

```
<212> TYPE: DNA
<213> ORGANISM: Homo sapiens

<400> SEQUENCE: 360
agagttcttg ggagcagcgc                                              20

<210> SEQ ID NO 361
<211> LENGTH: 20
<212> TYPE: DNA
<213> ORGANISM: Homo sapiens

<400> SEQUENCE: 361
atttgagtcc tacctgctgc                                              20

<210> SEQ ID NO 362
<211> LENGTH: 20
<212> TYPE: DNA
<213> ORGANISM: Homo sapiens

<400> SEQUENCE: 362
gacccacctg gtggcagcac                                              20

<210> SEQ ID NO 363
<211> LENGTH: 20
<212> TYPE: DNA
<213> ORGANISM: Homo sapiens

<400> SEQUENCE: 363
agactccgag aacatgacca                                              20

<210> SEQ ID NO 364
<211> LENGTH: 20
<212> TYPE: DNA
<213> ORGANISM: Homo sapiens

<400> SEQUENCE: 364
ttctccatgg accagactga                                              20

<210> SEQ ID NO 365
<211> LENGTH: 20
<212> TYPE: DNA
<213> ORGANISM: Homo sapiens

<400> SEQUENCE: 365
ccatgaggag attcgtgaga                                              20

<210> SEQ ID NO 366
<211> LENGTH: 20
<212> TYPE: DNA
<213> ORGANISM: Homo sapiens

<400> SEQUENCE: 366
tttggataac gacctgaaga                                              20

<210> SEQ ID NO 367
<211> LENGTH: 20
<212> TYPE: DNA
<213> ORGANISM: Homo sapiens

<400> SEQUENCE: 367
ctcctgcaag gagggggacct                                             20

<210> SEQ ID NO 368
<211> LENGTH: 20
```

```
<212> TYPE: DNA
<213> ORGANISM: Homo sapiens

<400> SEQUENCE: 368
gtgttctatg agctggccca                                              20

<210> SEQ ID NO 369
<211> LENGTH: 20
<212> TYPE: DNA
<213> ORGANISM: Homo sapiens

<400> SEQUENCE: 369
tggcagcacc tcacatttga                                              20

<210> SEQ ID NO 370
<211> LENGTH: 20
<212> TYPE: DNA
<213> ORGANISM: Homo sapiens

<400> SEQUENCE: 370
ccgaagctga ccagcagatg                                              20

<210> SEQ ID NO 371
<211> LENGTH: 20
<212> TYPE: DNA
<213> ORGANISM: Homo sapiens

<400> SEQUENCE: 371
ggaccagact gaatccctgt                                              20

<210> SEQ ID NO 372
<211> LENGTH: 20
<212> TYPE: DNA
<213> ORGANISM: Mus musculus

<400> SEQUENCE: 372
ccctacgggg ttaaggaacc                                              20

<210> SEQ ID NO 373
<211> LENGTH: 20
<212> TYPE: DNA
<213> ORGANISM: Mus musculus

<400> SEQUENCE: 373
cggggttaag gaacccaggt                                              20

<210> SEQ ID NO 374
<211> LENGTH: 20
<212> TYPE: DNA
<213> ORGANISM: Mus musculus

<400> SEQUENCE: 374
ttaaggaacc caggtgctcc                                              20

<210> SEQ ID NO 375
<211> LENGTH: 20
<212> TYPE: DNA
<213> ORGANISM: Mus musculus

<400> SEQUENCE: 375
gcgacaatga cagctgacaa                                              20

<210> SEQ ID NO 376
<211> LENGTH: 20
```

```
<212> TYPE: DNA
<213> ORGANISM: Mus musculus

<400> SEQUENCE: 376
aatgacagct gacaaggaga                                              20

<210> SEQ ID NO 377
<211> LENGTH: 20
<212> TYPE: DNA
<213> ORGANISM: Mus musculus

<400> SEQUENCE: 377
gcaaggagac ggaggtcttc                                              20

<210> SEQ ID NO 378
<211> LENGTH: 20
<212> TYPE: DNA
<213> ORGANISM: Mus musculus

<400> SEQUENCE: 378
acagtgtgag ctcccacctg                                              20

<210> SEQ ID NO 379
<211> LENGTH: 20
<212> TYPE: DNA
<213> ORGANISM: Mus musculus

<400> SEQUENCE: 379
atgcgcctgg ccatcagctt                                              20

<210> SEQ ID NO 380
<211> LENGTH: 20
<212> TYPE: DNA
<213> ORGANISM: Mus musculus

<400> SEQUENCE: 380
atggataact tgtacctgaa                                              20

<210> SEQ ID NO 381
<211> LENGTH: 20
<212> TYPE: DNA
<213> ORGANISM: Mus musculus

<400> SEQUENCE: 381
aacttgtacc tgaaagcctt                                              20

<210> SEQ ID NO 382
<211> LENGTH: 20
<212> TYPE: DNA
<213> ORGANISM: Mus musculus

<400> SEQUENCE: 382
aagccttgga gggtttcatt                                              20

<210> SEQ ID NO 383
<211> LENGTH: 20
<212> TYPE: DNA
<213> ORGANISM: Mus musculus

<400> SEQUENCE: 383
catcagcaag ttcatgggac                                              20

<210> SEQ ID NO 384
<211> LENGTH: 20
```

```
<212> TYPE: DNA
<213> ORGANISM: Mus musculus

<400> SEQUENCE: 384
ttcatgggac ttacccaggt                                        20

<210> SEQ ID NO 385
<211> LENGTH: 20
<212> TYPE: DNA
<213> ORGANISM: Mus musculus

<400> SEQUENCE: 385
ttacccaggt agaactaaca                                        20

<210> SEQ ID NO 386
<211> LENGTH: 20
<212> TYPE: DNA
<213> ORGANISM: Mus musculus

<400> SEQUENCE: 386
caggacacag catctttgac                                        20

<210> SEQ ID NO 387
<211> LENGTH: 20
<212> TYPE: DNA
<213> ORGANISM: Mus musculus

<400> SEQUENCE: 387
atctttgact tcactcatcc                                        20

<210> SEQ ID NO 388
<211> LENGTH: 20
<212> TYPE: DNA
<213> ORGANISM: Mus musculus

<400> SEQUENCE: 388
accgagcgtg acttcttcat                                        20

<210> SEQ ID NO 389
<211> LENGTH: 20
<212> TYPE: DNA
<213> ORGANISM: Mus musculus

<400> SEQUENCE: 389
gacttcttca tgaggatgaa                                        20

<210> SEQ ID NO 390
<211> LENGTH: 20
<212> TYPE: DNA
<213> ORGANISM: Mus musculus

<400> SEQUENCE: 390
cttcatgagg atgaagtgca                                        20

<210> SEQ ID NO 391
<211> LENGTH: 20
<212> TYPE: DNA
<213> ORGANISM: Mus musculus

<400> SEQUENCE: 391
caacagaggc cggactgtca                                        20

<210> SEQ ID NO 392
<211> LENGTH: 20
```

```
<212> TYPE: DNA
<213> ORGANISM: Mus musculus

<400> SEQUENCE: 392
tgcaccgggc aagtgagagt                                              20

<210> SEQ ID NO 393
<211> LENGTH: 20
<212> TYPE: DNA
<213> ORGANISM: Mus musculus

<400> SEQUENCE: 393
aagtgagagt ctacaacaac                                              20

<210> SEQ ID NO 394
<211> LENGTH: 20
<212> TYPE: DNA
<213> ORGANISM: Mus musculus

<400> SEQUENCE: 394
atcatcatgt gtgagccaat                                              20

<210> SEQ ID NO 395
<211> LENGTH: 20
<212> TYPE: DNA
<213> ORGANISM: Mus musculus

<400> SEQUENCE: 395
gtgagccaat ccagcaccca                                              20

<210> SEQ ID NO 396
<211> LENGTH: 20
<212> TYPE: DNA
<213> ORGANISM: Mus musculus

<400> SEQUENCE: 396
ttcctgagcc gccacagcat                                              20

<210> SEQ ID NO 397
<211> LENGTH: 20
<212> TYPE: DNA
<213> ORGANISM: Mus musculus

<400> SEQUENCE: 397
gaactgattg gttaccaccc                                              20

<210> SEQ ID NO 398
<211> LENGTH: 20
<212> TYPE: DNA
<213> ORGANISM: Mus musculus

<400> SEQUENCE: 398
agtcaccaga acttgtgcac                                              20

<210> SEQ ID NO 399
<211> LENGTH: 20
<212> TYPE: DNA
<213> ORGANISM: Mus musculus

<400> SEQUENCE: 399
ccagaacttg tgcaccaagg                                              20

<210> SEQ ID NO 400
<211> LENGTH: 20
```

```
<212> TYPE: DNA
<213> ORGANISM: Mus musculus

<400> SEQUENCE: 400
tggctggaga cccaggggac                                       20

<210> SEQ ID NO 401
<211> LENGTH: 20
<212> TYPE: DNA
<213> ORGANISM: Mus musculus

<400> SEQUENCE: 401
ggagacccag gggacggtca                                       20

<210> SEQ ID NO 402
<211> LENGTH: 20
<212> TYPE: DNA
<213> ORGANISM: Mus musculus

<400> SEQUENCE: 402
cccaggggac ggtcatctac                                       20

<210> SEQ ID NO 403
<211> LENGTH: 20
<212> TYPE: DNA
<213> ORGANISM: Mus musculus

<400> SEQUENCE: 403
gggacggtca tctacaaccc                                       20

<210> SEQ ID NO 404
<211> LENGTH: 20
<212> TYPE: DNA
<213> ORGANISM: Mus musculus

<400> SEQUENCE: 404
gacgtggtgt tctccatgga                                       20

<210> SEQ ID NO 405
<211> LENGTH: 20
<212> TYPE: DNA
<213> ORGANISM: Mus musculus

<400> SEQUENCE: 405
ggtgttctcc atggaccaga                                       20

<210> SEQ ID NO 406
<211> LENGTH: 20
<212> TYPE: DNA
<213> ORGANISM: Mus musculus

<400> SEQUENCE: 406
tggccatgaa cagcatcttt                                       20

<210> SEQ ID NO 407
<211> LENGTH: 20
<212> TYPE: DNA
<213> ORGANISM: Mus musculus

<400> SEQUENCE: 407
gagcaactac ctgttcacca                                       20

<210> SEQ ID NO 408
<211> LENGTH: 20
```

```
<212> TYPE: DNA
<213> ORGANISM: Mus musculus

<400> SEQUENCE: 408
aaggaggagc ccgaggagct                                               20

<210> SEQ ID NO 409
<211> LENGTH: 20
<212> TYPE: DNA
<213> ORGANISM: Mus musculus

<400> SEQUENCE: 409
cctcagccta tggcaaggcc                                               20

<210> SEQ ID NO 410
<211> LENGTH: 20
<212> TYPE: DNA
<213> ORGANISM: Mus musculus

<400> SEQUENCE: 410
gcctatggca aggccatcct                                               20

<210> SEQ ID NO 411
<211> LENGTH: 20
<212> TYPE: DNA
<213> ORGANISM: Mus musculus

<400> SEQUENCE: 411
agctgctcca cgcccagcag                                               20

<210> SEQ ID NO 412
<211> LENGTH: 20
<212> TYPE: DNA
<213> ORGANISM: Mus musculus

<400> SEQUENCE: 412
cagtacccag acggacttca                                               20

<210> SEQ ID NO 413
<211> LENGTH: 20
<212> TYPE: DNA
<213> ORGANISM: Mus musculus

<400> SEQUENCE: 413
aagtacccgc agcagttgga                                               20

<210> SEQ ID NO 414
<211> LENGTH: 20
<212> TYPE: DNA
<213> ORGANISM: Mus musculus

<400> SEQUENCE: 414
ctgggagcaa agggtccctg                                               20

<210> SEQ ID NO 415
<211> LENGTH: 20
<212> TYPE: DNA
<213> ORGANISM: Mus musculus

<400> SEQUENCE: 415
tgctgtggcc aggccagcac                                               20

<210> SEQ ID NO 416
<211> LENGTH: 20
```

```
<212> TYPE: DNA
<213> ORGANISM: Mus musculus

<400> SEQUENCE: 416
ctcatgtctc catgttcaag                                              20

<210> SEQ ID NO 417
<211> LENGTH: 20
<212> TYPE: DNA
<213> ORGANISM: Mus musculus

<400> SEQUENCE: 417
catgttcaag atgaggtctg                                              20

<210> SEQ ID NO 418
<211> LENGTH: 20
<212> TYPE: DNA
<213> ORGANISM: Mus musculus

<400> SEQUENCE: 418
tcaagatgag gtctgcaaag                                              20

<210> SEQ ID NO 419
<211> LENGTH: 20
<212> TYPE: DNA
<213> ORGANISM: Mus musculus

<400> SEQUENCE: 419
gccctgtcca acaagctgaa                                              20

<210> SEQ ID NO 420
<211> LENGTH: 20
<212> TYPE: DNA
<213> ORGANISM: Mus musculus

<400> SEQUENCE: 420
tccaggcacc agcagttcac                                              20

<210> SEQ ID NO 421
<211> LENGTH: 20
<212> TYPE: DNA
<213> ORGANISM: Mus musculus

<400> SEQUENCE: 421
atgaagagcc tcatgggcgg                                              20

<210> SEQ ID NO 422
<211> LENGTH: 20
<212> TYPE: DNA
<213> ORGANISM: Mus musculus

<400> SEQUENCE: 422
tcatgggcgg gacctgtcct                                              20

<210> SEQ ID NO 423
<211> LENGTH: 20
<212> TYPE: DNA
<213> ORGANISM: Mus musculus

<400> SEQUENCE: 423
gacctgtcct ttgatgcctg                                              20

<210> SEQ ID NO 424
<211> LENGTH: 20
```

```
<212> TYPE: DNA
<213> ORGANISM: Mus musculus

<400> SEQUENCE: 424
aaggtgtcag gcgtggccag                                          20

<210> SEQ ID NO 425
<211> LENGTH: 20
<212> TYPE: DNA
<213> ORGANISM: Mus musculus

<400> SEQUENCE: 425
agtcgactgc tggggccatc                                          20

<210> SEQ ID NO 426
<211> LENGTH: 20
<212> TYPE: DNA
<213> ORGANISM: Mus musculus

<400> SEQUENCE: 426
actgctgggg ccatcgttcg                                          20

<210> SEQ ID NO 427
<211> LENGTH: 20
<212> TYPE: DNA
<213> ORGANISM: Mus musculus

<400> SEQUENCE: 427
ccatcgttcg agccttacct                                          20

<210> SEQ ID NO 428
<211> LENGTH: 20
<212> TYPE: DNA
<213> ORGANISM: Mus musculus

<400> SEQUENCE: 428
gaactgacca gatatgactg                                          20

<210> SEQ ID NO 429
<211> LENGTH: 20
<212> TYPE: DNA
<213> ORGANISM: Mus musculus

<400> SEQUENCE: 429
gaccagatat gactgtgagg                                          20

<210> SEQ ID NO 430
<211> LENGTH: 20
<212> TYPE: DNA
<213> ORGANISM: Mus musculus

<400> SEQUENCE: 430
gatatgactg tgaggtgaac                                          20

<210> SEQ ID NO 431
<211> LENGTH: 20
<212> TYPE: DNA
<213> ORGANISM: Mus musculus

<400> SEQUENCE: 431
gactgtgagg tgaacgtgcc                                          20

<210> SEQ ID NO 432
<211> LENGTH: 20
```

```
<212> TYPE: DNA
<213> ORGANISM: Mus musculus

<400> SEQUENCE: 432
tgaggtgaac gtgcccgtgc                                          20

<210> SEQ ID NO 433
<211> LENGTH: 20
<212> TYPE: DNA
<213> ORGANISM: Mus musculus

<400> SEQUENCE: 433
acactcctgc agggagaga                                           20

<210> SEQ ID NO 434
<211> LENGTH: 20
<212> TYPE: DNA
<213> ORGANISM: Mus musculus

<400> SEQUENCE: 434
aggggagaga ccttctcaga                                          20

<210> SEQ ID NO 435
<211> LENGTH: 20
<212> TYPE: DNA
<213> ORGANISM: Mus musculus

<400> SEQUENCE: 435
ccttctcaga gctctggacc                                          20

<210> SEQ ID NO 436
<211> LENGTH: 20
<212> TYPE: DNA
<213> ORGANISM: Mus musculus

<400> SEQUENCE: 436
ctggaccagg ccacctgagc                                          20

<210> SEQ ID NO 437
<211> LENGTH: 20
<212> TYPE: DNA
<213> ORGANISM: Mus musculus

<400> SEQUENCE: 437
aactcaagtg ttcttgttct                                          20

<210> SEQ ID NO 438
<211> LENGTH: 20
<212> TYPE: DNA
<213> ORGANISM: Mus musculus

<400> SEQUENCE: 438
actgtcatgt ctcaactgtt                                          20

<210> SEQ ID NO 439
<211> LENGTH: 20
<212> TYPE: DNA
<213> ORGANISM: Mus musculus

<400> SEQUENCE: 439
tcaagatgag gttagtgaca                                          20

<210> SEQ ID NO 440
<211> LENGTH: 20
```

<212> TYPE: DNA
<213> ORGANISM: Mus musculus

<400> SEQUENCE: 440
cccagaaaag tgactcctgt                                                    20

<210> SEQ ID NO 441
<211> LENGTH: 20
<212> TYPE: DNA
<213> ORGANISM: Mus musculus

<400> SEQUENCE: 441
cagtgtcctg agactgtatg                                                    20

<210> SEQ ID NO 442
<211> LENGTH: 20
<212> TYPE: DNA
<213> ORGANISM: Artificial Sequence
<220> FEATURE:
<223> OTHER INFORMATION: Synthetic Construct

<400> SEQUENCE: 442
ttcgcggctg gacgattcag                                                    20

<210> SEQ ID NO 443
<211> LENGTH: 20
<212> TYPE: DNA
<213> ORGANISM: Artificial Sequence
<220> FEATURE:
<223> OTHER INFORMATION: Synthetic Construct

<400> SEQUENCE: 443
cctcatggtc gcaggatga                                                     20

<210> SEQ ID NO 444
<211> LENGTH: 20
<212> TYPE: DNA
<213> ORGANISM: Artificial Sequence
<220> FEATURE:
<223> OTHER INFORMATION: Synthetic Construct

<400> SEQUENCE: 444
tctcctcatg gtcgcaggga                                                    20

<210> SEQ ID NO 445
<211> LENGTH: 20
<212> TYPE: DNA
<213> ORGANISM: Artificial Sequence
<220> FEATURE:
<223> OTHER INFORMATION: Synthetic Construct

<400> SEQUENCE: 445
tcatggtcac atggatgagt                                                    20

<210> SEQ ID NO 446
<211> LENGTH: 20
<212> TYPE: DNA
<213> ORGANISM: Artificial Sequence
<220> FEATURE:
<223> OTHER INFORMATION: Synthetic Construct

<400> SEQUENCE: 446
cctcatggtc acatggatga                                                    20

<210> SEQ ID NO 447
<211> LENGTH: 20

```
<212> TYPE: DNA
<213> ORGANISM: Artificial Sequence
<220> FEATURE:
<223> OTHER INFORMATION: Synthetic Construct

<400> SEQUENCE: 447
ctcatggtca catggatgag                                              20

<210> SEQ ID NO 448
<211> LENGTH: 20
<212> TYPE: DNA
<213> ORGANISM: Artificial Sequence
<220> FEATURE:
<223> OTHER INFORMATION: Synthetic Construct

<400> SEQUENCE: 448
atttcctcat ggtcacatgg                                              20

<210> SEQ ID NO 449
<211> LENGTH: 20
<212> TYPE: DNA
<213> ORGANISM: Artificial Sequence
<220> FEATURE:
<223> OTHER INFORMATION: Synthetic Construct

<400> SEQUENCE: 449
aaaccctcca aggctttcag                                              20

<210> SEQ ID NO 450
<211> LENGTH: 20
<212> TYPE: DNA
<213> ORGANISM: Artificial Sequence
<220> FEATURE:
<223> OTHER INFORMATION: Synthetic Construct

<400> SEQUENCE: 450
tcctcatggt cgcagggatg                                              20

<210> SEQ ID NO 451
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: n = inosine
<220> FEATURE:
<221> NAME/KEY: misc_feature
<222> LOCATION: (15)..(15)
<223> OTHER INFORMATION: n = pseudouridine

<400> SEQUENCE: 451
tcctcatggt cncanggatg                                              20

<210> SEQ ID NO 452
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: n = inosine
<220> FEATURE:
<221> NAME/KEY: misc_feature
<222> LOCATION: (14)..(14)
<223> OTHER INFORMATION: n = pseudouridine
```

-continued

<400> SEQUENCE: 452
cctcatggtc ncanggatga                                                20

<210> SEQ ID NO 453
<211> LENGTH: 20
<212> TYPE: DNA
<213> ORGANISM: Artificial Sequence
<220> FEATURE:
<223> OTHER INFORMATION: Control Oligonucleotide
<220> FEATURE:
<221> NAME/KEY: misc_feature
<222> LOCATION: (1)..(20)
<223> OTHER INFORMATION: equal mixture of the bases A, C, G and T

<400> SEQUENCE: 453
nnnnnnnnnn nnnnnnnnnn                                                20

<210> SEQ ID NO 454
<211> LENGTH: 20
<212> TYPE: DNA
<213> ORGANISM: Artificial Sequence
<220> FEATURE:
<223> OTHER INFORMATION: Control Oligonucleotide

<400> SEQUENCE: 454
ccttccctga aggttcctcc                                                20

<210> SEQ ID NO 455
<211> LENGTH: 19
<212> TYPE: DNA
<213> ORGANISM: Artificial Sequence
<220> FEATURE:
<223> OTHER INFORMATION: Synthetic Construct

<400> SEQUENCE: 455
cgagaggcgg acgggaccg                                                 19

<210> SEQ ID NO 456
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxythymidine

<400> SEQUENCE: 456
cgagaggcgg acgggaccgt t                                              21

<210> SEQ ID NO 457
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxythymidine

<400> SEQUENCE: 457
cggtcccgtc cgcctctcgt t                                              21

<210> SEQ ID NO 458
<211> LENGTH: 19

```
<212> TYPE: DNA
<213> ORGANISM: Artificial Sequence
<220> FEATURE:
<223> OTHER INFORMATION: Synthetic Construct

<400> SEQUENCE: 458
cggtcccgtc cgcctctcg                                                    19
```

MODULATION OF HIF1α AND HIF2α EXPRESSION

RELATED APPLICATIONS

This application is a continuation of U.S. application Ser. No. 11/527,876, filed Sep. 26, 2006, which is a continuation of U.S. application Ser. No. 10/719,370, filed Nov. 21, 2003, which is a continuation-in-part of U.S. application Ser. No. 10/304,126, filed Nov. 23, 2002. The contents of each application are hereby incorporated by reference in their entirety.

INCORPORATION OF SEQUENCE LISTING

A computer-readable form of the sequence listing, on diskette, containing the file name PTS0070USC2SEQ.txt, which is 280 kilo-bytes and was created on Dec. 7, 2009, is herein incorporated by reference.

FIELD OF THE INVENTION

The present invention provides compositions and methods for modulating the expression of HIF1α (HIF1α) and hypoxia-inducible factor 2 alpha (HIF2α). In particular, this invention relates to compounds, particularly oligonucleotide compounds, which, in preferred embodiments, hybridize with nucleic acid molecules encoding HIF1α and HIF2α. Such compounds are shown herein to modulate the expression of HIF1α and HIF2α.

BACKGROUND OF THE INVENTION

Oxygen homeostasis is an essential cellular and systemic function; hypoxia leads to metabolic demise, but this must be balanced by the risk of oxidative damage to cellular lipids, nucleic acids, and proteins resulting from hyperoxia. As a result, cellular and systemic oxygen concentrations are tightly regulated via response pathways that affect the activity and expression of a multitude of cellular proteins. This balance is disrupted in heart disease, cancer, cerebrovascular disease, and chronic obstructive pulmonary disease (Semenza, *Genes Dev.*, 2000, 14, 1983-1991)(Semenza, G., 2001, *Trends Mol. Med.*, 7, 345-350. Cells are typically cultured in the laboratory at an ambient oxygen concentration of 21%, but cells in the human body are exposed to much lower oxygen concentrations ranging from 16% in the lungs to less than 6% in most other organs of the body—often significantly less in tumors. Semenza G., 2001, *Trends Mol. Med.*, 7, 345-350.

Solid tumor growth depends on a continuous supply of oxygen and nutrients through neovascularization (angiogenesis). Tumors often become hypoxic, often because new blood vessels are aberrant and have poor blood flow. Cancer cells make adaptive changes that allow them to proliferate even at hypoxia. These changes include an increase in glycolysis and an increase in production of angiogenic factors. Hypoxia in tumors is associated with resistance to radio-and chemotherapy, and thus is an indicator of poor survival.

The transcriptional complex, hypoxia inducible factor (HIF), is a key regulator of oxygen homeostasis. Hypoxia induces the expression of genes participating in many cellular and physiological processes, including oxygen transport and iron metabolism, erythropoiesis, angiogenesis, glycolysis and glucose uptake, transcription, metabolism, pH regulation, growth-factor signaling, response to stress and cell adhesion. These gene products participate in either increasing oxygen delivery to hypoxic tissues or activating an alternative metabolic pathway (glycolysis) which does not require oxygen. Hypoxia-induced pathways, in addition to being required for normal cellular processes, can also aid tumor growth by allowing or aiding angiogenesis, immortalization, genetic instability, tissue invasion and metastasis (Harris, *Nat. Rev. Cancer,* 2002, 2, 38-47; Maxwell et al., *Curr. Opin. Genet. Dev.,* 2001, 11, 293-299).

HIF is a heterodimer composed of an alpha subunit complexed with a beta subunit, both of which are basic helix-loop-helix transcription factors. The beta subunit of HIF is a constitutive nuclear protein. The alpha subunit is the regulatory subunit specific to the oxygen response pathway, and can be one of three subunits, HIF1α, 2 alpha or 3 alpha (HIF-1α, HIF-2α and HIF-3α, respectively) (Maxwell et al., *Curr. Opin. Genet. Dev.,* 2001, 11, 293-299; Safran and Kaelin, *J. Clin. Invest.,* 2003, 111, 779-783).

The transcription factor hypoxia-inducible factor 1 (HIF-1) plays an essential role in homeostatic responses to hypoxia by binding to the DNA sequence 5'-TACGTGCT-3' and activating the transcription of dozens of genes in vivo under hypoxic conditions (Wang and Semenza, *J. Biol. Chem.,* 1995, 270, 1230-1237). These gene products participate in either increasing oxygen delivery to hypoxic tissues or activating an alternative metabolic pathway (glycolysis) which does not require oxygen. This list includes: aldolase C, enolase 1, glucose transporter 1, glucose transporter 3, glyceraldehyde-3-phosphate dehydrogenase, hexokinase 1, hexokinase 2, insulin-like growth factor-2 (IGF-2), IGF binding protein 1, IGF binding protein 3, lactate dehydrogenase A, phosphoglycerate kinase 1, pyruvate kinase M, p21, transforming growth factor B3, ceruloplasmin, erythropoietin, transferrin, transferrin receptor, alb-adrenergic receptor, adrenomedullin, endothelin-1, heme oxygenase 1, nitric oxide synthase 2, plasminogen activator inhibitor 1, vascular endothelial growth factor (VEGF), VEGF receptor FTL-1, and p35 (Semenza, *Genes Dev.,* 2000, 14, 1983-1991). Expression of HIF1α is also sensitive to oxygen concentration: increased levels of protein are detected in cells exposed to 1% oxygen and these decay rapidly upon return of the cells to 20% oxygen (Wang et al., *Proc. Natl. Acad. Sci. U.S.A.,* 1995, 92, 5510-5514).

Hypoxia-inducible factor-1 alpha is a heterodimer composed of a 120 kDa alpha subunit complexed with a 91 to 94 kDa beta subunit, both of which contain a basic helix-loop-helix (Wang and Semenza, *J. Biol. Chem.,* 1995, 270, 1230-1237). The gene encoding hypoxia-inducible factor-1 alpha (HIF1α, also called HIF-1 alpha, HIF1A, HIF-1A, HIF1-A, and MOP1) was cloned in 1995 (Wang et al., *Proc. Natl. Acad. Sci. U.S.A.,* 1995, 92, 5510-5514). A nucleic acid sequence encoding HIF1α is disclosed and claimed in U.S. Pat. No. 5,882,914, as are expression vectors expressing the recombinant DNA, and host cells containing said vectors (Semenza, 1999).

HIF1α expression and HIF-1 transcriptional activity are precisely regulated by cellular oxygen concentration. The beta subunit is a constitutive nuclear protein, while the alpha subunit is the regulatory subunit. HIF1α mRNA is expressed at low levels in tissue culture cells, but it is markedly induced by hypoxia or ischemia in vivo (Yu et al., *J. Clin. Invest.,* 1999, 103, 691-696). HIF1α protein is negatively regulated in non-hypoxic cells by ubiquitination and proteasomal degradation (Huang et al., *Proc. Natl. Acad. Sci. U.S.A.,* 1998, 95, 7987-7992). Under hypoxic conditions, the degradation pathway is inhibited, HIF1α protein levels increase dramatically, and the fraction that is ubiquitinated decreases. HIP1α then translocates to the nucleus and dimerizes with a beta subunit (Sutter et al., *Proc. Natl. Acad. Sci. U.S.A.*, 2000, 97, 4748-4753).

A natural antisense transcript that is complementary to the 3' untranslated region of HIF1α mRNA has been discovered and is named "aHIF" (Thrash-Bingham and Tartof, *J. Natl. Cancer Inst.*, 1999, 91, 143-151). This is the first case of overexpression of a natural antisense transcript exclusively associated with a specific human malignant disease. aHIF is specifically overexpressed in nonpapillary clear-cell renal carcinoma under both normoxic and hypoxic conditions, but not in papillary renal carcinoma. Although aHIF is not further induced by hypoxia in nonpapillary disease, it can be induced in lymphocytes where there is a concomitant decrease in HIF1α mRNA.

HIF1α plays an important role in promoting tumor progression and is overexpressed in common human cancers, including breast, colon, lung, and prostate carcinoma. Overexpression of HIFs is sometimes observed in cancers, such as clear cel renal cell carcinoma, even at normoxia. Mutations that inactivate tumor suppressor genes or activate oncogenes have, as one of their consequences, upregulation of HIF1α activity, either through an increase in HIF1α protein expression, HIF1α transcriptional activity, or both (Semenza, *Pediatr. Res.*, 2001, 49, 614-617).

Until a tumor establishes a blood supply, the hypoxic conditions limit tumor growth. Subsequent increases in HIF1α activity result in increased expression of target genes such as vascular endothelial growth factor (VEGF). VEGF expression is essential for vascularization and the establishment of angiogenesis in most solid tumors (Iyer et al., *Genes Dev.*, 1998, 12, 149-162). A significant association between hypoxia-inducible factor-1 alpha, VEGF overexpression and tumor grade is also seen in human glioblastoma multiforme, the highest grade glioma in which mean patient survival time is less than one year. The rapidly proliferating tumor outgrows its blood supply, resulting in extensive necrosis, and these regions express high levels of HIF1α protein and VEGF mRNA, suggesting a response of the tumor to hypoxia (Zagzag et al., *Cancer*, 2000, 88, 2606-2618).

The action of the von Hippel-Landau (VHL) tumor suppressor gene product is implicated in hypoxic gene regulation, in both normal and diseased cells. Individuals with VHL disease are predisposed to renal cysts, clear cell renal carcinoma, phaeochromocytoma, haemangioblastomas of the central nervous system, angiomas of the retina, islet cell tumors of the pancreas, and endolymphatic sac tumors (Pugh and Ratcliffe, *Semin. Cancer. Biol.*, 2003, 13, 83-89). The VHL gene product participates in ubiquitin-mediated proteolysis by acting as the recognition component of the E3-ubiquitin ligase complex involved in the degradation of hypoxia-inducible factor alpha subunits (Cockman et al., *J. Biol. Chem.*, 2000, 275, 25733-25741; Ohh et al., *Nat. Cell Biol.*, 2000, 2, 423-427). In normal cells, VHL/HIF complexes form and target HIF alpha subunits for destruction (Maxwell et al., *Nature*, 1999, 399, 271-275). This is proposed to occur through hydroxylation of the oxygen-dependent domain of HIF2α and subsequent recognition by the VHL gene product, as recognition of a homologous oxygen-dependent domain is the mechanism by which the VHL protein recognizes HIF1α (Maxwell et al., *Nature*, 1999, 399, 271-275). HIF2α is in fact hydroxylated by the enzyme prolyl 4-hydroxylases in vitro (Hirsila et al., *J. Biol. Chem.*, 2003).

The p53 tumor suppressor also targets HIF1α for degradation by the proteasome. Loss of p53 activity occurs in the majority of human cancers and indicates that amplification of normal HIF1α levels contributes to the angiogenic switch during tumorigenesis (Ravi et al., *Genes Dev.*, 2000, 14, 34-44).

A mouse model of pulmonary hypertension has shown that local inhibition of HIF1α activity in the lung might represent a therapeutic strategy for treating or preventing pulmonary hypertension in at risk individuals. In pulmonary hypertension hypoxia-induced vascular remodeling leads to decreased blood flow, which leads to progressive right heart failure and death. This hypoxia-induced vascular remodeling is markedly impaired in mice that are partially HIF1α deficient (Yu et al., *J. Clin. Invest.*, 1999, 103, 691-696). Decreased vascular density and retarded solid tumor growth is also seen in mouse embryonic stem cells which are deficient for HIF1α (Ryan et al., *Embo J*, 1998, 17, 3005-3015).

During hypoxia, cells shift to a glycolytic metabolic mode for their energetic needs and HIF1α is known to upregulate the expression of many glycolytic genes. HIF1α may play a pivotal role in the Warburg effect in tumors, a paradoxical situation in which tumor cells growing under normoxic conditions show elevated glycolytic rates, which enhances tumor growth and expansion. HIF1α mediates the expression of 6-phosphofructo-2-kinase/fructose-2,6-bisphosphatase-3, a gene whose protein product maintains levels of the key regulator of glycolytic flux, fructose-2,6-bisphosphate (Minchenko et al., *J. Biol. Chem.*, 2001, 14, 14).

Currently, there are no known therapeutic agents which effectively inhibit the synthesis of HIF1α and to date, investigative strategies aimed at modulating HIF1α function have involved the use of antisense expression vectors and oligonucleotides. These studies have served to define the involvement of HIF1α in disease progression and to identify novel roles of HIF1α in vivo including unique roles for HIF1α as a transcription factor under non-hypoxic conditions and as an inhibitor of gene expression.

Gene transfer of an antisense HIF1α plasmid has been shown to enhance the efficacy of cancer immunotherapy. Antisense therapy was shown to slow, but not eradicate, the growth of EL-4 tumors established in mice. In addition, endogenously expression of HIF1α was almost completely inhibited in these tumors. When antisense therapy was combined with T-cell costimulator B7-1 immunotherapy, the tumors completely and rapidly regressed within 1 week. Furthermore, when these tumor-free mice were rechallenged with EL-4 cells, no tumors emerged, indicating that systemic antitumor immunity had been achieved (Sun et al., *Gene Ther.*, 2001, 8, 638-645).

Activation of HIF1α is thought to aggravate heart failure by upregulation of cardiac ET-1, a gene product involved in heart failure and whose inhibition improves the survival rate of rats with heart failure. In a failing heart, a metabolic switch occurs, and HIF1α activates the expression of glycolytic enzymes as compensation for impaired b-oxidation of fatty acid. Another consequence of increased HIF1α activity is that in rat cardiomyocytes, HIF1α was shown to bind to the 5'-promoter region of the ET-1 gene and increase ET-1 expression. In vitro, an antisense oligonucleotide targeted to hypoxia-inducible factor-1 alphalargely inhibited the increased gene expression of ET-1, confirming the role of HIF1α in heart failure (Kakinuma et al., *Circulation*, 2001, 103, 2387-2394). This antisense oligonucleotide is comprised of 20 nucleotides and targets bases 11 to 31 of the rat HIF1α with GenBank accession number AF_057308 incorporated herein by reference.

Preeclampsia is a disorder of unknown etiology that is the leading cause of fetal and maternal morbidity and mortality. Defective downregulation of HIF1α may play a major role in the pathogenesis of preeclampsia. For most of the first trimester, the human fetus develops under hypoxic conditions but at 10-12 weeks the intervillous space opens, the fetus is exposed to maternal blood and at this stage the trophoblast cells invade the maternal decidua. The switch of the trophoblasts from a proliferative to an invasive phenotype is controlled by cellular oxygen concentration. The proliferative, non-invasive trophoblast phenotype appears to be maintained by HIF1α mediated expression of TGFbeta3 because treatment of human villous explants with an antisense oligonucleotide against HIF1α or TGF beta 3 induces invasion under hypoxic conditions. In this case the HIF1α antisense oligonucleotide was comprised of phosphorothioate oligonucleotides, 16 nucleotides in length, and targeted to the AUG codon (Caniggia et al., *J. Clin. Invest.*, 2000, 105, 577-587;. Caniggia et al., *Placenta*, 2000, 21 Suppl A, S25-30).

The human intestinal trefoil factor (ITF) gene product protects the epithelial barrier during episodes of intestinal hypoxia. The ITF gene promoter bears a binding site for hypoxia-inducible factor-1 alpha, and the function of HIF1α as a transcription factor for ITF was confirmed in vitro. T84 colonic epithelial cells were treated with a phosphorothioate antisense oligonucleotide, 15 nucleotides in length and targeted to the AUG codon of HIF1α and this resulted in a loss of ITF hypoxia inducibility (Furuta et al., *J. Exp. Med.*, 2001, 193, 1027-1034).

Human epidemiological and animal studies have associated inhalation of nickel dusts with an increased incidence of pulmonary fibrosis. Nickel transcriptionally activates plasminogen activator inhibitor (PAI-1), an inhibitor of fibrinolysis, through the HIF1α signaling pathway. This was evidenced by decreases in PAI-1 mRNA levels when human airway epithelial cells were treated with an antisense oligonucleotide directed against HIF1α identical to the one used in the preeclampsia study discussed above. These data may be critical for understanding the pathology of pulmonary fibrosis and other diseases associated with nickel exposure (Andrew et al., *Am J Physiol Lung Cell Mol Physiol*, 2001, 281, L607-615).

HIF1α is constitutively expressed in cerebral neurons under normoxic conditions. A second dimerization partner for HIF1α is ARNT2, a cerebral translocator homologous to hypoxia-inducible factor-1 beta. One splice variant of HIF1α found in rat neurons dimerizes with ARNT2 more avidly than it does with HIF1b, and the resulting hypoxia-inducible factor-1 alpha-ARNT2 heterodimer does not recognize the HIF1α binding site of the erythropoietin gene. This suggests that transcription of a different set of genes is controlled by the hypoxia-inducible factor-1 alpha-ARNT2 heterodimer controls in neurons under nonhypoxic conditions than the hypoxia-inducible factor-1 alpha-HIF1α heterodimer controls under hypoxic conditions. This was evidenced by antisense oligonucleotide downregulation of HIF1α expression in which the antisense oligonucleotide consisted of 16 phosphorothioate nucleotides targeted to bases 38 to 54 of the rat hypoxia-inducible factor-1 with GenBank accession number AF_057308 (Drutel et al., *Eur. J. Neurosci.*, 2000, 12, 3701-3708).

A role for HIF1α in mediating a down-regulatory pathway was recently discovered using antisense oligonucleotide depletion of hypoxia-inducible factor-1 alpha. The peroxisome proliferator-activated receptors (PPARs) are a nuclear hormone-binding proteins that regulate transcriptional activities. Ligands which bind the PPAR-gamma isoform man amplify or inhibit the expression of inflammation-related gene products and may regulate the duration of inflammatory response. Hypoxia elicits a down-regulation of PPAR-gamma in intestinal epithelial cells which is effected through a binding site for HIF1α on the antisense strand of the PPAR-gamma gene. The expression of PPAR-gamma was upregulated in hypoxic cells when treated with an antisense oligonucleotide targeted to HIF1α identical to the one used in the preeclampsia study discussed above (Narravula and Colgan, *J. Immunol.*, 2001, 166, 7543-7548).

The gene encoding hypoxia-inducible factor 2 alpha (HIF2α; also called HIF-2 alpha, endothelial PAS domain protein 1, EPAS1, MOP2, hypoxia-inducible factor 2, HIF-related factor, HRF, HIF1 alpha-like factor, HLF) was initially identified as a transcription factor expressed in endothelial cells (Ema et al., *Proc. Natl. Acad. Sci. U.S.A.*, 1997, 94, 4273-4278; Flamme et al., *Mech. Dev.*, 1997, 63, 51-60; Hogenesch et al., *J. Biol. Chem.*, 1997, 272, 8581-8593; Tian et al., *Genes Dev.*, 1997, 11, 72-82). A nucleic acid sequence encoding human HIF2α is disclosed and claimed in U.S. Pat. No. 5,695,963 (McKnight et al., 1997).

HIF2α mRNA is primarily expressed in highly vascularized adult tissues, such as lung, heart and liver, and in the placenta and endothelial cells of the embryonic and adult mouse (Hogenesch et al., *J. Biol. Chem.*, 1997, 272, 8581-8593). Comparison of normal human tissues and cancers reveals that HIF2α protein is not detectable in normal tissue, but is easily visualized in malignant tissues (Talks et al., *Am. J. Pathol.*, 2000, 157, 411-421). The requirement for expression of HIF2α in development is demonstrated by the abnormalities observed in HIF2α gene deficient mouse embryos, which include the disruption of catecholamine homeostasis and lack of protection against heart failure observed (Tian et al., *Genes Dev.*, 1998, 12, 3320-3324). Targeted disruption of the HIF2α gene and generation of embryos deficient for HIF2α is disclosed in the PCT publication WO 02/086497 (Compernolle et al., 2002). This publication also discloses antisense oligodeoxyribonucleotides for use in inhibiting HIF2α expression targeted to the translation initiation codon of HIF2α (Compernolle et al., 2002).

HIF2α expression and HIF transcriptional activity are precisely regulated by cellular oxygen concentration. Whereas changes in oxygen levels do not affect HIF1-beta protein levels, the abundance of the alpha subunits is markedly increased upon exposure of cells to hypoxia, primarily due to stabilization of the alpha subunit protein (Safran and Kaelin, *J. Clin. Invest.*, 2003, 111, 779-783). HIF2α mRNA and protein is expressed at low levels in tissue culture cells, but protein expression is markedly induced by exposure to 1% oxygen, a hypoxic state (Wiesener et al., *Blood*, 1998, 92, 2260-2268). The hypoxia-inducible factor 2 alpha/hypoxia-inducible factor 1 beta heterodimer protein binds to the hypoxic response element, which contains the core recognition sequence 5'-TACGTG-3' and is found in the cis-regulatory regions of hypoxia-regulated genes (Ema et al., *Proc. Natl. Acad. Sci. U.S.A.*, 1997, 94, 4273-4278; Hogenesch et al., *J. Biol. Chem.*, 1997, 272, 8581-8593). Binding of the heterodimer to the HRE induces gene expression. Upon return to normoxic conditions, HIF2α protein is rapidly degraded (Wiesener et al., *Blood*, 1998, 92, 2260-2268).

The mitogen-activated protein kinase (MAPK) pathway is critical for HIF2α activation. Inhibition of a dual specificity protein kinase that directly phosphorylates MAPK prevents HIF2α trans-activation during hypoxia (Conrad 1999; Conrad, 2001). However, the inhibitor does not prevent HIF2α phosphorylation, thus, while the MAPK pathway regulates the activity of hypoxia-inducible factor 2 alpha, it does not directly phosphorylate the protein (Conrad et al., *Comp. Biochem. Physiol. B. Biochem. Mol Biol.*, 2001, 128, 187-204; Conrad et al., *J. Biol. Chem.*, 1999, 274, 33709-33713). The Src family kinase pathway is also implicated in regulation of hypoxia-inducible factor 2 alpha. A specific inhibitor of the Src family of kinases abolishes the hypoxia-induced expression of HIF2α mRNA in human lung adenocarcinoma cells (Sato et al., *Am. J. Respir. Cell Mol. Biol.*, 2002, 26, 127-134).

The maintenance of oxygen homeostasis, in addition to being required in physiological development, is also required in tumor growth. Tumor cells experience hypoxia because blood circulates poorly through the aberrant blood vessel that tumors establish. Although hypoxia is toxic to cancer cells, they survive as a result of genetic and adaptive changes that allow them to thrive in a hypoxic environment. One such adaptation is an increase in the expression of the angiogenic growth factor named vascular endothelial growth factor (VEGF). VEGF is a key angiogenic factor secreted by cancer cells, as well as normal cells, in response to hypoxia (Harris, *Nat. Rev. Cancer*, 2002, 2, 38-47; Maxwell et al., *Curr. Opin. Genet. Dev.*, 2001, 11, 293-299).

Hemangioblastomas, the most frequent manifestation of VHL gene mutations, exhibit overexpression of VEGF mRNA in their associated stromal cells. The VEGF mRNA overexpression is highly correlated with elevated expression of HIF2α mRNA. This finding suggests a relationship between loss of function of the VHL gene, and transcriptional activation of the VEGF gene, possibly through HIF2α activity in VEGF-dependent vascular growth (Flamme et al., *Am. J. Pathol.*, 1998, 153, 25-29).

The tumor suppressive activity of the VHL gene product can be overridden by the activation of HIF target genes in human renal carcinoma cells in vivo. VHL gene product mutants lose the ability to target HIF for ubiquitin-mediated destruction, suggesting that down regulation of HIF and VHL tumor suppressor function are intimately linked (Kondo et al., *Cancer Cell*, 2002, 1, 237-246). In contrast to human renal cell carcinoma, the product of the tuberous sclerosis complex-2 (Tsc-2) gene, product rather than VEIL gene, is the primary target for rodent renal cell carcinoma (Liu et al., *Cancer Res.*, 2003, 63, 2675-2680). Rat RCC cells lacking Tsc-2 function exhibit stabilization of HIF2α protein and upregulation of VEGF, and were highly vascularized (Liu et al., *Cancer Res.*, 2003, 63, 2675-2680).

A link between elevated HIF2α activity and angiogenesis has also been demonstrated by experiments that show how HIF activity regulates VEGF expression. Normal human kidney cells typically have low levels of hypoxia-inducible factor 2 alpha, but upon introduction of a vector encoding HIF2α into these cells, VEGF mRNA and protein levels increase significantly (Xia et al., *Cancer*, 2001, 91, 1429-1436). When HIF2α was inhibited, VEGF expression was significantly decreased, thus demonstrating a direct link between HIF2α activity and VEGF expression (Xia et al., *Cancer*, 2001, 91, 1429-1436). Similarly, a dose-dependent increase in VEGF mRNA is observed when human umbulical vein cells are transduced with a virus encoding HIF2α (Maemura et al., *J. Biol. Chem.*, 1999, 274, 31565-31570). Expression of a mutated HIF2α that lacks a transactivation domain inhibits the induction of VEGF mRNA during hypoxia, a finding that further suggests that HIF2α is an important regulator of VEGF expression (Maemura et al., *J. Biol. Chem.*, 1999, 274, 31565-31570).

A correlation between HIF activity and VEGF expression is also observed in malignant cells and tissues. HIF2α can be readily detected in renal cell carcinoma (RCC) cell lines in the absence of a vector encoding HIF2α (Xia et al., *Cancer*, 2001, 91, 1429-1436). Significant increases in HIF2α and VEGF mRNA in renal cell carcinoma tissue samples, compared to normal tissue, suggest that abnormal activation of HIF2α may be involved in the angiogenesis of RCC (Xia et al., *Cancer*, 2001, 91, 1429-1436).

In addition to RCC, the expression of HIF2α in other malignancies has also been reported. HIF2α is expressed at the levels of mRNA and protein in human bladder cancers, especially in those with an invasive phenotype (Xia et al., *Urology*, 2002, 59, 774-778). Another example of overexpression of HIF2α is seen in squamous cell head-and-neck cancer (SCHNC). Higher levels of HIF2α were associated with locally aggressive behavior of SCHNC, as well as intensification of angiogenesis (Koukourakis et al., *Int. J. Radiat. Oncol. Biol. Phys.*, 2002, 53, 1192-1202). These findings also demonstrated a link between overexpression of HIF2α and resistance to chemotherapy. Yet another correlation between overexpression of HIF2α and cancer is seen in malignant pheochromocytomas, which exhibit a higher level of HIF2α and an induced VEGF pathway, when compared to benign counterparts (Favier et al., *Am. J. Pathol.*, 2002, 161, 1235-1246). HIF2α overexpression is also a common event in non-small-cell lung cancer (NSCLC) and is related to the up-regulation of multiple angiogenic factors and overexpression of angiogenic receptors by cancer cells. HIF2α overexpression in NSCLC is an indicator of poor prognosis (Giatromanolaki et al., *Br. J. Cancer*, 2001, 85, 881-890). Taken together, these studies demonstrate that elevated HIF2α confers aggressive tumor behavior, and that targeting the HIF pathway may aid the treatment of several different types of cancers.

Overexpression of HIF2α has also been observed in several cancer cell lines in addition to RCC cell lines. Elevated levels of HIF2α mRNA and protein are seen in human lung adenocarcinoma cells, and exposure of these cells to hypoxia further increases HIF2α expression (Sato et al., *Am. J. Respir. Cell Mol. Biol.*, 2002, 26, 127-134). Furthermore, the hypoxia response element plays a role in constitutively upregulating an isoform of VEGF in cancer cell lines under normoxic conditions. The HRE located within a cell type-specific enhancer element in glioblastoma cells participates in the up-regulation of VEGF expression through enhanced binding of HIF2α to the HRE (Liang et al., *J. Biol. Chem.*, 2002, 277, 20087-20094). A truncated version of HIF2α that can bind to hypoxia-inducible factor 1 beta, but not to the HRE, was unable to transactivate the VEGF promoter (Liang et al., *J. Biol. Chem.*, 2002, 277, 20087-20094). This further demonstrates the capability of cancer cells to combat hypoxic conditions by enhancing expression of factors required for vascularization and angiogenesis.

Short interfering RNAs (siRNAs) have been used to specifically inhibit the expression of HIF1α and HIF2α in human breast and renal carcinoma cell lines and in a human endothelial cell line. SiRNA duplexes with dTdT overhangs at both ends were designed to target nucleotides 1521-1541 and 1510-1530 of the HIF1α mRNA sequence (NM001530) and nucleotides 1260-1280 and 328-348 of the HIF2α sequence (NM001430). It was found that in the breast carcinoma and endothelial cell lines, gene expression and cell migration patterns were critically dependent on HIF1α but not hypoxia-inducible factor-2 alpha, but critically dependent on HIF2α in the renal carcinoma cells. Sowter et al., 2003, *Cancer Res.*, 63, 6130-6134.

Defective downregulation of HIF2α may play a major role in the pathogenesis of preeclampsia. HIF2α protein levels are increased during early development, as expected in a hypoxic environment, and then decrease significantly with gestational age (Rajakumar and Conrad, *Biol. Reprod.*, 2000, 63, 559-569). However, HIF2α protein expression is significantly increased in preeclamptic relative to normal term placentas (Rajakumar et al., *Biol. Reprod.*, 2001, 64, 499-506). This result suggests that failure to down-regulate HIF2α protein expression during early pregnancy could prevent the switch of the trophoblast to an invasive phenotype and ultimately lead to preeclampsia (Rajakumar et al., *Biol. Reprod*, 2001, 64, 499-506).

Overexpression of hypoxia-inducible factor 2 alpha, as well as hypoxia-inducible factor 1, has been observed in the inflammatory bowel diseases Crohn's disease and ulcerative colitis (Giatromanolaki et al., *J. Clin. Pathol.*, 2003, 56, 209-213). However, VEGF expression was weak in ulcerative colitis samples, and absent in Crohn's disease samples. The discordant expression of VEGF and HIF2α may lead to a reduced ability of a tissue to produce or respond to VEGF, which may in turn lead to reduced endothelial and epithelial cell viability (Giatromanolaki et al., *J. Clin. Pathol.*, 2003, 56, 209-213).

In addition to participating in adaptive changes in response to hypoxia, HIF2α may also function in an inflammatory response in cardiac myocytes. In cultured cardiac myocytes, interleukin-1 beta (IL-1beta) significantly increased both HIF2α mRNA and protein levels (Tanaka et al., *J. Mol. Cell Cardiol.*, 2002, 34, 739-748). Transduction of cardiac myocytes with adenovirus expressing HIF2α dramatically increased the levels of adrenomedullin (AM) mRNA, which is also upregulated by IL-1beta (Tanaka et al., *J. Mol. Cell Cardiol.*, 2002, 34, 739-748). Since IL-1 beta has been implicated in the pathogenesis of heart failure, and AM is known to improve cardiac function during heart failure, these results suggest that HIF2α plays a role in the adaptation of the cardiac myocytes during heart failure (Tanaka et al., *J. Mol. Cell Cardiol.*, 2002, 34, 739-748).

Disclosed and claimed in the PCT publication WO 00/09657 is a method of inhibiting angiogenesis in a mammal through administration of a compound which inhibits the binding of human HIF2α protein to the DNA regulatory element of an angiogenic factor, wherein the compound can be an antisense nucleic acid molecule complementary to all or part of the mRNA encoding human HIF2α (Lee et al., 2000). This publication also discloses a nucleic acid encoding human hypoxia-inducible factor 2 alpha.

The PCT publication WO 01/62965 discloses and claims a differential screening method for identifying a genetic element involved in a cellular process, which method includes introducing HIF2α into cells (Kingsman, 2001). This publication also discloses the development of HIF2α agonists or antagonists.

The PCT publication WO 02/34291 claims methods and reagents, including the use of antisense oligonucleotides, for the inhibition of human HIF1α transcription (Colgan, 2002). This publication also discloses a nucleic acid encoding human hypoxia-inducible factor 2 alpha.

U.S. Pat. No. 6,395,548 claims a nucleic acid encoding a deletion mutant of human HIF2α and the use of this deletion mutant as a method of inhibiting expression of an angiogenic factor in vitro. This patent also discloses a nucleic acid encoding human hypoxia-inducible factor 2 alpha, as well as nucleic acids complementary to all or part of the human HIF2α cDNA for use in antisense treatment to inhibit the expression of HIF2α (Lee et al., 2002).

U.S. Pat. No. 6,432,927 discloses nucleic acid sequences, including sense and antisense oligonucleotides, which are derived from an HIF2α and incorporated into recombinant nucleic acid molecules for the purpose of sustaining HIF2α expression in cells (Gregory and Vincent, 2002).

The nucleic acid sequence encoding a human HIF2α and insertion of this sequence into a viral expression vector, for the purpose of driving human HIF2α expression in mammalian cells, is disclosed in the PCT publication WO 02/068466 (White et al., 2002).

The PCT publication WO 02/094862 discloses a method for introducing into a muscle cell a nucleic acid sequence encoding hypoxia-inducible factor 2 alpha, for the purpose of overexpressing HIF2α and stimulating angiogenesis or metabolic activity (Guy, 2002).

Disclosed and claimed in the US pre-grant publication 2003/0045686 is a nucleic acid encoding human hypoxia-inducible factor 2 alpha, and a method of delivering a therapeutically effective amount of this nucleic acid to a subject for the purpose of reducing or preventing hypoxia (Kaelin Jr. and Ivan, 2003). This publication also discloses and claims human HIF muteins, including HIF2α mutein, which are designed to be more stable and/or resistant to degradation.

As a consequence of HIF2α involvement in many diseases, there remains a long felt need for additional agents capable of effectively regulating HIF2α function. As such, inhibition is especially important in the treatment of cancer, given that the upregulation of expression of HIF2α is associated with so many different types of cancer.

As a consequence of HIF1α and HIF2α involvement in many diseases, there remains a long felt need for additional agents capable of effectively inhibiting HIF1α and HIF2α function.

Antisense technology is emerging as an effective means for reducing the expression of specific gene products and may therefore prove to be uniquely useful in a number of therapeutic, diagnostic, and research applications for the modulation of HIF1α and HIF2α expression.

The present invention provides compositions and methods for modulating HIF1α and HIF2α expression. In particular antisense compositions for modulating HIF1α and/or HIF2α expression are believed to be useful in treatment of abnormal proliferative conditions associated with HIF1α and/or HIF2α. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following antioplasty. It is presently believed that inhibition of both HIF1α and HIF2α may be a particularly useful approach to treatment of such disorders.

SUMMARY OF THE INVENTION

The present invention is directed to compounds, especially nucleic acid and nucleic acid-like oligomers, which are targeted to a nucleic acid encoding HIF1α and/or HIF2α, and which modulate the expression of HIF1α and/or HIF2α. Pharmaceutical and other compositions comprising the compounds of the invention are also provided. Further provided are methods of screening for modulators of HIF1α and/or HIF2α and methods of modulating the expression of HIF1α and/or HIF2α in cells, tissues or animals comprising contacting said cells, tissues or animals with one or more of the compounds or compositions of the invention. Methods of treating an animal, particularly a human, suspected of having or being prone to a disease or condition associated with expression of HIF1α and/or HIF2α are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding HIF1α or HIF2α. This is accomplished by providing oligonucleotides which specifically hybridize with one or more nucleic acid molecules encoding HIF1α or HIF2α. Thus "target nucleic acid" refers to a nucleic acid molecule encoding HIF1α or HIF2α. As used herein, the term "nucleic acid molecule encoding HIF1α" has been used for convenience to encompass DNA encoding HIF1α, RNA (including pre-mRNA and mRNA or portions thereof) transcribed from such DNA, and also cDNA derived from such RNA. Similarly, the term "nucleic acid molecule encoding HIF2α" has been used for convenience to encompass DNA encoding HIF2α, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of HIF1α or HIF2α. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. These oligonucleotides are then tested using the methods described herein to determine their ability to inhibit expression of HIF2α mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes HIP1α or HIF2α.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding HIF1α or HIF2α, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of HIF1α or HIF2α. "Modulators" are those compounds that decrease or increase the expression of a nucleic acid molecule encoding HIF1α or HIF2α and which comprise at least an 8-nucleobase portion which is complementary to a preferred target segment. The screening method comprises the steps of contacting a preferred target segment of a nucleic acid molecule encoding HIF1α or HIF2α with one or more candidate modulators, and selecting for one or more candidate modulators which decrease or increase the expression of a nucleic acid molecule encoding HIF1α or HIF2α. Once it is shown that the candidate modulator or modulators are capable of modulating (e.g. either decreasing or increasing) the expression of a nucleic acid molecule encoding HIF1α or HIF2α, the modulator may then be employed in further investigative studies of the function of HIF1α or HIF2α, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al. *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between HIF1α or HIF2α and a disease state, phenotype, or condition. These methods include detecting or modulating HIF1α or HIF2α comprising contacting a sample, tissue, cell, or organism with the compounds of the present invention, measuring the nucleic acid or protein level of HIF1α or HIF2α and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81); protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF)

(Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The compounds of the invention are useful for research and diagnostics, because these compounds hybridize to nucleic acids encoding HIF1α or HIF2α. For example, oligonucleotides that are shown to hybridize with such efficiency and under such conditions as disclosed herein as to be effective HIF1α or HIF2α inhibitors will also be effective primers or probes under conditions favoring gene amplification or detection, respectively. These primers and probes are useful in methods requiring the specific detection of nucleic acid molecules encoding HIF1α or HIF2α and in the amplification of said nucleic acid molecules for detection or for use in further studies of HIF1α or HIF2α. Hybridization of the antisense oligonucleotides, particularly the primers and probes, of the invention with a nucleic acid encoding HIF1α or HIF2α can be detected by means known in the art. Such means may include conjugation of an enzyme to the oligonucleotide, radiolabelling of the oligonucleotide or any other suitable detection means. Kits using such detection means for detecting the level of HIF1α or HIF2α in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of HIF1α or HIF2α is treated by administering one or more antisense compounds in accordance with this invention. For example, in one non-limiting embodiment, the methods comprise the step of administering to the animal in need of treatment, a therapeutically effective amount of a HIF1α or HIF2α inhibitor. The HIF1α or HIF2α inhibitors of the present invention effectively inhibit the activity of the HIF target protein or inhibit the expression of the HIF1α or HIF2α protein. In one embodiment, the activity or expression of HIF1α or HIF2α in an animal is inhibited by about 10%. Preferably, the activity or expression of HIF1α or HIF2α in an animal is inhibited by about 30%. More preferably, the activity or expression of HIF1α and/or HIF2α in an animal is inhibited by 50% or more.

For example, the reduction of the expression of HIF1α may be measured in serum, adipose tissue, liver or any other body fluid, tissue or organ of the animal. Preferably, the cells contained within said fluids, tissues or organs being analyzed contain a nucleic acid molecule encoding HIF1α or HIF2α protein and/or the HIF1α or HIF2α protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$—[wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodo-benzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315, 298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287, 860, which is incorporated herein in its entirety. Also preferred are combinations of penetration enhancers, for example, fatty acids/salts in combination with bile acids/ salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Antiinflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxy-ethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], T-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH₄OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

present invention and their complements can be designed to target HIF1α or HIF2α. The nucleobase sequence of the antisense strand of the duplex preferably comprises at least a portion of an oligonucleotide in Tables 1, 3, 4, 5, 6, 13, or 14. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 455) and having a two-nucleobase overhang of deoxythymidine(dT) would have the following structure:

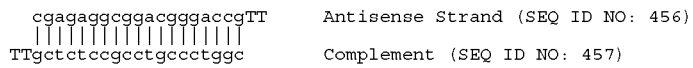

Antisense Strand (SEQ ID NO: 456)
Complement (SEQ ID NO: 457)

As another example, a duplex comprising an antisense strand having the sequence CGAGAGGCGGACGGGACCG (SEQ ID NO: 455) and having no overhangs would have the following structure:

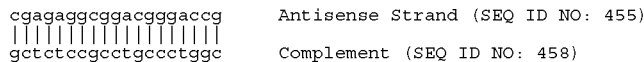

Antisense Strand (SEQ ID NO: 455)
Complement (SEQ ID NO: 458)

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting HIF1α or HIF2α

In accordance with the present invention, a series of nucleic acid duplexes comprising the antisense compounds of the RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate HIF1α or HIF2α expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of HIF1α and/or HIF2α Expression

Antisense modulation of HIF1α and/or HIF2α expression can be assayed in a variety of ways known in the art. For example, HIF1α or HIF2α mRNA levels can be quantitated by, e.g., Northern blot analysis, competitive polymerase chain reaction (PCR), or real-time PCR(RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of HIF1α or HIF2α can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to HIF1α or HIF2α can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of HIF1α or HIF2α Inhibitors Phenotypic Assays Once HIF1α or HIF2α inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of HIF1α and/or HIF2α in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with HIF1α and/or HIF2α inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the HIF1α and/or HIF2α inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.
Total RNA Isolation Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIA-VAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIA-VAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of HIF1α mRNA Levels

Quantitation of HIF1α mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATI-NUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human HIF1α were designed to hybridize to a human HIF1α sequence, using published sequence information (GenBank accession number U29165.1, incorporated herein by reference and incorporated herein as SEQ ID NO:4). For human HIF1α the PCR primers were:
forward primer: CCAGTTACGTTCCTTCGATCAGT (SEQ ID NO: 5)
reverse primer: TTTGAGGACTTGCGCTTTCA (SEQ ID NO: 6) and the PCR probe was: FAM-TCACCATTA-GAAAGCAGTTCCGCAAGCC-TAMRA
(SEQ ID NO: 7) where FAM is the fluorescent dye and TAMRA is the quencher dye. For human GAPDH the PCR primers were:
forward primer: GAAGGTGAAGGTCGGAGTC(SEQ ID NO:8)
reverse primer: GAAGATGGTGATGGGATTTC (SEQ ID NO:9) and the PCR probe was: 5' JOE-CAAGCTTCCCGT-TCTCAGCC-TAMRA 3' (SEQ ID NO: 10) where JOE is the fluorescent reporter dye and TAMRA is the quencher dye.

Example 14

Northern Blot Analysis of HIF1α mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBONDT™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ LTV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human HIF1α, a human HIF1α specific probe was prepared by PCR using the forward primer CCAGT-TACGTTCCTTCGATCAGT (SEQ ID NO: 5) and the reverse primer TTTGAGGACTTGCGCTTTCA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human HIF1α Expression by Chimeric Phosphorothioate Oligonucleotides Having 2'-MOE Wings and a Deoxy Gap In accordance with the present invention, a series of antisense compounds were designed to target different regions of the human HIF1α RNA, using published sequences (GenBank accession number U29165.1, incorporated herein by reference and incorporated herein as SEQ ID NO: 4, positions 82000 to 139500 of the sequence with GenBank accession number AL137129.4, incorporated herein by reference and incorporated herein as SEQ ID NO: 11, GenBank accession number AU123241.1, incorporated herein by reference and incorporated herein as SEQ ID NO: 12, and GenBank accession number AB073325.1, incorporated herein by reference and incorporated herein as SEQ ID NO: 13). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human HIF1α mRNA levels by quantitative real-time PCR as described in other examples herein. Data are averages from three experiments in which A549 cells were treated with the antisense oligonucleotides of the present invention. If present, "N.D." indicates "no data".

TABLE 1

Inhibition of human HIF1α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 175477 | Coding | 4 | 2496 | aaagtgatgtagtagctgca | 54 | 14 |
| 175478 | Coding | 4 | 854 | ggtatcatatacgtgaatgt | 73 | 15 |

TABLE 1-continued

Inhibition of human HIF1α mRNA levels by
chimeric phosphorothioate oligonucleotides having
2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 175479 | 3'UTR | 4 | 3179 | taccacgtactgctggcaaa | 31 | 16 |
| 175480 | Coding | 4 | 2039 | tgtgctttgaggacttgcgc | 94 | 17 |
| 175481 | Coding | 4 | 583 | gaaatgtaaatcatgtcacc | 56 | 18 |
| 175482 | Coding | 4 | 1408 | tcaaagaggctacttgtatc | 75 | 19 |
| 175483 | Coding | 4 | 1674 | ttaatgcaacttcttgattg | 45 | 20 |
| 175484 | 3'UTR | 4 | 3333 | atcattattatatgattaac | 60 | 21 |
| 175485 | 5'UTR | 4 | 152 | gaaaggcaagtccagaggtg | 42 | 22 |
| 175486 | 3'UTR | 4 | 3027 | taaactccctagccaaaaat | 40 | 23 |
| 175487 | Coding | 4 | 2085 | cattagcagtaggttcttgt | 75 | 24 |
| 175488 | 3'UTR | 4 | 3101 | gatcatgatgaaaggttact | 86 | 25 |
| 175489 | Coding | 4 | 1001 | aaatttcatatccaggctgt | 85 | 26 |
| 175490 | Coding | 4 | 460 | agtttcctcacacgcaaata | 38 | 27 |
| 175491 | Coding | 4 | 1983 | actgatcgaaggaacgtaac | 87 | 28 |
| 175492 | Coding | 4 | 2404 | cgctttctctgagcattctg | 44 | 29 |
| 175493 | Coding | 4 | 649 | aaatcaaacacactgtgtcc | 79 | 30 |
| 175494 | Coding | 4 | 1139 | tcctttagtaaacatatcat | 71 | 31 |
| 175495 | Coding | 4 | 1442 | caaagttaaagcatcaggtt | 79 | 32 |
| 175496 | Coding | 4 | 1765 | ctagtgcttccatcggaagg | 37 | 33 |
| 175497 | 3'UTR | 4 | 3424 | aatgccacatacctctaga | 24 | 34 |
| 175498 | 5'UTR | 4 | 110 | tcgtgagactagagagaagc | 71 | 35 |
| 175499 | 3'UTR | 4 | 3094 | atgaaaggttactgccttct | 81 | 36 |
| 175500 | Coding | 4 | 912 | tcagcaccaagcaggtcata | 8 | 37 |
| 175501 | 3'UTR | 4 | 2841 | aagtttgtgcagtattgtag | 33 | 38 |
| 175502 | Coding | 4 | 2396 | ctgagcattctgcaaagcta | 0 | 39 |
| 175503 | Coding | 4 | 350 | ttcagattctttacttcgcc | 54 | 40 |
| 175504 | Coding | 4 | 2320 | gataacacgttagggcttct | 41 | 41 |
| 175505 | Coding | 4 | 2331 | tcaaagcgacagataacacg | 51 | 42 |
| 175506 | Coding | 4 | 1091 | caaagcatgataatattcat | 56 | 43 |
| 175507 | Coding | 4 | 565 | ccatcatctgtgagaaccat | 86 | 44 |
| 175508 | Coding | 4 | 2222 | atatggtgatgatgtggcac | 76 | 45 |
| 175509 | 5'UTR | 4 | 51 | ctcctcaggtggcttgtcag | 33 | 46 |
| 175510 | 3'UTR | 4 | 2931 | tgagctgtctgtgatccagc | 94 | 47 |
| 175511 | Coding | 4 | 2321 | agataacacgttagggcttc | 86 | 48 |
| 175512 | Start Codon | 4 | 248 | catggtgaatcggtccccgc | 76 | 49 |
| 175513 | Coding | 4 | 1224 | tgttatatatgacagttgct | 73 | 50 |
| 224184 | Coding | 4 | 414 | ccttatcaagatgcgaactc | 63 | 51 |

TABLE 1-continued

Inhibition of human HIF1α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 224185 | Coding | 4 | 480 | ccaaatcaccagcatccaga | 32 | 52 |
| 224186 | Coding | 4 | 619 | aactgagttaatcccatgta | 72 | 53 |
| 224187 | Coding | 4 | 627 | ttagttcaaactgagttaat | 31 | 54 |
| 224188 | Coding | 4 | 706 | aggccatttctgtgtgtaag | 62 | 55 |
| 224189 | Coding | 4 | 961 | ctatctaaaggaatttcaat | 10 | 56 |
| 224190 | Coding | 4 | 1036 | cccatcaattcggtaattct | 41 | 57 |
| 224191 | Coding | 4 | 1125 | tatcatgatgagttttggtc | 81 | 58 |
| 224192 | Coding | 4 | 1283 | aataataccactcacaacgt | 60 | 59 |
| 224193 | Coding | 4 | 1380 | caactttggtgaatagctga | 71 | 60 |
| 224194 | Coding | 4 | 1699 | agtgactctggatttggttc | 44 | 61 |
| 224195 | Coding | 4 | 1928 | catctccaagtctaaatctg | 36 | 62 |
| 224196 | Coding | 4 | 1995 | ctaatggtgacaactgatcg | 72 | 63 |
| 224197 | Coding | 4 | 2126 | cactgtttttaattcatcag | 65 | 64 |
| 224198 | Coding | 4 | 2457 | ataatgttccaattcctact | 31 | 65 |
| 224199 | Stop Codon | 4 | 2735 | agaaaaagctcagttaactt | 57 | 66 |
| 224200 | 3'UTR | 4 | 2828 | attgtagccaggcttctaaa | 68 | 67 |
| 224201 | 3'UTR | 4 | 3056 | atcttcttaaaaataattcg | 18 | 68 |
| 224202 | 3'UTR | 4 | 3193 | tgtgcaattgtggctaccac | 76 | 69 |
| 224203 | 3'UTR | 4 | 3316 | aacaatgtcatgttccaggt | 88 | 70 |
| 224204 | 3'UTR | 4 | 3486 | gctggcaaagtgactataga | 72 | 71 |
| 224205 | 3'UTR | 4 | 3896 | ttccacagaagatgtttatt | 30 | 72 |
| 224206 | 3'UTR | 4 | 3899 | tttttccacagaagatgttt | 14 | 73 |
| 224207 | intron | 11 | 11258 | tagagctaaacgatctagaa | 47 | 74 |
| 224208 | intron | 11 | 23630 | taactctttctggccttgaa | 93 | 75 |
| 224209 | intron | 11 | 25682 | attggccctaacagaaaatc | 19 | 76 |
| 224210 | intron: exon junction | 11 | 27616 | agaacttatcctacttaaca | 7 | 77 |
| 224211 | intron | 11 | 39357 | gtttccctcgtgttgctcag | 63 | 78 |
| 224212 | exon: intron junction | 11 | 39759 | ttgtacttactatcatgatg | 25 | 79 |
| 224213 | exon: intron junction | 11 | 41520 | acttacttacctcacaacgt | 9 | 80 |
| 224214 | intron: exon junction | 11 | 47989 | aatctgtgtcctttaaaaca | 35 | 81 |
| 224215 | exon | 11 | 2745 | tgtgcactgaggagctgagg | 19 | 82 |
| 224216 | exon | 4 | 296 | acgttcagaacttatcttt | 45 | 83 |
| 224217 | Stop Codon | 13 | 2221 | catgctaaataattcctact | 0 | 84 |

As shown in Table 1, SEQ ID NOs 14, 15, 17, 18, 19, 20, 21, 22, 23, 24, 25, 26, 28, 29, 30, 31, 32, 35, 36, 40, 41, 42, 43, 44, 45, 47, 48, 49, 50, 51, 53, 55, 57, 58, 59, 60, 61, 63, 64, 66, 67, 69, 70, 71, 74, 75, 78 and 83 demonstrated at least 40% inhibition of human HIF1α expression in this assay and are therefore preferred. More preferred are SEQ ID NOs 47, 48 and 25. The target regions to which these preferred sequences are complementary are herein referred to as "preferred target segments" and are therefore preferred for targeting by compounds of the present invention. These preferred target segments are shown in Table 2. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in HIF1α.

| SITE ID | TARGET SEQ ID NO | TARGET SITE | SEQUENCE | REV COMP OF SEQ ID | ACTIVE IN | SEQ ID NO |
|---|---|---|---|---|---|---|
| 90592 | 4 | 2496 | tgcagctactacatcacttt | 14 | H. sapiens | 85 |
| 90593 | 4 | 854 | acattcacgtatatgatacc | 15 | H. sapiens | 86 |
| 90595 | 4 | 2039 | gcgcaagtcctcaaagcaca | 17 | H. sapiens | 87 |
| 90596 | 4 | 583 | ggtgacatgatttacatttc | 18 | H. sapiens | 88 |
| 90597 | 4 | 1408 | gatacaagtagcctctttga | 19 | H. sapiens | 89 |
| 90598 | 4 | 1674 | caatcaagaagttgcattaa | 20 | H. sapiens | 90 |
| 90599 | 4 | 3333 | gttaatcatataataatgat | 21 | H. sapiens | 91 |
| 90600 | 4 | 152 | cacctctggacttgcctttc | 22 | H. sapiens | 92 |
| 90601 | 4 | 3027 | attttttggctagggagttta | 23 | H. sapiens | 93 |
| 90602 | 4 | 2085 | acaagaacctactgctaatg | 24 | H. sapiens | 94 |
| 90603 | 4 | 3101 | agtaacctttcatcatgatc | 25 | H. sapiens | 95 |
| 90604 | 4 | 1001 | acagcctggatatgaaattt | 26 | H. sapiens | 96 |
| 90606 | 4 | 1983 | gttacgttccttcgatcagt | 28 | H. sapiens | 97 |
| 90607 | 4 | 2404 | cagaatgctcagagaaagcg | 29 | H. sapiens | 98 |
| 90608 | 4 | 649 | ggacacagtgtgtttgattt | 30 | H. sapiens | 99 |
| 90609 | 4 | 1139 | atgatatgtttactaaagga | 31 | H. sapiens | 100 |
| 90610 | 4 | 1442 | aacctgatgctttaactttg | 32 | H. sapiens | 101 |
| 90613 | 4 | 110 | gcttctctctagtctcacga | 35 | H. sapiens | 102 |
| 90614 | 4 | 3094 | agaaggcagtaacctttcat | 36 | H. sapiens | 103 |
| 90618 | 4 | 350 | ggcgaagtaaagaatctgaa | 40 | H. sapiens | 104 |
| 90619 | 4 | 2320 | agaagccctaacgtgttatc | 41 | H. sapiens | 105 |
| 90620 | 4 | 2331 | cgtgttatctgtcgctttga | 42 | H. sapiens | 106 |
| 90621 | 4 | 1091 | atgaatattatcatgctttg | 43 | H. sapiens | 107 |
| 90622 | 4 | 565 | atggttctcacagatgatgg | 44 | H. sapiens | 108 |
| 90623 | 4 | 2222 | gtgccacatcatcaccatat | 45 | H. sapiens | 109 |
| 90625 | 4 | 2931 | gctggatcacagacagctca | 47 | H. sapiens | 110 |
| 90626 | 4 | 2321 | gaagccctaacgtgttatct | 48 | H. sapiens | 111 |
| 90627 | 4 | 248 | gcggggaccgattcaccatg | 49 | H. sapiens | 112 |
| 90628 | 4 | 1224 | agcaactgtcatatataaca | 50 | H. sapiens | 113 |
| 140838 | 4 | 414 | gagttcgcatcttgataagg | 51 | H. sapiens | 114 |
| 140840 | 4 | 619 | tacatgggattaactcagtt | 53 | H. sapiens | 115 |

TABLE 2-continued

Sequence and position of preferred target
segments identified in HIF1α.

| SITE ID | TARGET SEQ ID NO | TARGET SITE | SEQUENCE | REV COMP OF SEQ ID | ACTIVE IN | SEQ ID NO |
|---|---|---|---|---|---|---|
| 140842 | 4 | 706 | cttacacacagaaatggcct | 55 | H. sapiens | 116 |
| 140844 | 4 | 1036 | agaattaccgaattgatggg | 57 | H. sapiens | 117 |
| 140845 | 4 | 1125 | gaccaaaactcatcatgata | 58 | H. sapiens | 118 |
| 140846 | 4 | 1283 | acgttgtgagtggtattatt | 59 | H. sapiens | 119 |
| 140847 | 4 | 1380 | tcagctattcaccaaagttg | 60 | H. sapiens | 120 |
| 140848 | 4 | 1699 | gaaccaaatccagagtcact | 61 | H. sapiens | 121 |
| 140850 | 4 | 1995 | cgatcagttgtcaccattag | 63 | H. sapiens | 122 |
| 140851 | 4 | 2126 | ctgatgaattaaaaacagtg | 64 | H. sapiens | 123 |
| 140853 | 4 | 2735 | aagttaactgagcttttct | 66 | H. sapiens | 124 |
| 140854 | 4 | 2828 | tttagaagcctggctacaat | 67 | H. sapiens | 125 |
| 140856 | 4 | 3193 | gtggtagccacaattgcaca | 69 | H. sapiens | 126 |
| 140857 | 4 | 3316 | acctggaacatgacattgtt | 70 | H. sapiens | 127 |
| 140858 | 4 | 3486 | tctatagtcactttgccagc | 71 | H. sapiens | 128 |
| 140861 | 11 | 11258 | ttctagatcgtttagctcta | 74 | H. sapiens | 129 |
| 140862 | 11 | 23630 | ttcaaggccagaaagagtta | 75 | H. sapiens | 130 |
| 140865 | 11 | 39357 | ctgagcaacacgagggaaac | 78 | H. sapiens | 131 |
| 140870 | 4 | 296 | aaaagataagttctgaacgt | 83 | H. sapiens | 132 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of HIF1α.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 16

Western Blot Analysis of HIF1α or HIF2α Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to HIF1α or HIF2α is used, with a radiolabeled or fluorescently labeled secondary antibody directed against the primary antibody species. Bands are visualized using a PHOSPHORIMAGER™ (Molecular Dynamics, Sunnyvale Calif.).

Example 17

Additional Antisense Oligonucleotides Against Human HIF1α

A series of antisense compounds were designed to target different regions of the human HIF1α RNA, using published sequences (GenBank accession number U29165.1, incorporated herein by reference and incorporated herein as SEQ ID NO: 133). The compounds are shown in Table 3. "Target site" indicates the first (5'-most) nucleotide number on the particular target sequence to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human HIF1α mRNA levels by quantitative real-time PCR as described in other examples herein. Data are averages from three experiments in which A549 cells were treated with the antisense oligonucleotides of the present invention. "Species" indicates the animal species of HIF1α nucleic acid to which the compounds are fully complementary (H=human, M=mouse, R=rat). As noted many of the compounds are fully complementary to more than one species.

TABLE 3

Inhibition of human HIF1α mRNA levels by additional chimeric phosphorothioate oligonucleotides having 2'-MOE wings and a deoxy gap

| ISIS # | REGION | TARGET seq id no | TARGET site | Sequence | % INHIB | SEQ ID NO | Species |
|---|---|---|---|---|---|---|---|
| 298690 | Coding | 133 | 373 | tgatgagcaagctcataaaa | 51 | 134 | H, M, R |
| 298691 | Coding | 133 | 378 | gcaactgatgagcaagctca | 77 | 135 | H, M, R |
| 298692 | Coding | 133 | 385 | ggaagtggcaactgatgagc | 62 | 136 | H, M, R |
| 298693 | Coding | 133 | 631 | ccagttagttcaaactgagt | 79 | 137 | H, M, R |
| 298694 | Coding | 133 | 636 | tgtgtccagttagttcaaac | 79 | 138 | H, M, R |
| 298695 | Coding | 133 | 641 | cacactgtgtccagttagtt | 79 | 139 | H, M, R |
| 298696 | Coding | 133 | 663 | cacatggatgagtaaaatca | 69 | 140 | H, M |
| 298697 | Coding | 133 | 673 | tcctcatggtcacatggatg | 84 | 141 | H, M, R |
| 298698 | Coding | 133 | 682 | tctctcatttcctcatggtc | 80 | 142 | H, M, R |
| 298699 | Coding | 133 | 687 | gcatttctctcatttcctca | 73 | 143 | H, M, R |
| 298700 | Coding | 133 | 695 | gtgtgtaagcatttctctca | 67 | 144 | H, M, R |
| 298701 | Coding | 133 | 705 | ggccatttctgtgtgtaagc | 78 | 145 | H, M, R |
| 298702 | Coding | 133 | 865 | tggttactgttggtatcata | 85 | 146 | H, M |
| 298703 | Coding | 133 | 919 | tcacaaatcagcaccaagca | 57 | 147 | H, M, R |
| 298704 | Coding | 133 | 924 | tgggttcacaaatcagcacc | 71 | 148 | H, M, R |
| 298705 | Coding | 133 | 931 | tgaggaatgggttcacaaat | 69 | 149 | H, M, R |
| 298706 | Coding | 133 | 967 | gtcttgctatctaaaggaat | 58 | 150 | H, M |
| 298707 | Coding | 133 | 1078 | tattcataaattgagcggcc | 80 | 151 | H, M |
| 298708 | Coding | 133 | 1084 | tgataatattcataaattga | 13 | 152 | H, M, R |
| 298709 | Coding | 133 | 1117 | tgagttttggtcagatgatc | 64 | 153 | H, M, R |
| 298710 | Coding | 133 | 1144 | acttgtcctttagtaaacat | 58 | 154 | H, M, R |
| 298711 | Coding | 133 | 1149 | tggtgacttgtcctttagta | 75 | 155 | H, M, R |
| 298712 | Coding | 133 | 1154 | tcctgtggtgacttgtcctt | 76 | 156 | H, M, R |
| 298713 | Coding | 133 | 1159 | tactgtcctgtggtgacttg | 62 | 157 | H, M, R |
| 298714 | Coding | 133 | 1164 | tcctgtactgtcctgtggtg | 83 | 158 | H, M, R |
| 298715 | Coding | 133 | 1171 | gcaagcatcctgtactgtcc | 67 | 159 | H, M, R |
| 298716 | Coding | 133 | 1192 | cagacatatccacctcttt | 56 | 160 | H, M, R |
| 298717 | Coding | 133 | 1198 | tcaacccagacatatccacc | 53 | 161 | H, M, R |
| 298718 | Coding | 133 | 1217 | tatgacagttgcttgagttt | 64 | 162 | H, M |
| 298719 | Coding | 133 | 1222 | ttatatatgacagttgcttg | 69 | 163 | H, M |
| 298720 | Coding | 133 | 1308 | gaagggagaaaatcaagtcg | 46 | 164 | H, M, R |
| 298721 | Coding | 133 | 1320 | attctgtttgttgaagggag | 43 | 165 | H, M, R |
| 298722 | Coding | 133 | 1354 | ttcatatctgaagattcaac | 53 | 166 | H, M, R |
| 298723 | Coding | 133 | 1387 | tctgattcaactttggtgaa | 59 | 167 | H, M |
| 298724 | Coding | 133 | 1549 | attacatcattatataatgg | 39 | 168 | H, M |
| 298725 | Coding | 133 | 1639 | ctacttcgaagtggctttgg | 77 | 169 | H, M, R |

TABLE 3-continued

Inhibition of human HIF1α mRNA levels by
additional chimeric phosphorothioate oligonucleotides
having 2'-MOE wings and a deoxy gap

| ISIS # | REGION | TARGET seq id no | TARGET site | Sequence | % INHIB | SEQ ID NO | Species |
|---|---|---|---|---|---|---|---|
| 298726 | Coding | 133 | 1645 | tcagcactacttcgaagtgg | 80 | 170 | H, M, R |
| 298727 | Coding | 133 | 1771 | ctttgtctagtgcttccatc | 73 | 171 | H, M, R |
| 298728 | Coding | 133 | 1955 | atcatccattgggatatagg | 74 | 172 | H, M, R |
| 298729 | Coding | 133 | 1996 | tctaatggtgacaactgatc | 78 | 173 | H, M, R |
| 298730 | Coding | 133 | 2421 | catcatgttccatttttcgc | 69 | 174 | H, M, R |
| 298731 | Coding | 133 | 2632 | gtcagctgtggtaatccact | 69 | 175 | H, M, R |
| 298732 | Coding | 133 | 2638 | taactggtcagctgtggtaa | 58 | 176 | H, M, R |
| 298733 | Coding | 133 | 2659 | ggagcattaacttcacaatc | 39 | 177 | H, M, R |
| 298734 | Coding | 133 | 2680 | aggtttctgctgccttgtat | 65 | 178 | H, M, R |
| 298735 | Coding | 133 | 2689 | ccctgcagtaggtttctgct | 63 | 179 | H, M, R |
| 298736 | Coding | 133 | 2694 | cttcaccctgcagtaggttt | 76 | 180 | H, M, R |
| 298737 | Coding | 133 | 2699 | taattcttcaccctgcagta | 71 | 181 | H, M, R |
| 298738 | Coding | 133 | 2704 | ctgagtaattcttcaccctg | 77 | 182 | H, M, R |
| 298739 | Coding | 133 | 2709 | aagctctgagtaattcttca | 84 | 183 | H, M, R |
| 298740 | Coding | 133 | 2714 | atccaaagctctgagtaatt | 66 | 184 | H, M, R |
| 298741 | Coding | 133 | 2719 | acttgatccaaagctctgag | 72 | 185 | H, M, R |
| 298742 | Stop codon | 133 | 2728 | gctcagttaacttgatccaa | 80 | 186 | H, M, R |
| 298743 | 3' UTR | 133 | 2770 | tgagccaccagtgtccaaaa | 85 | 187 | H, M, R |
| 298744 | 3' UTR | 133 | 2821 | ccaggcttctaaaattagat | 68 | 188 | H, M |
| 298745 | 3' UTR | 133 | 2835 | gtgcagtattgtagccaggc | 78 | 189 | H, M |
| 298746 | 3' UTR | 133 | 2840 | agtttgtgcagtattgtagc | 74 | 190 | H, M |
| 298747 | 3' UTR | 133 | 3004 | taaataaaaaggtgcatttt | 0 | 191 | H, M, R |
| 298749 | 3' UTR | 133 | 3110 | actgcctatgatcatgatga | 74 | 192 | H, M |
| 298750 | 3' UTR | 133 | 3194 | ttgtgcaattgtggctacca | 79 | 193 | H, M, R |
| 298751 | 3' UTR | 133 | 3199 | atatattgtgcaattgtggc | 0 | 194 | H, M, R |
| 298752 | 3' UTR | 133 | 3204 | agaaaatatattgtgcaatt | 31 | 195 | H, M, R |
| 298753 | 3' UTR | 133 | 3264 | cttaaaaactagttttataa | 21 | 196 | H, M, R |
| 298754 | 3' UTR | 133 | 3382 | atgtaaatggctttacccat | 68 | 197 | H, M, R |
| 298755 | 3' UTR | 133 | 3437 | ttttatccaaataaatgcca | 59 | 198 | H, M, R |
| 298756 | 3' UTR | 133 | 3443 | tgagaattttatccaaataa | 44 | 199 | H, M, R |
| 298757 | 3' UTR | 133 | 3701 | taatagcgacaaagtgcata | 81 | 200 | H, M, R |
| 298758 | 3' UTR | 133 | 3706 | gatgttaatagcgacaaagt | 54 | 201 | H, M, R |
| 298759 | 3' UTR | 133 | 3711 | aaaaggatgttaatagcgac | 77 | 202 | H, M, R |
| 298760 | 3' UTR | 133 | 3752 | aatgcttctaaaattactca | 62 | 203 | H, M, R |

TABLE 3-continued

Inhibition of human HIF1α mRNA levels by additional chimeric phosphorothioate oligonucleotides having 2'-MOE wings and a deoxy gap

| ISIS # | REGION | TARGET seq id no | TARGET site | Sequence | % INHIB | SEQ ID NO | Species |
|---|---|---|---|---|---|---|---|
| 298761 | 3' UTR | 133 | 3766 | tatattcctaaaataatgct | 30 | 204 | H, M |
| 298762 | 3' UTR | 133 | 3892 | acagaagatgtttatttgat | 44 | 205 | H, M, R |

In Table 3, SEQ ID NO 134, 135, 136, 137, 138, 139, 140, 141, 142, 143, 144, 145, 146, 147, 148, 149, 150, 151, 153, 154, 155, 156, 157, 158, 159, 160, 161, 162, 163, 166, 167, 169, 170, 171, 172, 173, 174, 175, 176, 178, 179, 180, 181, 182, 184, 185, 186, 187, 188, 189, 190, 192, 193, 197, 198, 200, 201, 202 and 203 demonstrated at least 50% inhibition of HIF1α expression and are therefore preferred.

Example 18

Antisense Inhibition of Mouse HIF1α Expression by Chimeric Phosphorothioate Oligonucleotides Having 2'-MOE Wings and a Deoxy Gap In accordance with the present invention, a series of antisense compounds were designed to target different regions of the mouse HIF1α RNA, using published sequences (GenBank accession number NM_010431.1, incorporated herein by reference and incorporated herein as SEQ ID NO: 206. The compounds are shown in Table 4. "Target site" indicates the first (5'-most) nucleotide number on the particular target sequence to which the compound binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse HIF1α mRNA levels by quantitative real-time PCR as described in other examples herein. Unlike previous examples, the oligonucleotide concentration in this experiment is 50 nM. Data are averages from three experiments in which b.END cells were treated with the antisense oligonucleotides of the present invention. In Table 4, "Species" indicates the animal species of HIF1α nucleic acid to which the compounds are fully complementary (H=human, M=mouse, R=rat). As noted many of the compounds are fully complementary to more than one species.

TABLE 4

Inhibition of mouse HIF1α mRNA levels by chimeric phosphorothioate oligonucleotides having 2'-MOE wings and a deoxy gap

| ISIS # | REGION | TARGET SEQ ID | TARGET SITE | Sequence | % INHIB | SEQ ID NO | Species |
|---|---|---|---|---|---|---|---|
| 298690 | Coding | 206 | 366 | tgatgagcaagctcataaaa | 32 | 134 | H, M, R |
| 298691 | Coding | 206 | 371 | gcaactgatgagcaagctca | 67 | 135 | H, M, R |
| 298692 | Coding | 206 | 378 | ggaagtggcaactgatgagc | 33 | 136 | H, M, R |
| 298693 | Coding | 206 | 624 | ccagttagttcaaactgagt | 58 | 137 | H, M, R |
| 298694 | Coding | 206 | 629 | tgtgtccagttagttcaaac | 39 | 138 | H, M, R |
| 298695 | Coding | 206 | 634 | cacactgtgtccagttagtt | 71 | 139 | H, M, R |
| 298696 | Coding | 206 | 656 | cacatggatgagtaaaatca | 60 | 140 | H, M |
| 298697 | Coding | 206 | 666 | tcctcatggtcacatggatg | 56 | 141 | H, M, R |
| 298698 | Coding | 206 | 675 | tctctcatttcctcatggtc | 69 | 142 | H, M, R |
| 298699 | Coding | 206 | 680 | gcatttctctcatttcctca | 70 | 143 | H, M, R |
| 298700 | Coding | 206 | 688 | gtgtgtaagcatttctctca | 64 | 144 | H, M, R |
| 298701 | Coding | 206 | 698 | ggccatttctgtgtgtaagc | 46 | 145 | H, M, R |
| 298702 | Coding | 206 | 858 | tggttactgttggtatcata | 69 | 146 | H, M |
| 298703 | Coding | 206 | 912 | tcacaaatcagcaccaagca | 45 | 147 | H, M, R |
| 298704 | Coding | 206 | 917 | tgggttcacaaatcagcacc | 34 | 148 | H, M, R |

TABLE 4-continued

Inhibition of mouse HIF1α mRNA levels by
chimeric phosphorothioate oligonucleotides
having 2'-MOE wings and a deoxy gap

| ISIS # | REGION | TARGET SEQ ID | TARGET SITE | Sequence | % INHIB | SEQ ID NO | Species |
|---|---|---|---|---|---|---|---|
| 298705 | Coding | 206 | 924 | tgaggaatgggttcacaaat | 64 | 149 | H, M, R |
| 298706 | Coding | 206 | 960 | gtcttgctatctaaaggaat | 42 | 150 | H, M |
| 298707 | Coding | 206 | 1071 | tattcataaattgagcggcc | 64 | 151 | H, M |
| 298708 | Coding | 206 | 1077 | tgataatattcataaattga | 0 | 152 | H, M, R |
| 298709 | Coding | 206 | 1110 | tgagttttggtcagatgatc | 26 | 153 | H, M, R |
| 298710 | Coding | 206 | 1137 | acttgtcctttagtaaacat | 47 | 154 | H, M, R |
| 298711 | Coding | 206 | 1142 | tggtgacttgtcctttagta | 64 | 155 | H, M, R |
| 298712 | Coding | 206 | 1147 | tcctgtggtgacttgtcctt | 58 | 156 | H, M, R |
| 298713 | Coding | 206 | 1152 | tactgtcctgtggtgacttg | 48 | 157 | H, M, R |
| 298714 | Coding | 206 | 1157 | tcctgtactgtcctgtggtg | 61 | 158 | H, M, R |
| 298715 | Coding | 206 | 1164 | gcaagcatcctgtactgtcc | 70 | 159 | H, M, R |
| 298716 | Coding | 206 | 1185 | cagacatatccacctctttt | 43 | 160 | H, M, R |
| 298717 | Coding | 206 | 1191 | tcaacccagacatatccacc | 55 | 161 | H, M, R |
| 298718 | Coding | 206 | 1210 | tatgacagttgcttgagttt | 39 | 162 | H, M |
| 298719 | Coding | 206 | 1215 | ttatatatgacagttgcttg | 42 | 163 | H, M |
| 298720 | Coding | 206 | 1301 | gaagggagaaaatcaagtcg | 23 | 164 | H, M, R |
| 298721 | Coding | 206 | 1313 | attctgtttgttgaagggag | 30 | 165 | H, M, R |
| 298722 | Coding | 206 | 1347 | ttcatatctgaagattcaac | 5 | 166 | H, M, R |
| 298723 | Coding | 206 | 1380 | tctgattcaactttggtgaa | 52 | 167 | H, M |
| 298724 | Coding | 206 | 1542 | attacatcattatataatgg | 29 | 168 | H, M |
| 298725 | Coding | 206 | 1629 | ctacttcgaagtggcttttgg | 57 | 169 | H, M, R |
| 298726 | Coding | 206 | 1635 | tcagcactacttcgaagtgg | 59 | 170 | H, M, R |
| 298727 | Coding | 206 | 1761 | ctttgtctagtgcttccatc | 46 | 171 | H, M, R |
| 298728 | Coding | 206 | 1987 | atcatccattgggatatagg | 29 | 172 | H, M, R |
| 298729 | Coding | 206 | 2028 | tctaatggtgacaactgatc | 19 | 173 | H, M, R |
| 298730 | Coding | 206 | 2444 | catcatgttccatttttcgc | 55 | 174 | H, M, R |
| 298731 | Coding | 206 | 2655 | gtcagctgtggtaatccact | 59 | 175 | H, M, R |
| 298732 | Coding | 206 | 2661 | taactggtcagctgtggtaa | 62 | 176 | H, M, R |
| 298733 | Coding | 206 | 2682 | ggagcattaacttcacaatc | 32 | 177 | H, M, R |
| 298734 | Coding | 206 | 2703 | aggtttctgctgccttgtat | 50 | 178 | H, M, R |
| 298735 | Coding | 206 | 2712 | ccctgcagtaggtttctgct | 53 | 179 | H, M, R |
| 298736 | Coding | 206 | 2717 | cttcaccctgcagtaggttt | 46 | 180 | H, M, R |
| 298737 | Coding | 206 | 2722 | taattcttcaccctgcagta | 42 | 181 | H, M, R |
| 298738 | Coding | 206 | 2727 | ctgagtaattcttcaccctg | 62 | 182 | H, M, R |
| 298739 | Coding | 206 | 2732 | aagctctgagtaattcttca | 44 | 183 | H, M, R |
| 298740 | Coding | 206 | 2737 | atccaaagctctgagtaatt | 42 | 184 | H, M, R |

TABLE 4-continued

Inhibition of mouse HIF1α mRNA levels by chimeric phosphorothioate oligonucleotides having 2'-MOE wings and a deoxy gap

| ISIS # | REGION | TARGET SEQ ID | TARGET SITE | Sequence | % INHIB | SEQ ID NO | Species |
|---|---|---|---|---|---|---|---|
| 298741 | Coding | 206 | 2742 | acttgatccaaagctctgag | 47 | 185 | H, M, R |
| 298742 | Stop codon | 206 | 2751 | gctcagttaacttgatccaa | 67 | 186 | H, M, R |
| 298743 | 3' UTR | 206 | 2853 | tgagccaccagtgtccaaaa | 56 | 187 | H, M, R |
| 298744 | 3' UTR | 206 | 2895 | ccaggcttctaaaattagat | 48 | 188 | H, M |
| 298745 | 3' UTR | 206 | 2909 | gtgcagtattgtagccaggc | 72 | 189 | H, M |
| 298746 | 3' UTR | 206 | 2914 | agtttgtgcagtattgtagc | 62 | 190 | H, M |
| 298747 | 3' UTR | 206 | 3067 | taaataaaaaggtgcatttt | 4 | 191 | H, M, R |
| 298748 | 3' UTR | 206 | 3162 | gatcatgatgagaatttact | 56 | 207 | M |
| 298749 | 3' UTR | 206 | 3171 | actgcctatgatcatgatga | 64 | 192 | H, M, |
| 298750 | 3' UTR | 206 | 3253 | ttgtgcaattgtggctacca | 74 | 193 | H, M, R |
| 298751 | 3' UTR | 206 | 3258 | atatattgtgcaattgtggc | 67 | 194 | H, M, R |
| 298752 | 3' UTR | 206 | 3263 | agaaaatatattgtgcaatt | 24 | 195 | H, M, R |
| 298753 | 3' UTR | 206 | 3322 | cttaaaaactagttttataa | 0 | 196 | H, M, R |
| 298754 | 3' UTR | 206 | 3428 | atgtaaatggctttacccat | 51 | 197 | H, M, R |
| 298755 | 3' UTR | 206 | 3483 | ttttatccaaataaatgcca | 28 | 198 | H, M, R |
| 298756 | 3' UTR | 206 | 3489 | tgagaattttatccaaataa | 14 | 199 | H, M, R |
| 298757 | 3' UTR | 206 | 3739 | taatagcgacaaagtgcata | 43 | 200 | H, M, R |
| 298758 | 3' UTR | 206 | 3744 | gatgttaatagcgacaaagt | 23 | 201 | H, M, R |
| 298759 | 3' UTR | 206 | 3749 | aaaaggatgttaatagcgac | 45 | 202 | H, M, R |
| 298760 | 3' UTR | 206 | 3789 | aatgcttctaaaattactca | 30 | 203 | H, M, R |
| 298761 | 3' UTR | 206 | 3803 | tatattcctaaaataatgct | 0 | 204 | H, M |
| 298762 | 3' UTR | 206 | 3928 | acagaagatgtttatttgat | 21 | 205 | H, M, R |

In Table 4, SEQ ID NOs 134, 135, 136, 137, 138, 139, 140, 141, 142, 143, 144, 145, 146, 147, 148, 149, 150, 151, 154, 155, 156, 157, 158, 159, 160, 161, 162, 163, 167, 169, 170, 171, 174, 175, 176, 177, 178, 179, 180, 181, 182, 183, 184, 185, 186, 187, 188, 189, 190, 207, 192, 193, 194, 197, 200, and 202 demonstrated at least 32% inhibition of HIF1α expression and are therefore preferred.

Example 19

Real-Time Quantitative PCR Analysis of HIF2α mRNA Levels

Quantitation of HIF2α mRNA levels was accomplished by real-time quantitative PCR using the ABI PRISM™ 7600, 7700, or 7900 Sequence Detection System (PE-Applied Biosystems, Foster City, Calif.) as described in previous examples.

Probes and primers to human HIF2α were designed to hybridize to a human HIF2α sequence, using published sequence information (GenBank accession number NM_001430.1, incorporated herein by reference and incorporated herein as SEQ ID NO: 208). For human HIF2α the PCR primers were:

forward primer: AAGCCTTGGAGGGTTTCATTG (SEQ ID NO: 209)
reverse primer: TGCTGATGTTTTCTGACAGAAAGAT (SEQ ID NO: 210) and the PCR probe was: FAM-CGTGGT-GACCCAAGATGGCGACA-TAMRA (SEQ ID NO: 211) where FAM is the fluorescent dye and TAMRA is the quencher dye. For human GAPDH the PCR primers and probe were those listed in previous examples (SEQ ID NOs: 8, 9, 10).

Probes and primers to mouse HIF2α were designed to hybridize to a mouse HIF2α sequence, using published sequence information (GenBank accession number NM_010137.1, incorporated herein by reference and incorporated herein as SEQ ID NO: 212). For mouse HIF2α the PCR primers were:

forward primer: GGCCATCGTTCGAGCCTTA (SEQ ID NO: 213)
reverse primer: GGCACGGGCACGTTCA (SEQ ID NO: 214) and the PCR probe was: FAM-CTGTTGCCGGAACTGACCAGATAT-GACTG-TAMRA
(SEQ ID NO: 215) where FAM is the fluorescent reporter dye and TAMRA is the quencher dye. For mouse GAPDH the PCR primers were:
forward primer: GGCAAATTCAACGGCACAGT (SEQ ID NO: 216)
reverse primer: GGGTCTCGCTCCTGGAAGAT (SEQ ID NO: 217) and the PCR probe was: 5' JOE-AAGGC-CGAGAATGGGAAGCTTGTCATC-TAMRA 3' (SEQ ID NO: 218) where JOE is the fluorescent reporter dye and TAMRA is the quencher dye.

Example 20

Northern Blot Analysis of HIF2α mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Electrophoresis and blotting was performed as described in previous examples.

To detect human HIF2α, a human HIF2α specific probe was prepared by PCR using the forward primer AAGCCT-TGGAGGGTTTCATTG (SEQ ID NO: 209) and the reverse primer TGCTGATGTTTTCTGACAGAAAGAT (SEQ ID NO: 210). To normalize for variations in loading and transfer efficiency membranes were stripped and probed for human glyceraldehyde-3-phosphate dehydrogenase (GAPDH) RNA (Clontech, Palo Alto, Calif.).

To detect mouse HIF2α, a mouse HIF2α specific probe was prepared by PCR using the forward primer GGC-CATCGTTCGAGCCTTA (ID NO: 213) and the reverse primer GGCACGGGCACGTTCA (SEQ ID NO: 214). To normalize for variations in loading and transfer efficiency membranes were stripped and probed for mouse glyceraldehyde-3-phosphate dehydrogenase (GAPDH) RNA (Clontech, Palo Alto, Calif.).

Example 21

Antisense Inhibition of Human HIF2α Expression by Chimeric Phosphorothioate Oligonucleotides Having 2'-MOE Wings and a Deoxy Gap In accordance with the present invention, a series of antisense compounds were designed to target different regions of the human HIF2α RNA, using published sequences (GenBank accession number NM_001430.1, incorporated herein by reference and incorporated herein as SEQ ID NO: 208). The compounds are shown in Table 5. "Target site" indicates the first (5'-most) nucleotide number on the particular target sequence to which the compound binds. All compounds in Table 5 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human HIF2α mRNA levels by quantitative real-time PCR as described in other examples herein. Data are averages from three experiments in which A549 cells were treated with the antisense oligonucleotides of the present invention.

TABLE 5

Inhibition of human HIF2α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 221985 | Start Codon | 208 | 142 | gtcagctgtcattgtcgctg | 74 | 219 |
| 221987 | Stop Codon | 208 | 2751 | ggcctggctcaggtggcctg | 54 | 220 |
| 221989 | Coding | 208 | 1000 | ggtcatgttctcggagtcta | 82 | 221 |
| 221991 | Coding | 208 | 1572 | gtggagcagctgctgctgct | 80 | 222 |
| 221993 | Coding | 208 | 2412 | ggtacatttgcgctcagtgg | 76 | 223 |
| 221995 | Coding | 208 | 2206 | tgggcctcgagcccaaaac | 15 | 224 |
| 221997 | Coding | 208 | 1300 | gaataggaagttactcttct | 51 | 225 |
| 221999 | Coding | 208 | 1752 | tggaagtcttccccgtccat | 69 | 226 |
| 222001 | Coding | 208 | 947 | gcagctcctcagggtggtaa | 82 | 227 |
| 222003 | Coding | 208 | 977 | catggtagaattcataggct | 82 | 228 |
| 222005 | Coding | 208 | 1631 | tcacttcaatcttcaggtcg | 55 | 229 |
| 222007 | Coding | 208 | 2691 | gagcttcccagcacgggcac | 79 | 230 |

TABLE 5-continued

Inhibition of human HIF2α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 222009 | Coding | 208 | 1502 | tgaaggcaggcaggctccca | 77 | 231 |
| 222011 | Coding | 208 | 2008 | ggtgctggcctggccacagc | 72 | 232 |
| 222013 | Coding | 208 | 561 | cgaatctcctcatggtcgca | 89 | 233 |
| 222015 | Coding | 208 | 1247 | tgctgttcatggccatcagg | 78 | 234 |
| 222017 | Coding | 208 | 1679 | tactgcattggtccttggcc | 78 | 235 |
| 222019 | Coding | 208 | 1488 | ctcccagcctcgctctgggt | 63 | 236 |
| 222021 | Coding | 208 | 2700 | aggagcgtggagcttcccag | 59 | 237 |
| 222023 | Coding | 208 | 623 | ctgtggacatgtctttgctt | 79 | 238 |
| 222025 | Coding | 208 | 1716 | agtgtctccaagtccagctc | 84 | 239 |
| 222027 | Coding | 208 | 759 | ctattgtgaggagggcagtt | 75 | 240 |
| 222029 | Coding | 208 | 237 | tcatagaacacctccgtctc | 37 | 241 |
| 222031 | Coding | 208 | 2334 | aaatgtgaggtgctgccacc | 67 | 242 |
| 222033 | Coding | 208 | 1578 | ttgggcgtggagcagctgct | 54 | 243 |
| 222035 | Coding | 208 | 2126 | gcgctgctcccaagaactct | 89 | 244 |
| 222037 | Coding | 208 | 2639 | gcagcaggtaggactcaaat | 64 | 245 |
| 222039 | Coding | 208 | 2325 | gtgctgccaccaggtgggtc | 79 | 246 |
| 222041 | Coding | 208 | 1001 | tggtcatgttctcggagtct | 82 | 247 |
| 222043 | Coding | 208 | 1209 | tcagtctggtccatggagaa | 80 | 248 |
| 222045 | Coding | 208 | 566 | tctcacgaatctcctcatgg | 68 | 249 |
| 222047 | Coding | 208 | 1622 | tcttcaggtcgttatccaaa | 56 | 250 |
| 222049 | Coding | 208 | 2715 | aggtcccctccttgcaggag | 66 | 251 |
| 222051 | Coding | 208 | 246 | tgggccagctcatagaacac | 82 | 252 |
| 222053 | Coding | 208 | 2336 | tcaaatgtgaggtgctgcca | 73 | 253 |
| 222055 | Coding | 208 | 391 | catctgctggtcagcttcgg | 85 | 254 |
| 222057 | Coding | 208 | 1217 | acagggattcagtctggtcc | 84 | 255 |

As shown in Table 5, SEQ ID NOs 219, 220, 221, 211, 223, 225, 226, 227, 228, 229, 230, 231, 232, 233, 234, 235, 236, 237, 238, 239, 240, 242, 243, 244, 245, 246, 247, 248, 249, 250, 251, 252, 253, 254 and 255 demonstrated at least 40% inhibition of HIF2α expression and are therefore preferred. More preferred are SEQ ID NOs 233, 239 and 244. The target regions to which these preferred sequences are complementary are herein referred to as "preferred target segments" and are therefore preferred for targeting by compounds of the present invention. These preferred target segments are shown in Table 7. These sequences are shown to contain thymine (T) but one of skill in the art will appreciate that thymine (T) is generally replaced by uracil (U) in RNA sequences. The sequences represent the reverse complement of the preferred antisense compounds shown in Table 5. "Target site" indicates the first (5'-most) nucleotide number on the particular target nucleic acid to which the oligonucleotide binds. Also shown in Table 7 is the species in which each of the preferred target segments was found.

Example 22

Antisense Inhibition of Mouse HIF2α Expression by Chimeric Phosphorothioate Oligonucleotides Having 2'-MOE Wings and a Deoxy Gap In accordance with the present invention, a second series of antisense compounds were designed to target different regions of the mouse HIF2α RNA, using published sequences (GenBank accession number NM_010137.1, incorporated herein by reference and incorporated herein as SEQ ID NO: 212, nucleotides 20468925 to 20547619 of the sequence with GenBank accession number NW_000133.1, incorporated herein by reference and incorporated herein as SEQ ID NO: 257, GenBank accession number BY229956.1, incorporated herein by reference and incorporated herein as SEQ ID NO: 258, and GenBank accession number AK087208.1, incorporated herein by reference and incorporated herein as SEQ ID NO: 259). The compounds are shown in Table 6. "Target site" indicates the first (5'-most) nucleotide number on the particular target nucleic acid to which the compound binds. All compounds in Table 6 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse HIF2α mRNA levels by quantitative real-time PCR as described in other examples herein. Data are averages from three experiments in which b.END cells were treated with the antisense oligonucleotides of the present invention.

TABLE 6

Inhibition of mouse HIF2α mRNA levels by chimeric phosphorothioate oligonucleotides having 2'-MOE wings and a deoxy gap

| ISIS # | REGION | TARGET SEQ ID NO: | TARGET SITE | SEQUENCE | % INHIB | SEQ ID NO |
|---|---|---|---|---|---|---|
| 320972 | 5'UTR | 212 | 130 | ggttccttaaccccgtaggg | 70 | 260 |
| 320973 | 5'UTR | 212 | 135 | acctgggttccttaaccccg | 61 | 261 |
| 320974 | 5'UTR | 212 | 140 | ggagcacctgggttccttaa | 70 | 262 |
| 320975 | Start Codon | 212 | 178 | ttgtcagctgtcattgtcgc | 72 | 263 |
| 320976 | Start Codon | 212 | 183 | tctccttgtcagctgtcatt | 84 | 264 |
| 320977 | Coding | 212 | 266 | gaagacctccgtctccttgc | 83 | 265 |
| 320978 | Coding | 212 | 317 | caggtgggagctcacactgt | 76 | 266 |
| 320979 | Coding | 212 | 352 | aagctgatggccaggcgcat | 64 | 267 |
| 320980 | Coding | 212 | 442 | ttcaggtacaagttatccat | 78 | 268 |
| 320981 | Coding | 212 | 448 | aaggctttcaggtacaagtt | 73 | 269 |
| 320982 | Coding | 212 | 461 | aatgaaaccctccaaggctt | 87 | 270 |
| 320983 | Coding | 212 | 520 | atgaacttgctgatgttttc | 29 | 271 |
| 320984 | Coding | 212 | 525 | gtcccatgaacttgctgatg | 57 | 272 |
| 320985 | Coding | 212 | 535 | acctgggtaagtcccatgaa | 63 | 273 |
| 320986 | Coding | 212 | 545 | tgttagttctacctgggtaa | 62 | 274 |
| 320987 | Coding | 212 | 563 | gtcaaagatgctgtgtcctg | 83 | 275 |
| 320988 | Coding | 212 | 574 | ggatgagtgaagtcaaagat | 50 | 276 |
| 320989 | Coding | 212 | 673 | atgaagaagtcacgctcggt | 63 | 277 |
| 320990 | Coding | 212 | 682 | ttcatcctcatgaagaagtc | 53 | 278 |
| 320991 | Coding | 212 | 687 | tgcacttcatcctcatgaag | 58 | 279 |
| 320992 | Coding | 212 | 714 | tgacagtccggcctctgttg | 52 | 280 |
| 320993 | Coding | 212 | 766 | actctcacttgcccggtgca | 87 | 281 |
| 320994 | Coding | 212 | 776 | gttgttgtagactctcactt | 64 | 282 |
| 320995 | Coding | 212 | 850 | attggctcacacatgatgat | 76 | 283 |
| 320996 | Coding | 212 | 860 | tgggtgctggattggctcac | 75 | 284 |
| 320997 | Coding | 212 | 913 | atgctgtggcggctcaggaa | 87 | 285 |
| 320998 | Coding | 212 | 970 | gggtggtaaccaatcagttc | 76 | 286 |
| 320999 | Coding | 212 | 1057 | gtgcacaagttctggtgact | 50 | 287 |
| 321000 | Coding | 212 | 1062 | ccttggtgcacaagttctgg | 74 | 288 |

TABLE 6-continued

Inhibition of mouse HIF2α mRNA levels by
chimeric phosphorothioate oligonucleotides
having 2'-MOE wings and a deoxy gap

| ISIS # | REGION | TARGET SEQ ID NO: | TARGET SITE | SEQUENCE | % INHIB | SEQ ID NO |
|---|---|---|---|---|---|---|
| 321001 | Coding | 212 | 1135 | gtcccctgggtctccagcca | 78 | 289 |
| 321002 | Coding | 212 | 1140 | tgaccgtccctgggtctcc | 63 | 290 |
| 321003 | Coding | 212 | 1145 | gtagatgaccgtccctggg | 68 | 291 |
| 321004 | Coding | 212 | 1150 | gggttgtagatgaccgtccc | 62 | 292 |
| 321005 | Coding | 212 | 1191 | catagttgacacacatgata | 37 | 293 |
| 321006 | Coding | 212 | 1234 | tccatggagaacaccacgtc | 76 | 294 |
| 321007 | Coding | 212 | 1239 | tctggtccatggagaacacc | 83 | 295 |
| 321008 | Coding | 212 | 1286 | aaagatgctgttcatggcca | 51 | 296 |
| 321009 | Coding | 212 | 1338 | tggtgaacaggtagttgctc | 64 | 297 |
| 321010 | Coding | 212 | 1363 | agctcctcgggctcctcctt | 83 | 298 |
| 321011 | Coding | 212 | 1454 | ggccttgccataggctgagg | 49 | 299 |
| 321012 | Coding | 212 | 1459 | aggatggccttgccataggc | 53 | 300 |
| 321013 | Coding | 212 | 1612 | ctgctgggcgtggagcagct | 40 | 301 |
| 321014 | Coding | 212 | 1725 | tgaagtccgtctgggtactg | 58 | 302 |
| 321015 | Coding | 212 | 1939 | tccaactgctgcgggtactt | 82 | 303 |
| 321016 | Coding | 212 | 2002 | ttgctcccagcatcaaagaa | 0 | 304 |
| 321017 | Coding | 212 | 2012 | cagggacccttttgctcccag | 81 | 305 |
| 321018 | Coding | 212 | 2038 | gtgctggcctggccacagca | 66 | 306 |
| 321019 | Coding | 212 | 2216 | cttgaacatggagacatgag | 65 | 307 |
| 321020 | Coding | 212 | 2226 | cagacctcatcttgaacatg | 72 | 308 |
| 321021 | Coding | 212 | 2231 | ctttgcagacctcatcttga | 73 | 309 |
| 321022 | Coding | 212 | 2296 | ttcagcttgttggacagggc | 51 | 310 |
| 321023 | Coding | 212 | 2376 | gtgaactgctggtgcctgga | 79 | 311 |
| 321024 | Coding | 212 | 2386 | cacatcaagtgtgaactgct | 0 | 312 |
| 321025 | Coding | 212 | 2413 | ccgcccatgaggctcttcat | 70 | 313 |
| 321026 | Coding | 212 | 2423 | aggacaggtcccgcccatga | 85 | 314 |
| 321027 | Coding | 212 | 2433 | caggcatcaaaggacaggtc | 55 | 315 |
| 321028 | Coding | 212 | 2482 | gatttttgggtgaattcatc | 38 | 316 |
| 321029 | Coding | 212 | 2647 | ctggccacgcctgacacctt | 65 | 317 |
| 321030 | Coding | 212 | 2665 | gatggccccagcagtcgact | 64 | 318 |
| 321031 | Coding | 212 | 2670 | cgaacgatggccccagcagt | 48 | 319 |
| 321032 | Coding | 212 | 2680 | aggtaaggctcgaacgatgg | 65 | 320 |
| 321033 | Coding | 212 | 2707 | cagtcatatctggtcagttc | 78 | 321 |
| 321034 | Coding | 212 | 2712 | cctcacagtcatatctggt | 83 | 322 |
| 321035 | Coding | 212 | 2717 | gttcacctcacagtcatatc | 66 | 323 |
| 321036 | Coding | 212 | 2722 | ggcacgttcacctcacagtc | 81 | 324 |

TABLE 6-continued

Inhibition of mouse HIF2α mRNA levels by
chimeric phosphorothioate oligonucleotides
having 2'-MOE wings and a deoxy gap

| ISIS # | REGION | TARGET SEQ ID NO: | TARGET SITE | SEQUENCE | % INHIB | SEQ ID NO |
|---|---|---|---|---|---|---|
| 321037 | Coding | 212 | 2727 | gcacgggcacgttcacctca | 90 | 325 |
| 321038 | Coding | 212 | 2758 | tctctcccctgcaggagtgt | 79 | 326 |
| 321039 | Coding | 212 | 2768 | tctgagaaggtctctcccct | 51 | 327 |
| 321040 | Coding | 212 | 2778 | ggtccagagctctgagaagg | 73 | 328 |
| 321041 | Stop Codon | 212 | 2791 | gctcaggtggcctggtccag | 69 | 329 |
| 321042 | Stop Codon | 212 | 2798 | ggccctggctcaggtggcct | 12 | 330 |
| 321043 | 3'UTR | 212 | 3199 | agaacaagaacacttgagtt | 66 | 331 |
| 321044 | intron | 257 | 12633 | aacagttgagacatgacagt | 67 | 332 |
| 321045 | exon: intron junction | 257 | 74580 | tgtcactaacctcatcttga | 45 | 333 |
| 321046 | 5'UTR | 258 | 235 | acaggagtcacttttctggg | 43 | 334 |
| 321047 | 5'UTR | 258 | 82 | catacagtctcaggacactg | 47 | 335 |
| 321048 | Genomic | 259 | 116 | aatctgtccatgaaaagaca | 33 | 336 |

As shown in Table 6, SEQ ID NO, 260, 261, 262, 263, 264, 265, 266, 267, 268, 269, 270, 272, 273, 274, 275, 276, 277, 278, 279, 280, 281, 282, 283, 284, 285, 286, 287, 288, 289, 290, 291, 292, 294, 295, 296, 297, 298, 299, 300, 301, 302, 303, 305, 306, 307, 308, 309, 310, 311, 313, 314, 315, 317, 318, 319, 320, 321, 322, 323, 324, 325, 326, 327, 328, 329, 331, 332, 333, 334 and 335 demonstrated at least 40% inhibition of mouse HIF2α expression in this experiment and are therefore preferred. More preferred are SEQ ID NOs 270, 281 and 285. The target regions to which these preferred sequences are complementary are herein referred to as "preferred target segments" and are therefore preferred for targeting by compounds of the present invention. These preferred target segments are shown in Table 7. These sequences are shown to contain thymine (T) but one of skill in the art will appreciate that thymine (T) is generally replaced by uracil (U) in RNA sequences. The sequences represent the reverse complement of the preferred antisense compounds shown in Tables 5 and 6. "Target site" indicates the first (5'-most) nucleotide number on the particular target nucleic acid to which the oligonucleotide binds. Also shown in Table 3 is the species in which each of the preferred target segments was found.

TABLE 7

Sequence and position of preferred target segments
identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 138730 | 208 | 142 | cagcgacaatgacagctgac | 291 | H. sapiens | 337 |
| 138731 | 208 | 2751 | caggccacctgagccaggcc | 292 | H. sapiens | 338 |
| 138732 | 208 | 1000 | tagactccgagaacatgacc | 293 | H. sapiens | 339 |
| 138733 | 208 | 1572 | agcagcagcagctgctccac | 294 | H. sapiens | 340 |
| 138734 | 208 | 2412 | ccactgagcgcaaatgtacc | 295 | H. sapiens | 341 |
| 138736 | 208 | 1300 | agaagagtaacttcctattc | 297 | H. sapiens | 342 |
| 138737 | 208 | 1752 | atggacggggaagacttcca | 298 | H. sapiens | 343 |
| 138738 | 208 | 947 | ttaccaccctgaggagctgc | 299 | H. sapiens | 344 |
| 138739 | 208 | 977 | agcctatgaattctaccatg | 300 | H. sapiens | 345 |
| 138740 | 208 | 1631 | cgacctgaagattgaagtga | 301 | H. sapiens | 346 |

TABLE 7-continued

Sequence and position of preferred target segments
identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 138741 | 208 | 2691 | gtgcccgtgctgggaagctc | 302 | H. sapiens | 347 |
| 138742 | 208 | 1502 | tgggagcctgcctgccttca | 303 | H. sapiens | 348 |
| 138743 | 208 | 2008 | gctgtggccaggccagcacc | 304 | H. sapiens | 349 |
| 138744 | 208 | 561 | tgcgaccatgaggagattcg | 305 | H. sapiens | 350 |
| 138745 | 208 | 1247 | cctgatggccatgaacagca | 306 | H. sapiens | 351 |
| 138746 | 208 | 1679 | ggccaaggaccaatgcagta | 307 | H. sapiens | 352 |
| 138747 | 208 | 1488 | acccagagcgaggctgggag | 308 | H. sapiens | 353 |
| 138748 | 208 | 2700 | ctgggaagctccacgctcct | 309 | H. sapiens | 354 |
| 138749 | 208 | 623 | aagcaaagacatgtccacag | 310 | H. sapiens | 355 |
| 138750 | 208 | 1716 | gagctggacttggagacact | 311 | H. sapiens | 356 |
| 138751 | 208 | 759 | aactgccctcctcacaatag | 312 | H. sapiens | 357 |
| 138753 | 208 | 2334 | ggtggcagcacctcacattt | 314 | H. sapiens | 358 |
| 138754 | 208 | 1578 | agcagctgctccacgcccaa | 315 | H. sapiens | 359 |
| 138755 | 208 | 2126 | agagttcttgggagcagcgc | 316 | H. sapiens | 360 |
| 138756 | 208 | 2639 | atttgagtcctacctgctgc | 317 | H. sapiens | 361 |
| 138757 | 208 | 2325 | gacccacctggtggcagcac | 318 | H. sapiens | 362 |
| 138758 | 208 | 1001 | agactccgagaacatgacca | 319 | H. sapiens | 363 |
| 138759 | 208 | 1209 | ttctccatggaccagactga | 320 | H. sapiens | 364 |
| 138760 | 208 | 566 | ccatgaggagattcgtgaga | 321 | H. sapiens | 365 |
| 138761 | 208 | 1622 | tttggataacgacctgaaga | 322 | H. sapiens | 366 |
| 138762 | 208 | 2715 | ctcctgcaaggaggggacct | 323 | H. sapiens | 367 |
| 138763 | 208 | 246 | gtgttctatgagctggccca | 324 | H. sapiens | 368 |
| 138764 | 208 | 2336 | tggcagcacctcacatttga | 325 | H. sapiens | 369 |
| 138765 | 208 | 391 | ccgaagctgaccagcagatg | 326 | H. sapiens | 370 |
| 138766 | 208 | 1217 | ggaccagactgaatccctgt | 327 | H. sapiens | 371 |
| 237138 | 212 | 130 | ccctacggggttaaggaacc | 332 | M. musculus | 372 |
| 237139 | 212 | 135 | cggggttaaggaacccaggt | 333 | M. musculus | 373 |
| 237140 | 212 | 140 | ttaaggaacccaggtgctcc | 334 | M. musculus | 374 |
| 237141 | 212 | 178 | gcgacaatgacagctgacaa | 335 | M. musculus | 375 |
| 237142 | 212 | 183 | aatgacagctgacaaggaga | 336 | M. musculus | 376 |
| 237143 | 212 | 266 | gcaaggagacggaggtcttc | 337 | M. musculus | 377 |
| 237144 | 212 | 317 | acagtgtgagctcccacctg | 338 | M. musculus | 378 |
| 237145 | 212 | 352 | atgcgcctggccatcagctt | 339 | M. musculus | 379 |
| 237146 | 212 | 442 | atggataacttgtacctgaa | 340 | M. musculus | 380 |
| 237147 | 212 | 448 | aacttgtacctgaaagcctt | 341 | M. musculus | 381 |
| 237148 | 212 | 461 | aagccttggagggtttcatt | 342 | M. musculus | 382 |
| 237150 | 212 | 525 | catcagcaagttcatgggac | 344 | M. musculus | 383 |

TABLE 7-continued

Sequence and position of preferred target segments identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 237151 | 212 | 535 | ttcatgggacttacccaggt | 345 | M. musculus | 384 |
| 237152 | 212 | 545 | ttacccaggtagaactaaca | 346 | M. musculus | 385 |
| 237153 | 212 | 563 | caggacacagcatctttgac | 347 | M. musculus | 386 |
| 237154 | 212 | 574 | atctttgacttcactcatcc | 348 | M. musculus | 387 |
| 237155 | 212 | 673 | accgagcgtgacttcttcat | 349 | M. musculus | 388 |
| 237156 | 212 | 682 | gacttcttcatgaggatgaa | 350 | M. musculus | 389 |
| 237157 | 212 | 687 | cttcatgaggatgaagtgca | 351 | M. musculus | 390 |
| 237158 | 212 | 714 | caacagaggccggactgtca | 352 | M. musculus | 391 |
| 237159 | 212 | 766 | tgcaccgggcaagtgagagt | 353 | M. musculus | 392 |
| 237160 | 212 | 776 | aagtgagagtctacaacaac | 354 | M. musculus | 393 |
| 237161 | 212 | 850 | atcatcatgtgtgagccaat | 355 | M. musculus | 394 |
| 237162 | 212 | 860 | gtgagccaatccagcaccca | 356 | M. musculus | 395 |
| 237163 | 212 | 913 | ttcctgagccgccacagcat | 357 | M. musculus | 396 |
| 237164 | 212 | 970 | gaactgattggttaccaccc | 358 | M. musculus | 397 |
| 237165 | 212 | 1057 | agtcaccagaacttgtgcac | 359 | M. musculus | 398 |
| 237166 | 212 | 1062 | ccagaacttgtgcaccaagg | 360 | M. musculus | 399 |
| 237167 | 212 | 1135 | tggctggagacccaggggac | 361 | M. musculus | 400 |
| 237168 | 212 | 1140 | ggagacccaggggacggtca | 362 | M. musculus | 401 |
| 237169 | 212 | 1145 | cccaggggacggtcatctac | 363 | M. musculus | 402 |
| 237170 | 212 | 1150 | gggacggtcatctacaaccc | 364 | M. musculus | 403 |
| 237172 | 212 | 1234 | gacgtggtgttctccatgga | 366 | M. musculus | 404 |
| 237173 | 212 | 1239 | ggtgttctccatggaccaga | 367 | M. musculus | 405 |
| 237174 | 212 | 1286 | tggccatgaacagcatcttt | 368 | M. musculus | 406 |
| 237175 | 212 | 1338 | gagcaactacctgttcacca | 369 | M. musculus | 407 |
| 237176 | 212 | 1363 | aaggaggagcccgaggagct | 370 | M. musculus | 408 |
| 237177 | 212 | 1454 | cctcagcctatggcaaggcc | 371 | M. musculus | 409 |
| 237178 | 212 | 1459 | gcctatggcaaggccatcct | 372 | M. musculus | 410 |
| 237179 | 212 | 1612 | agctgctccacgcccagcag | 373 | M. musculus | 411 |
| 237180 | 212 | 1725 | cagtacccagacggacttca | 374 | M. musculus | 412 |
| 237181 | 212 | 1939 | aagtacccgcagcagttgga | 375 | M. musculus | 413 |
| 237183 | 212 | 2012 | ctgggagcaaagggtccctg | 377 | M. musculus | 414 |
| 237184 | 212 | 2038 | tgctgtggccaggccagcac | 378 | M. musculus | 415 |
| 237185 | 212 | 2216 | ctcatgtctccatgttcaag | 379 | M. musculus | 416 |
| 237186 | 212 | 2226 | catgttcaagatgaggtctg | 380 | M. musculus | 417 |
| 237187 | 212 | 2231 | tcaagatgaggtctgcaaag | 381 | M. musculus | 418 |
| 237188 | 212 | 2296 | gccctgtccaacaagctgaa | 382 | M. musculus | 419 |

TABLE 7-continued

Sequence and position of preferred target segments identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 237189 | 212 | 2376 | tccaggcaccagcagttcac | 383 | M. musculus | 420 |
| 237191 | 212 | 2413 | atgaagagcctcatgggcgg | 385 | M. musculus | 421 |
| 237192 | 212 | 2423 | tcatgggcgggacctgtcct | 386 | M. musculus | 422 |
| 237193 | 212 | 2433 | gacctgtcctttgatgcctg | 387 | M. musculus | 423 |
| 237195 | 212 | 2647 | aaggtgtcaggcgtggccag | 389 | M. musculus | 424 |
| 237196 | 212 | 2665 | agtcgactgctggggccatc | 390 | M. musculus | 425 |
| 237197 | 212 | 2670 | actgctggggccatcgttcg | 391 | M. musculus | 426 |
| 237198 | 212 | 2680 | ccatcgttcgagccttacct | 392 | M. musculus | 427 |
| 237199 | 212 | 2707 | gaactgaccagatatgactg | 393 | M. musculus | 428 |
| 237200 | 212 | 2712 | gaccagatatgactgtgagg | 394 | M. musculus | 429 |
| 237201 | 212 | 2717 | gatatgactgtgaggtgaac | 395 | M. musculus | 430 |
| 237202 | 212 | 2722 | gactgtgaggtgaacgtgcc | 396 | M. musculus | 431 |
| 237203 | 212 | 2727 | tgaggtgaacgtgcccgtgc | 397 | M. musculus | 432 |
| 237204 | 212 | 2758 | acactcctgcaggggagaga | 398 | M. musculus | 433 |
| 237205 | 212 | 2768 | aggggagagaccttctcaga | 399 | M. musculus | 434 |
| 237206 | 212 | 2778 | ccttctcagagctctggacc | 400 | M. musculus | 435 |
| 237207 | 212 | 2791 | ctggaccaggccacctgagc | 401 | M. musculus | 436 |
| 237209 | 212 | 3199 | aactcaagtgttcttgttct | 403 | M. musculus | 437 |
| 237210 | 257 | 12633 | actgtcatgtctcaactgtt | 404 | M. musculus | 438 |
| 237211 | 257 | 74580 | tcaagatgaggttagtgaca | 405 | M. musculus | 439 |
| 237212 | 258 | 235 | cccagaaaagtgactcctgt | 406 | M. musculus | 440 |
| 237213 | 258 | 82 | cagtgtcctgagactgtatg | 407 | M. musculus | 441 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of HIF2α.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 23

Expression of HIF1α and HIF2α in Various Human Cell Lines

U87-MG human glioblastoma, PC-3 human prostate cancer, JEG-3 human choriocarcinoma, HeLa human cervix cancer, SK-N-BE(2) neuroblastoma, MCF-7 human breast cancer, 786-O human clear-cell renal cell carcinoma, Calu-1 human lung cancer, and Hep3B human hepatocellular carcinoma cells were purchased from American Type Culture Collection (ATCC; Manassas, Va.) and cultured according to ATCC directions. Human umbilical endothelial cells (HU-VEC) were obtained from Cascade Biologics (Portland Oreg.). Hypoxic treatments of cells (0.5–0.8×10⁶/60 mm dish or 1–2×10⁶/100 mm dish) were performed at 1% $O_2$ in a chamber controlled by ProOx oxygen sensor (BioSpherix, Redfield, N.Y.) for 16 h. To achieve the optimal hypoxic induction, 3 or 6 ml of medium was used for 60 mm and 100 mm dish culture, respectively during incubation. $CoCl_2$ (150 μM) was added to the cells to mimic hypoxic condition in some experiments.

Cultured cells at normoxia, hypoxia, or with $CoCl_2$ were harvested and whole cell lysates prepared with RIPA buffer containing protease inhibitor cocktails (Roche), 0.5 mM sodium orthovanadate, 10 mM β-glycerophophate, 250 ng/ml ubiquitin aldehyde, and 400 nM epoxomicin were separated on 12% SDS-PAGE and transferred to PVDF membranes (Amersham Biosciences). Typically, 35-50 μg of proteins were loaded per lane. Immunoblotting was performed with the following antibodies: anti-HIF-1α (BD Transduction Laboratories) at 1:250 (v/v); anti-HIF-2α (EPAS1) (Santa Cruz Biotechnology Inc) at 1:150; anti-HIF-1β (BD Transduction Laboratories) at 1:1000; anti-VHL (BD Transduction Laboratories) at 1:500; anti-GLUT-1 (Alpha Diagnostic International) at 1:600, and anti-α-tubulin (Sigma) at 1:2000 in 0.05% Tween-20/Tris-buffered saline (T-TBS) blocking buffer containing 5% nonfat skim milk at 4° C. overnight, followed by washing with T-TBS for 30 min. Goat anti-mouse or rabbit IgGs coupled with HRP (BioRad) were used as secondary antibodies at 1:3000. Immunospecific bands were detected by enhanced chemiluminescence plus (ECL-Plus) detection kit (Amersham Biosciences).

Hif1α expression was shown to be increased in hypoxic conditions and in the presence of $CoCl_2$ (which mimics hypoxia) in U87-MG human glioblastoma, PC-3 human prostate cancer, JEG-3 human choriocarcinoma, HeLa human cervix cancer, SK-N-BE(2) neuroblastoma, MCF-7 human breast cancer, Calu-1 human lung cancer, and Hep3B human hepatocellular carcinoma cells but not 786-O human clear-cell renal cell carcinoma cells.

Hif2α expression was shown to be increased in hypoxic (1% $O_2$) conditions and in the presence of $CoCl_2$ in U87-MG human glioblastoma, PC-3 human prostate cancer, JEG-3 human choriocarcinoma, MCF-7 human breast cancer, 786-O human clear-cell renal cell carcinoma, Calu-1 human lung cancer, Hep3B human hepatocellular carcinoma cells and HUVECs.

Example 24

Antisense Modulation of HIF1α mRNA Expression in Cancer Cells

Dose Response

HeLa, Hep3B, or U87-MG cells were plated in 96-well plates (8-10,000/well) 16 h prior to transfection. The following antisense oligonucleotides were delivered into cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides).

The transfection medium was switched to complete growth medium (120 μl/well) 4 h after transfection. Sixty microliters of medium was removed from the well 3 h after media switch and the cells were further incubated at normoxia or hypoxia for 16-20 h.

TABLE 8

HIF1α mRNA expression in antisense treated HeLa cells Shown as percent inhibition relative to control oligonucleotide

| Oligo-nucleotide and conditions: | Normoxia or Hypoxia | Percent inhibition of HIF1α mRNA expression after treatment with oligonucleotide at concentrations shown: | | | | |
|---|---|---|---|---|---|---|
| | | 0 | 6.25 nM | 25 nM | 100 nM | 200 nM |
| 129688 | N | 0 | 0 | 0 | 30 | 47 |
| 129688 | H | 1 | 1 | 10 | 30 | 57 |
| 175510 | N | 0 | 24 | 77 | 94 | 94 |
| 175510 | H | 1 | 39 | 82 | 95 | 96 |
| 298697 | N | 0 | 44 | 72 | 91 | 93 |
| 298697 | H | 3 | 30 | 75 | 92 | 93 |
| 222035 | N | 0 | 0 | 0 | 1 | 24 |
| 222035 | H | 3 | 3 | 0 | 11 | 35 |
| 10/35 | N | 0 | 33 | 82 | 94 | 94 |
| 10/35 | H | 3 | 35 | 85 | 94 | 95 |
| 97/35 | N | 0 | 16 | 66 | 84 | 85 |
| 97/35 | H | 3 | 34 | 79 | 88 | 89 |

N = Normoxia (21% $O_2$)
H = Hypoxia (1% $O_2$)

It can be seen that the HIF1α antisense oligonucleotides ISIS 175510 and 298697 specifically inhibited HIF1α and not HIF2α. Similar results were obtained in Hep3b human hepatocellular carcinoma cells and in U87-MG human glioblastoma cells.

Example 25

Antisense Modulation of HIF2α mRNA Expression in Cancer Cells

Dose Response

HeLa, Hep3B, or U87-MG cells were plated in 96-well plates (8-10,000/well) 16 h prior to transfection. The following antisense oligonucleotides were delivered into cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides). The transfection medium was switched to complete growth medium (120 μl/well) 4 h after transfection. Sixty microliters of medium was removed from the well 3 h after media switch and the cells were further incubated at normoxia or hypoxia for 16-20 h.

TABLE 9

HIF2α mRNA expression in ASO treated HeLa cells Shown as percent inhibition relative to control oligonucleotide

| Oligo-nucleotide and conditions: | Normoxia or Hypoxia | Percent inhibition of HIF1α mRNA expression after treatment with oligonucleotide at concentrations shown: | | | | |
|---|---|---|---|---|---|---|
| | | 0 | 6.25 nM | 25 nM | 100 nM | 200 nM |
| 129688 | N | 0 | 0 | 16 | 12 | 21 |
| 129688 | H | 0 | 0 | 4 | 12 | 50 |
| 175510 | N | 0 | 1 | 0 | 0 | 0 |
| 175510 | H | 0 | 8 | 0 | 4 | 0 |
| 298697 | N | 0 | 0 | 10 | 48 | 65 |

TABLE 9-continued

HIF2α mRNA expression in ASO treated HeLa cells
Shown as percent inhibition relative to control oligonucleotide

| Oligo-nucleotide and conditions: | Normoxia or Hypoxia | Percent inhibition of HIF1α mRNA expression after treatment with oligonucleotide at concentrations shown: | | | | |
|---|---|---|---|---|---|---|
| | | 0 | 6.25 nM | 25 nM | 100 nM | 200 nM |
| 298697 | H | 0 | 0 | 11 | 52 | 58 |
| 222035 | N | 0 | 0 | 62 | 93 | 96 |
| 222035 | H | 0 | 19 | 73 | 94 | 96 |
| 10/35 | N | 0 | 0 | 77 | 96 | 96 |
| 10/35 | H | 0 | 21 | 78 | 94 | 95 |
| 97/35 | N | 0 | 0 | 63 | 89 | 95 |
| 97/35 | H | 0 | 34 | 79 | 96 | 96 |

N = Normoxia (21% $O_2$)
H = Hypoxia (1% $O_2$)

It can be seen that the HIF2α antisense oligonucleotide ISIS 222035 specifically inhibited HIF2α relative to HIF1α. The oligonucleotide ISIS 298697, designed to target human HIF1α, showed some ability to inhibit HIF2α expression as well.
This oligonucleotide has perfect complementarity to the HIF1α target sequence and was found to have only two mismatches to the human HIF2α. Similar results were seen in U87-MG human glioblastoma cells and HepG3 hepatocellular carcinoma cells.

Example 26

HIF2α Plays a Major Role in the Induction of VEGF by Hypoxia in U87-MG Cells Genes whose products are dramatically induced by hypoxia (or $CoCl_2$, a mimic of hypoxia) include erythropoietin (Epo), glucose transporter-1 (Glut-1), vascular endothelial growth factor (VEGF) and Phosphofructokinase-L (PFK-L). They are induced by hypoxia to varying extents in various cell lines. As shown in previous examples, VEGF expression is induced by hypoxia in U87-MG cells. The following antisense oligonucleotides were delivered into cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides).

TABLE 10

HIF2α plays a major role in the induction of
EGF by hypoxia in U87-MG cells

| Oligo-nucleotide and conditions: | Normoxia or Hypoxia | Relative VEGF mRNA expression after treatment with oligonucleotide at concentrations shown: | | | | |
|---|---|---|---|---|---|---|
| | | 0 | 6.25 nM | 25 nM | 100 nM | 200 nM |
| 129688 | N | 100 | 103 | 111 | 73 | 81 |
| 129688 | H | 372 | 378 | 346 | 363 | 383 |
| 175510 | N | 100 | 86 | 65 | 61 | 62 |
| 175510 | H | 372 | 397 | 407 | 338 | 392 |
| 298697 | N | 100 | 111 | 81 | 56 | 73 |
| 298697 | H | 372 | 413 | 342 | 312 | 275 |
| 222035 | N | 100 | 94 | 69 | 48 | 45 |
| 222035 | H | 372 | 399 | 257 | 131 | 108 |
| 10/35 | N | 100 | 81 | 48 | 45 | 44 |
| 10/35 | H | 372 | 431 | 254 | 110 | 80 |
| 97/35 | N | 100 | 119 | 63 | 45 | 47 |
| 97/35 | H | 372 | 409 | 289 | 124 | 85 |

ISIS 175510, which specifically inhibits HIF1α and not HIF2α, was found to have no effect on VEGF induction by hypoxia in U87-MG cells. In contrast, ISIS 222035, which specifically inhibits HIF2α and not HIF1α, caused a dose-dependent decrease in VEGF induction. ISIS 298697, which was designed to target HIF1α but was found to have crossreactivity with HIF2α, also interfered with VEGF induction by hypoxia.
Thus HIF2α plays a major role in the induction of VEGF by hypoxia in U87-MG cells.

Example 27

HIF2α Plays a Major Role in the Induction of Epo by Hypoxia in Hep3B Cells

Genes whose products are dramatically induced by hypoxia (or $CoCl_2$, a mimic of hypoxia) include Epo, Glut-1, VEGF and PFK-L. They are induced by hypoxia to varying extents in various cell lines. Epo (erythropoietin) expression is induced by hypoxia in Hep3B cells. The following antisense oligonucleotides were delivered into Hep3B cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides).

TABLE 11

HIF2α plays a major role in the induction
of Epo by hypoxia in Hep3B cells

| Oligo-nucleotide and conditions: | Normoxia or Hypoxia | Relative Epo mRNA expression after treatment with oligonucleotide at concentrations shown: Shown as - Fold induction over control | | | | |
|---|---|---|---|---|---|---|
| | | 0 | 6.25 nM | 25 nM | 100 nM | 200 nM |
| 129688 | N | 1 | 1 | 0 | 3 | 11 |
| 129688 | H | 531 | 586 | 433 | 261 | 128 |
| 175510 | N | 1 | 8 | 3 | 3 | 2 |
| 175510 | H | 531 | 577 | 542 | 326 | 144 |
| 298697 | N | 1 | 9 | 11 | 12 | 3 |
| 298697 | H | 531 | 436 | 326 | 52 | 6 |
| 222035 | N | 1 | 3 | 3 | 2 | 1 |
| 222035 | H | 531 | 302 | 101 | 2 | 2 |
| 10/35 | N | 1 | 2 | 0 | 0 | 3 |

TABLE 11-continued

HIF2α plays a major role in the induction
of Epo by hypoxia in Hep3B cells

| Oligo-nucleotide and conditions: | Normoxia or Hypoxia | Relative Epo mRNA expression after treatment with oligonucleotide at concentrations shown: Shown as - Fold induction over control | | | | |
|---|---|---|---|---|---|---|
| | | 0 | 6.25 nM | 25 nM | 100 nM | 200 nM |
| 10/35 | H | 531 | 212 | 30 | 0 | 1 |
| 97/35 | N | 1 | 2 | 0 | 1 | 4 |
| 97/35 | H | 531 | 194 | 29 | 2 | 1 |

ISIS 175510, which specifically inhibits HIF1α and not HIF2α, was found to have no effect on Epo induction by hypoxia in Hep3B cells. In contrast, ISIS 222035, which specifically inhibits HIF2α and not HIF1α, caused a dose-dependent decrease in Epo induction. ISIS 298697, which was designed to target HIF1α but was found to have crossreactivity with HIF2α, also interfered with Epo induction by hypoxia.

Thus HIF2α plays a major role in the induction of Epo by hypoxia in Hep3B cells.

Example 28

Both HIF1α and HIF2α Play a Major Role in the Induction of VEGF by Hypoxia in HeLa Cells Genes whose products are dramatically induced by hypoxia (or $CoCl_2$) include Epo (erythropoietin), Glut-1, VEGF and Phosphofructokinase (PFK)-L. They are induced by hypoxia to varying extents in various cell lines. VEGF expression is induced by hypoxia in HeLa cells. The following antisense oligonucleotides were delivered into cells by lipofectin (3 µg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides).

TABLE 12

HIF1α and HIF2α play a major role in the induction
of VEGF by hypoxia in HeLa cells

| Oligo-nucleotide and conditions: | Normoxia or Hypoxia | Relative VEGF mRNA expression after treatment with oligonucleotide at concentrations shown: | | | | |
|---|---|---|---|---|---|---|
| | | 0 | 6.25 nM | 25 nM | 100 nM | 200 nM |
| 129688 | N | 100 | 119 | 100 | 85 | 93 |
| 129688 | H | 284 | 283 | 289 | 234 | 209 |
| 175510 | N | 100 | 95 | 132 | 110 | 113 |
| 175510 | H | 284 | 249 | 157 | 113 | 106 |
| 298697 | N | 100 | 84 | 105 | 93 | 93 |
| 298697 | H | 284 | 211 | 144 | 106 | 108 |
| 222035 | N | 100 | 111 | 114 | 92 | 67 |
| 222035 | H | 284 | 260 | 209 | 144 | 77 |
| 10/35 | N | 100 | 94 | 97 | 76 | 58 |
| 10/35 | H | 284 | 214 | 104 | 74 | 70 |
| 97/35 | N | 100 | 106 | 80 | 65 | 56 |
| 97/35 | H | 284 | 207 | 108 | 73 | 60 |

In this experiment all oligonucleotides except for the control (129688) interfered with induction of VEGF by hypoxia in HeLa cells. Thus both HIF1α and HIF2α play a major role in the induction of VEGF by hypoxia in HeLa cells. Because the relative role of HIF1α and HIF2α in hypoxic induction depends both on cell type and by induced gene (e.g., VEGF vs Epo), it is believed to be preferred to target both HIF1α and HIF2α for antisense inhibition. This may be achieved by a single cross-HIF antisense compound (such as ISIS 298697) or by a combination of one or more antisense compounds targeted to HIF1α and one or more antisense compounds targeted to HIF2α. Compounds administered in combination may be given simultaneously or sequentially.

Example 29

Designing and Testing HIF1α/HIF2α Cross-Reacting Antisense Compounds

The human HIF1α and HIF2α target sequences were compared for regions of identity but none were found to be as long as 20 nucleotides. However, based on the somewhat limited sequence homology between the human HIF1α and HIF2α target sequences, a series of antisense sequences were designed which were perfectly complementary to either HIF1α or HIF2α and which had no more than 4 mismatches to the other HIFα. These compounds are shown in Table 13. The primary target sequence (perfect complementarity) is shown in the "target" column and the number of mismatches against the other HIF is shown in subsequent columns. "Target site" refers to position on the primary target sequence.

TABLE 13

HIF1α/HIF2α crossreacting antisense sequences

| ISISNO | OLIGO_SEQ | SEQ ID NO | Target | # Mismatch vs HIF1α | #Mismatches vs HIF2α | Target site | HIF1α ~EC50 | HIF2α ~EC50 |
|---|---|---|---|---|---|---|---|---|
| 129688 | TTCGCGGCTGGACGATTCAG | 442 | Control | | | | | |
| 330460 | CCTCATGGTCGCAGGGATGA | 443 | HIF2α | 2 (G-A, G-U) | | 554 | | |
| 330462 | TCTCCTCATGGTCGCAGGGA | 444 | HIF2α | 3 (G-A, G-U, C-A) | | 557 | | |

TABLE 13-continued

HIF1α/HIF2α crossreacting antisense sequences

| ISISNO | OLIGO_SEQ | SEQ ID NO | Target | # Mismatch vs HIF1α | #Mismatches vs HIF2α | Target site | HIF1α ~EC50 | HIF2α ~EC50 |
|---|---|---|---|---|---|---|---|---|
| 222013 | CGAATCTCCTCATGGTCGCA | 233 | HIF2α | 4 (G-U, C-A, A-G, G-A) | | 561 | | |
| 298697 | TCCTCATGGTCACATGGATG | 141 | HIF1α | | 2 (A-C, T-C) | 673 | 5 | 30 |
| 330447 | TCATGGTCACATGGATGAGT | 445 | HIF1α | | 2 A-C, T-C) | 670 | 8 | 50 |
| 330449 | CCTCATGGTCACATGGATGA | 446 | HIF1α | | 2 A-C, T-C) | 672 | 5 | 30 |
| 330448 | CTCATGGTCACATGGATGAG | 447 | HIF1α | | 2 (A-C, T-C) | 671 | | |
| 330452 | ATTTCCTCATGGTCACATGG | 448 | HIF1α | | 3 (A-C, T-C, G-T) | 676 | | |
| 330470 | AAACCCTCCAAGGCTTTCAG | 449 | HIF2α | 2 (G-U, C-U) | | 423 | 45 | 20 |
| 326743 | TCCTCATGGTCGCAGGGATG | 450 | HIF2α | 2 G-A, G-U | | 555 | 40 | 10 |

Thus it is possible to inhibit both HIF1α and HIF2α with a single crossreacting oligonucleotide, although the relative antisense efficacy is not equal for the two forms because of imperfect homology to one HIFα or the other.

Example 30

Crossreacting HIF1α/HIF2α Antisense Compounds Containing "Universal" Bases

In order to try to get antisense compounds that were highly potent against both HIF1α and HIF2α targets, the nucleobases at the sites of the mismatches against one or the other HIF were replaced with the "universal bases" inosine or 3' nitro-pyrrole. Inosine has the ability to pair with G, U or C. If there was an A at the particular position of either of the sequences, we used 3-nitropyrrole. This is a base that does not have binding affinity to any of the bases, but also does not cause steric hindrance of the duplex. These oligos were screened and found to be active against both targets with an intermediate potency. This is shown in Table 14. In the table, "I" indicates inosine and "P" indicates 3-nitropyrrole.

TABLE 14

HIF1α/HIF2α crossreacting antisense compounds containing universal bases

| ISISNO | OLIGO_SEQ | SEQ ID NO | Target | # Mismatch vs HIF1α | #Mismatch vs HIF2α | Target site | HIF1α ~EC50 | HIF2α ~EC50 |
|---|---|---|---|---|---|---|---|---|
| 326743 | TCCTCATGGTCGCAGGGATG | 450 | HIF2α | 2 (G-A, G-U) | | 555 | 40 | 10 |
| 298697 | TCCTCATGGTCACATGGATG | 141 | HIF1α | | 2 (A-C, T-C) | 673 | 5 | 30 |
| 330449 | CCTCATGGTCACATGGATGA | 446 | HIF1α | | 2 (A-C, T-C) | 672 | 5 | 30 |
| 337223 | TCCTCATGGTCICAPGGATG | 451 | HIF1α and HIF2α | 2 (I-T, P-A) | 2 (I-C, P-C) | 673 | 25 | 15 |
| 337224 | CCTCATGGTCICAPGGATGA | 452 | HIF1α and HIF2α | 2 (I-T, P-A) | 2 (I-C, P-C) | 672 | 25 | 15 |

Introduction of universal bases into the antisense compounds at the site of mismatches resulted in a more equal inhibitory effect for both HIF1α and HIF2α.

Example 31

Tube Formation Assay to Determine Effect of HIF1α and HIF2α Antisense Inhibitors on Angiogenesis Angiogenesis is stimulated by numerous factors that promote interaction of endothelial cells with each other and with extracellular matrix molecules, resulting in the formation of capillary tubes. This process can be reproduced in tissue culture by the formation of tube-like structures by endothelial cells. Loss of tube formation in vitro has been correlated with the inhibition of angiogenesis in vivo (Carmeliet et al., (2000) Nature 407:249-257; and Zhang et al., (2002) Cancer Research 62:2034-42), which supports the use of in vitro tube formation as an endpoint for angiogenesis.

Angiogenesis, or neovascularization, is the formation of new capillaries from existing blood vessels. In adult organisms this process is typically controlled and short-lived, for example in wound repair and regeneration. However, aberrant capillary growth can occur and this uncontrolled growth plays a causal and/or supportive role in many pathologic conditions such as tumor growth and metastasis. In the context of this invention "aberrant angiogenesis" refers to unwanted or uncontrolled angiogenesis. Angiogenesis inhibitors are being evaluated for use as antitumor drugs. Other diseases and conditions associated with angiogenesis include arthritis, cardiovascular diseases, skin conditions, and aberrant wound healing. Aberrant angiogenesis can also occur in the eye, causing loss of vision. Examples of ocular conditions involving aberrant angiogenesis include macular degeneration, diabetic retinopathy and retinopathy of prematurity.

The tube formation assay is performed using an in vitro Angiogenesis Assay Kit (Chemicon International, Temecula, Calif.), or growth factor reduced Matrigel (BD Biosciences, Bedford, Mass.). HUVECs were plated at 4000 cells/well in 96-well plates. One day later, cells were transfected with antisense and control oligonucleotides according to standard published procedures (Monia et al., (1993) J Biol Chem. 1993 Jul. 5; 268(19):14514-22) using 75 nM oligonucleotide in lipofectin (Gibco, Grand Island, N.Y.). Approximately fifty hours post-transfection, cells were transferred to 96-well plates coated with ECMatrix™ (Chemicon Inter-national) or growth factor depleted Matrigel. Under these conditions, untreated HUVECs form tube-like structures. After an overnight incubation at 37° C., treated and untreated cells were inspected by light microscopy. Individual wells were assigned discrete scores from 1 to 5 depending on the extent of tube formation. A score of 1 refers to a well with no tube formation while a score of 5 is given to wells where all cells are forming an extensive tubular network.

ISIS 29848; (NNNNNNNNNNNNNNNNNNNN; SEQ ID NO: 453) is a control oligonucleotide containing an equal mixture of the bases A, C, G and T at every position. ISIS 298695 (SEQ ID NO: 139) and ISIS 298750 (Seq; SEQ ID NO: 193) are targeted to HIF1α; ISIS 330447 (Seq; SEQ ID NO: 445) is a cross-HIF oligonucleotide having perfect complementarity to HIF1α target and imperfect complementarity (and thus less inhibitory effect) for HIF2α; ISIS 222035 (SEQ ID NO: 244) and 222025 (SEQ ID NO: 239) are targeted to HIF2α and ISIS 326743 is a cross-HIF oligonucleotide having perfect complementarity to HIF2α target and imperfect complementarity (and thus less inhibitory effect) for HIF1α.

TABLE 15

Effect of HIF1α and HIF2α antisense oligonucleotides on angiogenic tube formation

| ISIS # | Target | 0 | 10 nM | 35 nM | 75 nM |
|---|---|---|---|---|---|
| 29848 | control | 5 | 5 | 4.75 | 4.375 |
| 298695 | HIF1α | 5 | 5 | 5 | 3.75 |
| 298750 | HIF1α | 5 | 5 | 4.75 | 3.25 |
| 330447 | HIF 1α/2α | 5 | 5 | 4.25 | 3 |
| 222035 | HIF2α | 5 | 5 | 3.75 | 1.75 |
| 222025 | HIF2α | 5 | 5 | 3.5 | 1.75 |
| 326743 | HIF2α/1α | 5 | 5 | 4.75 | 5 |

As calculated from the assigned discrete scores, it is apparent that HUVEC tube formation is inhibited by reduction of HIF2α and HIF1α, singly or in combination.

Example 32

Inhibition of HIF1α Expression In Vivo

C57Bl/6 mice are maintained on a standard rodent diet and are used as control (lean) animals. Seven-week old male C57Bl/6 mice are injected subcutaneously with oligonucleotides at a dose of 25 mg/kg two times per week for 4 weeks. Saline-injected animals serve as a control. After the treatment period, mice are sacrificed and target levels are evaluated in liver using RNA isolation and target mRNA expression level quantitation (RT-PCR) as described in other examples herein.

Oligonucleotides used in this experiment were ISIS 298695 (SEQ ID NO: 139), ISIS 298697 (SEQ ID NO: 141), and ISIS 298750, (SEQ ID NO: 193), all targeted to mouse HIF1α and crossreactive to human HIF1α. ISIS 141923 (CCTTCCCTGAAGGTTCCTCC; SEQ ID NO: 454) is an unrelated negative control oligonucleotide. Results are shown in Table 16.

TABLE 16

Antisense inhibition of HIF1α expression in mouse liver by antisense to HIF1α

| ISIS # | % inhib. of HIF1α |
|---|---|
| Saline | 0 |
| ISIS 298695 | 76 |
| ISIS 298697 | 70 |
| ISIS 298750 | 74 |
| ISIS 141923 (control) | 0 |

The effect of inhibiting HIF1α on levels of VEGF and GLUT1 in mouse liver was also determined. These are both hypoxia-inducible targets. Results are shown in Table 17 and 18.

TABLE 17

Effect of Antisense inhibition of HIF1α on VEGF expression in mouse liver

| ISIS # | % inhib. of VEGF |
|---|---|
| Saline | 0 |
| ISIS 298695 | 12 |
| ISIS 298697 | 4 |
| ISIS 298750 | 0 |
| ISIS 141923 (control) | 0 |

TABLE 18

Effect of antisense inhibition of HIF1α
on GLUT1 expression in mouse liver

| ISIS # | % inhib. of VEGF |
|---|---|
| Saline | 0 |
| ISIS 298695 | 0 |
| ISIS 298697 | 15 |
| ISIS 298750 | 0 |
| ISIS 141923 (control) | 22 |

Example 33

Antisense Inhibition of HIF1α in a Mouse Model of Hepatocellular Carcinoma (HCC)

An HCC mouse model (C57BL/6-TgN(CRP-TagSV40) 60-4, Taconic, Germantown N.Y.) for hepatocellular carcinoma was used in which transgenic male mice express SV40 T-antigen (Tag) in their livers, which leads to spontaneous development of well-differentiated hepatocellular carcinoma (HCC) carcinomas (Ruther et al., 1993, *Oncogene* 8, 87-93). HCC mice were treated with ISIS 298695, ISIS 298697 or ISIS 298750, all targeted to HIF1α or with an unrelated control oligonucleotide. HCC and wild type mice were also treated with saline alone. Results are shown in Table 19.

TABLE 19

Antisense inhibition of HIF1α in HCC mouse liver

| ISIS # | SEQ ID NO | % inhib. of HIF1α |
|---|---|---|
| Saline | | 0 |
| ISIS 298695 | 139 | 43 |
| ISIS 298697 | 141 | 33 |
| ISIS 298750 | 193 | 40 |
| ISIS 141923 (control) | 454 | 11 |
| C57BL6/saline | | 43 |

The effect of HIF1α inhibition on GLUT1 expression in HCC mice was also evaluated. Results are shown in Table 20.

TABLE 20

Effect of antisense inhibition of HIF1α
on GLUT1 levels in HCC mouse liver

| ISIS # | SEQ ID NO | % inhib. of GLUT1 |
|---|---|---|
| Saline | | 0 |
| ISIS 298695 | 139 | 0 |
| ISIS 298697 | 141 | 0 |
| ISIS 298750 | 193 | 13 |
| ISIS 141923 (control) | 454 | 18 |
| C57BL6/saline | | 2 |

Example 34

Inhibition of HIF2α Expression in Tumor Cells by Wild-Type p53 Under Hypoxia in T47D Tumor Cells T47D breast adenocarcinoma cells were obtained from the American Type Culture Collection (ATCC) (Manassas, Va.). Cells were cultured in Gibco DMEM High glucose media supplemented with 10% FBS. p53 is a tumor suppressor gene product which is inactive or aberrant in approximately 50% of human tumors. T47D cells are p53 null, i.e. they contain inactive mutant p53. These cells express high levels of HIF2α even in normoxic conditions. Hypoxia or $CoCl_2$ induces even higher levels of HIF2α expression. In contrast, T47D cells which have been transfected with a plasmid expressing p53, thus restoring p53 function in these cells, express extremely low levels of HIF2α, even in hypoxic conditions or in $CoCl_2$ simulation of hypoxia. This increase in HIF2α in cells with aberrant p53 is believed to be a novel observation and is believed to indicate a link between p53 and the HIF pathway.

Example 35

Effects of Antisense Inhibition of HIF1α and/or HIF2α on Cancer Cell Proliferation Under Hypoxia/Glucose Deprivation PC-3 human prostate cancer cells were cultured as described in previous examples. Cells were electroporated with oligonucleotide at concentrations described below and grown for 16 hours at normoxia and 0.45 g/l glucose. The medium was then replaced with either glucose (4.5 g/l glucose) or low-glucose medium (no added glucose) and cells were then kept at hypoxia (1% $O_2$) or normoxia (21% $O_2$) for another 48 hours. The effect of antisense treatment on cell proliferation was measured. Oligonucleotides were ISIS 129688 (unrelated control), ISIS 175510 (HIF1α), ISIS 222035 (HIF2α) and ISIS 298697 (HIF1α with some cross-reactivity to HIF2α). Results are shown in the tables below, one table for each culture condition.

TABLE 21

Effect of HIF antisense on proliferation
of PC-3 cancer cells Normoxia/Glucose

| | Cell proliferation as percent of saline control | | | |
|---|---|---|---|---|
| ISIS # | 0 nM | 10 nM | 20 nM | SEQ ID NO |
| 129688 | 100 | 103 | 103 | 442 |
| 175510 | 100 | 126 | 93 | 47 |
| 222035 | 100 | 130 | 116 | 244 |
| 298697 | 100 | 118 | 86 | 141 |

TABLE 22

Effect of HIF antisense on proliferation
of PC-3 cancer cells Hypoxia/Glucose

| | Cell proliferation as percent of saline control | | | |
|---|---|---|---|---|
| ISIS # | 0 nM | 10 nM | 20 nM | SEQ ID NO |
| 129688 | 100 | 104 | 99 | 442 |
| 175510 | 100 | 113 | 105 | 47 |
| 222035 | 100 | 106 | 91 | 244 |
| 298697 | 100 | 113 | 83 | 141 |

TABLE 23

Effect of HIF antisense on proliferation
of PC-3 cancer cells Normoxia/Low Glucose

| | Cell proliferation as percent of saline control | | | |
|---|---|---|---|---|
| ISIS # | 0 nM | 10 nM | 20 nM | SEQ ID NO |
| 129688 | 100 | 107 | 105 | 442 |
| 175510 | 100 | 96 | 89 | 47 |
| 222035 | 100 | 91 | 68 | 244 |

TABLE 23-continued

Effect of HIF antisense on proliferation
of PC-3 cancer cells Normoxia/Low Glucose

| | Cell proliferation as percent of saline control | | | |
|---|---|---|---|---|
| ISIS # | 0 nM | 10 nM | 20 nM | SEQ ID NO |
| 298697 | 100 | 91 | 88 | 141 |

TABLE 24

Effect of HIF antisense on proliferation
of PC-3 cancer cells Hypoxia/Low Glucose

| | Cell proliferation as percent of saline control | | | |
|---|---|---|---|---|
| ISIS # | 0 nM | 10 nM | 20 nM | SEQ ID NO |
| 129688 | 100 | 105 | 103 | 442 |
| 175510 | 100 | 90 | 85 | 47 |
| 222035 | 100 | 88 | 80 | 244 |
| 298697 | 100 | 88 | 61 | 141 |

Example 36

Effect of Antisense Inhibitors of HIFs on Human Tumor Cell Xenografts in Mice

Nude mice are injected in the flank with approximately $10^6$ U87-MG human glioblastoma cells. Mice are dosed with antisense compound beginning the day after tumor inoculation and continuing every other day. Oligonucleotides used are ISIS 129688 (unrelated control), ISIS 175510 (HIF1α), ISIS 222035 (HIF2α) and ISIS 298697 (HIF1α with some crossreactivity to HIF2α). Tumor volume is measured every few days beginning 10 days after inoculation.

Similar xenograft studies are performed with MDA-MB231 human breast cancer cells, which are p53-deficient. Nude mice are injected in the flank with approximately $10^6$ MDA-MB231 human breast cancer cells. Mice are dosed with antisense compound beginning the day after tumor inoculation and continuing every other day. Oligonucleotides used are ISIS 129688 (unrelated control), ISIS 175510 (HIF1α), ISIS 222035 (HIF2α) and ISIS 298697 (HIF1α with some crossreactivity to HIF2α). Tumor volume is measured every few days beginning 10 days after inoculation.

Example 37

Effect of Antisense Inhibitors of HIFs on Angiogenic Conditions in the Eye

It is believed that antisense inhibitors of HIF2α and possibly HIF1α will be useful in treatment of angiogenic conditions, because of their effect on endothelial tube formation in an in vitro model for angiogenesis (see previous examples).

A pig model of ocular neovascularization, the branch retinal vein occlusion (BVO) model, is used to study ocular neovascularization. Male farm pigs (8-10 kg) are subjected to branch retinal vein occlusions (BVO) by laser treatment in both eyes. The extent of BVO is determined by indirect opthalmoscopy after a 2 week period. Intravitreous injections (10 μM) of ISIS 129688 (unrelated control), ISIS 175510 (HIF1α), ISIS 222035 (HIF2α) or ISIS 298697 (HIF1α with some crossreactivity to HIF2α) are started on the day of BVO induction and are repeated at weeks 2, 6, and 10 after BVO (Right eye—vehicle, Left eye—antisense molecule). Stereo fundus photography and fluorescein angiography are performed at baseline BVO and at weeks 1, 6 and 12 following intravitreous injections to measure the neovascular response. In addition capillary gel electrophoresis analysis of the eye sections containing sclera, choroid, and the retina are performed to determine antisense concentrations, and gross and microscopic evaluations are performed to determine eye histopathology.

What is claimed is:

1. A compound comprising a chimeric oligonucleotide consisting of 8 to 80 linked nucleosides, wherein said oligonucleotide is fully complementary to the nucleotide sequence within the range of nucleotides 1139 to 1218 of SEQ ID NO: 4.

2. A compound comprising a chimeric oligonucleotide consisting of 8 to 80 linked nucleosides, wherein said oligonucleotide comprises an at least 8 consecutive nucleobase portion that is fully complementary to an equal length portion of the nucleotide sequence within the range of nucleotides 1151 to 1230 of SEQ ID NO: 4, and wherein said chimeric oligonucleotide is fully complementary to SEQ ID NO: 4.

3. The compound of claim 1 or 2, wherein the oligonucleotide comprises 12 to 50 linked nucleosides.

4. The compound of claim 1 or 2, wherein the oligonucleotide comprises 15 to 30 linked nucleosides.

5. A composition comprising the compound of claim 1 or 1 with a pharmaceutically acceptable carrier.

6. A method of inhibiting the expression of HIF1α in cells or tissues comprising contacting said cells or tissues with the compound of claim 1 or 2, so that expression of HIF1α is inhibited.

7. A method of treating an animal having a disease or condition associated with HIF1α comprising administering to said animal a therapeutically or prophylactically effective amount of the compound of claim 1 or 2, so that expression of HIF1α is inhibited.

8. The compound of claim 3, consisting of a single-stranded modified oligonucleotide.

9. The compound of claim 8, wherein at least one internucleoside linkage is a modified internucleoside linkage.

10. The compound of claim 9, wherein each internucleoside linkage is a phosphorothioate internucleoside linkage.

11. The compound of claim 8, wherein at least one nucleoside comprises a modified sugar.

12. The compound of claim 11, wherein at least one modified sugar is a bicyclic sugar.

13. The compound of claim 11, wherein at least one modified sugar comprises a 2'-O-methoxyethyl or a 4'-$(CH_2)_n$-O-2' bridge, wherein n is 1 or 2.

14. The compound of claim 8, wherein at least one nucleoside comprises a modified nucleobase.

15. The compound of claim 14, wherein the modified nucleobase is a 5-methylcytosine.

16. The compound of claim 3, wherein the chimeric oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

17. The compound of claim 16, wherein the chimeric oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar; wherein each cytosine in said chimeric oligonucleotide is a 5-methylcytosine, and wherein each internucleoside linkage of said chimeric oligonucleotide is a phosphorothioate linkage.

18. The compound of claim 17, wherein the chimeric oligonucleotide consists of 20 linked nucleosides.

* * * * *